(12) United States Patent
Roschke et al.

(10) Patent No.: US 9,676,833 B2
(45) Date of Patent: Jun. 13, 2017

(54) ANG-2-BINDING MODULAR RECOGNITION DOMAIN COMPLEXES AND PHARMACEUTICAL COMPOSITIONS THEREOF

(71) Applicant: Zyngenia, Inc., Gaithersburg, MD (US)

(72) Inventors: Viktor Roschke, Bethesda, MD (US); David Lafleur, Washington, DC (US); David M. Hilbert, Bethesda, MD (US); Peter Kiener, Potomac, MD (US)

(73) Assignee: Zyngenia, Inc., Washington, DC (US)

( * ) Notice: Subject to any disclaimer, the term of this patent is extended or adjusted under 35 U.S.C. 154(b) by 0 days.

(21) Appl. No.: 14/527,656

(22) Filed: Oct. 29, 2014

(65) Prior Publication Data

US 2016/0176934 A1 Jun. 23, 2016

Related U.S. Application Data

(63) Continuation of application No. 13/840,227, filed on Mar. 15, 2013, now abandoned, which is a continuation of application No. 13/184,485, filed on Jul. 15, 2011, now abandoned.

(60) Provisional application No. 61/364,764, filed on Jul. 15, 2010, provisional application No. 61/364,765, filed on Jul. 15, 2010, provisional application No. 61/364,766, filed on Jul. 15, 2010, provisional application No. 61/364,771, filed on Jul. 15, 2010, provisional application No. 61/364,774, filed on Jul. 15, 2010, provisional application No. 61/383,644, filed on Sep. 16, 2010, provisional application No. 61/481,063, filed on Apr. 29, 2011, provisional application No. 61/485,486, filed on May 12, 2011, provisional application No. 61/485,484, filed on May 12, 2011, provisional application No. 61/485,502, filed on May 12, 2011, provisional application No. 61/485,505, filed on May 12, 2011.

(51) Int. Cl.
| | | |
|---|---|---|
| *C07K 14/47* | (2006.01) | |
| *A61K 38/00* | (2006.01) | |
| *A61K 47/48* | (2006.01) | |
| *C07K 16/22* | (2006.01) | |
| *C07K 16/24* | (2006.01) | |
| *C07K 16/28* | (2006.01) | |
| *C07K 16/30* | (2006.01) | |
| *C12N 9/00* | (2006.01) | |
| *C07K 16/32* | (2006.01) | |

(52) U.S. Cl.
CPC ........ *C07K 14/47* (2013.01); *A61K 47/48415* (2013.01); *A61K 47/48546* (2013.01); *A61K 47/48561* (2013.01); *A61K 47/48584* (2013.01); *A61K 47/48676* (2013.01); *C07K 16/22* (2013.01); *C07K 16/24* (2013.01); *C07K 16/241* (2013.01); *C07K 16/2863* (2013.01); *C07K 16/2866* (2013.01); *C07K 16/3046* (2013.01); *C07K 16/32* (2013.01); *C12N 9/0002* (2013.01); *A61K 38/00* (2013.01); *C07K 2317/73* (2013.01); *C07K 2317/77* (2013.01); *C07K 2319/01* (2013.01); *C07K 2319/30* (2013.01)

(58) Field of Classification Search
CPC ........ C07K 14/47; C07K 16/22; C07K 16/24; C07K 16/241; C07K 16/2863; C07K 16/2866; C07K 16/3046; C07K 16/32; C07K 2317/73; C07K 2317/77; C07K 2319/01; C07K 2319/30; A61K 38/00; A61K 47/48415; A61K 47/48546; A61K 47/48561; A61K 47/48584; A61K 47/48676; C12N 9/0002
See application file for complete search history.

(56) References Cited

U.S. PATENT DOCUMENTS

| | | |
|---|---|---|
| 5,196,193 A | 3/1993 | Carroll |
| 5,637,481 A | 6/1997 | Ledbetter et al. |
| 5,677,171 A | 10/1997 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,821,337 A | 10/1998 | Carter et al. |
| 5,844,094 A | 12/1998 | Hudson et al. |
| 5,877,289 A | 3/1999 | Thorpe et al. |
| 5,977,322 A | 11/1999 | Marks et al. |
| 6,054,561 A | 4/2000 | Ring |
| 6,103,889 A | 8/2000 | Whitlow et al. |
| 6,132,992 A | 10/2000 | Ledbetter et al. |
| 6,165,464 A | 12/2000 | Hudziak et al. |
| 6,166,185 A | 12/2000 | Davis et al. |

(Continued)

FOREIGN PATENT DOCUMENTS

| | | |
|---|---|---|
| EP | 1 591 527 A1 | 11/2005 |
| EP | 1 600 459 A2 | 11/2005 |

(Continued)

OTHER PUBLICATIONS

International Search Report for International Application No. PCT/US08/88337, United States Patent and Trademark Office, Alexandria, VA, U.S.A., mailed on Jul. 20, 2009.

(Continued)

*Primary Examiner* — Robert Landsman
(74) *Attorney, Agent, or Firm* — Sterne, Kessler, Goldstein & Fox P.L.L.C.

(57) ABSTRACT

Complexes containing one or more modular recognition domains (MRDs) and MRDs attached to scaffolds including antibodies are described. The manufacture of these complexes are the use of these complexes to treat and diagnose diseases and disorders are also described.

12 Claims, 20 Drawing Sheets

(56) References Cited

U.S. PATENT DOCUMENTS

| | | |
|---|---|---|
| 6,194,177 B1 | 2/2001 | Campbell et al. |
| 6,267,958 B1 | 7/2001 | Andya et al. |
| 6,268,488 B1 | 7/2001 | Barbas, III et al. |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,413,932 B1 | 7/2002 | Cerretti et al. |
| 6,417,168 B1 | 7/2002 | Greene et al. |
| 6,458,356 B1 | 10/2002 | Arakawa et al. |
| 6,512,096 B2 | 1/2003 | Weiner et al. |
| 6,515,110 B1 | 2/2003 | Whitlow et al. |
| 6,521,424 B2 | 2/2003 | Cerretti et al. |
| 6,627,196 B1 | 9/2003 | Baughman et al. |
| 6,719,971 B1 | 4/2004 | Carter et al. |
| 6,800,738 B1 | 10/2004 | Carter et al. |
| 6,821,515 B1 | 11/2004 | Cleland et al. |
| 7,063,840 B2 | 6/2006 | Davis et al. |
| 7,067,475 B2 | 6/2006 | Cerretti et al. |
| 7,074,404 B2 | 7/2006 | Basey et al. |
| 7,112,317 B2 | 9/2006 | Thorpe et al. |
| 7,125,541 B2 | 10/2006 | Thorpe et al. |
| 7,138,370 B2 | 11/2006 | Oliner et al. |
| 7,148,321 B2 | 12/2006 | Gillies et al. |
| 7,183,076 B2 | 2/2007 | Arathoon et al. |
| 7,205,275 B2 | 4/2007 | Oliner et al. |
| 7,211,252 B2 | 5/2007 | Mundy et al. |
| 7,226,592 B2 | 6/2007 | Kreysch |
| 7,365,054 B2 | 4/2008 | Lode et al. |
| 7,371,379 B2 | 5/2008 | Baughman et al. |
| 7,449,184 B2 | 11/2008 | Allison et al. |
| 7,456,016 B2 | 11/2008 | Young et al. |
| 7,462,352 B2 | 12/2008 | Hansen et al. |
| 7,485,302 B2 | 2/2009 | Adams et al. |
| 7,521,053 B2 | 4/2009 | Oliner |
| 7,537,931 B2 | 5/2009 | Adams et al. |
| 7,541,440 B2 | 6/2009 | Goldenberg et al. |
| 7,612,181 B2 | 11/2009 | Wu et al. |
| 7,625,558 B2 | 12/2009 | Greene et al. |
| 7,638,124 B2 | 12/2009 | Reiter et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,666,832 B2 | 2/2010 | Oliner et al. |
| 7,666,839 B2 | 2/2010 | Oliner et al. |
| 7,682,609 B2 | 3/2010 | Andya et al. |
| 7,723,499 B2 | 5/2010 | Oliner et al. |
| 7,736,652 B2 | 6/2010 | Penichet et al. |
| 7,749,501 B2 | 7/2010 | Gelfand |
| 7,750,127 B2 | 7/2010 | Gegg et al. |
| 7,750,128 B2 | 7/2010 | Gegg et al. |
| 7,786,267 B2 | 8/2010 | Zurawski et al. |
| 7,790,674 B2 | 9/2010 | Oliner et al. |
| 7,862,817 B2 | 1/2011 | Adams et al. |
| 7,951,369 B2 | 5/2011 | Goldenberg et al. |
| 7,973,140 B2 | 7/2011 | Green et al. |
| 7,981,418 B2 | 7/2011 | Amler et al. |
| 7,993,834 B2 | 8/2011 | Mass |
| 8,008,453 B2 | 8/2011 | Gegg et al. |
| 2003/0130496 A1 | 7/2003 | Winter et al. |
| 2003/0229023 A1 | 12/2003 | Oliner et al. |
| 2004/0001827 A1 | 1/2004 | Dennis |
| 2004/0052785 A1 | 3/2004 | Goodman et al. |
| 2004/0057969 A1 | 3/2004 | Smith et al. |
| 2005/0287153 A1 | 12/2005 | Dennis |
| 2006/0106203 A1 | 5/2006 | Winter et al. |
| 2006/0128944 A1 | 6/2006 | Botti et al. |
| 2006/0140936 A1 | 6/2006 | Goldenberg et al. |
| 2006/0222653 A1 | 10/2006 | Abel et al. |
| 2006/0269540 A1 | 11/2006 | Robert et al. |
| 2007/0031402 A1 | 2/2007 | Zhang et al. |
| 2007/0086998 A1 | 4/2007 | Nagy |
| 2007/0166753 A1 | 7/2007 | Mass |
| 2007/0196274 A1 | 8/2007 | Sun |
| 2007/0202041 A1 | 8/2007 | Young et al. |
| 2007/0248994 A1 | 10/2007 | Su |
| 2007/0254316 A1 | 11/2007 | Rodriguez et al. |
| 2008/0233130 A1 | 9/2008 | Tomlinson et al. |
| 2008/0241145 A1 | 10/2008 | Goldenberg et al. |
| 2008/0299120 A1 | 12/2008 | Miller et al. |
| 2009/0054323 A1 | 2/2009 | Oliner et al. |
| 2009/0087432 A1 | 4/2009 | Sliwkowski |
| 2009/0148905 A1 | 6/2009 | Ashman et al. |
| 2009/0181022 A1 | 7/2009 | Nielsen et al. |
| 2009/0191212 A1 | 7/2009 | Oliner et al. |
| 2009/0226447 A1 | 9/2009 | Boone et al. |
| 2009/0246206 A1 | 10/2009 | Nielsen et al. |
| 2009/0298195 A1 | 12/2009 | Rüker et al. |
| 2009/0304694 A1 | 12/2009 | Oliner et al. |
| 2010/0016556 A1 | 1/2010 | Carter et al. |
| 2010/0021379 A1 | 1/2010 | Lam et al. |
| 2010/0021473 A1 | 1/2010 | De Angelis et al. |
| 2010/0047239 A1 | 2/2010 | Wu et al. |
| 2010/0048877 A1 | 2/2010 | Ruker et al. |
| 2010/0104588 A1 | 4/2010 | Dennis |
| 2010/0111967 A1 | 5/2010 | Baehner et al. |
| 2010/0158926 A1 | 6/2010 | Cartilage et al. |
| 2010/0159587 A1 | 6/2010 | Brinkmann et al. |
| 2010/0166695 A1 | 7/2010 | Bundle et al. |
| 2010/0166746 A1 | 7/2010 | Chowdhury et al. |
| 2010/0178298 A1 | 7/2010 | Lindhofer |
| 2010/0233173 A1 | 9/2010 | Wu et al. |
| 2010/0286060 A1 | 11/2010 | Oliner et al. |
| 2010/0297103 A1 | 11/2010 | Murakami |
| 2010/0322934 A1 | 12/2010 | Imhof-Jung et al. |
| 2010/0330115 A1 | 12/2010 | Zurawski et al. |
| 2011/0020332 A1 | 1/2011 | Greene et al. |
| 2011/0027286 A1 | 2/2011 | Thurston et al. |
| 2011/0044998 A1 | 2/2011 | Bedian et al. |
| 2011/0046355 A1 | 2/2011 | Himmler et al. |
| 2011/0076723 A1 | 3/2011 | Min et al. |
| 2011/0097300 A1 | 4/2011 | Van Slyke et al. |
| 2011/0097321 A1 | 4/2011 | Blakey et al. |
| 2011/0110851 A1 | 5/2011 | Chang et al. |
| 2011/0129464 A1 | 6/2011 | Adams et al. |
| 2011/0150895 A1 | 6/2011 | Ryu et al. |
| 2011/0158978 A1 | 6/2011 | Kirchner et al. |
| 2011/0189206 A1 | 8/2011 | Barbas, III |
| 2012/0020966 A1 | 1/2012 | Barbas, III |
| 2012/0020967 A1 | 1/2012 | Barbas, III |
| 2012/0034211 A1 | 2/2012 | Barbas, III |
| 2012/0058114 A1 | 3/2012 | Barbas, III |
| 2012/0100166 A1 | 4/2012 | Roschke et al. |
| 2013/0259868 A1 | 10/2013 | Roschke et al. |

FOREIGN PATENT DOCUMENTS

| | | |
|---|---|---|
| EP | 1 517 921 B1 | 6/2006 |
| EP | 1 752 471 B9 | 11/2008 |
| EP | 2 070 944 A1 | 6/2009 |
| EP | 1 189 641 B1 | 7/2009 |
| EP | 1 210 115 B1 | 8/2009 |
| EP | 1 434 791 B1 | 10/2009 |
| EP | 2 110 138 A1 | 10/2009 |
| EP | 2 116 262 A2 | 11/2009 |
| EP | 2 272 869 A2 | 1/2011 |
| EP | 2 275 119 A1 | 1/2011 |
| EP | 2 284 194 A1 | 2/2011 |
| EP | 2 311 849 A1 | 4/2011 |
| EP | 2 316 845 A1 | 5/2011 |
| EP | 2 336 180 A1 | 6/2011 |
| WO | WO 95/24220 A1 | 9/1995 |
| WO | WO 96/11269 A2 | 4/1996 |
| WO | WO 97/20858 A1 | 6/1997 |
| WO | WO 98/50431 A2 | 11/1998 |
| WO | WO 01/81377 A2 | 11/2001 |
| WO | WO 03/016330 A2 | 2/2003 |
| WO | WO 2004/032857 A2 | 4/2004 |
| WO | WO 2004/032961 A1 | 4/2004 |
| WO | WO 2004/092215 A2 | 10/2004 |
| WO | WO 2005/023859 A1 | 3/2005 |
| WO | WO 2005/070966 A2 | 8/2005 |
| WO | WO 2005/117973 A2 | 12/2005 |
| WO | WO 2006/063150 A2 | 6/2006 |

(56) References Cited

FOREIGN PATENT DOCUMENTS

| | | |
|---|---|---|
| WO | WO 2006/078307 A1 | 7/2006 |
| WO | WO 2006/091209 A2 | 8/2006 |
| WO | WO 2007/001457 A2 | 1/2007 |
| WO | WO 2007/016185 A2 | 2/2007 |
| WO | WO 2007/019232 A2 | 2/2007 |
| WO | WO 2007/024715 A2 | 3/2007 |
| WO | WO 2007/060192 A1 | 5/2007 |
| WO | WO 2007/066109 A1 | 6/2007 |
| WO | WO 2007/068895 A1 | 6/2007 |
| WO | WO 2007/075270 A2 | 7/2007 |
| WO | WO 2007/136892 A2 | 11/2007 |
| WO | WO 2008/003103 A2 | 1/2008 |
| WO | WO 2008/019290 A2 | 2/2008 |
| WO | WO 2008/088658 A2 | 7/2008 |
| WO | WO 2008/116293 A1 | 10/2008 |
| WO | WO 2008/132568 A2 | 11/2008 |
| WO | WO 2008/144029 A1 | 11/2008 |
| WO | WO 2009/088805 A2 | 7/2009 |
| WO | WO 2009/097325 A1 | 8/2009 |
| WO | WO 2009/105269 A1 | 8/2009 |
| WO | WO 2009/132876 A1 | 11/2009 |
| WO | WO 2009/158432 A2 | 12/2009 |
| WO | WO 2010/010551 A2 | 1/2010 |
| WO | WO 2010/040508 A1 | 4/2010 |
| WO | WO 2010/066836 A2 | 6/2010 |
| WO | WO 2010/108153 A2 | 9/2010 |
| WO | WO 2011/014469 A1 | 2/2011 |
| WO | WO 2012/009705 A1 | 1/2012 |

OTHER PUBLICATIONS

International Preliminary Report on Patentability, including the Written Opinion of the International Searching Authority, for International Application No. PCT/US08/88337, The International Bureau of WIPO, Geneva, Switzerland, issued Jul. 6, 2010.

Ruoslahti, Erkki, "Integrins," *J. Clin. Invest.* 87:1-5, The American Society for Clinical Investigation, Inc., United States (1991).

Stancovski, I., et al., "Mechanistic aspects of the opposing effects of monoclonal antibodies to the ERBB2 receptor on tumor growth," *Proc. Natl. Acad Sci.* 88:8691-95, United States National Academy of Sciences, United States (1991).

Taipale, J. and Keski-Oja, J., "Growth factors in the extracellular matrix," *The FASEB Journal* 11:51-59, Federation of American Societies for Experimental Biology, United States (1997).

Kutty, G., et al., "Identification of a new member of transforming growth factor=beta superfamily in *Drosophila*: the first invertebrate activin gene," *Biochem. Biophys. Res. Common.* 246(3):644-49, Elsevier B.V., Netherlands (1998).

Grzesik, W.J., et al., "Synthetic integrin-binding peptides promote adhesion and proliferation of human periodontal ligament cells in vitro," *J. Dent. Res.* 77(8):1606-12, International & American Associations for Dental Research, United States (1998).

Dennis, M.S., et al., "Albumin Binding as a General Strategy for Improving the Pharmacokinetics of Proteins," *JBC* 277(33):35035-43, The American Society for Biochemistry and Molecular Biology, Inc., United States (2002).

Li, L.-S., et al., "Chemical Adaptor Immunotherapy: Design, Synthesis, and Evaluation of Novel Integrin-Targeting Devices," *J. Med. Chem.* 47:5630-40, American Chemical Society, United States (2004).

Riemer, A.B., et al., "Matching of trastuzumab (Herceptin) epitope mimics onto the surface of her-2/neu—a new method of epitope definition," *Mol. Immunol.* 42(9):1121-24, Elsevier B.V., Netherlands (2005).

Corte-Real, S., et al., "Intrabodies targeting the Kaposi sarcoma-associated herpesvirus latency antigen inhibit persistence in lymphoma cells," *Blood* 106:3797-802, American Society of Hematology, United States (2005).

Niu, G. and Carter, B., "Human Epidermal Growth Factor Receptor 2 Regulates Angiopoietin-2 Expression in Breast Cancer via AKT and Mitogen-Activated Protein Kinase Pathways," *Cancer Res.* 67:1487-93, American Association for Cancer Research, United States (2007).

Asano, R., et al., "Highly Effective Recombinant Format of a Humanized IgG-like Bispecific Antibody for Cancer Immunotherapy with Retargeting of Lymphocytes to Tumor Cells," *JBC* 282(38):27659-65, The American Society for Biochemistry and Molecular Biology, Inc., United States (2007).

Yu, L., et al., "Interaction between Bevavizumab and Murine VEGF-A: A Reassessment,"*IOVS* 49(2):522-27, Association for Research in Vision and Ophthalmology, United States (2008).

Dela Cruz, J.S., et al., "Recombinant Anti-Human HER2/neu IgG3-(GM-CSF) Fusion Protein Retains Antigen Specificity and Cytokine Function and Demonstrates Antitumor Activity," *J Immunol.* 165:5112-21, The American Association of Immunologists, United States (2000).

Helguera, G., et al., "Vaccination with novel combinations of anti-HER2/neu cytokines fusion proteins and soluble protein antigen elicits a protective immune response against HER2/neu expressing tumors," *Vaccine* 24:304-16, Elsevier B.V., Netherlands (2006).

Figure 17B

| Protein | Clone ID | MRD Sequence | EC50, nM |
|---|---|---|---|
| L1-7D MDD | 2G12 | PGKGGGSMGAQTNFMPMDDDEQRLYEQFILQQGLE (SEQ ID NO:114) | 0.133 |
| L1-7D MQD | 1A12 | PGKGGGSMGAQTNFMPMQDDEQRLYEQFILQQGLE (SEQ ID NO:115) | >100 |
| L1-7D MVD | 2A1 | PGKGGGSMGAQTNFMPMVDDEQRLYEQFILQQGLE (SEQ ID NO:116) | >100 |
| L1-7D MID | 3C3 | PGKGGGSMGAQTNFMPMIDDEQRLYEQFILQQGLE (SEQ ID NO:117) | 17.00 |
| L1-7D MND | 4B4 | PGKGGGSMGAQTNFMPMNDDEQRLYEQFILQQGLE (SEQ ID NO:118) | 0.411 |
| L1-7D MKD | 5A8 | PGKGGGSMGAQTNFMPMKDDEQRLYEQFILQQGLE (SEQ ID NO:119) | >100 |
| L1-7D MAD | 6A3 | PGKGGGSMGAQTNFMPMADDEQRLYEQFILQQGLE (SEQ ID NO:120) | >100 |
| L1-7D MSD | 7B2 | PGKGGGSMGAQTNFMPMSDDEQRLYEQFILQQGLE (SEQ ID NO:121) | 1.380 |
| L1-7D MRD | 8B12 | PGKGGGSMGAQTNFMPMRDDEQRLYEQFILQQGLE (SEQ ID NO:122) | >100 |
| L1-7D MGD | 9C7 | PGKGGGSMGAQTNFMPMGDDEQRLYEQFILQQGLE (SEQ ID NO:123) | 0.660 |
| L1-7D MTD | 10B12 | PGKGGGSMGAQTNFMPMTDDEQRLYEQFILQQGLE (SEQ ID NO:124) | 7.340 |
| L1-7D MYD | 11B10 | PGKGGGSMGAQTNFMPMYDDEQRLYEQFILQQGLE (SEQ ID NO:125) | >100 |
| L1-7D MPD | 12C12 | PGKGGGSMGAQTNFMPMPDDEQRLYEQFILQQGLE (SEQ ID NO:126) | >100 |
| L1-7D MfD | 13D5 | PGKGGGSMGAQTNFMPMfDDEQRLYEQFILQQGLE (SEQ ID NO:127) | >100 |
| L1-7D MWD | 14F11 | PGKGGGSMGAQTNFMPMWDDEQRLYEQFILQQGLE (SEQ ID NO:128) | >100 |
| L1-7D MLD | 15G12 | PGKGGGSMGAQTNFMPMLDDEQRLYEQFILQQGLE (SEQ ID NO:129) | >100 |
| L1-7D MED | 16E5 | PGKGGGSMGAQTNFMPMEDDEQRLYEQFILQQGLE (SEQ ID NO:130) | >100 |
| L1-7D MHD | 17F9 | PGKGGGSMGAQTNFMPMHDDEQRLYEQFILQQGLE (SEQ ID NO:131) | >100 |
| L1-7D MMD | 18E3 | PGKGGGSMGAQTNFMPMMDDEQRLYEQFILQQGLE (SEQ ID NO:132) | >100 |
| L1-7D MFD* | 14G4* | PGKGGGSMGAQTNFMPMFDDEGRLYDQFILQQGLE (SEQ ID NO:133) | >100 |
| Lm32 Kis5 | ZC10 | PGKSGGSMGAQTNFMPMDNDELLYEQFILQQGLE (SEQ ID NO:134) | 0.199 |
| Lm32 2X | ZC39 | PGKGGGSMGAQTNFMPMDNDELLYEQFILQQGLEGGGSMGAQTNFMPMDNDELL | 0.005 |
| | | LLYEQFILQQGLE (SEQ ID NO:135) | |

Figure 17C

SEQUENCE LISTING

```
<160> NUMBER OF SEQ ID NOS: 143

<210> SEQ ID NO 1
<211> LENGTH: 4
<212> TYPE: PRT
<213> ORGANISM: Artificial
<220> FEATURE:
<223> OTHER INFORMATION: linker peptide

<400> SEQUENCE: 1

Gly Gly Gly Ser
1

<210> SEQ ID NO 2
<211> LENGTH: 15
<212> TYPE: PRT
<213> ORGANISM: Artificial
<220> FEATURE:
<223> OTHER INFORMATION: linker peptide

<400> SEQUENCE: 2

Ser Ser Gly Gly Gly Gly Ser Gly Gly Gly Gly Gly Gly Ser Ser
1               5                  10                  15

<210> SEQ ID NO 3
<211> LENGTH: 7
<212> TYPE: PRT
<213> ORGANISM: Artificial
<220> FEATURE:
<223> OTHER INFORMATION: integrin targeting MRD peptide

<400> SEQUENCE: 3

Tyr Cys Arg Gly Asp Cys Thr
1               5

<210> SEQ ID NO 4
<211> LENGTH: 7
<212> TYPE: PRT
<213> ORGANISM: Artificial
<220> FEATURE:
<223> OTHER INFORMATION: integrin targeting MRD peptide

<400> SEQUENCE: 4

Pro Cys Arg Gly Asp Cys Leu
1               5

<210> SEQ ID NO 5
<211> LENGTH: 7
<212> TYPE: PRT
<213> ORGANISM: Artificial
<220> FEATURE:
<223> OTHER INFORMATION: integrin targeting MRD peptide

<400> SEQUENCE: 5

Thr Cys Arg Gly Asp Cys Tyr
1               5

<210> SEQ ID NO 6
```

```
<211> LENGTH: 7
<212> TYPE: PRT
<213> ORGANISM: Artificial
<220> FEATURE:
<223> OTHER INFORMATION: integrin targeting M

```
<210> SEQ ID NO 11
<211> LENGTH: 28
<212> TYPE: PRT
<213> ORGANISM: Artificial
<220> FEATURE:
<223> OTHER INFORMATION: angiogenic cytokine targeting MRD

<400> SEQUENCE: 11

Met Gly Ala Gln Thr Asn Phe Met Pro Met Asp Asn Asp Glu Leu Leu
1               5                   10                  15

Asn Tyr Glu Gln Phe Ile Leu Gln Gln Gly Leu Glu
            20                  25

<210> SEQ ID NO 12
<211> LENGTH: 10
<212> TYPE: PRT
<213> ORGANISM: Artificial
<220> FEATURE:
<223> OTHER INFORMATION: angiogenic cytokine targeting MRD
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Pro Xaa Asp Asn Asp Xaa Leu Leu Asn Tyr
1               5                   10

<210> SEQ ID NO 13
<211> LENGTH: 19
<212> TYPE: PRT
<213> ORGANISM: Artificial
<220> FEATURE:
<223> OTHER INFORMATION: VEGF targeting MRD

<400> SEQUENCE: 13

Val Glu Pro Asn Cys Asp Ile His Val Met Trp Glu Trp Glu Cys Phe
1               5                   10                  15

Glu Arg Leu

<210> SEQ ID NO 14
<211> LENGTH: 27
<212> TYPE: PRT
<213> ORGANISM: Artificial
<220> FEATURE:
<223> OTHER INFORMATION: insulin-like growth factor-I receptor targeting
      MRD

<400> SEQUENCE: 14

Ser Phe Tyr Ser Cys Leu Glu Ser Leu Val Asn Gly Pro Ala Glu Lys
1               5                   10                  15

Ser Arg Gly Gln Trp Asp Gly Cys Arg Lys Lys
            20                  25

<210> SEQ ID NO 15
<211> LENGTH: 11
<212> TYPE: PRT
<213> ORGANISM: Artificial
<220> FEATURE:
<223> OTHER INFORMATION: vascular homing peptide MRD
```

```
<400> SEQUENCE: 15

Ala Cys Asp Cys Arg Gly Asp Cys Phe Cys Gly
1               5                   10

<210> SEQ ID NO 16
<211> LENGTH: 58
<212> TYPE: PRT
<213> ORGANISM: Artificial
<220> FEATURE:
<223> OTHER INFORMATION: EGFR targeting MRD

<400> SEQUENCE: 16

Val Asp Asn Lys Phe Asn Lys Glu Leu Glu Lys Ala Tyr Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 17
<211> LENGTH: 58
<212> TYPE: PRT
<213> ORGANISM: Artificial
<220> FEATURE:
<223> OTHER INFORMATION: EGFR targeting MRD

<400> SEQUENCE: 17

Val Asp Asn Lys Phe Asn Lys Glu Met Trp Ile Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Artificial
<220> FEATURE:
<223> OTHER INFORMATION: ErbB2 targeting MRD

<400> SEQUENCE: 18

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 19
<211> LENGTH: 18
<212> TYPE: PRT
<213> ORGANISM: Artificial
<220> FEATURE:
<223> OTHER INFORMATION: linker peptide
```

```
<400> SEQUENCE: 19

Ser Ser Gly Gly Gly Ser Gly Gly Gly Gly Ser Ser Arg
1               5                   10                  15

Ser Ser

<210> SEQ ID NO 20
<211> LENGTH: 60
<212> TYPE: PRT
<213> ORGANISM: Artificial
<220> FEATURE:
<223> OTHER INFORMATION: angiogenic cytokine targeting MRD

<400> SEQUENCE: 20

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu Gly Gly Ser Gly
                20                  25                  30

Ser Thr Ala Ser Ser Gly Ser Gly Ser Ser Leu Gly Ala Gln Thr Asn
            35                  40                  45

Phe Met Pro Met Asp Asn Asp Glu Leu Leu Leu Tyr
        50                  55                  60

<210> SEQ ID NO 21
<211> LENGTH: 16
<212> TYPE: PRT
<213> ORGANISM: Artificial
<220> FEATURE:
<223> OTHER INFORMATION: angiogenic cytokine targeting MRD

<400> SEQUENCE: 21

Ala Gln Gln Glu Glu Cys Glu Phe Ala Pro Trp Thr Cys Glu His Met
1               5                   10                  15

<210> SEQ ID NO 23
<211> LENGTH: 54
<212> TYPE: PRT
<213> ORGANISM: Artificial
<220> FEATURE:
<223> OTHER INFORMATION: 2xConFA

<400> SEQUENCE: 23

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ala Pro Trp Thr
        35                  40                  45

Cys Glu His Met Leu Glu
    50

<210> SEQ ID NO 24
<211> LENGTH: 16
<212> TYPE: PRT
<213> ORGANISM: Artificial
<220> FEATURE:
<223> OTHER INFORMATION: ConLA

<400> SEQUENCE: 24

Ala Gln Gln Glu Glu Cys Glu Leu Ala Pro Trp Thr Cys Glu His Met
1               5                   10                  15

<210> SEQ ID NO 25
<211> LENGTH: 106
<212> TYPE: PRT
<213> ORGANISM: Artificial
<220> FEATURE:
<223> OTHER INFORMATION: MRD peptide core
<220> FEATURE:
<221> NAME/KEY: misc_feature
<222> LOCATION: (1)..(50)
<223> OTHER INFORMATION: X is any amino acid or may be missing
<220> FEATURE:
<221> NAME/KEY: misc_feature
<222> LOCATION: (57)..(106)
<223> OTHER INFORMATION: X is any amino acid or may be missing

<400> SEQUENCE: 25

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Glu Leu Ala Pro Trp Thr Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa
                100                 105

<210> SEQ ID NO 26
<211> LENGTH: 54

```
<212> TYPE: PRT
<213> ORGANISM: Artificial
<220> FEATURE:
<223> OTHER INFORMATION: MRD peptide with a core sequence

<400> SEQUENCE: 26

Ala Gln Gln Glu Glu Cys Glu Leu Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Ala Pro Trp Thr
        35                  40                  45

Cys Glu His Met Leu Glu
    50

<210> SEQ ID NO 27
<211> LENGTH: 16
<212> TYPE: PRT
<213> ORGANISM: artificial
<220> FEATURE:
<223> OTHER INFORMATION: MRD peptide with a core sequence

<400> SEQUENCE: 27

Ala Gln Gln Glu Glu Cys Glu Phe Ser Pro Trp Thr Cys Glu His Met
1               5                   10                  15

<210> SEQ ID NO 28
<211> LENGTH: 106
<212> TYPE: PRT
<213> ORGANISM: Artificial
<220> FEATURE:
<223> OTHER INFORMATION: MRD peptide core
<220> FEATURE:
<221> NAME/KEY: misc_feature
<222> LOCATION: (1)..(50)
<223> OTHER INFORMATION: X is any amino acid or may be missing
<220> FEATURE:
<221> NAME/KEY: misc_feature
<222> LOCATION: (57)..(106)
<223> OTHER INFORMATION: X is any amino acid or may be missing

<400> SEQUENCE: 28

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Glu Phe Ser Pro Trp Thr Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa
            100                 105

<210> SEQ ID NO 29
<211> LENGTH: 54
<212> TYPE: PRT
<213> ORGANISM: artificial
<220> FEATURE:
<223> OTHER INFORMATION: 2xConFS
```

<400> SEQUENCE: 29

Ala Gln Gln Glu Glu Cys Glu Phe Ser Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ser Pro Trp Thr
        35                  40                  45

Cys Glu His Met Leu Glu
            50

<210> SEQ ID NO 30
<211> LENGTH: 16
<212> TYPE: PRT
<213> ORGANISM: Artificial
<220> FEATURE:
<223> OTHER INFORMATION: MRD peptide with a core sequence

<400> SEQUENCE: 30

Ala Gln Gln Glu Glu Cys Glu Leu Glu Pro Trp Thr Cys Glu His Met
1               5                   10                  15

<210> SEQ ID NO 31
<211> LENGTH: 106
<212> TYPE: PRT
<213> ORGANISM: artificial
<220> FEATURE:
<223> OTHER INFORMATION: MRD peptide core
<220> FEATURE:
<221> NAME/KEY: misc_feature
<222> LOCATION: (1)..(50)
<223> OTHER INFORMATION: X is any amino acid or may be missing
<220> FEATURE:
<221> NAME/KEY: misc_feature
<222> LOCATION: (57)..(106)
<223> OTHER INFORMATION: X is any amino acid or may be missing

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Glu Leu Glu Pro Trp Thr Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa
                100                 105

<210> SEQ ID NO 32
<211> LENGTH: 54
<212> TYPE: PRT
<213> ORGANISM: artificial
<220> FEATURE:
<223> OTHER INFORMATION: 2xConLE

<400> SEQUENCE: 32

Ala Gln Gln Glu Glu Cys Glu Leu Glu Pro Trp Thr Cys Glu His Met
1               5                   10                  15

-continued

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Glu Pro Trp Thr
        35                  40                  45

Cys Glu His Met Leu Glu
    50

<210> SEQ ID NO 33
<211> LENGTH: 54
<212> TYPE: PRT
<213> ORGANISM: artificial
<220> FEATURE:
<223> OTHER INFORMATION: ConFA-LA

<400> SEQUENCE: 33

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Ala Pro Trp Thr
        35                  40                  45

Cys Glu His Met Leu Glu
    50

<210> SEQ ID NO 34
<211> LENGTH: 54
<212> TYPE: PRT
<213> ORGANISM: artificial
<220> FEATURE:
<223> OTHER INFORMATION: ConFA-FS

<400> SEQUENCE: 34

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ser Pro Trp Thr
        35                  40                  45

Cys Glu His Met Leu Glu
    50

<210> SEQ ID NO 35
<211> LENGTH: 28
<212> TYPE: PRT
<213> ORGANISM: artificial
<220> FEATURE:
<223> OTHER INFORMATION: IGF1R binding MRD

<400> SEQUENCE: 35

Asn Phe Tyr Gln Cys Ile Glu Met Leu Ala Ser His Pro Ala Glu Lys
1               5                   10                  15

Ser Arg Gly Gln Trp Gln Glu Cys Arg Thr Gly Gly
            20                  25

<210> SEQ ID NO 36
<211> LENGTH: 28
<212> TYPE: PRT
<213> ORGANISM: artificial
<220> FEATURE:
<223> OTHER INFORMATION: IGF1R binding MRD

<400> SEQUENCE: 36

-continued

```
Asn Phe Tyr Gln Cys Ile Glu Gln Leu Ala Leu Arg Pro Ala Glu Lys
1               5                   10                  15

Ser Arg Gly Gln Trp Gln Glu Cys Arg Thr Gly Gly
            20                  25
```

<210> SEQ ID NO 37
<211> LENGTH: 28
<212> TYPE: PRT
<213> ORGANISM: artificial
<220> FEATURE:
<223> OTHER INFORMATION: IGF1R binding MRD

<400> SEQUENCE: 37

```
Asn Phe Tyr Gln Cys Ile Asp Leu Leu Met Ala Tyr Pro Ala Glu Lys
1               5                   10                  15

Ser Arg Gly Gln Trp Gln Glu Cys Arg Thr Gly Gly
            20                  25
```

<210> SEQ ID NO 38
<211> LENGTH: 28
<212> TYPE: PRT
<213> ORGANISM: artificial
<220> FEATURE:
<223> OTHER INFORMATION: IGF1R binding MRD

<400> SEQUENCE: 38

```
Asn Phe Tyr Gln Cys Ile Glu Arg Leu Val Thr Gly Pro Ala Glu Lys
1               5                   10                  15

Ser Arg Gly Gln Trp Gln Glu Cys Arg Thr Gly Gly
            20                  25
```

<210> SEQ ID NO 39
<211> LENGTH: 28
<212> TYPE: PRT
<213> ORGANISM: artificial
<220> FEATURE:
<223> OTHER INFORMATION: IGF1R binding MRD

<400> SEQUENCE: 39

```
Asn Phe Tyr Gln Cys Ile Glu Tyr Leu Ala Met Lys Pro Ala Glu Lys
1               5                   10                  15

Ser Arg Gly Gln Trp Gln Glu Cys Arg Thr Gly Gly
            20                  25
```

<210> SEQ ID NO 40
<211> LENGTH: 28
<212> TYPE: PRT
<213> ORGANISM: artificial
<220> FEATURE:
<223> OTHER INFORMATION: IGF1R binding MRD

<400> SEQUENCE: 40

```
Asn Phe Tyr Gln Cys Ile Glu Ala Leu Gln Ser Arg Pro Ala Glu Lys
1               5                   10                  15

Ser Arg Gly Gln Trp Gln Glu Cys Arg Thr Gly Gly
            20                  25
```

<210> SEQ ID NO 41
<211> LENGTH: 28
<212> TYPE: PRT
<213> ORGANISM: artificial
<220> FEATURE:
<223> OTHER INFORMATION: IGF1R binding MRD

<400> SEQUENCE: 41

Asn Phe Tyr Gln Cys Ile Glu Ala Leu Ser Arg Ser Pro Ala Glu Lys
1               5                   10                  15

Ser Arg Gly Gln Trp Gln Glu Cys Arg Thr Gly Gly
            20                  25

<210> SEQ ID NO 42
<211> LENGTH: 27
<212> TYPE: PRT
<213> ORGANISM: artificial
<220> FEATURE:
<223> OTHER INFORMATION: IGF1R binding MRD

<400> SEQUENCE: 42

Asn Phe Tyr Gln Cys Ile Glu His Leu Ser Gly Ser Pro Ala Glu Lys
1               5                   10                  15

Ser Arg Gly Gln Trp Gln Glu Cys Arg Thr Gly
            20                  25

<210> SEQ ID NO 43
<211> LENGTH: 27
<212> TYPE: PRT
<213> ORGANISM: artificial
<220> FEATURE:
<223> OTHER INFORMATION: IGF1R binding MRD

<400> SEQUENCE: 43

Asn Phe Tyr Gln Cys Ile Glu Ser Leu Ala Gly Gly Pro Ala Glu Lys
1               5                   10                  15

Ser Arg Gly Gln Trp Gln Glu Cys Arg Thr Gly
            20                  25

<210> SEQ ID NO 44
<211> LENGTH: 27
<212> TYPE: PRT
<213> ORGANISM: artificial
<220> FEATURE:
<223> OTHER INFORMATION: IGF1R binding MRD

<400> SEQUENCE: 44

Asn Phe Tyr Gln Cys Ile Glu Ala Leu Val Gly Val Pro Ala Glu Lys
1               5                   10                  15

Ser Arg Gly Gln Trp Gln Glu Cys Arg Thr Gly
            20                  25

<210> SEQ ID NO 45
<211> LENGTH: 27
<212> TYPE: PRT
<213> ORGANISM: artificial
<220> FEATURE:
<223> OTHER INFORMATION: IGF1R binding MRD

<400> SEQUENCE: 45

Asn Phe Tyr Gln Cys Ile Glu Met Leu Ser Leu Pro Pro Ala Glu Lys
1               5                   10                  15

Ser Arg Gly Gln Trp Gln Glu Cys Arg Thr Gly
            20                  25

<210> SEQ ID NO 46
<211> LENGTH: 27
<212> TYPE: PRT
<213> ORGANISM: artificial
<220> FEATURE:
<223> OTHER INFORMATION: IGF1R binding MRD -continued

<400> SEQUENCE: 46

Asn Phe Tyr Gln Cys Ile Glu Val Phe Trp Gly Arg Pro Ala Glu Lys
1               5                   10                  15

Ser Arg Gly Gln Trp Gln Glu Cys Arg Thr Gly
            20                  25

<210> SEQ ID NO 47
<211> LENGTH: 27
<212> TYPE: PRT
<213> ORGANISM: artificial
<220> FEATURE:
<223> OTHER INFORMATION: IGF1R binding MRD

<400> SEQUENCE: 47

Asn Phe Tyr Gln Cys Ile Glu Gln Leu Ser Ser Gly Pro Ala Glu Lys
1               5                   10                  15

Ser Arg Gly Gln Trp Gln Glu Cys Arg Thr Gly
            20                  25

<210> SEQ ID NO 48
<211> LENGTH: 27
<212> TYPE: PRT
<213> ORGANISM: artificial
<220> FEATURE:
<223> OTHER INFORMATION: IGF1R binding MRD

<400> SEQUENCE: 48

Asn Phe Tyr Gln Cys Ile Glu Leu Leu Ser Arg Pro Ala Glu Lys
1               5                   10                  15

Ser Arg Gly Gln Trp Ala Glu Cys Arg Ala Gly
            20                  25

<210> SEQ ID NO 49
<211> LENGTH: 27
<212> TYPE: PRT
<213> ORGANISM: artificial
<220> FEATURE:
<223> OTHER INFORMATION: IGF1R binding MRD

<400> SEQUENCE: 49

Asn Phe Tyr Gln Cys Ile Glu Ala Leu Ala Arg Thr Pro Ala Glu Lys
1               5                   10                  15

Ser Arg Gly Gln Trp Val Glu Cys Arg Ala Pro
            20                  25

<210> SEQ ID NO 50
<211> LENGTH: 18
<212> TYPE: DNA
<213> ORGANISM: artificial
<220> FEATURE:
<223> OTHER INFORMATION: Rm2-2-218

<400> SEQUENCE: 50
gtggagtgca gggcgccg                                                 18

<210> SEQ ID NO 51
<211> LENGTH: 6
<212> TYPE: PRT
<213> ORGANISM: artificial
<220> FEATURE:
<223> OTHER INFORMATION: Rm2-2-218

<400> SEQUENCE: 51

Val Glu Cys Arg Ala Pro
1               5

<210> SEQ ID NO 52
<211> LENGTH: 18
<212> TYPE: DNA
<213> ORGANISM: artificial
<220> FEATURE:
<223> OTHER INFORMATION: Rm2-2-316

<400> SEQUENCE: 52
gctgagtgca gggctggg                                                 18

<210> SEQ ID NO 53
<211> LENGTH: 6
<212> TYPE: PRT
<213> ORGANISM: artificial
<220> FEATURE:
<223> OTHER INFORMATION: Rm2-2-316

<400> SEQUENCE: 53

Ala Glu Cys Arg Ala Gly
1               5

<210> SEQ ID NO 54
<211> LENGTH: 18
<212> TYPE: DNA
<213> ORGANISM: artificial
<220> FEATURE:
<223> OTHER INFORMATION: Rm2-2-319

<400> SEQUENCE: 54
caggagtgca ggacgggg                                                 18

<210> SEQ ID NO 55
<211> LENGTH: 6
<212> TYPE: PRT
<213> ORGANISM: artificial
<220> FEATURE:
<223> OTHER INFORMATION: Rm2-2-319

<400> SEQUENCE: 55

Gln Glu Cys Arg Thr Gly
1               5

<210> SEQ ID NO 56
<211> LENGTH: 26
<212> TYPE: PRT
<213> ORGANISM: artificial
<220> FEATURE:
<223> OTHER INFORMATION: targeting MRD peptide core
<220> FEATURE:
<221> NAME/KEY: misc_feature
<222> LOCATION: (12)..(26)
<223> OTHER INFORMATION: X is any amino acid or may be missing

<400> SEQUENCE: 56

Met Gly Ala Gln Thr Asn Phe Met Pro Met Asp Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 57
<211> LENGTH: 117
<212> TYPE: PRT
<213> ORGANISM: artificial
<220> FEATURE:
<223> OTHER INFORMATION: MRD peptide core

```
<220> FEATURE:
<221> NAME/KEY: MISC_FEATURE
<222> LOCATION: (1)..(50)
<223> OTHER INFORMATION: X is any amino acid or may be missing
<220> FEATURE:
<221> NAME/KEY: MISC_FEATURE
<222> LOCATION: (58)..(58)
<223> OTHER INFORMATION: X is any amino acid
<220> FEATURE:
<221> NAME/KEY: MISC_FEATURE
<222> LOCATION: (59)..(59)
<223> OTHER INFORMATION: X is any amino acid
<220> FEATURE:
<221> NAME/KEY: misc_feature
<222> LOCATION: (67)..(117)
<223> OTHER INFORMATION: X is any amino acid or may be missing

<400> SEQUENCE: 57

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Ala Gln Gln Glu Glu Cys Glu Xaa Xaa Pro Trp Thr Cys Glu
    50                  55                  60

His Met Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa
        115

<210> SEQ ID NO 58
<211> LENGTH: 28
<212> TYPE: PRT
<213> ORGANISM: artificial
<220> FEATURE:
<223> OTHER INFORMATION: IGF1R targeting MRD
<220> FEATURE:
<221> NAME/KEY: MISC_FEATURE
<222> LOCATION: (7)..(7)
<223> OTHER INFORMATION: X is E or D
<220> FEATURE:
<221> NAME/KEY: MISC_FEATURE
<222> LOCATION: (8)..(8)
<223> OTHER INFORMATION: X is any amino acid
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid

<400> SEQUENCE: 58

Asn Phe Tyr Gln Cys Ile Xaa Xaa Leu Xaa Xaa Xaa Pro Ala Glu Lys
1               5                   10                  15

Ser Arg Gly Gln Trp Gln Glu Cys Arg Thr Gly Gly
            20                  25
```

```
<210> SEQ ID NO 59
<211> LENGTH: 12
<212> TYPE: PRT
<213> ORGANISM: artificial
<220> FEATURE:
<223> OTHER INFORMATION: VL-CDR1 trastuzumab

<400> SEQUENCE: 59

Arg Ala Ser Gln Asp Val Asn Thr Ala Val Ala Trp
1               5                   10

<210> SEQ ID NO 60
<211> LENGTH: 7
<212> TYPE: PRT
<213> ORGANISM: artificial
<220> FEATURE:
<223> OTHER INFORMATION: VL-CDR2 trastuzumab

<400> SEQUENCE: 60

Ser Ala Ser Phe Leu Tyr Ser
1               5

<210> SEQ ID NO 61
<211> LENGTH: 9
<212> TYPE: PRT
<213> ORGANISM: Artificial
<220> FEATURE:
<223> OTHER INFORMATION: VL-CDR3 trastuzumab

<400> SEQUENCE: 61

Gln Gln His Tyr Thr Thr Pro Pro Thr
1               5

<210> SEQ ID NO 62
<211> LENGTH: 10
<212> TYPE: PRT
<213> ORGANISM: Artificial
<220> FEATURE:
<223> OTHER INFORMATION: VH-CDR1 trastuzumab

<400> SEQUENCE: 62

Gly Arg Asn Ile Lys Asp Thr Tyr Ile His
1               5                   10

<210> SEQ ID NO 63
<211> LENGTH: 17
<212> TYPE: PRT
<213> ORGANISM: artificial
<220> FEATURE:
<223> OTHER INFORMATION: VH-CDR2 trastuzumab

<400> SEQUENCE: 63

Arg Ile Tyr Pro Thr Asn Gly Tyr Thr Arg Tyr Ala Asp Ser Val Lys
1               5                   10                  15

Gly

<210> SEQ ID NO 64
<211> LENGTH: 11
<212> TYPE: PRT
<213> ORGANISM: artificial
<220> FEATURE:
<223> OTHER INFORMATION: VH-CDR3 trastuzumab

<400> SEQUENCE: 64

Trp Gly Gly Asp Gly Phe Tyr Ala Met Asp Tyr
1               5                   10
```

```
<210> SEQ ID NO 65
<211> LENGTH: 109
<212> TYPE: PRT
<213> ORGANISM: artificial
<220> FEATURE:
<223> OTHER INFORMATION: VL trastuzumab

<400> SEQUENCE: 65
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

```
<210> SEQ ID NO 66
<211> LENGTH: 120
<212> TYPE: PRT
<213> ORGANISM: artificial
<220> FEATURE:
<223> OTHER INFORMATION: VH trastuzumab

<400> SEQUENCE: 66
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

```
<210> SEQ ID NO 67
<211> LENGTH: 27
<212> TYPE: PRT
<213> ORGANISM: Artificial
<220> FEATURE:
<223> OTHER INFORMATION: Rm1-67

<400> SEQUENCE: 67
```

Asn Phe Tyr Gln Cys Ile Glu Ser Leu Val Asn Gly Pro Ala Glu Lys
1               5                   10                  15

Ser Arg Gly Gln Trp Asp Gly Cys Arg Lys Lys
            20                  25

<210> SEQ ID NO 68
<211> LENGTH: 27
<212> TYPE: PRT
<213> ORGANISM: Artificial
<220> FEATURE:
<223> OTHER INFORMATION: Rm2-2-218

<400> SEQUENCE: 68

Asn Phe Tyr Gln Cys Ile Glu Ser Leu Val Asn Gly Pro Ala Glu Lys
1               5                   10                  15

Ser Arg Gly Gln Trp Val Glu Cys Arg Ala Pro
            20                  25

<210> SEQ ID NO 69
<211> LENGTH: 27
<212> TYPE: PRT
<213> ORGANISM: artificial
<220> FEATURE:
<223> OTHER INFORMATION: Rm2-2-316

<400> SEQUENCE: 69

Asn Phe Tyr Gln Cys Ile Glu Ser Leu Val Asn Gly Pro Ala Glu Lys
1               5                   10                  15

Ser Arg Gly Gln Trp Ala Glu Cys Arg Ala Gly
            20                  25

<210> SEQ ID NO 70
<211> LENGTH: 27
<212> TYPE: PRT
<213> ORGANISM: artificial
<220> FEATURE:
<223> OTHER INFORMATION: Rm2-2-319

<400> SEQUENCE: 70

Asn Phe Tyr Gln Cys Ile Glu Ser Leu Val Asn Gly Pro Ala Glu Lys
1               5                   10                  15

Ser Arg Gly Gln Trp Gln Glu Cys Arg Thr Gly
            20                  25

<210> SEQ ID NO 71
<211> LENGTH: 7
<212> TYPE: PRT
<213> ORGANISM: artificial
<220> FEATURE:
<223> OTHER INFORMATION: MRD

<400> SEQUENCE: 71

Ala Thr Trp Leu Pro Pro Pro
1               5

<210> SEQ ID NO 72
<211> LENGTH: 11
<212> TYPE: PRT
<213> ORGANISM: artificial
<220> FEATURE:
<223> OTHER INFORMATION: VL-CDR1 bevacizumab

<400> SEQUENCE: 72

Ser Ala Ser Gln Asp Ile Ser Asn Tyr Leu Asn
1               5                   10

<210> SEQ ID NO 73

```
<211> LENGTH: 7
<212> TYPE: PRT
<213> ORGANISM: artificial
<220> FEATURE:
<223> OTHER INFORMATION: VL-CDR2 bevacizumab

<400> SEQUENCE: 73

Phe Thr Ser Ser Leu His Ser
1               5

<210> SEQ ID NO 74
<211> LENGTH: 9
<212> TYPE: PRT
<213> ORGANISM: artificial
<220> FEATURE:
<223> OTHER INFORMATION: VL-CDR3 bevacizumab

<400> SEQUENCE: 74

Gln Gln Tyr Ser Thr Val Pro Trp Thr
1               5

<210> SEQ ID NO 75
<211> LENGTH: 10
<212> TYPE: PRT
<213> ORGANISM: artificial
<220> FEATURE:
<223> OTHER INFORMATION: VH-CDR1 bevacizumab

<400> SEQUENCE: 75

Gly Tyr Thr Phe Thr Asn Tyr Gly Met Asn
1               5                   10

<210> SEQ ID NO 76
<211> LENGTH: 17
<212> TYPE: PRT
<213> ORGANISM: artificial
<220> FEATURE:
<223> OTHER INFORMATION: VH-CDR2 bevacizumab

<400> SEQUENCE: 76

Trp Ile Asn Thr Tyr Thr Gly Glu Pro Thr Tyr Ala Ala Asp Phe Lys
1               5                   10                  15

Arg

<210> SEQ ID NO 77
<211> LENGTH: 14
<212> TYPE: PRT
<213> ORGANISM: artificial
<220> FEATURE:
<223> OTHER INFORMATION: VH-CDR3 bevacizumab

<400> SEQUENCE: 77

Tyr Pro His Tyr Tyr Gly Ser Ser His Trp Tyr Phe Asp Val
1               5                   10

<210> SEQ ID NO 78
<211> LENGTH: 108
<212> TYPE: PRT
<213> ORGANISM: artificial
<220> FEATURE:
<223> OTHER INFORMATION: VL bevacizumab

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
```

```
                    20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 79
<211> LENGTH: 123
<212> TYPE: PRT
<213> ORGANISM: artificial
<220> FEATURE:
<223> OTHER INFORMATION: VH bevacizumab

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 80
<211> LENGTH: 11
<212> TYPE: PRT
<213> ORGANISM: artificial
<220> FEATURE:
<223> OTHER INFORMATION: VL-CDR1 adaliumumab

<400> SEQUENCE: 80

Arg Ala Ser Gln Gly Ile Arg Asn Tyr Leu Ala
1               5                   10

<210> SEQ ID NO 81
<211> LENGTH: 7
<212> TYPE: PRT
<213> ORGANISM: artificial
<220> FEATURE:
<223> OTHER INFORMATION: VL-CDR2 adaliumumab

<400> SEQUENCE: 81

Ala Ala Ser Thr Leu Gln Ser
1               5

<210> SEQ ID NO 82
```

```
<211> LENGTH: 9
<212> TYPE: PRT
<213> ORGANISM: artificial
<220> FEATURE:
<223> OTHER INFORMATION: VL-CDR3 adaliumumab

<400> SEQUENCE: 82

Gln Arg Tyr Asn Arg Ala Pro Tyr Thr
1               5

<210> SEQ ID NO 83
<211> LENGTH: 5
<212> TYPE: PRT
<213> ORGANISM: artificial
<220> FEATURE:
<223> OTHER INFORMATION: VH-CDR1 adaliumumab

<400> SEQUENCE: 83

Asp Tyr Ala Met His
1               5

<210> SEQ ID NO 84
<211> LENGTH: 17
<212> TYPE: PRT
<213> ORGANISM: artificial
<220> FEATURE:
<223> OTHER INFORMATION: VH-CDR2 adaliumumab

<400> SEQUENCE: 84

Ala Ile Thr Trp Asn Ser Gly His Ile Asp Tyr Ala Asp Ser Val Glu
1               5                   10                  15

Gly

<210> SEQ ID NO 85
<211> LENGTH: 12
<212> TYPE: PRT
<213> ORGANISM: artificial
<220> FEATURE:
<223> OTHER INFORMATION: VH-CDR3 adaliumumab

<400> SEQUENCE: 85

Val Ser Tyr Leu Ser Thr Ala Ser Ser Leu Asp Tyr
1               5                   10

<210> SEQ ID NO 86
<211> LENGTH: 108
<212> TYPE: PRT
<213> ORGANISM: artificial
<220> FEATURE:
<223> OTHER INFORMATION: VL adaliumumab

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95
```

```
Thr Phe Gly Gln Gly Thr Lys Val Glu Ile Lys Arg
            100                 105

<210> SEQ ID NO 87
<211> LENGTH: 121
<212> TYPE: PRT
<213> ORGANISM: artificial
<220> FEATURE:
<223> OTHER INFORMATION: VH adaliumumab

<400> SEQUENCE: 87

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 88
<211> LENGTH: 41
<212> TYPE: PRT
<213> ORGANISM: artificial
<220> FEATURE:
<223> OTHER INFORMATION: MBP fusion protein

<400> SEQUENCE: 88

Lys Ser Leu Ser Leu Ser Pro Gly Ser Gly Gly Ser Met Gly Ala
1               5                   10                  15

Gln Thr Asn Phe Met Pro Met Asp Asn Asp Glu Gly Leu Leu Tyr Glu
            20                  25                  30

Gln Phe Ile Leu Gln Gln Gly Leu Glu
            35                  40

<210> SEQ ID NO 89
<211> LENGTH: 41
<212> TYPE: PRT
<213> ORGANISM: artificial
<220> FEATURE:
<223> OTHER INFORMATION: MBP fusion protein

<400> SEQUENCE: 89

Lys Ser Leu Ser Leu Ser Pro Gly Ser Gly Gly Ser Met Gly Ala
1               5                   10                  15

Gln Thr Asn Phe Met Pro Met Asp Asn Asp Glu Leu Gly Leu Tyr Glu
            20                  25                  30

Gln Phe Ile Leu Gln Gln Gly Leu Glu
            35                  40

<210> SEQ ID NO 90
<211> LENGTH: 41
```

```
<212> TYPE: PRT
<213> ORGANISM: artificial
<220> FEATURE:
<223> OTHER INFORMATION: MBP fusion protein

<400> SEQUENCE: 90

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Ala Leu Leu Tyr Glu
                20                  25                  30

Gln Phe Ile Leu Gln Gln Gly Leu Glu
            35                  40

<210> SEQ ID NO 91
<211> LENGTH: 41
<212> TYPE: PRT
<213> ORGANISM: artificial
<220> FEATURE:
<223> OTHER INFORMATION: MBP fusion protein

<400> SEQUENCE: 91

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Leu Thr Leu Tyr Glu
                20                  25                  30

Gln Phe Ile Leu Gln Gln Gly Leu Glu
            35                  40

<210> SEQ ID NO 92
<211> LENGTH: 41
<212> TYPE: PRT
<213> ORGANISM: artificial
<220> FEATURE:
<223> OTHER INFORMATION: MBP fusion protein

<400> SEQUENCE: 92

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Leu Leu Leu Tyr Glu
                20                  25                  30

Gln Phe Ile Tyr Gln Gln Gly Leu Glu
            35                  40

<210> SEQ ID NO 93
<211> LENGTH: 41
<212> TYPE: PRT
<213> ORGANISM: artificial
<220> FEATURE:
<223> OTHER INFORMATION: MBP fusion protein

<400> SEQUENCE: 93

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Gly Leu Leu Tyr Glu
                20                  25                  30

Gln Phe Ile Tyr Gln Gln Gly Leu Glu
            35                  40

<210> SEQ ID NO 94
<211> LENGTH: 41
<212> TYPE: PRT
<213> ORGANISM: artificial
<220> FEATURE:
```

<223> OTHER INFORMATION: MBP fusion protein

<400> SEQUENCE: 94

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Ala Leu Leu Tyr Glu
            20                  25                  30

Gln Phe Ile Tyr Gln Gln Gly Leu Glu
        35                  40

<210> SEQ ID NO 95
<211> LENGTH: 39
<212> TYPE: PRT
<213> ORGANISM: artificial
<220> FEATURE:
<223> OTHER INFORMATION: MBP fusion protein

<400> SEQUENCE: 95

Lys Ser Leu Ser Leu Ser Pro Gly Ser Gly Gly Gly Ser Met Gly Ala
1               5                   10                  15

Gln Thr Asn Phe Met Pro Met Asp Asn Glu Glu Leu Thr Leu Tyr Glu
            20                  25                  30

Gln Phe Ile Phe Gln Gln Gly
        35

<210> SEQ ID NO 96
<211> LENGTH: 41
<212> TYPE: PRT
<213> ORGANISM: artificial
<220> FEATURE:
<223> OTHER INFORMATION: MBP fusion protein

<400> SEQUENCE: 96

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Gly Leu Leu Tyr Glu
            20                  25                  30

Glu Phe Ile Leu Gln Gln Gly Leu Glu
        35                  40

<210> SEQ ID NO 97
<211> LENGTH: 41
<212> TYPE: PRT
<213> ORGANISM: artificial
<220> FEATURE:
<223> OTHER INFORMATION: MBP fusion protein

<400> SEQUENCE: 97

Lys Ser Leu Ser Leu Ser Pro Gly Ser Gly Gly Gly Ser Met Gly Ala
1               5                   10                  15

Gln Thr Asn Phe Met Pro Met Asp Asn Asp Glu Ala Leu Leu Tyr Glu
            20                  25                  30

Glu Phe Ile Leu Gln Gln Gly Leu Glu
        35                  40

<210> SEQ ID NO 98
<211> LENGTH: 41
<212> TYPE: PRT
<213> ORGANISM: artificial
<220> FEATURE:
<223> OTHER INFORMATION: MBP fusion protein

<400> SEQUENCE: 98

```
Lys Ser Leu Ser Leu Ser Pro Gly Ser Gly Gly Gly Ser Met Gly Ala
1               5                   10                  15

Gln Thr Asn Phe Met Pro Met Asp Asn Glu Glu Leu Thr Leu Tyr Glu
            20                  25                  30

Glu Phe Ile Leu Gln Gln Gly Leu Glu
        35                  40

<210> SEQ ID NO 99
<211> LENGTH: 41
<212> TYPE: PRT
<213> ORGANISM: artificial
<220> FEATURE:
<223> OTHER INFORMATION: MBP fusion protein

<400> SEQUENCE: 99

Lys Ser Leu Ser Leu Ser Pro Gly Ser Gly Gly Gly Ser Met Gly Ala
1               5                   10                  15

Gln Thr Asn Phe Met Pro Met Asp Gln Asp Glu Leu Leu Leu Tyr Glu
            20                  25                  30

Gln Phe Ile Leu Gln Gln Gly Leu Glu
        35                  40

<210> SEQ ID NO 100
<211> LENGTH: 41
<212> TYPE: PRT
<213> ORGANISM: artificial
<220> FEATURE:
<223> OTHER INFORMATION: MBP fusion protein

<400> SEQUENCE: 100

Lys Ser Leu Ser Leu Ser Pro Gly Ser Gly Gly Gly Ser Met Gly Ala
1               5                   10                  15

Gln Thr Asn Phe Met Pro Met Asp Asp Asp Glu Leu Leu Leu Tyr Glu
            20                  25                  30

Gln Phe Ile Leu Gln Gln Gly Leu Glu
        35                  40

<210> SEQ ID NO 101
<211> LENGTH: 27
<212> TYPE: PRT
<213> ORGANISM: artificial
<220> FEATURE:
<223> OTHER INFORMATION: IGF1R targeting MRD
<220> FEATURE:
<221> NAME/KEY: MISC_FEATURE
<222> LOCATION: (1)..(4)
<223> OTHER INFORMATION: X is any amino acid
<220> FEATURE:
<221> NAME/KEY: MISC_FEATURE
<222> LOCATION: (6)..(6)
<223> OTHER INFORMATION: X is any amino acid
<220> FEATURE:
<221> NAME/KEY: MISC_FEATURE
<222> LOCATION: (8)..(12)
<223> OTHER INFORMATION: X is any amino acid
<220> FEATURE:
<221> NAME/KEY: MISC_FEATURE
<222> LOCATION: (22)..(23)
<223> OTHER INFORMATION: X is any amino acid
<220> FEATURE:
<221> NAME/KEY: MISC_FEATURE
<222> LOCATION: (25)..(27)
<223> OTHER INFORMATION: X is any amino acid

<400> SEQUENCE: 101

Xaa Xaa Xaa Xaa Cys Xaa Glu Xaa Xaa Xaa Xaa Xaa Pro Ala Glu Lys
```

```
                    1               5                  10                 15
Ser Arg Gly Gln Trp Xaa Xaa Cys Xaa Xaa Xaa
                    20                 25
```

<210> SEQ ID NO 102
<211> LENGTH: 105
<212> TYPE: PRT
<213> ORGANISM: artificial
<220> FEATURE:
<223> OTHER INFORMATION: MRD insertion site

<400> SEQUENCE: 102

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Lys Leu Gly Thr
            35                  40                  45

Asn Ser Gln Glu Ser Val Thr Glu Gln Asp Ser Lys Asp Ser Thr Tyr
        50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Leu Pro Val
                85                  90                  95

Thr Lys Ser Phe Asn Arg Gly Glu Cys
                100                 105
```

<210> SEQ ID NO 103
<211> LENGTH: 10
<212> TYPE: PRT
<213> ORGANISM: artificial
<220> FEATURE:
<223> OTHER INFORMATION: MRD

<400> SEQUENCE: 103

```
Ser Leu Phe Val Pro Arg Pro Glu Arg Lys
1               5                   10
```

<210> SEQ ID NO 104
<211> LENGTH: 10
<212> TYPE: PRT
<213> ORGANISM: artificial
<220> FEATURE:
<223> OTHER INFORMATION: MRD

<400> SEQUENCE: 104

```
Glu Ser Asp Val Leu His Phe Thr Ser Thr
1               5                   10
```

<210> SEQ ID NO 105
<211> LENGTH: 9
<212> TYPE: PRT
<213> ORGANISM: artificial
<220> FEATURE:
<223> OTHER INFORMATION: MRD

<400> SEQUENCE: 105

```
Leu Arg Lys Tyr Ala Asp Gly Thr Leu
1               5
```

<210> SEQ ID NO 106
<211> LENGTH: 9
<212> TYPE: PRT

<213> ORGANISM: artificial
<220> FEATURE:
<223> OTHER INFORMATION: MRD that targets integrin RGD4C

<400> SEQUENCE: 106

Cys Asp Cys Arg Gly Asp Cys Phe Cys
1               5

<210> SEQ ID NO 107
<211> LENGTH: 28
<212> TYPE: PRT
<213> ORGANISM: artificial
<220> FEATURE:
<223> OTHER INFORMATION: L17D

<400> SEQUENCE: 107

Met Gly Ala Gln Thr Asn Phe Met Pro Met Asp Asp Asp Glu Leu Leu
1               5                   10                  15

Leu Tyr Glu Gln Phe Ile Leu Gln Gln Gly Leu Glu
            20                  25

<210> SEQ ID NO 108
<211> LENGTH: 20
<212> TYPE: PRT
<213> ORGANISM: artificial
<220> FEATURE:
<223> OTHER INFORMATION: Ang2 binding MRD

<400> SEQUENCE: 108

Ala Gln Thr Asn Phe Met Pro Met Asp Gln Glu Glu Ala Leu Leu Tyr
1               5                   10                  15

Glu Glu Phe Ile
            20

<210> SEQ ID NO 109
<211> LENGTH: 20
<212> TYPE: PRT
<213> ORGANISM: artificial
<220> FEATURE:
<223> OTHER INFORMATION: Ang2 binding MRD

<400> SEQUENCE: 109

Ala Gln Thr Asn Phe Met Pro Met Asp Gln Asp Glu Ala Leu Leu Tyr
1               5                   10                  15

Glu Glu Phe Ile
            20

<210> SEQ ID NO 110
<211> LENGTH: 20
<212> TYPE: PRT
<213> ORGANISM: artificial
<220> FEATURE:
<223> OTHER INFORMATION: Ang2 binding MRD

<400> SEQUENCE: 110

Ala Gln Thr Asn Phe Met Pro Met Asp Gln Asp Glu Ala Leu Leu Tyr
1               5                   10                  15

Glu Gln Phe Ile
            20

<210> SEQ ID NO 111
<211> LENGTH: 20
<212> TYPE: PRT
<213> ORGANISM: artificial
<220> FEATURE:

<223> OTHER INFORMATION: Ang2 binding MRD

<400> SEQUENCE: 111

Ala Gln Thr Asn Phe Met Pro Met Asp Gln Asp Glu Leu Leu Leu Tyr
1               5                   10                  15

Glu Glu Phe Ile
            20

<210> SEQ ID NO 112
<211> LENGTH: 20
<212> TYPE: PRT
<213> ORGANISM: artificial
<220> FEATURE:
<223> OTHER INFORMATION: Ang2 binding MRD

<400> SEQUENCE: 112

Ala Gln Thr Asn Phe Met Pro Met Asp Asn Asp Glu Ala Leu Leu Tyr
1               5                   10                  15

Glu Gln Phe Ile
            20

<210> SEQ ID NO 113
<211> LENGTH: 21
<212> TYPE: PRT
<213> ORGANISM: artificial
<220> FEATURE:
<223> OTHER INFORMATION: Ang2 binding MRD

<400> SEQUENCE: 113

Ala Gln Thr Asn Phe Met Pro Met Asp Asn Asp Glu Leu Thr Leu Tyr
1               5                   10                  15

Glu Gln Phe Ile Leu
            20

<210> SEQ ID NO 114
<211> LENGTH: 20
<212> TYPE: PRT
<213> ORGANISM: artificial
<220> FEATURE:
<223> OTHER INFORMATION: Ang2 binding MRD

<400> SEQUENCE: 114

Ala Gln Thr Asn Phe Met Pro Met Asp Asn Asp Glu Gly Leu Leu Tyr
1               5                   10                  15

Glu Gln Phe Ile
            20

<210> SEQ ID NO 115
<211> LENGTH: 20
<212> TYPE: PRT
<213> ORGANISM: artificial
<220> FEATURE:
<223> OTHER INFORMATION: Ang2 binding MRD

<400> SEQUENCE: 115

Ala Gln Thr Asn Phe Met Pro Met Asp Asn Asp Glu Ala Leu Leu Tyr
1               5                   10                  15

Glu Gln Phe Ile
            20

<210> SEQ ID NO 116
<211> LENGTH: 20
<212> TYPE: PRT
<213> ORGANISM: artificial

```
<220> FEATURE:
<223> OTHER INFORMATION: Ang2 binding MRD

<400> SEQUENCE: 116

Ala Gln Thr Asn Phe Met Pro Met Asp Asn Asp Glu Gly Leu Leu Tyr
1               5                   10                  15

Glu Glu Phe Ile
            20

<210> SEQ ID NO 117
<211> LENGTH: 20
<212> TYPE: PRT
<213> ORGANISM: artificial
<220> FEATURE:
<223> OTHER INFORMATION: Ang2 binding MRD

<400> SEQUENCE: 117

Ala Gln Thr Asn Phe Met Pro Met Asp Asn Asp Glu Ala Leu Leu Tyr
1               5                   10                  15

Glu Glu Phe Ile
            20

<210> SEQ ID NO 118
<211> LENGTH: 20
<212> TYPE: PRT
<213> ORGANISM: artificial
<220> FEATURE:
<223> OTHER INFORMATION: Ang2 binding MRD

<400> SEQUENCE: 118

Ala Gln Thr Asn Phe Met Pro Met Asp Gln Asp Glu Leu Leu Leu Tyr
1               5                   10                  15

Glu Gln Phe Ile
            20

<210> SEQ ID NO 119
<211> LENGTH: 21
<212> TYPE: PRT
<213> ORGANISM: artificial
<220> FEATURE:
<223> OTHER INFORMATION: Ang2 binding MRD

<400> SEQUENCE: 119

Ala Gln Thr Asn Phe Met Pro Met Asp Asp Asp Glu Leu Leu Leu Tyr
1               5                   10                  15

Glu Gln Phe Ile Leu
            20

<210> SEQ ID NO 120
<211> LENGTH: 21
<212> TYPE: PRT
<213> ORGANISM: artificial
<220> FEATURE:
<223> OTHER INFORMATION: Ang2 binding MRD

<400> SEQUENCE: 120

Ala Gln Thr Asn Phe Met Pro Met Asp Gln Asp Glu Ala Leu Leu Tyr
1               5                   10                  15

Glu Glu Phe Ile Cys
            20

<210> SEQ ID NO 121
<211> LENGTH: 30
<212> TYPE: PRT
```

```
<213> ORGANISM: artificial
<220> FEATURE:
<223> OTHER INFORMATION: Ang2 binding MRD

<400> SEQUENCE: 121

Lys Ser Leu Ser Leu Ser Pro Gly Gly Asn Gly Thr Thr Asn Phe Met
1               5                   10                  15

Pro Met Asp Gln Asp Glu Ala Leu Leu Tyr Glu Glu Phe Ile
            20                  25                  30

<210> SEQ ID NO 122
<211> LENGTH: 30
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q, G, S, T, Y, L, V, P, I, W, F, M, K,
      R, or H
<220> FEATURE:
<221> NAME/KEY: MISC_FEATURE
<222> LOCATION: (21)..(21)
<223> OTHER INFORMATION: X is A, D, E, N, Q, G, S, T, Y, P, W, K, R or H
<220> FEATURE:
<221> NAME/KEY: MISC_FEATURE
<222> LOCATION: (23)..(23)
<223> OTHER INFORMATION: X  is A, D, N, G, S, T, Y, V, P, I, W, F, M, K,
      R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H

<400> SEQUENCE: 122

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Phe Ile
            20                  25                  30

<210> SEQ ID NO 123
<211> LENGTH: 30
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q, G, S, T, Y, L, V, P, I, W, F, M, K, R,
      or H
<220> FEATURE:
<221> NAME/KEY: MISC_FEATURE
<222> LOCATION: (21)..(21)
<223> OTHER INFORMATION: X is D, E, N, Q, G, S, T, Y, V,K, R, or H
```

-continued

```
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
      R, or H
<220> FEATURE:
<221> NAME/KEY: MISC_FEATURE
<222> LOCATION: (28)..(28)
<223> OTHER INFORMATION: X is E, N, D, G, S, T, Y, L, V, P, I, W, F, M,
      K, R, or H

<400> SEQUENCE: 123

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Phe Ile
            20                  25                  30

<210> SEQ ID NO 124
<211> LENGTH: 30
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: misc_feature
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D, E, N, Q, or G
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
      R, or H
<220> FEATURE:
<221> NAME/KEY: MISC_FEATURE
<222> LOCATION: (28)..(28)
<223> OTHER INFORMATION: X is E, N, D, G, S, T, Y, L, V, P, I, W, F, M,
      K, R, or H

<400> SEQUENCE: 124

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Phe Ile
            20                  25                  30

<210> SEQ ID NO 125
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
```

```
<223> OTHER INFORMATION: X is L, A, V, P, I, W, F, M, S, N, E, G, T, H,
      Y, or C
<220> FEATURE:
<221> NAME/KEY: MISC_FEATURE
<222> LOCATION: (12)..(12)
<223> OTHER INFORMATION: X is N, Q, G, S, T, E, D, Y, M, V, L, or I
<220> FEATURE:
<221> NAME/KEY: MISC_FEATURE
<222> LOCATION: (13)..(13)
<223> OTHER INFORMATION: X is N, Q, G, S, T, Y, F, E, P, A, or H
<220> FEATURE:
<221> NAME/KEY: MISC_FEATURE
<222> LOCATION: (14)..(14)
<223> OTHER INFORMATION: X is N, Q, G, S, T, Y, E, H, L, A, V, P, I, W,
      F, or M
<220> FEATURE:
<221> NAME/KEY: MISC_FEATURE
<222> LOCATION: (15)..(15)
<223> OTHER INFORMATION: X is V, M, A, F, L, P, I, W, or Y
<220> FEATURE:
<221> NAME/KEY: MISC_FEATURE
<222> LOCATION: (20)..(20)
<223> OTHER INFORMATION: X is Q, G, S, T, Y, L, V, P, I, W, F, M, K, R,
      or H
<220> FEATURE:
<221> NAME/KEY: MISC_FEATURE
<222> LOCATION: (21)..(21)
<223> OTHER INFORMATION: X is D, E, N, Q, G, S, T, Y, P, W, K, R, or H
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
      R, or H
<220> FEATURE:
<221> NAME/KEY: misc_feature
<222> LOCATION: (24)..(24)
<223> OTHER INFORMATION: X is V, M, A, F, L, P, I, W, Y, D, E, T, H, or
      Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine
<220> FEATURE:
<221> NAME/KEY: MISC_FEATURE
<222> LOCATION: (30)..(30)
<223> OTHER INFORMATION: X is V, M, A, F, L, P, I, W, C, Y, or
      Norleucine
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: MISC_FEATURE
<222> LOCATION: (32)..(40)
<223> OTHER INFORMATION: X is any amino acid or may be missing

<400> SEQUENCE: 125

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 126
<211> LENGTH: 40
<212> TYPE: PRT
<213> ORGANISM: artificial
<220> FEATURE:
```

-continued

```
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (12)..(12)
<223> OTHER INFORMATION: X is N, Q, G, S, T, E, D, Y, M, V, L, or I
<220> FEATURE:
<221> NAME/KEY: MISC_FEATURE
<222> LOCATION: (13)..(13)
<223> OTHER INFORMATION: X is N, Q, G, S, T, Y, F, E, P, A, or H
<220> FEATURE:
<221> NAME/KEY: MISC_FEATURE
<222> LOCATION: (14)..(14)
<223> OTHER INFORMATION: X is N, Q, G, S, T, Y, E, H, L, A, V, P, I, W,
      F, or M
<220> FEATURE:
<221> NAME/KEY: MISC_FEATURE
<222> LOCATION: (15)..(15)
<223> OTHER INFORMATION: X is V, M, A, F, L, P, I, W, or Y
<220> FEATURE:
<221> NAME/KEY: MISC_FEATURE
<222> LOCATION: (20)..(20)
<223> OTHER INFORMATION: X is Q, G, S, T, Y, L, V, P, I, W, F, M, K, R,
      or H
<220> FEATURE:
<221> NAME/KEY: MISC_FEATURE
<222> LOCATION: (21)..(21)
<223> OTHER INFORMATION: X is D, E, N, Q, G, S, T, Y, P, W, K, R, or H
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
      R, or H
<220> FEATURE:
<221> NAME/KEY: MISC_FEATURE
<222> LOCATION: (24)..(24)
<223> OTHER INFORMATION: X is V, M, A, F, L, P, I, W, Y, D, E, T, H, or
      Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine
<220> FEATURE:
<221> NAME/KEY: MISC_FEATURE
<222> LOCATION: (30)..(30)
<223> OTHER INFORMATION: X is V, M, A, F, L, P, I, W, C, Y, or
      Norleucine
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 126

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
```

```
                    20                  25                  30

Xaa Xaa Xaa Xaa Xaa Xaa Xaa Xaa
            35                  40

<210> SEQ ID NO 127
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (12)..(12)
<223> OTHER INFORMATION: X is N, Q, G, S, T, E, D, Y, M, V, L, or I
<220> FEATURE:
<221> NAME/KEY: MISC_FEATURE
<222> LOCATION: (13)..(13)
<223> OTHER INFORMATION: X is N, Q, G, S, T, Y, F, E, P, A, or H
<220> FEATURE:
<221> NAME/KEY: MISC_FEATURE
<222> LOCATION: (14)..(14)
<223> OTHER INFORMATION: X is Q, E, or N
<220> FEATURE:
<221> NAME/KEY: MISC_FEATURE
<222> LOCATION: (15)..(15)
<223> OTHER INFORMATION: X is V, M, A, F, L, P, I, W, or Y
<220> FEATURE:
<221> NAME/KEY: MISC_FEATURE
<222> LOCATION: (20)..(20)
<223> OTHER INFORMATION: X  is Q, G, S, T, Y, L, V, P, I, W, F, M, K, R,
      or H
<220> FEATURE:
<221> NAME/KEY: MISC_FEATURE
<222> LOCATION: (21)..(21)
<223> OTHER INFORMATION: X  is D, E, N, Q, G, S, T, Y, P, W, K, R, or H
<220> FEATURE:
<221> NAME/KEY: MISC_FEATURE
<222> LOCATION: (23)..(23)
<223> OTHER INFORMATION: X  is A, D, N, G, S, T, Y, V, P, I, W, F, M, K,
      R, or H
<220> FEATURE:
<221> NAME/KEY: MISC_FEATURE
<222> LOCATION: (24)..(24)
<223> OTHER INFORMATION: X is V, M, A, F, L, P, I, W, Y, D, E, T, H, or
      Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine
<220> FEATURE:
<221> NAME/KEY: MISC_FEATURE
<222> LOCATION: (30)..(30)
<223> OTHER INFORMATION: X is V, M, A, F, L, P, I, W, C, Y, or
      Norleucine
<220> FEATURE:
<221> NAME/KEY: MISC_FEATURE
<222> LOCATION: (31)..(31)
<223> OTHER INFORMATION: X is any amino acid
<220> FEATURE:
```

```
<221> NAME/KEY: misc_feature
<222> LOCATION: (32)..(40)
<223> OTHER INFORMATION: X is any amino acid or may be missing

<400> SEQUENCE: 127

Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 128
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (12)..(12)
<223> OTHER INFORMATION: X is  N, Q, G, S, T, E, D, Y, M, V, L, or I
<220> FEATURE:
<221> NAME/KEY: MISC_FEATURE
<222> LOCATION: (13)..(13)
<223> OTHER INFORMATION: X is N, Q, G, S, T, Y, F, E, P, A, or H
<220> FEATURE:
<221> NAME/KEY: MISC_FEATURE
<222> LOCATION: (14)..(14)
<223> OTHER INFORMATION: X is N, Q, G, S, T, Y, E, H, L, A, V, P, I, W,
    F, or M
<220> FEATURE:
<221> NAME/KEY: MISC_FEATURE
<222> LOCATION: (15)..(15)
<223> OTHER INFORMATION: X is V, M, A, F, L, P, I, W, or Y
<220> FEATURE:
<221> NAME/KEY: MISC_FEATURE
<222> LOCATION: (20)..(20)
<223> OTHER INFORMATION: X is Q or N
<220> FEATURE:
<221> NAME/KEY: MISC_FEATURE
<222> LOCATION: (21)..(21)
<223> OTHER INFORMATION: X an amino acid other than L or C
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
    R, or H
<220> FEATURE:
<221> NAME/KEY: MISC_FEATURE
<222> LOCATION: (24)..(24)
<223> OTHER INFORMATION: X is V, M, A, F, L, P, I, W, Y, D, E, T, H, or
    Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
    K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
    or Norleucine
```

```
<220> FEATURE:
<221> NAME/KEY: MISC_FEATURE
<222> LOCATION: (30)..(30)
<223> OTHER INFORMATION: X is V, M, A, F, L, P, I, W, C, Y, or
      Norleucine
<220> FEATURE:
<221> NAME/KEY: misc_feature
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 128

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 129
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (12)..(12)
<223> OTHER INFORMATION: X is N, Q, G, S, T, E, D, Y, M, V, L, or I
<220> FEATURE:
<221> NAME/KEY: MISC_FEATURE
<222> LOCATION: (13)..(13)
<223> OTHER INFORMATION: X is N, Q, G, S, T, Y, F, E, P, A, or H
<220> FEATURE:
<221> NAME/KEY: misc_feature
<222> LOCATION: (14)..(14)
<223> OTHER INFORMATION: X is N, Q, G, S, T, Y, E, H, L, A, V, P, I,
      W, F, or M
<220> FEATURE:
<221> NAME/KEY: misc_feature
<222> LOCATION: (15)..(15)
<223> OTHER INFORMATION: X is V, M, A, F, L, P, I, W, or Y
<220> FEATURE:
<221> NAME/KEY: MISC_FEATURE
<222> LOCATION: (20)..(20)
<223> OTHER INFORMATION: X is Q
<220> FEATURE:
<221> NAME/KEY: misc_feature
<222> LOCATION: (21)..(21)
<223> OTHER INFORMATION: X is D, E, S, K, or R
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
      R, or H
<220> FEATURE:
<221> NAME/KEY: MISC_FEATURE
<222> LOCATION: (24)..(24)
<223> OTHER INFORMATION: X is V, M, A, F, L, P, I, W, Y, D, E, T, H, or
      Norleucine
```

```
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine
<220> FEATURE:
<221> NAME/KEY: MISC_FEATURE
<222> LOCATION: (30)..(30)
<223> OTHER INFORMATION: X is V, M, A, F, L, P, I, W, C, Y, or
      Norleucine
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 129

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 130
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (12)..(12)
<223> OTHER INFORMATION: X is N, Q, G, S, T, E, D, Y, M, V, L, or I
<220> FEATURE:
<221> NAME/KEY: MISC_FEATURE
<222> LOCATION: (13)..(13)
<223> OTHER INFORMATION: X is N, Q, G, S, T, Y, F, E, P, A, or H
<220> FEATURE:
<221> NAME/KEY: MISC_FEATURE
<222> LOCATION: (14)..(14)
<223> OTHER INFORMATION: X is N, Q, G, S, T, Y, E, H, L, A, V, P, I, W,
      F, or M
<220> FEATURE:
<221> NAME/KEY: MISC_FEATURE
<222> LOCATION: (15)..(15)
<223> OTHER INFORMATION: X is V, M, A, F, L, P, I, W, or Y
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X  is D, E, S, K, or R
```

-continued

```
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
      R, or H
<220> FEATURE:
<221> NAME/KEY: MISC_FEATURE
<222> LOCATION: (24)..(24)
<223> OTHER INFORMATION: X is V, M, A, F, L, P, I, W, Y, D, E, T, H, or
      Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine
<220> FEATURE:
<221> NAME/KEY: MISC_FEATURE
<222> LOCATION: (30)..(30)
<223> OTHER INFORMATION: X is V, M, A, F, L, P, I, W, C, Y, or
      Norleucine
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 130

Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 131
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is A, V, I, or C
<220> FEATURE:
<221> NAME/KEY: MISC_FEATURE
<222> LOCATION: (12)..(12)
<223> OTHER INFORMATION: X is D, N, or Q
<220> FEATURE:
<221> NAME/KEY: MISC_FEATURE
<222> LOCATION: (13)..(13)
<223> OTHER INFORMATION: X is S or T
<220> FEATURE:
<221> NAME/KEY: MISC_FEATURE
<222> LOCATION: (14)..(14)
<223> OTHER INFORMATION: X is Q, E, or N
<220> FEATURE:
<221> NAME/KEY: MISC_FEATURE
<222> LOCATION: (15)..(15)
```

```
<223> OTHER INFORMATION: X is L, A, V, P, I, W, F, or M
<220> FEATURE:
<221> NAME/KEY: MISC_FEATURE
<222> LOCATION: (20)..(20)
<223> OTHER INFORMATION: X is Q, G, S, T, Y, L, V, P, I, W, F, M, K, R,
      or H
<220> FEATURE:
<221> NAME/KEY: MISC_FEATURE
<222> LOCATION: (21)..(21)
<223> OTHER INFORMATION: X is D, E, S, K, or R
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (24)..(24)
<223> OTHER INFORMATION: X is L, I, or Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is L, V, Norleucine, or F
<220> FEATURE:
<221> NAME/KEY: MISC_FEATURE
<222> LOCATION: (30)..(30)
<223> OTHER INFORMATION: X is L, A, V, I, or Norleucine
<220> FEATURE:
<221> NAME/KEY: misc_feature
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 131

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 132
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is A, V, I, or C
<220> FEATURE:
<221> NAME/KEY: MISC_FEATURE
<222> LOCATION: (12)..(12)
<223> OTHER INFORMATION: X is D, N, or Q
<220> FEATURE:
<221> NAME/KEY: MISC_FEATURE
<222> LOCATION: (13)..(13)
<223> OTHER INFORMATION: X is S, or T
<220> FEATURE:
```

-continued

```
<221> NAME/KEY: MISC_FEATURE
<222> LOCATION: (14)..(14)
<223> OTHER INFORMATION: X is Q, E, or N
<220> FEATURE:
<221> NAME/KEY: MISC_FEATURE
<222> LOCATION: (15)..(15)
<223> OTHER INFORMATION: X  is L, A, V, P, I, W, F, or M
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D, E, S, K, or R
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: misc_feature
<222> LOCATION: (24)..(24)
<223> OTHER INFORMATION: X is L, I, or Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: misc_feature
<222> LOCATION: (29)..(29)
<223> OTHER INFORMATION: X is L,V, Norleucine or F
<220> FEATURE:
<221> NAME/KEY: MISC_FEATURE
<222> LOCATION: (30)..(30)
<223> OTHER INFORMATION: X is L, A, V, I, or Norleucine
<220> FEATURE:
<221> NAME/KEY: misc_feature
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 132

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 133
<211> LENGTH: 40
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is A, V, I, or C
<220> FEATURE:
<221> NAME/KEY: MISC_FEATURE
<222> LOCATION: (12)..(12)
<223> OTHER INFORMATION: X is D, N, or Q
```

```
<220> FEATURE:
<221> NAME/KEY: MISC_FEATURE
<222> LOCATION: (13)..(13)
<223> OTHER INFORMATION: X is S, or T
<220> FEATURE:
<221> NAME/KEY: MISC_FEATURE
<222> LOCATION: (14)..(14)
<223> OTHER INFORMATION: X is Q, E, or N
<220> FEATURE:
<221> NAME/KEY: MISC_FEATURE
<222> LOCATION: (15)..(15)
<223> OTHER INFORMATION: X is L, A, V, P, I, W, F, or M
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (24)..(24)
<223> OTHER INFORMATION: X is L, I, or Norleucine
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is L, V, Norleucine, or F
<220> FEATURE:
<221> NAME/KEY: MISC_FEATURE
<222> LOCATION: (30)..(30)
<223> OTHER INFORMATION: X is L, A, V, I, or Norleucine
<220> FEATURE:
<221> NAME/KEY: misc_feature
<222> LOCATION: (31)..(31)
<223> OTHER INFORMATION: X is any amino acid
<220> FEATURE:
<221> NAME/KEY: misc_feature
<222> LOCATION: (32)..(40)
<223> OTHER INFORMATION: X is any amino acid or may be missing

<400> SEQUENCE: 133

Xaa Xaa Xaa Xaa Xaa Xaa Xaa Xaa Xaa Xaa Xaa Xaa Xaa Xaa Xaa Met
1               5                   10                  15

Pro Met Asp Xaa Xaa Glu Xaa Xaa Leu Tyr Glu Xaa Xaa Xaa Xaa Xaa
            20                  25                  30

Xaa Xaa Xaa Xaa Xaa Xaa Xaa Xaa
        35                  40

<210> SEQ ID NO 134
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
```

```
<223> OTHER INFORMATION: X is Q, G, S, T, Y, L, V, P, I, W, F, M, K, R,
      or H
<220> FEATURE:
<221> NAME/KEY: MISC_FEATURE
<222> LOCATION: (21)..(21)
<223> OTHER INFORMATION: X is D, E, N, Q, G, S, T, Y, P, W, K, R, or H
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H
      or Norleucine

<400> SEQUENCE: 134

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20                  25                  30

<210> SEQ ID NO 135
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D, E, N, Q, G, S, T, Y, P, W, K, R, or H
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine

<400> SEQUENCE: 135

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20                  25                  30

<210> SEQ ID NO 136
<211> LENGTH: 31
<212> TYPE: PRT
```

```
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is any amino acid other than L or C
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
     K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
     or Norleucine

<400> SEQUENCE: 136

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20                  25                  30

<210> SEQ ID NO 137
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D, E, S, K, or R
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
     K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
     or Norleucine
```

```
<400> SEQUENCE: 137

Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20              25                  30

<210> SEQ ID NO 138
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D
<220> FEATURE:
<221> NAME/KEY: MISC_FEATURE
<222> LOCATION: (23)..(23)
<223> OTHER INFORMATION: X is A, D, G, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
      K, R, or H
<220> FEATURE:
<221> NAME/KEY: MISC_FEATURE
<222> LOCATION: (29)..(29)
<223> OTHER INFORMATION: X is E, D, V, M, A, F, L, P, I, W, Y, K, R, H,
      or Norleucine

<400> SEQUENCE: 138

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20              25                  30

<210> SEQ ID NO 139
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q, Y, V, P, W, F, K, or R
<220> FEATURE:
<221> NAME/KEY: MISC_FEATURE
<222> LOCATION: (21)..(21)
<223> OTHER INFORMATION: X is D, E, N, Q, or G
<220> FEATURE:
```

<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M, K, R, or H
<220> FEATURE:
<221> NAME/KEY: MISC_FEATURE
<222> LOCATION: (29)..(29)
<223> OTHER INFORMATION: X is L, V, Norleucine, or F

<400> SEQUENCE: 139

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20                  25                  30

<210> SEQ ID NO 140
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D, E, N, Q, or G
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K, R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M, K, R, or H
<220> FEATURE:
<221> NAME/KEY: MISC_FEATURE
<222> LOCATION: (29)..(29)
<223> OTHER INFORMATION: X is L, V, Norleucine, or F

<400> SEQUENCE: 140

Xaa Xaa Xaa Xaa Xaa Xaa Xaa Xaa Xaa Xaa Ala Gln Thr Asn Phe Met
1               5                   10                  15

Pro Met Asp Xaa Xaa Glu Xaa Leu Leu Tyr Glu Xaa Xaa Phe Ile
            20                  25                  30

<210> SEQ ID NO 141
<211> LENGTH: 31
<212> TYPE: PRT
<213> ORGANISM: artificial
<220> FEATURE:
<223> OTHER INFORMATION: Ang2 binding MRD
<220> FEATURE:
<221> NAME/KEY: MISC_FEATURE
<222> LOCATION: (1)..(9)
<223> OTHER INFORMATION: X is any amino acid or may be missing

```
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (20)..(20)
<223> OTHER INFORMATION: X is Q
<220> FEATURE:
<221> NAME/KEY: MISC_FEATURE
<222> LOCATION: (21)..(21)
<223> OTHER INFORMATION: X is D
<220> FEATURE:
<221> NAME/KEY: MISC_FEATURE
<222> LOCATION: (23)..(23)
<223> OTHER INFORMATION: X is A, D, N, G, S, T, Y, V, P, I, W, F, M, K,
     R, or H
<220> FEATURE:
<221> NAME/KEY: MISC_FEATURE
<222> LOCATION: (28)..(28)
<223> OTHER INFORMATION: X is A, E, D, G, S, T, Y, L, V, P, I, W, F, M,
     K, R, or H
<220> FEATURE:
<221> NAME/KEY: MISC_FEATURE
<222> LOCATION: (29)..(29)
<223> OTHER INFORMATION: X is L, V, Norleucine, or F

<400> SEQUENCE: 141

Xaa Xaa Xaa Xaa Xaa Xaa Xaa Xaa Xaa Xaa Ala Gln Thr Asn Phe Met
1               5                  10                  15

Pro Met Asp Xaa Xaa Glu Xaa Leu Leu Tyr Glu Xaa Xaa Phe Ile
             20                  25                  30

<210> SEQ ID NO 142
<211> LENGTH: 35
<212> TYPE: PRT
<213> ORGANISM: artificial
<220> FEATURE:
<223> OTHER INFORMATION: MBP fusion protein

<400> SEQUENCE: 142

Lys Ser Leu Ser Leu Ser Pro Gly Ser Gly Gly Gly Ser Met Gly Ala
1               5                  10                  15

Gln Thr Asn Phe Met Pro Met Asp Asn Asp Glu Leu Leu Leu Tyr Glu
             20                  25                  30

Gln Phe Ile
        35

<210> SEQ ID NO 143
<211> LENGTH: 35
<212> TYPE: PRT
<213> ORGANISM: artificial
<220> FEATURE:
<223> OTHER INFORMATION: MBP fusion protein

<400> SEQUENCE: 143

Lys Ser Leu Ser Leu Ser Pro Gly Ser Gly Gly Gly Ser Met Gly Ala
1               5                  10                  15

Gln Thr Asn Phe Met Pro Met Asp Asn Glu Glu Leu Leu Leu Tyr Glu
             20                  25                  30

Gln Phe Ile
        35
```

＃ ANG-2-BINDING MODULAR RECOGNITION DOMAIN COMPLEXES AND PHARMACEUTICAL COMPOSITIONS THEREOF

Related Applications U.S. 61/364,764, filed Jul. 15, 2010; U.S. 61/364,765, filed Jul. 15, 2010; U.S. 61/364,766, filed Jul. 15, 2010; U.S. 61/364,771, filed Jul. 15, 2010; U.S. 61/364,774, filed Jul. 15, 2010; U.S. 61/383,644, filed Sep. 16, 2010; U.S. 61/481,063, filed Apr. 29, 2011; U.S. 61/485,486, filed May 12, 2011; U.S. 61/485,484, filed May 12, 2011; U.S. 61/485,502, filed May 12, 2011; U.S. 61/485,505, filed May 12, 2011; U.S. Ser. No. 13/184,485, filed Jul. 15, 2011; and U.S. Ser. No. 13/840,227, filed Mar. 15, 2013; are herein incorporated by reference in their entireties.

BACKGROUND OF THE INVENTION

Field of the Invention

The invention relates generally to complexes containing one or more modular recognition domains and includes complexes containing a scaffold such as an antibody. The invention also relates to methods of making these complexes and methods of treatment and diagnosis using these complexes.

Background Art

The development of bispecific or multi-specific molecules that target two or more targets simultaneously and/or activate prodrugs offers a novel and promising solution to attacking cancer and other diseases. Such molecules can be based, inter alia, on immunoglobulin-like domains or subdomains as exemplified in FIG. 1. Studies of bispecific antibodies that simultaneously target two tumor-associated antigens (e.g., growth factor receptors) for down-regulation of multiple cell proliferation/survival pathways have provided support for this approach. Traditionally, bispecific antibodies have been prepared by chemically linking two different monoclonal antibodies or by fusing two hybridoma cell lines to produce a hybrid-hybridoma. Other technologies that have created multispecific, and/or multi-valent molecules include dAbs, diabodies, TandAbs, nanobodies, BiTEs, SMIPs, DARPins, DNLs, affibodies, Duocalins, adnectins, fynomers, Kunitz Domains Albu-dabs, DARTs, DVD-IG, Covx-bodies, peptibodies, scFv-Igs, SVD-Igs, dAb-Igs, Knob-in-Holes, and triomAbs. Although each of these molecules may bind one or more targets, they each present challenges with respect to retention of typical Ig function (e.g., half-life, effector function), production (e.g., yield, purity), valency, and simultaneous target recognition.

Some of the smaller, Ig subdomain- and non-Ig-domain-based multi-specific molecules may possess some advantages over the full-length or larger IgG-like molecules for certain clinical applications, such as for tumor radio-imaging and targeting, because of better tissue penetration and faster clearance from the circulation. On the other hand, IgG-like molecules may prove to be preferred over smaller fragments for other in vivo applications, specifically for oncology indications, by providing the Fc domain that confers long serum half-life and supports secondary immune function, such as antibody-dependent cellular cytotoxicity and complement-mediated cytotoxicity. Unlike their fragment counterparts, engineering and production of recombinant IgG-like multi-specific, multi-valent molecules has been, however, rather technically challenging due to their large size (150-200 kDa) and structural complexity. Success in the field, as judged by successful application in animal models, has been very limited. Recently, with the examination of a variety of constructs, the efficient expression of Fc domain-containing bi-specific molecules in mammalian cells has made some strides.

Another approach that has been used to target antibodies is through the use of peptibodies. Peptibodies are essentially peptide fusions with antibody Fc regions. Given the success of studies using random peptide libraries to find high-affinity peptide ligands for a wide variety of targets, fusion of such peptides to antibody Fc regions provides a means of making peptides into therapeutic candidates by increasing their circulatory half-life and activity through increased valency.

Protein interactions with other molecules are basic to biochemistry. Protein interactions include receptor-ligand interactions, antibody-antigen interactions, cell-cell contact interactions, and pathogen interactions with target tissues. Protein interactions can involve contact with other proteins, with carbohydrates, oligosaccharides, lipids, metal ions and like materials. The basic unit of protein interaction is the region of the protein involved in contact and recognition, and is referred to as the binding site or target site. Such units may be linear sequence(s) of amino acids or discontinuous amino acids that collectively form the binding site or target site.

Peptides derived from phage display libraries typically retain their binding characteristics when linked to other molecules. Specific peptides of this type can be treated as modular specificity blocks or molecular recognition domains (MRDs) that can, independently, or in combination with other protein scaffolds, create a single protein with binding specificities for several defined targets.

An example of such a defined target site is integrin. Integrins are a family of transmembrane cell adhesion receptors that are composed of $\alpha$ and $\beta$ subunits and mediate cell attachment to proteins within the extracellular matrix. At present, eighteen a and eight $\beta$ subunits are known; these form 24 different $\alpha\beta$ heterodimers with different specificities for various extracellular matrix (ECM) cell-adhesive proteins. Ligands for various integrins include fibronectin, collagen, laminin, von Willebrand factor, osteopontin, thrombospondin, and vitronectin, which are all components of the ECM. Certain integrins can also bind to soluble ligands such as fibrinogen or to other adhesion molecules on adjacent cells. Integrins are known to exist in distinct activation states that exhibit different affinities for ligand. Recognition of soluble ligands by integrins strictly depends on specific changes in receptor conformation. This provides a molecular switch that controls the ability of cells to aggregate in an integrin dependent manner and to arrest under the dynamic flow conditions of the vasculature. This mechanism is well established for leukocytes and platelets that circulate within the blood stream in a resting state while expressing non-activated integrins. Upon stimulation through proinflammatory or prothrombotic agonists, these cell types promptly respond with a number of molecular changes including the switch of key integrins, $\beta 2$ integrins for leukocytes and $\alpha v\beta 3$ for platelets, from "resting" to "activated" conformations. This enables these cell types to arrest within the vasculature, promoting cell cohesion and leading to thrombus formation.

It has been demonstrated that a metastatic subset of human breast cancer cells expresses integrin $\alpha v\beta 3$ in a constitutively activated form. This aberrant expression of $\alpha v\beta 3$ plays a role in metastasis of breast cancer as well as prostate cancer, melanoma, and neuroblastic tumors. The activated receptor strongly promotes cancer cell migration and enables the cells to arrest under blood flow conditions. In this way, activation of $\alpha v\beta 3$ endows metastatic cells with key properties likely to be critical for successful dissemination and colonization of target organs. Tumor cells that have successfully entered a target organ may further utilize αvβ3 to thrive in the new environment, as αvβ3 matrix interactions can promote cell survival and proliferation. For example, αvβ3 binding to osteopontin promotes malignancy and elevated levels of osteopontin correlate with a poor prognosis in breast cancer.

For these reasons, and for its established role in angiogenesis, the αvβ3 integrin is one of the most widely studied integrins. Antagonists of this molecule have significant potential for use in targeted drug delivery. One approach that has been used to target αvβ3 integrin uses the high binding specificity to αvβ3 of peptides containing the Arg-Gly-Asp (RGD) sequence. This tripeptide, naturally present in extracellular matrix proteins, is the primary binding site of the αvβ3 integrin. However, RGD based reporter probes are problematic due to fast blood clearance, high kidney and liver uptake, and fast tumor washout. Chemical modification of cyclized RGD peptides has been shown to increase their stability and valency. These modified peptides are then coupled to radio-isotopes and used either for tumor imaging or to inhibit tumor growth.

Integrin αvβ3 is one of the most well characterized integrin heterodimers and is one of several heterodimers that have been implicated in tumor-induced angiogenesis. While sparingly expressed in mature blood vessels, αvβ3 is significantly up-regulated during angiogenesis in vivo. The expression of αvβ3 correlates with aggressiveness of disease in breast and cervical cancer as well as in malignant melanoma. Recent studies suggest that αvβ3 may be useful as a diagnostic or prognostic indicator for some tumors. Integrin αvβ3 is particularly attractive as a therapeutic target due to its relatively limited cellular distribution. Integrin αvβ3 is not generally expressed on epithelial cells, and minimally expressed on other cell types. Furthermore, αvβ3 antagonists, including both cyclic RGD peptides and monoclonal antibodies, significantly inhibit cytokine-induced angiogenesis and the growth of solid tumor on the chick chorioallantoic membrane.

Another integrin heterodimer, αvβ5, is more widely expressed on malignant tumor cells and is likely involved in VEGF-mediated angiogenesis. It has been shown that αvβ3 and αvβ5 promote angiogenesis via distinct pathways: αvβ3 through bFGF and TNF-a, and αvβ5 through VEGF and TGF-α. It has also been shown that inhibition of Src kinase can block VEGF-induced, but not FGF2-induced, angiogenesis. These results strongly imply that FGF2 and VEGF activate different angiogenic pathways that require αvβ3 and αvβ5, respectively.

Integrins have also been implicated in tumor metastasis. Metastasis is the primary cause of morbidity and mortality in cancer. Malignant progression of melanoma, glioma, ovarian, and breast cancer have all been strongly linked with the expression of the integrin αvβ3 and in some cases with αvβ5. More recently, it has been shown that activation of integrin αvβ3 plays a significant role in metastasis in human breast cancer. A very strong correlation between expression of αvβ3 and breast cancer metastasis has been noted where normal breast epithelia are αvβ3 negative and approximately 50% of invasive lobular carcinomas and nearly all bone metastases in breast cancer express αvβ3. Antagonism of αvβ3 with a cyclic peptide has been shown to synergize with radioimmunotherapy in studies involving breast cancer xenografts.

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular disease, arthritis and psoriasis, the process can go awry. The association of angiogenesis with disease has made the discovery of anti-angiogenic compounds attractive. Among the most promising phage-derived anti-angiogenic peptides described to date, are those that neutralize vascular endothelial growth factor (VEGF), and cytokine Ang2. See e.g., U.S. Pat. Nos. 6,660,843 and 7,138,370, respectively.

While the VEGFs and their receptors have been among the most extensively targeted molecules in the angiogenesis field, preclinical efforts targeting the more recently discovered angiopoietin-Tie2 pathway are underway. Both protein families involve ligand receptor interactions, and both include members whose functions are largely restricted postnatally to endothelial cells and some hematopoietic stem cell lineages. Tie2 is a receptor tyrosine kinase with four known ligands, angiopoietin-1 (Ang1) through angiopoietin-4 (Ang4), the best studied being Ang1 and Ang2. Ang1 stimulates phosphorylation of Tie2 and the Ang2 interaction with Tie2 has been shown to both antagonize and agonize Tie2 receptor phosphorylation. Elevated Ang2 expression at sites of normal and pathological postnatal angiogenesis circumstantially implies a proangiogenic role for Ang2. Vessel-selective Ang2 induction associated with angiogenesis has been demonstrated in diseases including cancer. In patients with colon carcinoma, Ang2 is expressed ubiquitously in tumor epithelium, whereas expression of Ang1 in tumor epithelium has been shown to be rare. The net gain of Ang2 activity has been suggested to be an initiating factor for tumor angiogenesis.

Other proteins directed towards cellular receptors are under clinical evaluation. HERCEPTIN® (Trastuzumab), developed by Genentech, is a recombinant humanized monoclonal antibody directed against the extracellular domain of the human epidermal tyrosine kinase receptor 2 (HER2 or ErbB2). The HER2 gene is overexpressed in 25% of invasive breast cancers, and is associated with poor prognosis and altered sensitivity to chemotherapeutic agents. HERCEPTIN® blocks the proliferation of ErbB2-overexpressing breast cancers, and is currently the only ErbB2 targeted antibody therapy approved by the FDA for the treatment of ErbB2 over-expressing metastatic breast cancer (MBC). In normal adult cells, few ErbB2 molecules exist at the cell surface ~20,000 per cell thereby limiting their signaling capacity and the likelihood of forming homo- and hetero-receptor complexes on the cell surface. When ErbB2 is overexpressed on the cell surface, ~500,000 per cell, multiple ErbB2 homo- and hetero-complexes are formed and cell signaling is stronger, resulting in enhanced responsiveness to growth factors and malignant growth. This explains why ErbB2 overexpression is an indicator of poor prognosis in breast tumors and may be predictive of response to treatment.

ErbB2 is a promising and validated target for breast cancer, where it is found both in primary tumor and metastatic sites. HERCEPTIN® induces rapid removal of ErbB2 from the cell surface, thereby reducing its availability to multimerize and ability to promote growth. Mechanisms of action of HERCEPTIN® observed in experimental in vitro and in vivo models include inhibition of proteolysis of ErbB2's extracellular domain, disruption of downstream signaling pathways such as phosphatidylinositiol 3-kinase (P13K) and mitogen-activated protein kinase (MAPK) cascades, GI cell-cycle arrest, inhibition of DNA repair, suppression of angiogenesis and induction of antibody dependent cellular cytotoxicity (ADCC). Many patients with metastatic breast cancer who initially respond to HERCEPTIN®, however, demonstrate disease progression within one year of treatment initiation.

Another target cellular receptor is type 1 insulin-like growth factor-1 receptor (IGF1R), IGF1R is a receptor-tyrosine kinase that plays a critical role in signaling cell survival and proliferation. The IGF system is frequently deregulated in cancer cells by the establishment of autocrine loops involving IGF-I or IGF-II and/or IGF1R overexpression. Moreover, epidemiological studies have suggested a link between elevated IGF levels and the development of major human cancers, such as breast, colon, lung and prostate cancer. Expression of IGFs and their cognate receptors has been correlated with disease stage, reduced survival, development of metastases and tumor de-differentiation.

Besides IGF1R, epidermal growth factor receptor (EGFR) has also been implicated in the tumorigenesis of numerous cancers. Effective tumor inhibition has been achieved both experimentally and clinically with a number of strategies that antagonize either receptor activity. Because of the redundancy of growth signaling pathways in tumor cells, inhibition of one receptor function (e.g., EGFR) could be effectively compensated by up-regulation of other growth factor receptor (e.g., IGF1R) mediated pathways. For example, a recent study has shown that malignant glioma cell lines expressing equivalent EGFR had significantly different sensitivity to EGFR inhibition depending on their capability to activate IGF1R and its downstream signaling pathways. Other studies have also demonstrated that overexpression and/or activation of IGF1R in tumor cells might contribute to their resistance to chemotherapeutic agents, radiation, or antibody therapy such as HERCEPTIN®. And consequently, inhibition of IGF1R signaling has resulted in increased sensitivity of tumor cells to HERCEPTIN®.

EGFR is a receptor tyrosine kinase that is expressed on many normal tissues as well as neoplastic lesions of most organs. Overexpression of EGFR or expression of mutant forms of EGFR has been observed in many tumors, particularly epithelial tumors, and is associated with poor clinical prognosis. Inhibition of signaling through EGFR induces an anti-tumor effect. With the FDA approval of cetuximab, also known as ERBITUX® (a mouse/human chimeric antibody) in February of 2004, EGFR became an approved antibody drug target for the treatment of metastatic colorectal cancer. In March of 2006, ERBITUX® also received FDA approval for the treatment of squamous cell carcinoma of the head and neck (SCCHN). More recently, panitumumab, also known as VECTIBIX®, a fully human antibody directed against EGFR, was approved for metastatic colorectal cancer. Neither ERBITUX® or VECTIBIX® is a stand-alone agent in colorectal cancer—they were approved as add-ons to existing colorectal regimens. In colorectal cancer, ERBITUX® is given in combination with the drug irinotecan and VECTIBIX® is administered after disease progression on, or following fluoropyrimidine-, oxaliplatin-, and irinotecan-containing chemotherapy regimens. ERBITUX® has been approved as a single agent in recurrent or metastatic SCCHN only where prior platinum-based chemotherapy has failed. Advanced clinical trials which use these drugs to target non-small cell lung carcinoma are ongoing. The sequence of the heavy and light chains of ERBITUX® are well known in the art (see for example, Goldstein, et al., Clin. Cancer Res. 1:1311 (1995); U.S. Pat. No. 6,217,866, which are herein incorporated by reference).

An obstacle in the utilization of a catalytic antibody for selective prodrug activation in cancer therapy has been systemic tumor targeting. An efficient alternative would be using the catalytic antibody fused to a targeting peptide located outside the antibody combining site, thereby leaving the active site available for the prodrug activation as described herein. For example, the fusion of Ab 38C2 to an integrin $\alpha v\beta 3$-binding peptide would selectively localize the antibody to the tumor and/or the tumor vasculature and trigger prodrug activation at that site. The potential therapy of this approach is supported by preclinical and clinical data suggesting that peptides can be converted into viable drugs through attachment to the isolated Fc domain of an immunoglobulin. The present invention describes an approach based on the adaptation of target binding peptides, or modular recognition domains (MRDs), which are fused to full-length antibodies that effectively target tumor cells or soluble molecules while retaining the prodrug activation capability of the catalytic antibody. The current invention calls for the fusion of MRDs to the N- and/or C-termini of an antibody. So as not to significantly mitigate binding to the antibody's traditional binding site, the antibody's specificity remains intact after MRD addition thereby resulting in a multi-specific antibody.

As depicted in FIG. 2, MRDs, designated by triangles, circles, diamonds, and squares, can be appended on any of the termini of either heavy or light chains of a typical IgG antibody. The first schematic represents a simple peptibody with a peptide fused to the C-terminus of an Fc. This approach provides for the preparation of bi-, tri-, tetra-, and penta-specific antibodies. Display of a single MRD at each N- and C-termini of an IgG provides for octavalent display of the MRD. As an alternative to the construction of bi- and multifunctional antibodies through the combination of antibody variable domains, high-affinity peptides selected from, for example, phage display libraries or derived from natural ligands, may offer a highly versatile and modular approach to the construction of multifunctional antibodies that retain both the binding and half-life advantages of traditional antibodies. MRDs can also extend the binding capacity of non-catalytic antibodies, providing for an effective approach to extend the binding functionality of antibodies, particularly for therapeutic purposes.

Therapeutic antibodies represent the most rapidly growing sector of the pharmaceutical industry. Treatment with bispecific antibodies and defined combinations of monoclonal antibodies are expected to show therapeutic advantages over established and emerging antibody monotherapy regimens. However, the cost of developing and producing such therapies has limited their consideration as viable treatments for most indications. There is, therefore, a great need for developing multispecific and multivalent antibodies or other scaffolds having superior drug properties with substantially reduced production costs as compared to conventional bispecific antibodies and combinations of monoclonal antibodies.

BRIEF SUMMARY OF THE INVENTION

The present invention is directed towards a full-length antibody comprising at least one modular recognition domain (MRD). In some embodiments, the full-length antibody comprises multiple MRDs. In additional non-exclusive embodiments, the full-length antibody comprises more than one type of MRD (i.e., multiple MRDs having the same or different specificities). Also embodied in the present invention are variants and derivatives of such antibodies comprising a MRD. Variants and derivatives of such antibodies comprising more than one type of MRD are also encompassed by the invention.

The MRDs of the MRD containing antibodies can be attached to the antibodies at any location on the antibody. In one aspect, the MRD is operably linked to the C-terminal end of the heavy chain of the antibody. In another aspect, the MRD is operably linked to the N-terminal end of the heavy chain of the antibody. In yet another aspect, the MRD is operably linked to the C-terminal end of the light chain of the antibody. In another aspect, the MRD is operably linked to the N-terminal end of the light chain of the antibody. In another aspect, two or more MRDs are operably linked to the same antibody location, e.g., any terminal end of the antibody. In another aspect, two or more MRDs are operably linked to at least two different antibody locations, e.g., two or more different terminal ends of the antibody. In another aspect, MRDs may possess activities in addition to antigen binding such as catalytic activity, carriers of therapeutic agents, prodrugs, or other modifications that do not prevent the antibody from binding to an antigen.

The antibodies of the MRD containing antibodies can be any immunoglobulin molecule that binds to an antigen and can be of any type, class, or subclass. In some embodiments, the antibody is an IgG. In some embodiments, the antibody is a polyclonal, monoclonal, multispecific, human, humanized, primatized or chimeric antibody. In a specific embodiment, the antibody is chimeric or humanized. In another specific embodiment, the antibody is human. In other non-exclusive embodiments, the antibodies also include modifications that do not interfere with their ability to bind antigen. In particular embodiments, the MRD-containing antibodies include modifications that increase ADCC, decrease ADCC, increase CDC, or decrease CDC compared to the antibody without the modification. In other embodiments, the MRD containing antibodies include modifications that increase antibody half life, or decrease antibody half-life compared to the antibody without the modification.

The antibodies of the MRD-containing antibodies of the invention can be any antibody that binds to a target of therapeutic or diagnostic value. In some embodiments, the antibodies corresponding to the MRD containing antibodies are marketed. In some embodiments, the antibodies corresponding to the MRD containing antibodies are in clinical trials for regulatory approval.

In preferred embodiments, the antibody of the MRD-containing antibody binds to a validated target. In one embodiment, the antibody binds to a cell surface antigen. In another embodiment, the antibody binds to an angiogenic factor. In a further embodiment, the antibody binds to an angiogenic receptor.

In some embodiments, the antibody binds to a target that is selected from the group consisting of EGFR, ErbB2, ErbB3, ErbB4, CD20, insulin-like growth factor-I receptor, VEGF, VEGF-R and prostate specific membrane antigen.

In one specific embodiment, the antibody the antibody of the MRD-containing antibody binds to EGFR. In another specific embodiment, the antibody binds to the same epitope as ERBITUX® antibody or competitively inhibits binding of the ERBITUX® antibody to EGFR. In a further specific embodiment, the antibody is the ERBITUX® antibody. In another specific embodiment, the antibody binds to the same epitope as zalutumumab (e.g., Genmab) antibody or competitively inhibits binding of the zalutumumab antibody to EGFR. In a further specific embodiment, the antibody is zalutumumab. In another specific embodiment, the antibody binds to the same epitope as nimotuzumab (e.g., BIOMAB® EGFR, YM Biosciences) antibody or competitively inhibits binding of the nimotuzumab antibody to EGFR. In a further specific embodiment, the antibody is nimotuzumab. In another specific embodiment, the antibody binds to the same epitope as matuzumab (e.g., EMD 72000, Merck Serono) antibody or competitively inhibits binding of the matuzumab antibody to EGFR. In a further specific embodiment, the antibody is matuzumab.

In a specific embodiment, the antibody of the MRD-containing antibody binds to ErbB2. In another specific embodiment, the antibody binds to the same epitope as HERCEPTIN® (trastuzumab) antibody or competitively inhibits HERCEPTIN® (trastuzumab) antibody. In another specific embodiment, the antibody is an antibody that comprises the CDR sequences of SEQ ID NOs: 59-64. In a further specific embodiment, the antibody is the HERCEPTIN® (trastuzumab) antibody.

In another specific embodiment, the antibody binds to VEGF. In another specific embodiment, the antibody binds to the same epitope as AVASTIN® (bevacizumab) antibody or competitively inhibits AVASTIN® antibody. In a further specific embodiment, the antibody is the AVASTIN® antibody.

In some embodiments, the antibody binds to a target that is associated with a disease or disorder of the immune system. In one embodiment, the antibody binds to TNF. In another specific embodiment, the antibody binds to the same epitope as HUMIRA® (adalimumab) antibody or competitively inhibits HUMIRA® antibody. In a further specific embodiment, the antibody is the HUMIRA® antibody. In one embodiment, the antibody binds to TNF. In another specific embodiment, the antibody binds to the same epitope as SIMPONI® (golimumab) antibody or competitively inhibits SIMPONI® antibody. In a further specific embodiment, the antibody is the SIMPONI® antibody.

In other embodiments, the antibody component of the MRD containing antibody binds to a target that is associated with a disease or disorder of the metabolic, cardiovascular, musculoskeletal, neurological, or skeletal system.

In other embodiments, the antibody component of the MRD containing antibody binds to a target that is associated with a yeast, fungal, viral or bacterial infections or disease.

MRDs can be linked to an antibody or other MRDs directly or through a linker. A linker can be any chemical structure that allows for the MRD that has been linked to an antibody to bind its target. In some embodiments, the linker is a chemical linker described herein or otherwise known in the art. In other embodiments the linker is a polypeptide linker described herein or otherwise known in the art. In one aspect, the antibody and the MRD are operably linked through a linker peptide. In one aspect, the linker peptide is between 2 to 20 peptides long, or between 4 to 10 or about 4 to 15 peptides long. In one aspect, the linker peptide comprises the sequence GGGS (SEQ ID NO:1), the sequence SSGGGGSGGGGGSS (SEQ ID NO:2), or the sequence SSGGGGSGGGGGSSRSS (SEQ ID NO:19). Other linkers containing a core sequence of GGGS as shown in SEQ ID NO:1 are also included herein wherein the linker peptide is from about 4-20 amino acids.

The MRDs can be any target binding peptide. In some embodiments, the MRD target is a soluble factor. In other embodiments, the MRD target is a transmembrane protein such as a cell surface receptor. For example, in some embodiments, the MRD target is selected from the group consisting of an angiogenic cytokine and an integrin. In a specific embodiment, the MRD comprises the sequence of SEQ ID NO:8. In another specific embodiment, the MRD comprises the sequence of SEQ ID NO:14. In another specific embodiment, the MRD comprises the sequence of SEQ ID NO:69.

In one embodiment, the MRD is about 2 to 150 amino acids. In another embodiment, the MRD is about 2 to 60 amino acids.

In an additional embodiment, the MRD-containing antibody comprises an MRD containing a sequence selected from the group consisting of SEQ ID NO:8, SEQ ID NO:14, and SEQ ID NO:70.

In one embodiment, the target of the MRD is a cellular antigen. In a specific embodiment of the present invention, the target of the MRD is CD20.

In another embodiment, the target of the MRD is an integrin. In one aspect, the peptide sequence of the integrin targeting MRD is YCRGDCT (SEQ ID NO:3). In another aspect, the peptide sequence of the integrin targeting MRD is PCRGDCL (SEQ ID NO:4). In yet another aspect, the peptide sequence of the integrin targeting MRD is TCRGDCY (SEQ ID NO:5). In another aspect, the peptide sequence of the integrin targeting MRD is LCRGDCF (SEQ ID NO:6).

In an additional embodiment, the target of the MRD is an angiogenic cytokine. In one aspect, the peptide sequence of the angiogenic cytokine targeting (i.e., binding) MRD is MGAQTNFMPMDDLEQRLYEQFILQQGLE (SEQ ID NO:7). In another aspect, the peptide sequence of the angiogenic cytokine targeting MRD is MGAQTNFMPMDNDELLLYEQFILQQGLE (SEQ ID NO:8). In yet another aspect, the peptide sequence of the angiogenic cytokine targeting MRD is MGAQTNFMPMDATETRLYEQFILQQGLE (SEQ ID NO:9). In another aspect, the peptide sequence of the angiogenic cytokine targeting MRD is AQQEECEWDPWTCEHMGSGSATG GSGSTASSGSGSATHQEECEWDPWTCEHMLE (SEQ ID NO:10). In another aspect, the peptide sequence of the angiogenic cytokine targeting MRD is MGAQTNFM PMDNDELLNYEQFILQQGLE (SEQ ID NO:11). In another aspect, the peptide sequence of the angiogenic cytokine targeting MRD is PXDNDXLLNY (SEQ ID NO:12), where X is one of the 20 naturally-occurring amino acids. In another aspect, the targeting MRD peptide has the core sequence MGAQTNFMPMDXn (SEQ ID NO:56), wherein X is any amino acid and n is from about 0 to 15.

In a further embodiment, the targeting MRD peptide contains a core sequence selected from:
XnEFAPWTXn where n is from about 0 to 50 amino acid residues (SEQ ID NO:22);
XnELAPWTXn where n is from about 0 to 50 amino acid residues (SEQ ID NO:25);
XnEFSPWTXn where n is from about 0 to 50 amino acid residues (SEQ ID NO:28);
XnELEPWTXn where n is from about 0 to 50 amino acid residues (SEQ ID NO:31); and
XnAQQEECEX$_1$X$_2$PWTCEHMXn where n is from about 0 to 50 amino acid residues and X, X$_1$ and X$_2$ are any amino acid (SEQ ID NO:57). Exemplary peptides containing such core peptides encompassed by the invention include for example: AQQEECEFAPWTCEHM (SEQ ID NO:21); AQQEECEFAPWTCEHMGSGSATGGSGSTASSGSGSATHQEECEFAPWTCEHMLE (SEQ ID NO:23); AQQEECELAPWTCEHM (SEQ ID NO:24); AQQEECELAPWTCEHM GSGSATG GSGSTASSGSGSATHQEECELAPWTCEHMLE (SEQ ID NO:26); AQQEECEFSPWTCEHM (SEQ ID NO:27); AQQEECEFSPWTCEHMGSGSATGGSGSTASSGSGSATHQEECEFSPW TCEHMLE 2×ConFS (SEQ ID NO:29); AQQEECELEPWTCEHM (SEQ ID NO:30); AQQEEC ELEPWTCEHMGSGSATGGSGSTASSGSGSATHQEECELEPWTCEHMLE (SEQ ID NO:32); AQQEECEFAPWTCEHMGSGSATGGSGSTASSGSGSATHQEECELAPWTCEHMLE (SEQ ID NO:33); AQQEECEFAPWTCEHMGSGSATGGSGSTASSGSGSATHQEECEFSPWTCE HMLE (SEQ ID NO:34); and AQQEECEWDPWTCEHMGSGSATGGSGSTASSGSGSATHQ EECEWDPWTCEHMLE (SEQ ID NO:10).

In one embodiment, the target of the MRD is ErbB2. In another embodiment, the target to which the MRD binds is ErbB3. In an additional embodiment, the target to which the MRD binds is tumor-associated surface antigen or an epithelial cell adhesion molecule (Ep-CAM).

In one embodiment, the target to which the MRD binds is VEGF. In one aspect, the peptide sequence of the VEGF targeting MRD is VEPNCDIHVMWEWECFERL (SEQ ID NO:13).

In one embodiment, the target to which the MRD binds is an insulin-like growth factor-I receptor (IGF1R). In one aspect, the peptide sequence of the insulin-like growth factor-1 receptor targeting MRD comprises SFYSCLESLVNGPAEKSRGQWDGCRKK (SEQ ID NO:14). Other illustrative IGF1R targeting MRDs include, for example, a peptide sequence having the formula NFYQCIX$_1$X$_2$LX$_3$X$_4$X$_5$PAEKSRGQWQECRTGG (SEQ ID NO:58), wherein X$_1$ is E or D; X$_2$ is any amino acid; X$_3$ is any amino acid; X$_4$ is any amino acid; and X$_5$ is any amino acid. Other illustrative IGF targeting MRDs include, for example, a peptide sequence having the formula of XXXXCXEXXXXXPAEKSRGQWXXCXXX (SEQ ID NO:101), wherein X is any amino acid. Illustrative peptides that contain such formula include:
NFYQCIEMLASHPAEKSRGQWQECRTGG (SEQ ID NO:35);
NFYQCIEQLALRPAEKSRGQWQECRTGG (SEQ ID NO:36);
NFYQCIERLVTGPAEKSRGQWQECRTGG (SEQ ID NO:38);
NFYQCIEYLAMKPAEKSRGQWQECRTGG (SEQ ID NO:39);
NFYQCIEALQSRPAEKSRGQWQECRTGG (SEQ ID NO:40);
NFYQCIEALSRSPAEKSRGQWQECRTGG (SEQ ID NO:41);
NFYQCIEHLSGSPAEKSRGQWQECRTG (SEQ ID NO:42);
NFYQCIESLAGGPAEKSRGQWQECRTG (SEQ ID NO:43);
NFYQCIEALVGVPAEKSRGQWQECRTG (SEQ ID NO:44);
NFYQCIEMLSLPPAEKSRGQWQECRTG (SEQ ID NO:45);
NFYQCIEVFWGRPAEKSRGQWQECRTG (SEQ ID NO:46);
NFYQCIEQLSSGPAEKSRGQWQECRTG (SEQ ID NO:47);
NFYQCIELLSARPAEKSRGQWAECRAG (SEQ ID NO:48);
NFYQCIEALARTPAEKSRGQWVECRAP (SEQ ID NO:49);
NFYQCIESLVNGPAEKSRGQWDGCRKK (SEQ ID NO:67) (Rm1-67);
NFYQCIESLVNGPAEKSRGQWVECRAP (SEQ ID NO:68) (Rm2-2-218);
NFYQCIESLVNGPAEKSRGQWAECRAG (SEQ ID NO:69) (Rm2-2-316); and NFYQCIESLVNGPAEKSRGQWQECRTG (SEQ ID NO:70) (Rm2-2-319). Another IGF1R targeting MRDs contains the sequence NFYQCIDLLMAYPAEKSRGQWQECRTGG (SEQ ID NO:37).

In one embodiment, the target of the MRD is a tumor antigen.

In one embodiment, the target of the MRD is an epidermal growth factor receptor (EGFR). In another embodiment of the present invention, the target of the MRD is an angiogenic factor. In an additional embodiment, the target of the MRD is an angiogenic receptor.

In another embodiment, the MRD is a vascular homing peptide. In one aspect, the peptide sequence of the vascular homing peptide MRD comprises the sequence ACDCRGDCFCG (SEQ ID NO:15).

In one embodiment, the target of the MRD is a nerve growth factor.

In another embodiment, the antibody and/or MRD binds to EGFR, ErbB2, ErbB3, ErbB4, CD20, insulin-like growth factor-I receptor, or prostate specific membrane antigen.

In one aspect, the peptide sequence of the EGFR targeting (binding) MRD is VDNKFNKELEKAYNEIRNLPNLNGWQMTAFIASLVDDPSQSANLLAEAKKLNDAQAPK (SEQ ID NO:16). In one aspect, the peptide sequence of the EGFR targeting MRD is VDNK FNKEMWIAWEEIRNLPNLNGWQMTAFIASLVDDPSQSANLLAEAKKLNDAQAPK (SEQ ID NO:17). In another aspect, the peptide sequence of the ErbB2 targeting MRD is VDNK FNKEMRNAYWEIALLPNLNNQQKRAFIRSLYDDPSQSANLLAEAKKLNDAQAPK (SEQ ID NO:18).

The present invention also relates to an isolated polynucleotide comprising a nucleotide sequence encoding an MRD containing antibody. In one aspect, a vector comprises a polynucleotide sequence encoding an MRD containing antibody. In another aspect, the polynucleotide sequence encoding an MRD containing antibody is operatively linked with a regulatory sequence that controls expression on the polynucleotide. In an additional aspect, a host cell comprises the polynucleotide sequence encoding an MRD containing antibody.

Methods of making MRD-antibody fusions (i.e., MRD-containing antibodies) are also provided, as are the use of these MRD-antibody fusions in diagnostic and therapeutic applications. The present invention also relates to methods of designing and making MRD-containing antibodies having a full-length antibody comprising a MRD. In one aspect, the MRD is derived from a phage display library. In another aspect, the MRD is derived from natural ligands. In another aspect, the MRD is derived from yeast display or RNA display technology.

The present invention also relates to a method of treating or preventing a disease or disorder in a subject in need thereof, comprising administering an antibody comprising an MRD to the subject. In one aspect, the disease is cancer. In another aspect, undesired angiogenesis in inhibited. In another aspect, angiogenesis is modulated. In yet another aspect, tumor growth is inhibited.

Certain embodiments provide for methods of treating or preventing a disease, disorder, or injury comprising administering a therapeutically effective amount of an antibody comprising an MRD (i.e., MRD-containing antibodies) to a subject in need thereof. In some embodiments, the disease, disorder or injury is cancer. In other embodiments, the disease, disorder or injury is a disorder of the immune system. In one embodiment, the disorder of the immune system is inflammation. In another embodiment, the disorder of the immune system is an autoimmune disease. In an additional embodiment, the disorder of the immune system is selected from the group consisting of: rheumatoid arthritis, Crohn's disease, systemic lupus erythematosus, inflammatory bowel disease, psoriasis, diabetes, ulcerative colitis, and multiple sclerosis. In one embodiment, the disease, disorder or injury is a metabolic disease. In another embodiment, the disease, disorder, or injury is an infectious disease. In specific embodiments, the infectious disease is human immunodeficiency virus (HIV) infection or AIDS, botulism, anthrax, or *clostridium difficile*. In other embodiments, the disease, disorder, or injury is neurological. In a specific embodiment, the neurological disease, disorder or injury is pain. In a more specific embodiment, the pain is, acute pain or chronic pain.

In another embodiment, a method of treatment or prevention comprising administering an additional therapeutic agent along with an antibody comprising an MRD is provided. In other embodiments, the methods of treatment or prevention comprise administering an antibody comprising more than one type of MRD.

BRIEF DESCRIPTION OF THE DRAWINGS/FIGURES

Figure 17A:
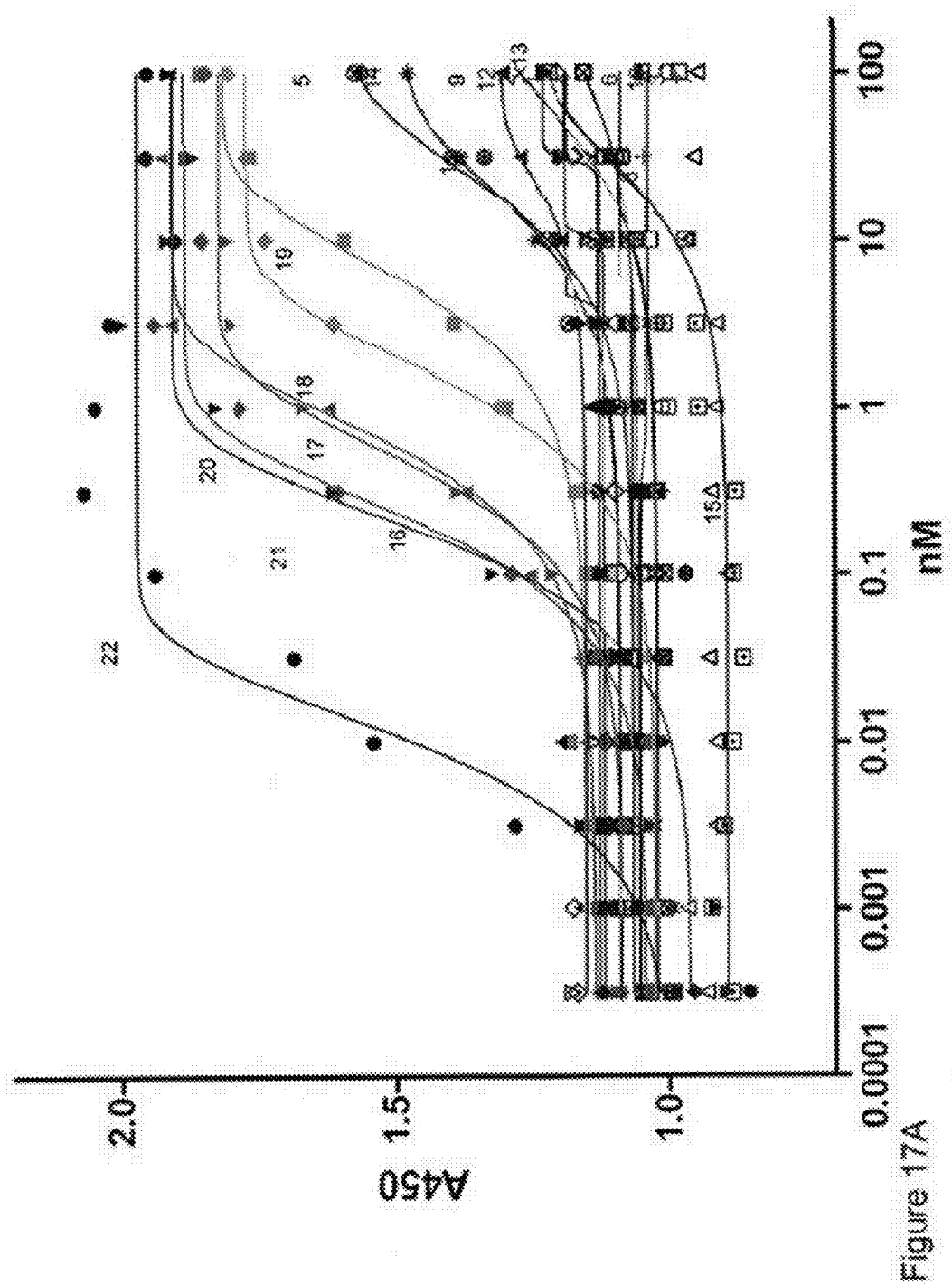
Figure 17B:
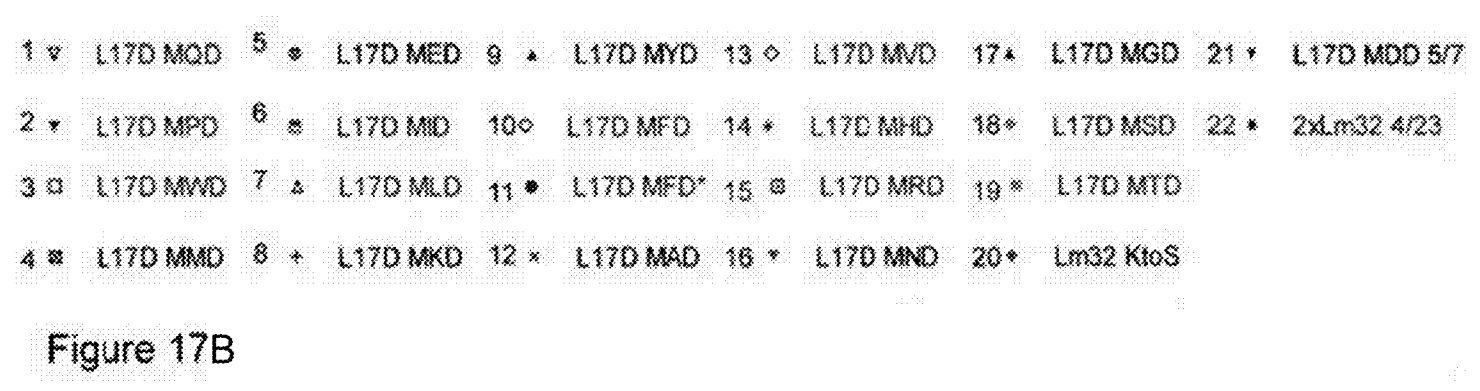

FIGS. 17A and B depict the dose response curves of MRD-maltose binding protein (MBP) fusions assayed for direct binding to Ang2.

FIG. 17C indicates MRD-MBP fusion proteins tested, the amino acid sequence of the MRD, and the EC50 values (calculated using a 4 parameter fit). The MXD sequence motif in the MRD components of the MRD-MBP fusions is underlined and mutated residues are in bold and italics.

Figure 18A:
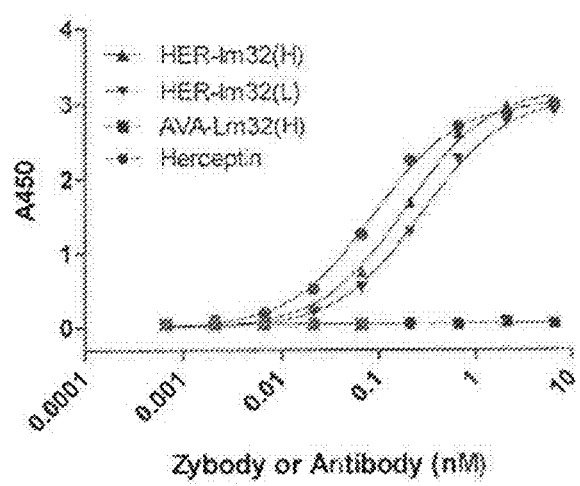

FIG. 18A depicts the results of an assay for direct binding of a HERCEPTIN® based zybody (i.e., an MRD containing HERCEPTIN® antibody sequences) antibody-MRDs and a HERCEPTIN® antibody to Her2 (ErbB2) Fc in the presence of biotinylated Ang2. Binding was detected with HRP-conjugated anti-human kappa chain mAb.

Figure 18B:
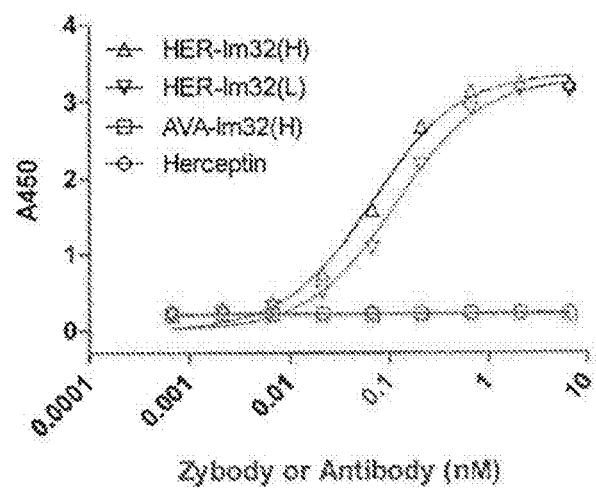

FIG. 18B depicts the results of an assay for direct binding of a HERCEPTIN® based zybody (i.e., an MRD containing HERCEPTIN® antibody sequences) and a HERCEPTIN® antibody to Her2 Fc in the presence of biotinylated Ang2. Binding was detected with horseradish peroxidase (HRP)-conjugated streptavidin.

Figure 19A:
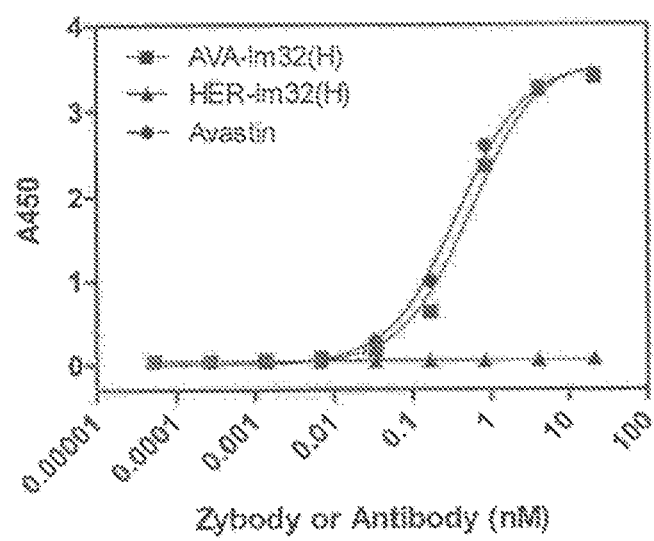

FIG. 19A depicts the results of an assay for direct binding of antibody-MRDs and an AVASTIN® antibody to VEGF in the presence of biotinylated Ang2. Binding was detected with HRP-conjugated anti-human kappa chain mAb.

Figure 19B:
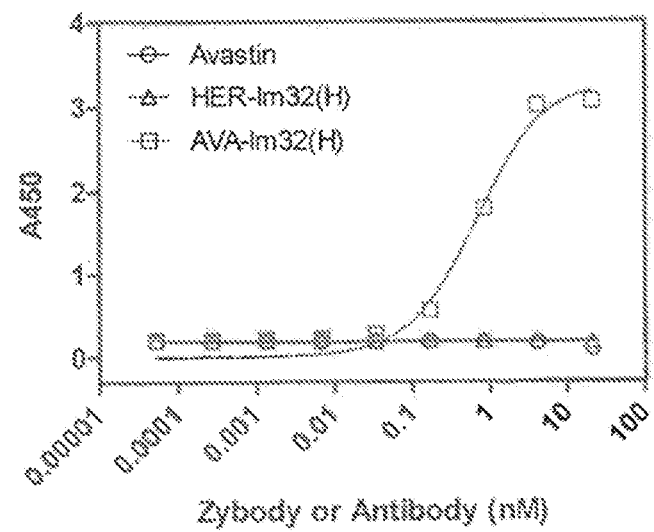

FIG. 19B depicts the results of an assay for direct binding of antibody-MRDs and an AVASTIN® antibody to VEGF in the presence of biotinylated Ang2. Binding was detected with HRP-conjugated streptavidin.

Figure 20A:
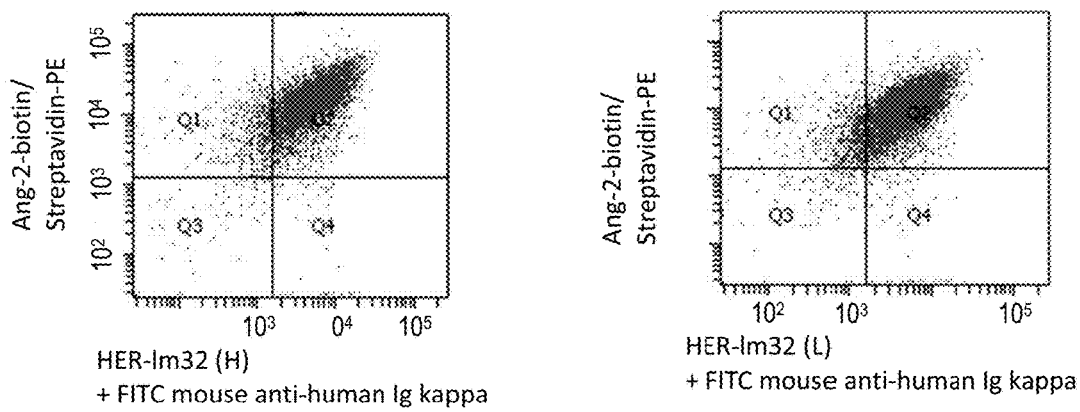

FIG. 20A depicts the results of a flow cytometry assay which demonstrates that antibody-MRDs simultaneously bind Her2 and Ang2 on BT-474 breast cancer cells.

Figure 20B:
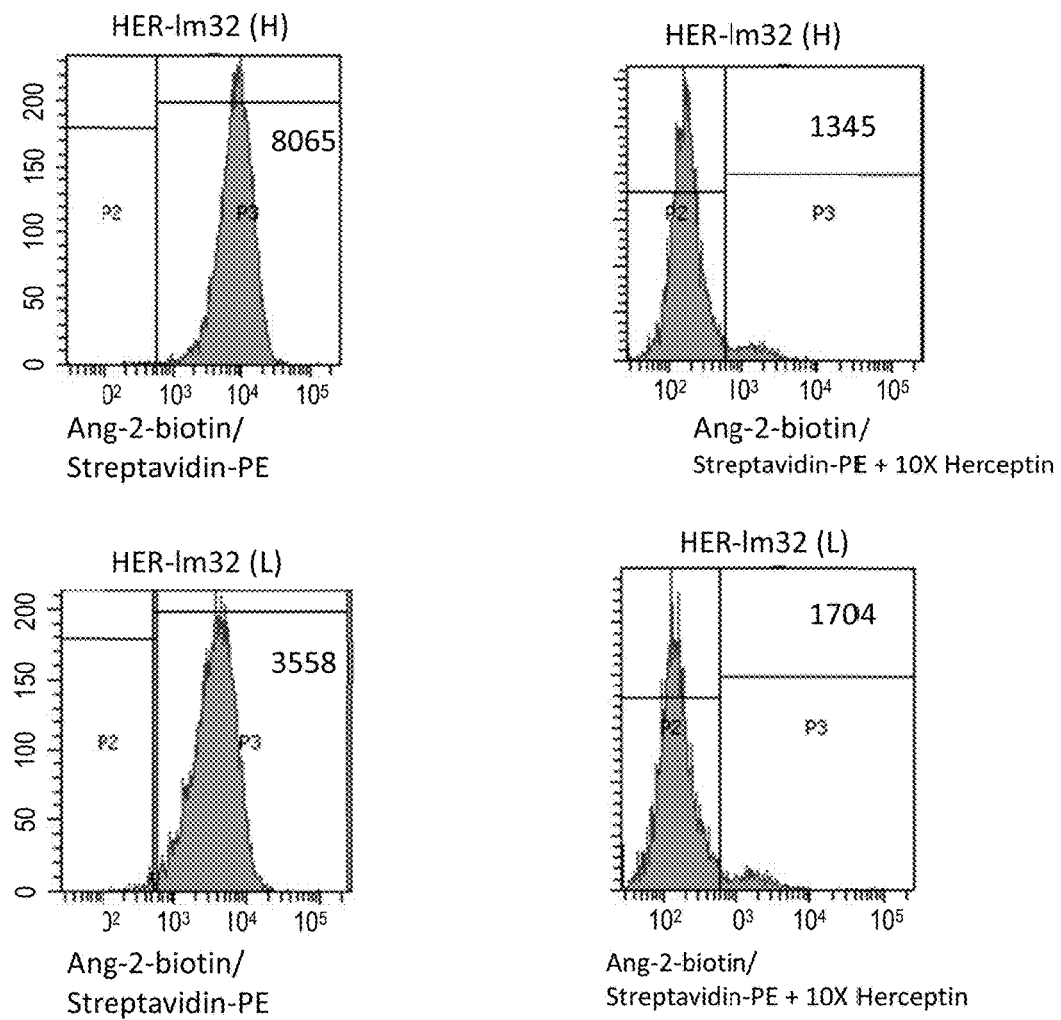

FIG. 20B depicts binding of antibody-MRDs to HER2 on BT-474 breast cancer cells.

Figure 21:
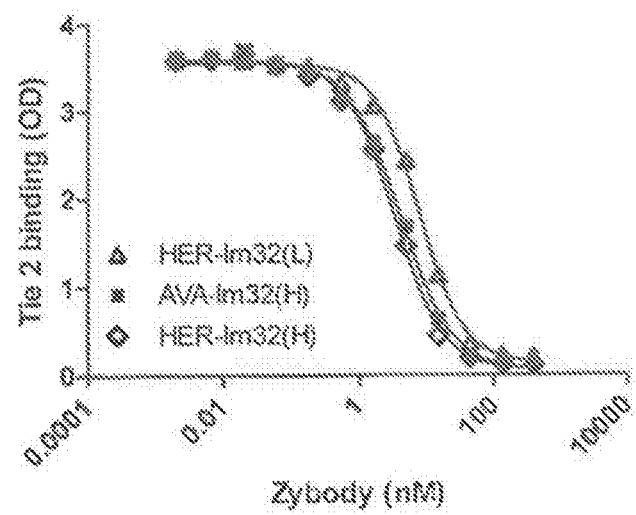

FIG. 21 depicts the results of an ELISA assay that demonstrates the inhibitory effect of antibody-MRDs on TIE-2 binding to plate immobilized Ang2.

Figure 22:
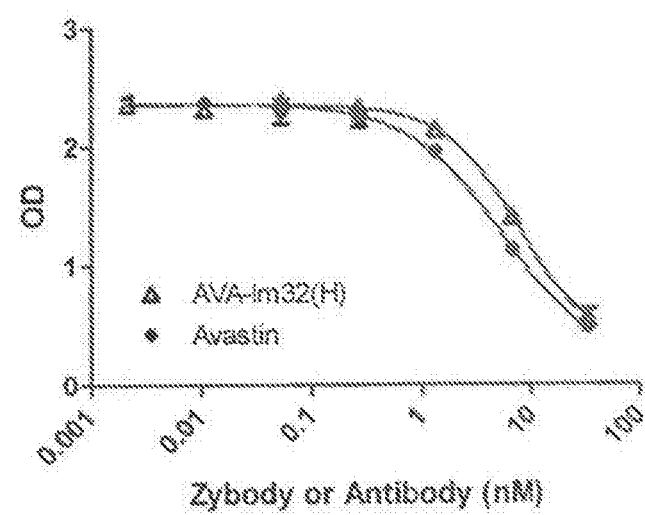

FIG. 22 depicts the results of a competitive binding assay that demonstrates the inhibition of binding of biotinylated antibody by antibody-MRD and unlabeled antibody.

Figure 23:
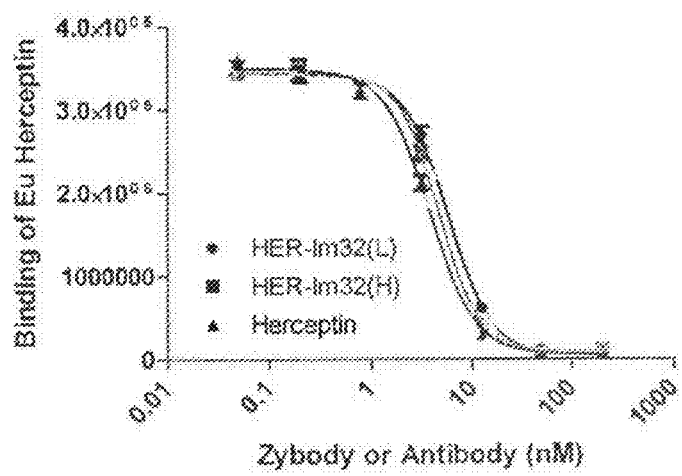

FIG. 23 depicts the results of a competitive binding assay that illustrates the inhibition of labeled antibody binding to BT-474 cells by antibody-MRDs and unlabeled antibody.

Figure 24A:
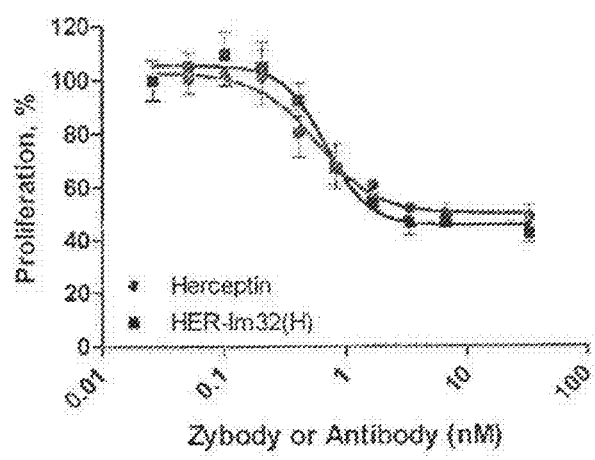

FIG. 24A depicts the fitted dose curves illustrating the inhibition of BT-474 cell proliferation by HERCEPTIN® with the lm32 MRD (SEQ ID NO:8) fused to the heavy chain and HERCEPTIN®.

Figure 24B:
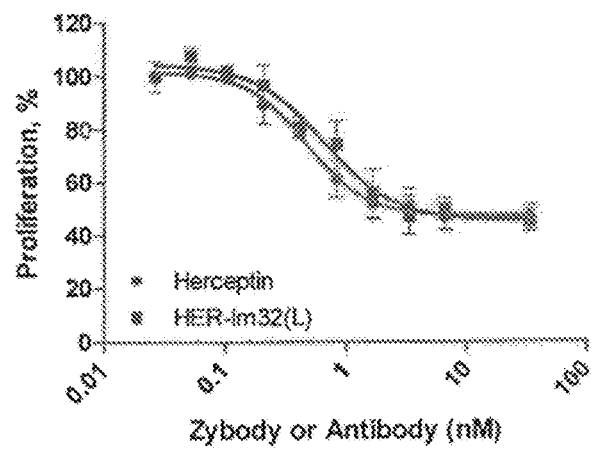

FIG. 24B depicts the fitted dose curves illustrating the inhibition of BT-474 cell proliferation by HERCEPTIN® with the lm32 MRD fused to the light chain and HERCEPTIN®.

Figure 24C:
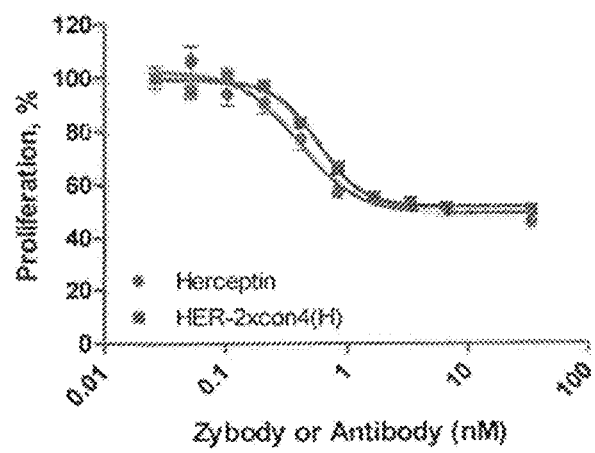

FIG. 24C depicts the fitted dose curves illustrating the inhibition of BT-474 cell proliferation by HERCEPTIN® with the 2×con4 MRD fused to the heavy chain and HERCEPTIN®.

Figure 25A:
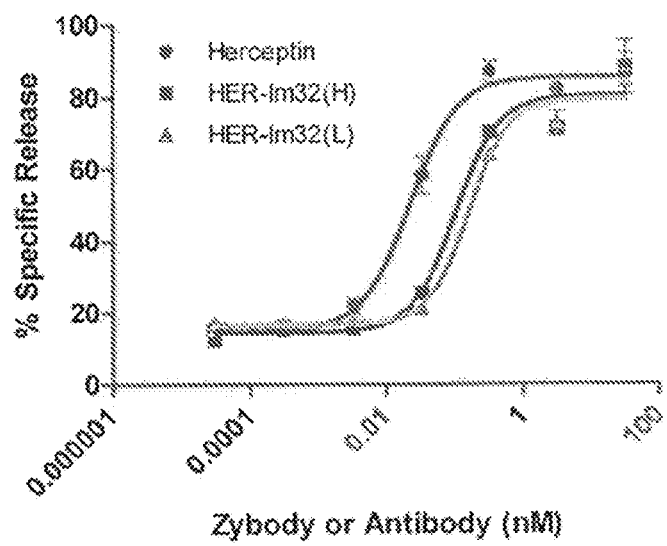

FIG. 25A depicts the results of a cytotoxicity assay illustrating ADCC-mediated killing of BT-474 cells by HERCEPTIN® with the lm32 MRD fused to the heavy chain, HERCEPTIN® with the lm32 MRD fused to the light chain, and HERCEPTIN®.

Figure 25B:
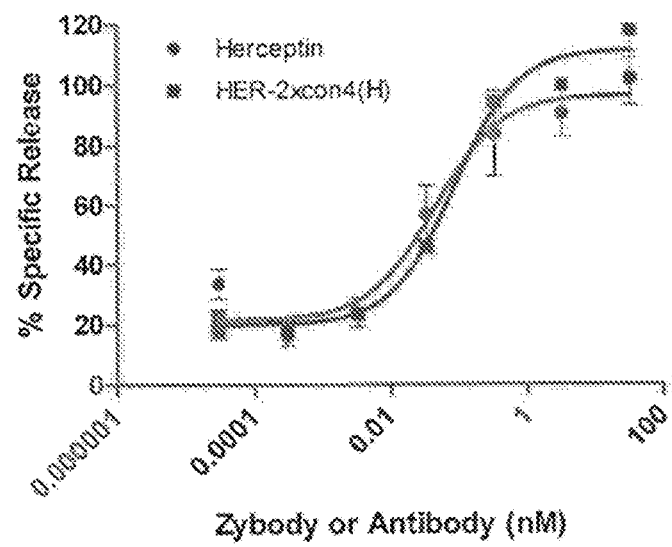

FIG. 25B depicts the results of a cytotoxicity assay illustrating ADCC-mediated killing of BT-474 cells by HERCEPTIN® with the 2×con4 MRD fused to the heavy chain, and HERCEPTIN®.

Figure 26A:
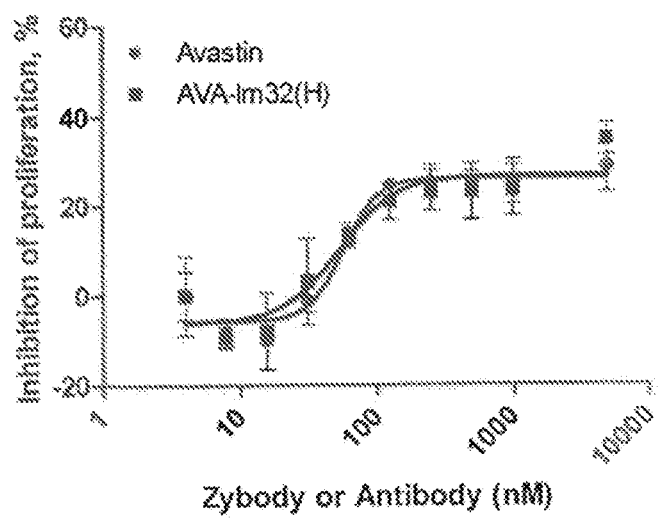

FIG. 26A depicts the inhibition of HUVEC proliferation by AVASTIN® with the lm32 MRD fused to the heavy chain and AVASTIN® using HUVECs obtained from GlycoTech (Gaithersburg, Md.).

Figure 26B:
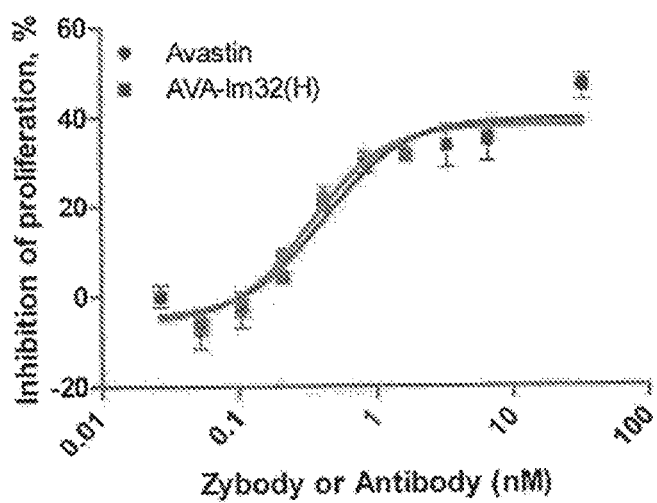

FIG. 26B depicts the inhibition of HUVEC proliferation by AVASTIN® with the lm32 MRD fused to the heavy chain and AVASTIN® using HUVECs obtained from Lonza.

Figure 27:
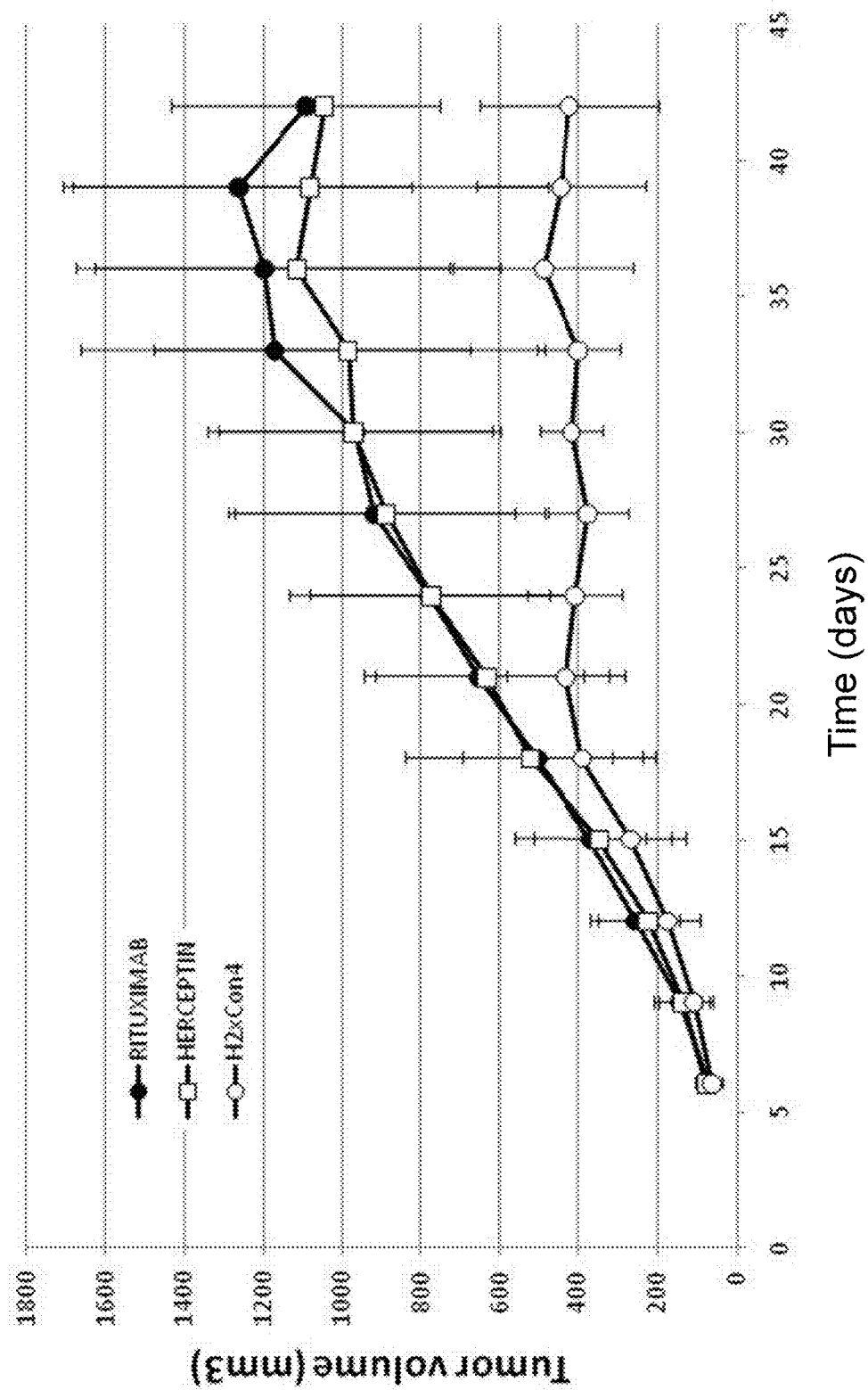

FIG. 27 depicts the effect of rituximab, HERCEPTIN®, and an MRD-containing antibody on tumor volume in vivo.

DETAILED DESCRIPTION OF THE INVENTION

The following provides a description of antibodies containing at least one modular recognition domain (MRD). The linkage of one or more MRDs to an antibody results in a multi-specific molecule of the invention that retains structural and functional properties of traditional antibodies or Fc optimized antibodies and can readily be synthesized using conventional antibody expression systems and techniques. The antibody can be any suitable antigen-binding immunoglobulin, and the MRDs can be any suitable target-binding peptide. The MRDs can be operably linked to any location on the antibody, and the attachment can be direct or indirect (e.g., through a chemical or polypeptide linker). Compositions of antibodies comprising an MRD, methods of manufacturing antibodies comprising an MRD, and methods of using antibodies comprising MRDs are also described in the sections below.

The section headings used herein are for organizational purposes only and are not to be construed as in any way limiting the subject matter described.

Standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures such as those set forth in Harlow et al., Antibodies: A Laboratory Manual, (Cold Spring Harbor Laboratory Press, 2nd ed. 1988) and Sambrook et al. (Molecular Cloning: A Laboratory Manual. Cold Spring Harbor Laboratory Press, Cold Spring Harbor, N.Y. (1989)) (both herein incorporated by reference), or as described herein. Unless specific definitions are provided, the nomenclature utilized in connection with, and the laboratory procedures and techniques of analytical chemistry, synthetic organic chemistry, and medicinal and pharmaceutical chemistry described herein, are those known and used in the art. Standard techniques may be used for chemical syntheses, chemical analyses, pharmaceutical preparation, formulation, delivery, and treatment of patients.

I. Definitions

The terms "MRD-containing antibodies," "antibody-MRD molecules," "MRD-antibody molecules," "antibodies comprising an MRD" and "Zybodies" are used interchangeably herein and do not encompass a peptibody. Each of these terms may also be used herein to refer to a "complex" of the invention.

The term "antibody" is used herein to refer to immunoglobulin molecules that are able to bind antigens through an antigen binding domain (i.e., antibody combining site). The term "antibody" includes polyclonal, oligoclonal (mixtures of antibodies), and monoclonal antibodies, chimeric, single chain, and humanized antibodies. The term "antibody" also includes human antibodies. In some embodiments, an antibody comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains: CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. In other embodiments, the antibody is a homomeric heavy chain antibody (e.g., camelid antibodies) which lacks the first constant region domain (CH1) but retains an otherwise intact heavy chain and is able to bind antigens through an antigen binding domain. The variable regions of the heavy and light chains in the antibody-MRD fusions of the invention contain a functional binding domain that interacts with an antigen.

The term "monoclonal antibody" typically refers to a population of antibody molecules that contain only one species of antibody combining site capable of immunoreacting with a particular epitope. A monoclonal antibody thus typically displays a single binding affinity for any epitope with which it immunoreacts. As used herein, a "monoclonal antibody" may also contain an antibody molecule having a plurality of antibody combining sites (i.e., a plurality of variable domains), each immunospecific for a different epitope, e.g., a bispecific monoclonal antibody. Thus, as used herein, a "monoclonal antibody" refers to a homogeneous antibody population involved in the highly specific recognition and binding of one or two (in the case of a bispecific monoclonal antibody) antigenic determinants, or epitopes. This is in contrast to polyclonal antibodies that typically include different antibodies directed against different antigenic determinants. The term "monoclonal antibody" refers to such antibodies made in any number of manners including but not limited to by hybridoma, phage selection, recombinant expression, yeast, and transgenic animals.

A "dual-specific antibody" is used herein to refer to an immunoglobulin molecule that contains dual-variable-domain immunoglobulins, where the dual-variable-domain can be engineered from any two monoclonal antibodies.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity and/or affinity while the constant regions are homologous to the sequences in antibodies derived from another species (usually human) to avoid eliciting an immune response in that species.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementarity determining region (CDR) are replaced by residues from the CDR of a non-human species (e.g., mouse, rat, rabbit, hamster) that have the desired specificity and/or affinity (Jones et al., Nature, 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody from a non-human species that has the desired specificity and/or affinity. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise an immunoglobulin constant region or domain (Fc), typically that of a human immunoglobulin. Examples of methods used to generate humanized antibodies are described in U.S. Pat. No. 5,225,539, U.S. Pat. No. 4,816,567, Morrison, Science 229:1202 (1985); Oi et al., BioTechniques 4:214 (1986); Cabilly et al., Taniguchi et al., EP 171496; Morrison et al., EP 173494; Neuberger et al., WO 86/01533; Robinson et al., WO 8702671; Boulianne et al., Nature 312:643 (1984); and Neuberger et al., Nature 314: 268 (1985) which are herein incorporated by reference.

As used herein, "human" antibodies include antibodies having the amino acid sequence of a human immunoglobulin or one or more human germlines and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al. A human antibody may still be considered "human" even if amino acid substitutions are made in the antibody. Examples of methods used to generate human antibodies are described in: PCT publications WO 98/24893, WO 92/01047, WO 96/34096, and WO 96/33735; European Patent No. 0 598 877; U.S. Pat. Nos. 5,413,923, 5,625,126, 5,633,425, 5,569,825, 5,661,016, 5,545,806, 5,814,318, 5,885,793, 5,916,771, and 5,939,598; and Lonberg and Huszar, Int. Rev. Immunol. 13:65-93 (1995), which are herein incorporated by reference.

An "antibody combining site" is that structural portion of an antibody molecule comprised of heavy and light chain variable and hypervariable regions that specifically binds (immunoreacts with) an antigen. The term "immunoreact" in its various forms means specific binding between an antigenic determinant-containing molecule and a molecule containing an antibody combining site such as a whole antibody molecule or a portion thereof.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain (i.e., antibody combining site) formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are herein incorporated by reference). "Humanized antibody" or "chimeric antibody" includes antibodies in which CDR sequences derived from the germline of another mammalian species, such as a mouse, have been grafted onto human framework sequences.

The term "peptibody" refers to a peptide or polypeptide which comprises less than a complete, intact antibody. A peptibody can be an antibody Fc domain attached to at least one peptide. A peptibody does not include antibody variable regions, an antibody combining site, CH1 domains, or Ig light chain constant region domains.

The term "naturally occurring" when used in connection with biological materials such as a nucleic acid molecules, polypeptides, host cells, and the like refers to those which are found in nature and not modified by a human being.

The term "domain" as used herein refers to a part of a molecule or structure that shares common physical or chemical features, for example hydrophobic, polar, globular, helical domains or properties, e.g., a protein binding domain, a DNA binding domain or an ATP binding domain. Domains can be identified by their homology to conserved structural or functional motifs.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence to the antigen(s) to which the polypeptide or antibody binds. Methods of identifying nucleotide and amino acid conservative substitutions and non-conservative substitutions which do not eliminate polypeptide or antigen binding are well-known in the art (see, e.g., Brummell et al., Biochem. 32:1180-1187 (1993); Kobayashi et al., Protein Eng. 12(10):879-884 (1999); and Burks et al., Proc. Natl. Acad. Sci. USA 94:412-417 (1997)).

A "modular recognition domain" (MRD) or "target binding peptide" is a molecule, such as a protein, glycoprotein and the like, that can specifically (non-randomly) bind to a target molecule. The amino acid sequence of a MRD can typically tolerate some degree of variability and still retain a degree of capacity to bind the target molecule. Furthermore, changes in the sequence can result in changes in the binding specificity and in the binding constant between a preselected target molecule and the binding site. In one embodiment, the MRD is an agonist of the target it binds. An MRD agonist refers to a MRD that in some way increases or enhances the biological activity of the MRD's target protein or has biological activity comparable to a known agonist of the MRD's target protein. In another embodiment, the MRD is an antagonist of the target it binds. An MRD antagonist refers to an MRD that blocks or in some way interferes with the biological activity of the MRD's target protein or has biological activity comparable to a known antagonist or inhibitor of the MRD's target protein.

"Cell surface receptor" refers to molecules and complexes of molecules capable of receiving a signal and the transmission of such a signal across the plasma membrane of a cell. An example of a cell surface receptor of the present invention is an activated integrin receptor, for example, an activated αvβ3 integrin receptor on a metastatic cell. As used herein, "cell surface receptor" also includes a molecule expressed on a cell surface that is capable of being bound by an MRD containing antibody of the invention.

As used herein, a "target binding site" or "target site" is any known, or yet to be defined, amino acid sequence having the ability to selectively bind a preselected agent. Exemplary reference target sites are derived from the RGD-dependent integrin ligands, namely fibronectin, fibrinogen, vitronectin, von Willebrand factor and the like, from cellular receptors such as ErbB2, VEGF, vascular homing peptide or angiogenic cytokines, from protein hormones receptors such as insulin-like growth factor-I receptor, epidermal growth factor receptor and the like, and from tumor antigens.

The term "epitope" or "antigenic determinant" are used interchangeably herein and refer to that portion of any molecule capable of being recognized and specifically bound by a particular binding agent (e.g., an antibody or an MRD). When the recognized molecule is a polypeptide, epitopes can be formed from contiguous amino acids and noncontiguous amino acids and/or other chemically active surface groups of molecules (such as carbohydrates) juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

An antibody, MRD, antibody-containing MRD, or other molecule is said to "competitively inhibit" binding of a reference molecule to a given epitope if it binds to that epitope to the extent that it blocks, to some degree, binding of the reference molecule to the epitope. Competitive inhibition may be determined by any method known in the art, for example, competition ELISA assays. As used herein, an antibody, MRD, antibody-containing MRD, or other molecule may be said to competitively inhibit binding of the reference molecule to a given epitope, for example, by at least 90%, at least 80%, at least 70%, at least 60%, or at least 50%.

The term "protein" is defined as a biological polymer comprising units derived from amino acids linked via peptide bonds; a protein can be composed of two or more chains.

A "fusion polypeptide" is a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature. The two polypeptides may be operably attached directly by a peptide bond or may be linked indirectly through a linker described herein or otherwise known in the art.

The term "operably linked," as used herein, indicates that two molecules are attached so as to each retain functional activity. Two molecules are "operably linked" whether they are attached directly (e.g., a fusion protein) or indirectly (e.g., via a linker).

The term "linker" refers to a peptide located between the antibody and the MRD or between two MRDs. Linkers can have from about 1 to 20 amino acids, about 2 to 20 amino acids, or about 4 to 15 amino acids. One or more of these amino acids may be glycosylated, as is well understood by those in the art. In one embodiment, the 1 to 20 amino acids are selected from glycine, alanine, proline, asparagine, glutamine, and lysine. In another embodiment, a linker is made up of a majority of amino acids that are sterically unhindered, such as glycine and alanine. Thus, in some embodiments, the linker is selected from polyglycines (such as $(Gly)_5$, and $(Gly)_8$), poly(Gly-Ala), and polyalanines. The linker can also be a non-peptide linker such as an alkyl linker, or a PEG linker. For example, alkyl linkers such as —NH—$(CH_2)$s-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker. In certain embodiments, the PEG linker has a molecular weight of about 100 to 5000 kDa, or about 100 to 500 kDa. The peptide linkers may be altered to form derivatives.

"Target cell" refers to any cell in a subject (e.g., a human or animal) that can be targeted by an antibody-containing MRD or MRD of the invention. The target cell can be a cell expressing or overexpressing the target binding site, such as an activated integrin receptor.

"Patient," "subject," "animal" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles. In some embodiments, the patient is a human.

"Treating" or "treatment" includes the administration of the antibody comprising an MRD of the present invention to prevent or delay the onset of the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder. Treatment can be with the antibody-MRD composition alone, the MRD alone, or in combination of either with an additional therapeutic agent.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of therapeutically prohibitive undesirable physiological effects such as nausea, dizziness, gastric upset and the like.

"Modulate," means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity).

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. A "cancerous tumor," or "malignant cell" is understood as a cell having specific structural properties, lacking differentiation and being capable of invasion and metastasis. Examples of cancers that may be treated using the antibody-MRD fusions of the invention include solid tumors and hematologic cancers. Additional, examples of cancers that may be treated using the antibody-MRD fusions of the invention include breast, lung, brain, bone, liver, kidney, colon, head and neck, ovarian, hematopoietic (e.g., leukemia), and prostate cancer. Further examples of cancer that may be treated using the MRD-containing antibodies include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers. Other types of cancer and tumors that may be treated using MRD-containing antibodies are described herein or otherwise known in the art.

An "effective amount" of an antibody, MRD, or MRD-containing antibody as disclosed herein is an amount sufficient to carry out a specifically stated purpose such as to bring about an observable change in the level of one or more biological activities related to the target to which the antibody, MRD, or MRD-containing antibody binds. In certain embodiments, the change increases the level of target activity. In other embodiments, the change decreases the level of target activity. An "effective amount" can be determined empirically and in a routine manner, in relation to the stated purpose.

The term "therapeutically effective amount" refers to an amount of an antibody, MRD, MRD-containing antibody, or other drug effective to "treat" a disease or disorder in a subject or mammal. In the case of cancer, the therapeutically effective amount of the drug can reduce angiogenesis and neovascularization; reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth or tumor incidence; stimulate immune responses against cancer cells and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

II. Modular Recognition Domains (MRDs)

The present invention describes an approach based on the adaptation of target binding peptides or modular recognition domains (MRDs) as fusions to catalytic or non-catalytic antibodies.

In certain embodiments, where the antibody component of the MRD-antibody fusion is a catalytic antibody, the MRD-antibody fusions provide for effective targeting to tumor cells or soluble molecules while leaving the prodrug activation capability of the catalytic antibody intact. MRDs can also extend the binding capacity of non-catalytic antibodies providing for an effective approach to extend the binding functionality of antibodies, particularly for therapeutic purposes.

One aspect of the present invention relates to development of a full-length antibody comprising at least one modular recognition domain (MRD). In another non-exclusive embodiment, the full-length antibody comprises more than one MRD, wherein the MRDs have the same or different specificities. In addition, a single MRD may be comprised of a tandem repeat of the same or different amino acid sequence that can allow for the binding of a single MRD to multiple targets and/or to a repeating epitope on a given target.

The interaction between a protein ligand and its target receptor site often takes place at a relatively large interface. However, only a few key residues at the interface contribute to most of the binding. The MRDs can mimic ligand binding. In certain embodiments, the MRD can mimic the biological activity of a ligand (an agonist MRD) or through competitive binding inhibit the bioactivity of the ligand (an antagonist MRD). MRDs in MRD-containing antibodies can also affect targets in other ways, e.g., by neutralizing, blocking, stabilizing, aggregating, or crosslinking the MRD target.

It is contemplated that MRDs of the present invention will generally contain a peptide sequence that binds to target sites of interests and have a length of about 2 to 150 amino acids, about 2 to 125 amino acids, about 2 to 100 amino acids, about 2 to 90 amino acids, about 2 to 80 amino acids, about 2 to 70 amino acids, about 2 to 60 amino acids, about 2 to 50 amino acids, about 2 to 40 amino acids, about 2 to 30 amino acids, or about 2 to 20 amino acids. It is also contemplated that MRDs have a length of about 10 to 150 amino acids, about 10 to 125 amino acids, about 10 to 100 amino acids, about 10 to 90 amino acids, about 10 to 80 amino acids, about 10 to 70 amino acids, about 10 to 60 amino acids, about 10 to 50 amino acids, about 10 to 40 amino acids, about 10 to 30 amino acids, or about 10 to 20 amino acids. It is further contemplated that MRDs have a length of about 20 to 150 amino acids, about 20 to 125 amino acids, about 20 to 100 amino acids, about 20 to 90 amino acids, about 20 to 80 amino acids, about 20 to 70 amino acids, about 20 to 60 amino acids, about 20 to 50 amino acids, about 20 to 40 amino acids, or about 20 to 30 amino acids. In certain embodiments, the MRDs have a length of about 2 to 60 amino acids. In other embodiments, the MRDs have a length of about 10 to 60 amino acids. In other embodiments, the MRDs have a length of about 10 to 50 amino acids. In additional embodiments, the MRDs have a length of about 10 to 40 amino acids. In additional embodiments, the MRDs have a length of about 10 to 30 amino acids.

In some embodiments, one or more of the MRD components of the MRD-containing antibodies have a dissociation constant or Kd of less than $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-14}$ M, $5 \times 10^{-14}$ M, $10^{-14}$ M, $5 \times 10^{-15}$ M, or $10^{-15}$ M. In one embodiment, one or more of the MRD components of the MRD-containing antibodies have a dissociation constant or Kd less than $5 \times 10^{-5}$ M. In another embodiment, one or more of the MRD components of the MRD-containing antibodies have a dissociation constant or Kd less than $5 \times 10^{-8}$ M. In another embodiment, one or more of the MRD components of the MRD-containing antibodies have a dissociation constant or Kd less than $5 \times 10^{-9}$ M. In another embodiment, one or more of the MRD components of the MRD-containing antibodies have a dissociation constant or Kd less than $5 \times 10^{-10}$ M. In another embodiment, one or more of the MRD components of the MRD-containing antibodies have a dissociation constant or Kd less than $5 \times 10^{-11}$ M. In another embodiment, one or more of the MRD components of the MRD-containing antibodies have a dissociation constant or Kd less than $5 \times 10^{-12}$ M.

In specific embodiments, one or more of the MRD components of the MRD-containing antibodies bind their targets with an off rate ($k_{off}$) of less than $5 \times 10^{-2}$ sec$^{-1}$, $10^{-2}$ sec$^{-1}$, $5 \times 10^{-3}$ sec$^{-1}$, or $10^{-3}$ sec$^{-1}$. More preferably, one or more of the MRD components of the MRD-containing antibodies bind their targets with an off rate ($k_{off}$) of less than $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$, or $10^{-7}$ sec$^{-1}$.

In other specific embodiments, one or more of the MRD components of the MRD-containing antibodies bind their targets with an on rate ($k_{on}$) of greater than $10^3$ M$^{-1}$sec$^{-1}$, $5 \times 10^3$ M$^{-1}$sec$^{-1}$, $10^4$ M$^{-1}$sec$^{-1}$, or $5 \times 10^4$ M$^{-1}$sec$^{-1}$. More preferably, one or more of the MRD components of the MRD-containing antibodies bind their targets with an on rate ($k_{on}$) of greater than $10^5$ M$^{-1}$sec$^{-1}$, $5 \times 10^5$ M$^{-1}$sec$^{-1}$, $10^6$ M$^{-1}$sec$^{-1}$, or $5 \times 10^6$ M$^{-1}$sec$^{-1}$, or $10^7$ M$^{-1}$sec$^{-1}$.

In some embodiments, the MRDs are affibodies. Affibodies represent a class of affinity proteins based on a 58-amino acid residue protein domain derived from one of the IgG-binding domains of staphylococcal protein A. This three helix bundle domain has been used as a scaffold for the construction of combinatorial phagemid libraries, from which affibody variants that bind a desired target molecule, such as one or more of the targets disclosed herein, can routinely be selected using phage display technology (see, e.g., Nord et al., Nat Biotechnol 15:772-7 (1997), and Ronmark et al., Eur J Biochem 269:2647-55 (2002)). Further details of Affibodies and methods of production thereof are provided by reference to U.S. Pat. No. 5,831,012, which is herein incorporated by reference in its entirety.

In some embodiments, the MRDs are fynomers or another SH3 domain based binding polypeptide. Fynomers, like other SH3 domain derived affinity peptides share a compact barrel conformation that is formed by two anti-parallel beta sheets. The Fyn SH3 domain is 63 residues in length and contains 2 flexible loops that have been modified using combinatorial protein design to create display libraries. Fynomers that bind a target of interest can routinely be selected using recombinant technology as described for example, in Grbulovski et al., J. Biol. Chem. 282(5) 3196-3204 (2007) and International Publication WO 2008/022759, which is herein incorporated by reference in its entirety.

In other embodiments, the MRDs comprise one or more amino acid residues or sequences of amino acid residues (including derivatives, analogs, and mimetics thereof), that are preferentially targeted by chemistries or other processes that covalently or non-covalently link a molecular entity to the MRD, as compared to the antibody component of the MRD-containing antibody. For example, in some embodiments, the amino acid sequence of the MRD contains one or more residues having reactive side chains (e.g., cysteine or lysine) that allow for selective or preferential linkage of the MRD to drug conjugates, imaging agents or bioactive ligands. The use of these "linking" MRDs to arm an MRD-comprising antibody with a "payload" overcomes many of the issues associated with antibody destabilization and reduction in antibody activity that have frequently been observed using conventional methods for generating immunotoxins. The "payload" component of an MRD-comprising antibody complex of the invention can be any composition that confers a beneficial therapeutic, diagnostic, or prognostic effect, or that provide an advantage in manufacturing, purifying or formulating an MRD-containing antibody. In some embodiments, the payload is a cytotoxin. In additional embodiments, the payload is another MRD, a toxin, a chemotherapeutic drug, a catalytic enzyme, a prodrug, a radioactive nuclide, or a chelator (e.g., for the attachment of lanthanides). In particular embodiments, the payload is a chemotherapeutic drug, or a prodrug, such as, doxorubicin or a maytansinoid-like drug. The payloads can be designed to be released from the MRD-comprising antibody complex using techniques known in the art. In certain embodiments, the payloads are released from the MRD-comprising antibody by cleavage of the MRD upon binding of the MRD-comprising-payload complex to a cell or other biomolecule. In other embodiments, the payloads of the MRD-comprising-antibody complex are released upon internalization of the complex into a cell.

In nonexclusive embodiments, the MRD does not contain an antigen binding domain, or another antibody domain such as a constant region, a variable region, a complementarity determining region (CDR), a framework region, an Fc domain, or a hinge region. In one non-exclusive embodiment, the MRD does not contain an antigen binding domain. In another non-exclusive embodiment, the MRD does not contain three CDRs. In another non-exclusive embodiment, the MRD does not contain CDR1 and CDR2. In yet another non-exclusive embodiment, the MRD does not contain CDR1. In one nonexclusive embodiment, the MRD is not derived from a natural cellular ligand. In another embodiment, the MRD is not a naturally occurring protein or functionally active (i.e., able to bind its natural target) fragment thereof. In another nonexclusive embodiment, the MRD is not a radioisotope. In another nonexclusive embodiment, the MRD is not a protein expression marker such as glutathione S-transferase (GST), His-tag, Flag, hemagglutinin (HA), MYC or a fluorescent protein (e.g., GFP or RFP). In another nonexclusive embodiment, the MRD does not bind serum albumin. In an additional nonexclusive embodiment, the MRD is not a small molecule that is a cytotoxin.

It yet another nonexclusive embodiment, the MRD does not have enzymatic activity. In another non-exclusive embodiment, the MRD has a therapeutic effect when administered alone and/or when fused to an Fc in a patient or animal model. In another non-exclusive embodiment, the MRD has a therapeutic effect when repeatedly administered alone and/or when fused to an Fc in a patient or animal model (e.g., 3 or more times over the course of at least six months).

In some embodiments, the MRD is conformationally constrained. In other embodiments, the MRD is not conformationally constrained. In some embodiments, the MRD contains at least two cysteine residues. Cysteine residues in the MRDs may produce either or both, intrachain or interchain disulfide bonds. In some embodiments, the MRD contains two cysteine residues outside the core target-binding domain. As used herein, the term "core binding domain means a region corresponding the minimal number of amino acids making up a portion of a binding protein that are required to competitively inhibit the binding of the full-length protein to a binding target. Alternatively, when dealing with proteins of less than 100 KDa, the core binding domain can conveniently be benchmarked as the minimum number of amino acids in a portion of a binding protein that retains greater than or equal to 80% of the biologic activity (e.g., binding) of the full-length protein Methods and reagents for assaying competitive binding inhibition between compounds are readily known in the art.

In additional embodiments, the MRD contains two cysteine residues located within the core target-binding domain at each end of the target-binding domain. In some embodiments, a first cysteine is located near the terminus of the molecule (i.e., at the C-terminus of an MRD on the C-terminus of a linker or antibody chain or at the N-terminus of an MRD on the N-terminus of a linker or antibody chain). Thus, in some embodiments, a first cysteine is located within one amino acid, within two amino acids, within three amino acids, within four amino acids, within five amino acids, or within six amino acids of the terminus of the molecule. In some embodiments, a second cysteine is located near the MRD fusion location (i.e., at the N-terminus of an MRD on the C-terminus of a linker or antibody chain or at the C-terminus of an MRD on the N-terminus of a linker or antibody chain). Thus, in some embodiments, a second cysteine is located within one amino acid, within two amino acids, within three amino acids, within four amino acids, within five amino acids, within 10 amino acids, or within 15 amino acids from the MRD fusion. In additional embodiments, the MRD one or two cysteine residues located outside of the core target-binding domain.

In some particular embodiments, the MRD has a particular hydrophobicity. For example, the hydrophobicity of MRDs can be compared on the basis of retention times determined using hydrophobic interaction chromatography or reverse phase liquid chromatography.

The MRD target can be any molecule that it is desirable for an MRD-containing antibody to interact with. For example, the MRD target can be a soluble factor or a transmembrane protein, such as a cell surface receptor. The MRD target can also be an extracellular component or an intracellular component. In certain non-exclusive embodiments, the MRD target is a factor that regulates cell proliferation, differentiation, or survival. In other nonexclusive embodiments, the MRD target is a cytokine. In another nonexclusive embodiment, the MRD target is a factor that regulates angiogenesis. In another nonexclusive embodiment, the MRD target is a factor that regulates cellular adhesion and/or cell-cell interaction. In certain non-exclusive embodiments, the MRD target is a cell signaling molecule. In another nonexclusive embodiment, the MRD target is a factor that regulates one or more immune responses, such as, autoimmunity, inflammation and immune responses against cancer cells. In another nonexclusive embodiment, the MRD target is a factor that regulates cellular adhesion and/or cell-cell interaction. In an additional nonexclusive embodiment, the MRD target is a cell signaling molecule. In another embodiment, an MRD can bind a target that is itself an MRD. The ability of MRDs to bind a target and block, increase, or interfere with the biological activity of the MRD target can be determined using or routinely modifying assays, bioassays, and/or animal models known in the art for evaluating such activity.

The MRDs are able to bind their respective target when the MRDs are attached to an antibody. In some embodiments, the MRD is able to bind its target when not attached to an antibody. In some embodiments, the MRD is a target agonist. In other embodiments, the MRD is a target antagonist. In certain embodiments, the MRD can be used to localize an MRD-containing antibody to an area where the MRD target is located.

The sequence of the MRD can be determined several ways. For example, MRD sequences can be derived from natural ligands or known sequences that bind to a specific target binding site. Additionally, phage display technologies have emerged as a powerful method in identifying peptides which bind to target receptors and ligands. In peptide phage display libraries, naturally occurring and non-naturally occurring (e.g., random peptide) sequences can be displayed by fusion with coat proteins of filamentous phage. The methods for elucidating binding sites on polypeptides using phage display vectors has been previously described, in particular in WO 94/18221, which is herein incorporated by reference. The methods generally involve the use of a filamentous phage (phagemid) surface expression vector system for cloning and expressing polypeptides that bind to the pre-selected target site of interest.

The methods of the present invention for preparing MRDs include the use of phage display vectors for their particular advantage of providing a means to screen a very large population of expressed display proteins and thereby locate one or more specific clones that code for a desired target binding reactivity. The ability of the polypeptides encoded by the clones to bind a target and/or alter the biological activity of the target can be determined using or routinely modifying assays and other methodologies described herein or otherwise known in the art.

For example, phage display technology can be used to identify and improve the binding properties of MRDs. See, for example, Scott et al., Science 249: 386 (1990); Devlin et al., Science 249: 404 (1990); U.S. Pat. Nos. 5,223,409, 5,733,731, 5,498,530, 5,432,018, 5,338,665, 5,922,545; WO 96/40987, and WO 98/15833, which are herein incorporated by reference. In peptide phage display libraries, natural and/or non-naturally occurring peptide sequences can be displayed by fusion with coat proteins of filamentous phage. The displayed peptides can be affinity-eluted against a target of interest if desired. The retained phage may be enriched by successive rounds of affinity purification and repropagation. The best binding peptides may be sequenced to identify key residues within one or more structurally related families of peptides. See, e.g., Cwirla et al., Science 276: 1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, Ann. Rev. Biophys. Biomol. Struct. 26: 401-24 (1997).

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide such as an MRD may be designed. See, e.g., Takasaki et al., Nature Biotech 15: 1266-70 (1997). These analytical methods may also be used to investigate the interaction between a target and an MRD selected by phage display, which can suggest further modification of the MRDs to increase binding affinity.

Other methods known in the art can be used to identify MRDs. For example, a peptide library can be fused to the carboxyl terminus of the lac repressor and expressed in *E. coli*. Another *E. coli*-based method allows display on the cell's outer membrane by fusion with a peptidoglycan-associated lipoprotein (PAL). These and related methods are collectively referred to as "*E. coli* display." In another method, translation of random RNA is halted prior to ribosome release, resulting in a library of polypeptides with their associated RNA still attached. This and related methods are collectively referred to as "ribosome display." Other known methods employ chemical linkage of peptides to RNA. See, for example, Roberts and Szostak, Proc Natl Acad Sci USA, 94:12297-303 (1997). This and related methods are collectively referred to as "RNA-peptide screening, RNA display and mRNA display." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. These and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, Curr. Opin. Biotechnol., 3:355-62 (1992). Furthermore, constrained libraries, linear libraries, and/or focused libraries (comprised of structurally related domains that share significant primary sequence homology) can be used to identify, characterize, and modify MRDs.

An improved MRD that specifically binds a desired target can also be prepared based on a known MRD sequence. For example, at least one, two, three, four, five, or more amino acid mutations (e.g., conservative or non-conservative substitutions), deletions or insertions can be introduced into a known MRD sequence and the resulting MRD can be screened for binding to the desired target and biological activity, such as the ability to antagonize target biological activity or agonize target biological activity.

Additionally, MRDs can be identified based on their effects in assays that measure particular pathways or activities. For example, assays that measure signaling pathways (e.g., phosphorylation studies or multimerization), ion channel fluxes, intracellular cAMP levels, cellular activities such as migration, adherence, proliferation, or apoptosis, and viral entry, replication, budding, or integration can be used to identify, characterize, and improve MRDs.

Variants and derivatives of the MRDs that retain the ability to bind the target antigen are included within the scope of the present invention. Included within variants are insertional, deletional, and substitutional variants, as well as variants that include MRDs presented herein with additional amino acids at the N- and/or C-terminus, including from about 0 to 50, 0 to 40, 0 to 30, 0 to 20 amino acids and the like. It is understood that a particular MRD of the present invention may be modified to contain one, two, or all three types of variants. Insertional and substitutional variants may contain natural amino acids, unconventional amino acids, or both. In some embodiments, the MRD contains a sequence with no more than 1, 2, 3, 4, 5, 6, 7, 8, 9, 10, 15, or 20 amino acid differences when compared to an MRD sequence described herein. In some embodiments, the amino acid differences are substitutions. These substitutions can be conservative or non-conservative in nature and can include unconventional or non-natural amino acids. In other embodiments the MRD contains a sequence that competitively inhibits the ability of an MRD-containing sequence described herein to bind with a target molecule. The ability of an MRD to competitively inhibit another MRD-containing sequence can be determined using techniques known in the art, including ELISA and BIAcore analysis.

The ability of an MRD to bind its target can be assessed using any technique that assesses molecular interaction. For example, MRD-target interaction can be assayed as described in the Examples below or alternatively, using in vitro or in vivo binding assays such as western blots, radioimmunoassays, ELISA (enzyme linked immunosorbant assay), "sandwich" immunoassays, immunoprecipitation assays, fluorescent immunoassays, protein A immunoassays, and immunohistochemistry (IHC). Assays evaluating the ability of an MRD to functionally affect its target (e.g., assays to measure signaling, proliferation, migration etc.) can also be used to indirectly assess MRD-target interaction.

Once the sequence of the MRD has been elucidated, the peptides may be prepared by any of the methods known in the art. For example, the MRD peptides can be chemically synthesized and operably attached to the antibody or can be synthesized using recombinant technology. For example, MRDs can be synthesized in solution or on a solid support using known techniques. Various automatic synthesizers are commercially available and can be used in accordance with known protocols. See, for example, Tam et al., J. Am. Chem. Soc., 105:6442 (1983); Merrifield, Science 232:341-347 (1986); Barany and Merrifield, The Peptides, Gross and Meienhofer, eds, Academic Press, New York, 1-284; Barany et al., Int. J. Pep. Protein Res., 30:705-739 (1987); and U.S. Pat. No. 5,424,398, which are herein incorporated by reference.

MRDs can be synthesized with covalently attached molecules that are not amino acids but aid in the purification, identification, and/or tracking of an MRD in vitro or in vivo. (e.g., biotin for reacting with avidin or avidin-labeled molecules).

The following MRD targets are described in more detail by way of example only.

In some embodiments described herein, the MRD targets an integrin. The role of integrins such as $\alpha v\beta 3$ and $\alpha v\beta 5$ as tumor-associated markers has been well documented. A recent study of 25 permanent human cell lines established from advanced ovarian cancer demonstrated that all lines were positive for $\alpha v\beta 5$ expression and many were positive for $\alpha v\beta 3$ expression. Studies have also shown that $\alpha v\beta 3$ and $\alpha v\beta 5$ is highly expressed on malignant human cervical tumor tissues. Integrins have also demonstrated therapeutic effects in animal models of Kaposi's sarcoma, melanoma, and breast cancer.

A number of integrin $\alpha v\beta 3$ and $\alpha v\beta 5$ antagonists are in clinical development. These include cyclic RGD peptides and synthetic small molecule RGD mimetics. Two antibody-based integrin antagonists are currently in clinical trials for the treatment of cancer. The first is VITAXIN® (MEDI-522, Abegrein), the humanized form of the murine anti-human $\alpha v\beta 3$ antibody LM609. A dose-escalating phase I study in cancer patients demonstrated that VITAXIN® is safe for use in humans. Another antibody in clinical trials is CNTO95, a fully human Ab that recognizes $\alpha v$ integrins. A Phase I study of CNTO95 in patients with a variety of solid tumors has shown that it is well tolerated. Cilengitide (EMD 121974), a peptide antagonist of $\alpha v\beta 3$ and $\alpha v\beta 5$, has also proven safe in phase I trials. Furthermore, there have been numerous drug targeting and imaging studies based on the use of ligands for these receptors. These preclinical and clinical observations demonstrate the importance of targeting $\alpha v\beta 3$ and $\alpha v\beta 5$ and studies involving the use of antibodies in this strategy have consistently reported that targeting through these integrins is safe.

Clinical trials are also ongoing for antagonists targeting $\alpha 5v\beta 1$ for treating metastatic melanoma, renal cell carcinoma, and non-small cell lung cancer (M200 (volociximab) and malignant glioma (ATN-161).

Integrin-binding MRDs containing one or more RGD tripeptide sequence motifs represent an example of MRDs of the invention. Ligands having the RGD motif as a minimum recognition domain and from which MRDs of the invention can be derived are well known, a partial list of which includes, with the corresponding integrin target in parenthesis, fibronectin ($\alpha 3\beta 1$, $\alpha 5\beta 1$, $\alpha v\beta 1$, $\alpha IIb\beta 3$, $\alpha v\beta 3$, and $\alpha 3\beta 1$) fibrinogen ($\alpha M\beta 2$ and $\alpha IIb\beta 1$) von Willebrand factor ($\alpha IIb\beta 3$ and $\alpha v\beta 3$), and vitronectin ($\alpha IIb\beta 3$, $\alpha v\beta 3$ and $\alpha v\beta 5$).

In one embodiment, the RGD containing targeting MRD is a member selected from the group consisting of: YCRGDCT (SEQ ID NO:3); PCRGDCL (SEQ ID NO:4); TCRGDCY (SEQ ID NO:5); and LCRGDCF (SEQ ID NO:6).

A MRD that mimics a non-RGD-dependent binding site on an integrin receptor and having the target binding specificity of a high affinity ligand that recognizes the selected integrin is also contemplated in the present invention. MRDs that bind to an integrin receptor and disrupt binding and/or signaling activity of the integrin are also contemplated.

In some embodiments, the MRD targets an angiogenic molecule. Angiogenesis is essential to many physiological and pathological processes. Ang2 has been shown to act as a proangiogenic molecule. Administration of Ang2-selective inhibitors is sufficient to suppress both tumor angiogenesis and corneal angiogenesis. Therefore, Ang2 inhibition alone or in combination with inhibition of other angiogenic factors, such as VEGF, can represent an effective antiangiogenic strategy for treating patients with solid tumors.

It is contemplated that MRDs useful in the present invention include those that bind to angiogenic receptors, angiogenic factors, and/or Ang2. In a specific embodiment, an MRD of the invention binds Ang2. In one embodiment, angiogenic cytokine targeting MRD sequences or MRD-containing sequences contain a sequence selected from the group: MGAQTNFMPMDD LEQRLYEQFILQQGLE (SEQ ID NO:7); MGAQTNFMPMDNDELLLYEQ-FILQQGLE (SEQ ID NO:8); MGAQTNFMPMDATET-RLYEQFILQQGLE (SEQ ID NO:9); AQQEECEWDPW TCEHMGSGSATGGSGSTASSGSGSATHQEECEWDP-WTCEHMLE (SEQ ID NO:10) (2×Con4); MGAQTNFMP-MDNDELLNYEQFILQQGLE (SEQ ID NO:11); and PXDNDXL LNY (SEQ ID NO:12) where X is one of the 20 naturally-occurring amino acids.

In another embodiment, the angiogenic cytokine targeting MRD sequences or MRD-containing sequences contain a sequence selected from the group: MGAQTNFMPMDN-DELLLYEQFILQ QGLEGGSGSTASSGSGSSLGAQTNF-MPMDNDELLLY (SEQ ID NO:20); AQQEECEWDPWT-CEHMGSGSATGGSGSTASSGSGSATHQEECEWDPWTC EHMLE (SEQ ID NO:10); AQQEE CEFAPWTCEHM (SEQ ID NO:21) (ConFA); core nEFAPWTn (SEQ ID NO:22) where n is from about 0 to 50 amino acid residues; AQQEECEFAPWTCEH-MGSGSATGGSGSTASSGSGSATHQEECEFAPWTCEH-MLE (SEQ ID NO:23) (2×ConFA); and AQQEECELAP-WTCEHM (SEQ ID NO:24) (ConLA).

In one embodiment, the Ang2 binding MRD contains the sequence AQTNFMPM DQEEALLYEEFI (SEQ ID NO:108). In another embodiment, the Ang2 binding MRD contains the sequence AQTNFMPMDQDEALLYEEFI (SEQ ID NO:109). In a further embodiment, the Ang2 binding MRD contains the sequence AQTNFMPM DQDEALLYEQFI (SEQ ID NO:110). In an additional embodiment, the Ang2 binding MRD contains the sequence AQTNFMPM DQDELLLYEEFI (SEQ ID NO:111).

In another embodiment, the Ang2 binding MRD contains a sequence selected from:

```
                            (SEQ ID NO: 112)
AQTNFMPMDNDEALLYEQFI;

(SEQ ID NO: 113)
AQTNFMPMDNDELTLYEQFIL;

(SEQ ID NO: 114)
AQTNFMPMDNDEGLLYEQFI;

(SEQ ID NO: 115)
AQTNFMPMDNDEALLYEQFI;

(SEQ ID NO: 116)
AQTNFMPMDNDEGLLYEEFI;

(SEQ ID NO: 117)
AQTNFMPMDNDEALLYEEFI;

((SEQ ID NO: 118)
AQTNFMPMDQDELLLYEQFI;

(SEQ ID NO: 119)
AQTNFMPMDDDELLLYEQFIL;

(SEQ ID NO: 120)
AQTNFMPMDQDEALLYEEFIC;
and (SEQ ID NO: 121)
KSLSLSPGGNGTTNFMPMDQDEALLYEEFI.
```

In one embodiment, the Ang2 binding MRD contains an amino acid sequence of the formula: $X_1$AQTNFMPMD$X_{11}X_{12}$E$X_{14}$LLYE$X_{19}$FI (SEQ ID NO:122) and wherein $X_1$ is 1-10 amino acid residues. According to one embodiment, $X_1$ is Q, G, S, T, Y, L, V, P, I, W, F, M, K, R, or H; $X_{12}$ is A, D, E, N, Q, G, S, T, Y, P, W, K, R, or H; $X_{14}$ is A, D, N, G, S, T, Y, V, P, I, W, F, M, K, R, or H, and $X_{19}$ is A, E, D, G, S, T, Y, L, V, P, I, W, F, M, K, R, or H (SEQ ID NO:122). In a further embodiment, $X_{11}$ is Q, G, S, T, Y, L, V, P, I, W, F, M, K, R, or H; $X_{12}$ is D, E, N, Q, G, S, T, Y, V, K, R, or H; $X_{14}$ is A, D, N, G, S, T, Y, V, P, I, W, F, M, K, R, or H, and $X_{19}$ is E, N, D, G, S, T, Y, L, V, P, 1, W, F, M, K, R, or H (SEQ ID NO:123). According to another embodiment, $X_{11}$ is Q, $X_{12}$ is D, E, N, Q, or G; $X_{14}$ is A A, D, N, G, S, T, Y, V, P, I, W, F, M, K, R, or H; and $X_{19}$ is E, N, D, G, S, T, Y, L, V, P, I, W, F, M, K, R, or H (SEQ ID NO:124).

In one embodiment, the Ang2 binding MRD contains a sequence having the formula $X_1X_2X_3X_4X_5X_6$MPMD$X_{11}X_{12}$E$X_{14}X_{15}$LYE$X_{19}X_{20}X_{21}X_{22}$ (SEQ ID NO:125) and wherein:

$X_1$ is 1-10 amino acid residues;
$X_2$ is L, A, V, P, I, W, F, M, S, N, E, G, T, H, Y, or C;
$X_3$ is N, Q, G, S, T, E, D, Y, M, V, L, or I;
$X_4$ is N, Q, G, S, T, Y, F, E, P, A, or H;
$X_5$ is N, Q, G, S, T, Y, E, H, L, A, V, P, I, W, F, or M;
$X_6$ is V, M, A, F, L, P, I, W, or Y;
$X_{11}$ is Q, G, S, T, Y, L, V, P, I, W, F, M, K, R, or H;
$X_{12}$ is D, E, N, Q, G, S, T, Y, P, W, K, R, or H;
$X_{14}$ is A, D, N, G, S, T, Y, V, P, I, W, F, M, K, R, or H;
$X_{15}$ is V, M, A, F, L, P, I, W, Y, D, E, T, H, or Norleucine;
$X_{19}$ is A, E, D, G, S, T, Y, L, V, P, I, W, F, M, K, R, or H;
$X_{20}$ is E, D, V, M, A, F, L, P, I, W, Y, K, R, H, or Norleucine;
$X_{21}$ is V, M, A, F, L, P, I, W, C, Y, or Norleucine; and
$X_{22}$ is 1-10 amino acid residues (SEQ ID NO:125). In additional embodiments the Ang2 binding MRD contains a sequence having the formula and sequences disclosed above, but wherein $X_2$ is any amino acid SEQ ID NO:126). In additional embodiments the Ang2 binding MRD contains a sequence having the formula and sequences disclosed above, but wherein $X_2$ is any amino acid, $X_5$ is Q, E, or N (SEQ ID NO:127). In additional embodiments the Ang2 binding MRD contains a sequence having the formula and sequences disclosed above, but wherein $X_2$ is any amino acid, $X_{11}$ is Q or N, and $X_{12}$ is not L or C (SEQ ID NO:128). In another embodiment, the Ang2 binding MRD contains a sequence having the formula and sequences disclosed above, but wherein $X_2$ is any amino acid, $X_{11}$ is Q, and $X_{12}$ is not L or C, and $X_{12}$ is D, E, S, K, or R (SEQ ID NO:129): In other embodiment, the Ang2 binding MRD contains a sequence having the formula and sequences disclosed above, but wherein $X_2$ is any amino acid, $X_{11}$ is Q, and $X_{12}$ is not L or C, and $X_{12}$ is D, E, S, K, or R (SEQ ID NO:130):

In another embodiment the Ang2 binding MRD contains a sequence having the formula: $X_1X_2X_3X_4X_5X_6$MPMD$X_{11}X_{12}$E$X_{14}X_{15}$LYE$X_{19}X_{20}X_{21}X_{22}$ (SEQ ID NO:131) and wherein:

$X_1$ is 1-10 amino acid residues;
$X_2$ is A, V, I, or C;
$X_3$ is D, N, or Q;
$X_4$ is S, or T;
$X_5$ is Q, E, or N;
$X_6$ is L, A, V, P, I, W, F, or M;
$X_{11}$ is Q, G, S, T, Y, L, V, P, I, W, F, M, K, R, or H;
$X_{12}$ is D, E, S, K, or R;
$X_{14}$ is A, D, G, V, P, I, W, F, M, K, R, or H, and
$X_{15}$ is L, I, or Norleucine;
$X_{19}$ is A, E, D, G, S, T, Y, L, V, P, I, W, F, M, K, R, or H;
$X_{20}$ is L, V, Norleucine, or F;
$X_{21}$ is L, A, V, I, or Norleucine; and
$X_{22}$ is 1-10 amino acid residues (SEQ ID NO:131). In additional embodiments the Ang2 binding MRD contains a sequence having the formula and sequences disclosed above, but wherein $X_{11}$ is Q (SEQ ID NO:132). In additional embodiments the Ang2 binding MRD contains a sequence having the formula and sequences disclosed above, but wherein $X_{11}$ is Q and $X_{12}$ is D (SEQ ID NO:133)

In one embodiment, the Ang2 binding MRD contains a sequence having the formula $X_1$AQTNFMPMDX$_{11}$ $X_{12}$EX$_{14}$LLYEX$_{19}$X$_{20}$FI (SEQ ID NO:134) wherein:
$X_1$ is 1-10 amino acid residues;
$X_{11}$ is Q, G, S, T, Y, L, V, P, I, W, F, M, K, R, or H;
$X_{12}$ is D, E, N, Q, G, S, T, Y, P, W, K, R, or H;
$X_{14}$ is A, D, G, V, P, I, W, F, M, K, R, or H;
$X_{19}$ is A, E, D, G, S, T, Y, L, V, P, I, W, F, M, K, R, or H; and
$X_{20}$ is E, D, V, M, A, F, L, P, I, W, Y, K, R, H, or Norleucine (SEQ ID NO:134). In additional embodiments the Ang2 binding MRD contains a sequence having the formula and sequences disclosed above, but wherein $X_{11}$ is Q (SEQ ID NO:135). In additional embodiments the Ang2 binding MRD contains a sequence having the formula and sequences disclosed above, but wherein $X_{11}$ is Q, and the amino acid at $X_{12}$ is any amino acid other than L or C (SEQ ID NO:136). In additional embodiments the Ang2 binding MRD contains a sequence having the formula and sequences disclosed above, but wherein $X_{11}$ is Q, and $X_{12}$ is D, E, S, K, or R (SEQ ID NO:137). In additional embodiments the Ang2 binding MRD contains a sequence having the formula and sequences disclosed above, but wherein $X_{11}$ is Q and $X_{12}$ is D (SEQ ID NO:138).

In another embodiment, the Ang2 binding MRD contains a sequence having the formula $X_1$ AQTNFMPMDX$_{11}$ $X_{12}$EX$_{14}$LLYE $X_{19}$X$_{20}$FI (SEQ ID NO:139)) wherein:
$X_1$ is 1-10 amino acid residues;
$X_{11}$ is Q, Y, V, P, W, F, K, or R;
$X_{12}$ is D, E, N, Q, or G;
$X_{14}$ is A, D, N, G, S, T, Y, V, P, I, W, F, M, K, R, or H;
$X_{19}$ is A, E, D, G, S, T, Y, L, V, P, I, W, F, M, K, R, or H; and
$X_{20}$ is L, V, Norleucine, or F (SEQ ID NO:139). In additional embodiments the Ang2 binding MRD contains a sequence having the formula and sequences disclosed above, but wherein $X_{11}$ is Q (SEQ ID NO:140). In additional embodiments the Ang2 binding MRD contains a sequence having the formula and sequences disclosed above, but wherein $X_{11}$ is Q and $X_{12}$ is D (SEQ ID NO:141).

In another embodiment, the angiogenic cytokine targeting MRD sequences or MRD-containing sequences contain a sequence selected from the group: XnELAPWTXn where n is from about 0 to 50 amino acid residues and X is any amino acid (SEQ ID NO:25); AQQEECELAPWTCEH-MGSGSATGGSGSTASSGSGSATHQEECELAPWTCEH-MLE (SEQ ID NO:26) (2×ConLA); AQQEECEFSPWTC EHM (SEQ ID NO:27) (ConFS); XnEFSPWTXn where n is from about 0 to 50 amino acid residues and X is any amino acid (SEQ ID NO:28); AQQEECEFSPWTCEH-MGSGSATGGSGSTASSGSGSATHQEECEFSPWTCEH-MLE (SEQ ID NO:29) (2×ConFS); AQQEECELEPWT-CEHM (SEQ ID NO:30) (ConLE); XnELEPWTXn where n is from about 0 to 50 amino acid residues (SEQ ID NO:31) and wherein X is any amino acid; and AQQEECELEPWT-CEHMGSGSATGGSGSTASSGSGSATHQEECELEP-WTCE HMLE (SEQ ID NO:32) (2×ConLE).

It should be understood that such the MRDs of the invention can be present in tandem dimers, trimers or other multimers either homologous or heterologous in nature. For example, one can dimerize identical Con-based sequences such as in 2×ConFA to provide a homologous dimer, or the Con peptides can be mixed such that ConFA is combined with ConLA to create ConFA-LA heterodimer with the sequence:

(SEQ ID NO: 33)
AQQEECEFAPWTCEHMGSGSATGGSGSTASSGSGSATHQEECELAPW

TCEHMLE.

Another heterodimer of the invention is ConFA combined with ConFS to create ConFA-FS with the sequence:

(SEQ ID NO: 34)
AQQEECEFAPWTCEHMGSGSATGGSGSTASSGSGSATHQEECEFSPWT

CEHMLE.

One of skill in the art, given the teachings herein, will appreciate that other such combinations will create functional Ang2 binding MRDs as described herein.

The invention also includes human Ang2 MRDs having a core sequence selected from:
XnEFAPWTXn where n is from about 0 to 50 amino acid residues (SEQ ID NO:22);
XnELAPWTXn where n is from about 0 to 50 amino acid residues (SEQ ID NO:25);
XnEFSPWTXn where n is from about 0 to 50 amino acid residues (SEQ ID NO:28);
XnELEPWTXn where n is from about 0 to 50 amino acid residues (SEQ ID NO:31); and Xn AQQEECEX$_1$X$_2$PWTCEHMXn where n is from about 0 to 50 amino acid residues and X represents any natural amino acid (SEQ ID NO:57).

In some embodiments, the MRD targets vascular endothelial growth factor (VEGF). Phage display selections and structural studies of VEGF neutralizing peptides in complex with VEGF have been reported. These studies have revealed that peptide vl 14 (VEPNCDIHVM WEWECFERL) (SEQ ID NO:13) is VEGF specific, binds VEGF with 0.2 µM affinity, and neutralizes VEGF-induced proliferation of Human Umbilical Vein Endothelial Cells (HUVEC). Since VEGF is a homodimer, the peptide occupies two identical sites at either end of the VEGF homodimer. In a specific embodiment, the antibody-MRD fusion of the invention comprises vl14. In other embodiments, the antibody-MRD fusion comprises variants/derivatives that competitively inhibit the ability of the antibody-vl14 fusion to bind to VEGF. In another embodiment, the antibody-MRD fusion comprises an MRD with the sequence ATWLPPP (SEQ ID NO:71), which inhibits VEGF-mediated angiogenesis. Binetruy-Tournaire, R. et. al., EMBO 19:1525-1533 (2000). In additional embodiments, an anti-VEGF antibody containing an MRD that targets VEGF is contemplated in the present invention. Anti-VEGF antibodies can be found for example in Presta et al., Cancer Research 57:4593-4599 (1997); and Fuh et al., J Biol Chem 281:10 6625 (2006), which are herein incorporated by reference.

Insulin-like growth factor-I receptor-specific MRDs can also be used in the present invention. In one embodiment, the MRD sequence that targets the insulin-like growth factor-I receptor is SFYSCLESLVNGPAEK-SRGQWDGCRKK (SEQ ID NO:14).

In one aspect, the invention includes an IGF1R binding MRD having the sequence: NFYQCIXIX2LX3X4 X5PAEKSRGQWQECRTGG (SEQ ID NO:58), wherein $X_1$ is E or D; $X_2$ is any amino acid; $X_3$ is any amino acid; $X_4$ is any amino acid and $X_5$ is any amino acid.

In another embodiment, the IGF1R binding MRD contains a sequence selected from the group: NFYQCIEM-LASHPAEKSRGQWQECRTGG (SEQ ID NO:35); NFY-QCIEQLALRPA EKSRGQWQECRTGG (SEQ ID NO:36);

NFYQCIDLLMAYPAEKS RGQWQECRTGG (SEQ ID NO:37); NFYQCIERLVTGPAEKSRGQWQECRTGG (SEQ ID NO:38); NFYQCIEYLAMK PAEKSRGQWQECRTGG (SEQ ID NO:39); and NFYQCIEALQSRPAEKSRGQWQECR TGG (SEQ ID NO:40).

In another embodiment, the IGF1R binding MRD contains a sequence selected from the group: NFYQCIEALSRSPAEKSRGQWQECRTGG (SEQ ID NO:41); NFYQCIEHLSGSPAEK SRGQWQECRTG (SEQ ID NO:42); NFYQCIESLAGGPAEKSRGQWQECRTG (SEQ ID NO:43); NFYQCIEALVGVPAEKSRGQWQECRTG (SEQ ID NO:44); and NFYQCIEMLSLP PAEKSRGQWQECRTG (SEQ ID NO:45).

In another embodiment, the IGF1R binding MRD contains a sequence selected from the group: NFYQCIEVFWGRPAEKSRGQWQECRTG (SEQ ID NO:46); NFYQCIE QLSSGPAE KSRGQWQECRTG (SEQ ID NO:47); NFYQCIELLSARPAEKSRGQWAECRAG (SEQ ID NO:48); and NFYQCIEALARTPAEKSRGQWVECRAP (SEQ ID NO:49).

Vascular homing-specific MRDs are also contemplated for use in the present invention. A number of studies have characterized the efficacy of linking the vascular homing peptide to other proteins like IL-12 or drugs to direct their delivery in live animals. One example of an MRD sequence that is a vascular homing peptide that is envisioned to be included within an antibody-MRD fusion of the invention is ACDCRGDCFCG (SEQ ID NO:15).

Numerous other target binding sites are contemplated as being the target of the antibody-MRD fusions of the present invention, including for example, epidermal growth factor receptor (EGFR), CD20, tumor antigens, ErbB2, ErbB3, ErbB4, insulin-like growth factor-I receptor, nerve growth factor (NGR), hepatocyte growth factor receptor, and tumor-associated surface antigen epithelial cell adhesion molecule (Ep-CAM). MRDs can be directed towards these target binding sites or the corresponding ligands.

In one embodiment, the MRD binds to IL6. In one embodiment, the MRD binds to IL6R.

In one embodiment, the MRD binds to HER2/3.

In one embodiment, the MRD sequence that binds to EGFR and that is envisioned to be included within an antibody-MRD fusion is selected from the group: VDNKFNKELEKAYN EIRNLPNLNGWQMTAFIASLVDDPSQSANLLAEAKKLNDAQAPK (SEQ ID NO:16); and VDNKFNKEMWIAWEEIRNLPNLNGWQMTAFIASLVDDPSQSANLLAEAKKLNDAQAPK (SEQ ID NO:17).

In another embodiment, the MRD binds ErbB2 and has the sequence:

(SEQ ID NO: 18)
VDNKFNKEMRNAYWEIALLPNLNNQQKRAFIRSLYDDPSQSANLLAEA

KKLNDAQAPK.

In some embodiments, the MRD binds to a human protein. In some embodiments, the MRD binds to both a human protein and its ortholog in mouse, rat, rabbit, or hamster.

Complexes comprising a modular recognition domain (MRD), such as those described herein are encompassed by the invention, as are complexes containing the MRD and an antibody. According to some embodiments, the MRD is part of a fusion protein, with for example an immunoglobulin heavy chain or an immunoglobulin light chain. According to some embodiments, the antibody and MRD ("the first MRD) bind to the same target. According to other embodiments, the antibody and the MRD bind to different targets. In additional embodiments, the MRD and antibody complex also contains at least a second MRD that is capable of binding to a different epitope or target than the first MRD. Complexes comprising an MRD having or associated with alternative scaffolds (e.g., platforms that confer or can be used in creating multispecific and/or multivalent compositions) are also encompassed by the invention. Such alternative scaffolds, include, but are not limited to, scaffolds based on, VASP polypeptides, Avian pancreatic polypeptides (aPP), tetranectins (based on CTLD3), affitins (based on Sac7d from the hyperthermophilic archaeon), affitins (based on γB-crystallin/ubiquitin), knottins, SH3 domains (e.g., fynomers, see e.g., PCT publications WO 2008/022759 and WO 2011/02368, which are herein incorporated by reference), PDZ domains, tendamistat, transferrin, an ankyrin repeat consensus domains (e.g., DARPins), lipocalin protein folds (e.g., anticalins amd duocalins), fibronectins (e.g., adnectins, see e.g., US Patent Application Publication 2003/0170753 and 20090155275 which are herein incorporated by reference), knottins, Z-domain of protein A (e.g., affibodies), thioredoxin, albumin (e.g., ALBUdAb (Domantis/GSK), Kunitz type domains, ALB-Kunitz sequences (e.g., Dyax)), unstructured repeat sequences of 3 or 6 amino acids (e.g., PASylation® technology and XTEN® technology), centyrin scaffolding, and sequences containing elastin-like repeat domains (see for example, U.S. Patent Application 61/442, 106, which is herein incorporated by reference). Polynucleotides encoding MRDs, vectors comprising these polynucleotides and host cells containing these vectors are also encompassed by the invention, as are pharmaceutical compositions containing these complexes. Methods of making and using these complexes to for example, inhibit cell growth or to inhibit cellular activity, or to treat cancer, diseases or disorder of the immune system (e.g., inflammation and autoimmune disease), infectious disease, or other diseases or disorders described herein or otherwise known in the art are also encompassed by the invention. According to one embodiment, a method for producing an MRD capable of binding a target is produced, wherin the method comprises culturing a host cell containing a vector that encodes the MRD under conditions wherein the nucleotide sequence encoding the MRD is expressed as a protein and recovering said protein.

According to some embodiments, the MRD is contained in a complex with an antibody that binds to a target selected from: VEGF, EGF, IGF-1, FGF1, FGF2, FGF3, FGF4, FGFR1, FGFR2, FGFR3, VEGFR1, EGFR, PDGFR, ErbB2, ErbB3, IGF-IR, cMET, CD19, and CD20. In additional emobidments, the antibody competitively inhibits: (a) binding of trastuzumab to ErbB2; binding of pertuzumab to ErbB2; binding of bevacizumab to VEGF; binding of cetuximab to EGFR; binding of panitumumab to EGFR; binding of zalutumumab to EGFR; binding of nimotuzumab to EGFR; or binding of matuzumab to EGFR; binding of figitumumab to IGF1R; binding of AMG 479 to IGF1R; binding of cixutumumab to IGF1R; binding of dalotuzumab to IGF1; binding of BIIB022 to IGF1; or binding of MEDI-573 to IGF1.

According to additional embodiments, the antibody binds a target selected from: interferon-alpha, interferon alpha receptor, interferon beta, interferon beta receptor, interferon-gamma, S1PR, integrin avb3, IL-1B, IL-2, IL-4, IL-4R, IL-5, IL-5R, IL-6, IL-6R, IL-7, IL-8, IL-9, IL-9R, IL-10R, IL-11, IL-12, IL-13, IL-15, IL-18, IL-21, ICOS, PD1, and LIF. In one embodiment, the antibody in the complex binds TNF. In additional embodiments, the antibody competitively inhibits binding of adalimumab, golumimab, or infliximab to TNF.

In additional embodiments, the complex contains two or more MRDs that bind to a target selected from, for example: ANG2, VEGF, EGF, IGF-1, FGF1, FGF2, FGF3, FGF4, FGFR1, FGFR2, FGFR3, VEGFR1, EGFR, PDGFR, ErbB2, ErbB3, IGF-IR, cMET, CD19, CD20, TNF alpha, IL-6, interferon-alpha, interferon alpha receptor, interferon beta, interferon beta receptor, interferon-gamma, S1PR, integrin avb3, IL-1B, IL-2, IL-4, IL-4R, IL-5, IL-5R, IL-6, IL-6R, IL-7, IL-8, IL-9, IL-9R, IL-10R, IL-11, IL-12, IL-13, IL-23, IL-15, IL-18, IL-21, ICOS, PD1, and LIF.

III. Antibodies

The antibody in the MRD-containing antibodies described herein can be any suitable antigen-binding immunoglobulin. In certain embodiments, the MRD-containing antibody molecules described herein retain the structural and functional properties of traditional monoclonal antibodies. Thus, the antibodies retain their epitope binding properties, but advantageously also incorporate one or more additional target-binding specificities.

Antibodies that can be used in the MRD-containing antibodies include, but are not limited to, monoclonal, multispecific, human, humanized, primatized, and chimeric antibodies. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. In specific embodiments, the antibodies are IgG1. In other specific embodiments, the antibodies are IgG3.

Antibodies that can be used as part of the MRD-containing antibodies can be naturally derived or the result of recombinant engineering (e.g., phage display, xenomouse, and synthetic). The antibodies can include modifications, for example, to enhance half-life or to increase or decrease antibody dependent cellular cytotoxicity (ADCC) and/or complement dependent cytotoxicity (CDC) activity. Antibodies can be from or derived from any animal origin including birds and mammals or generated synthetically. In some embodiments, the antibodies are human, murine, donkey, rabbit, goat, guinea pig, camel, llama, horse, or chicken antibodies. In specific embodiments, the antibodies are human.

In certain embodiments, the heavy chain portions of one polypeptide chain of a multimer are identical to those on a second polypeptide chain of the multimer. In alternative embodiments, the heavy chain portion-containing monomers of the invention are not identical. For example, each monomer may comprise a different target binding site, forming, for example, a bispecific antibody.

Bispecific, bivalent antibodies, and methods of making them, are described, for instance in U.S. Pat. Nos. 5,731, 168; 5,807,706; 5,821,333; and U.S. Appl. Publ. Nos. 2003/020734 and 2002/0155537, which are herein incorporated by reference. Bispecific tetravalent antibodies, and methods of making them are described, for instance, in WO 02/096948 and WO 00/44788, the disclosures of both of which are herein incorporated by reference. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992).

The heavy chain portions of the antibody component of the MRD-antibody fusions for use in the methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge region derived, in part, from an IgG I molecule and, in part, from an IgG4 molecule.

In some embodiments, the antigen binding domains of the antibody component of the MRD-containing antibodies bind to their target with a dissociation constant or Kd of less than $5 \times 10^{-3}$ M, $10^{-3}$ M, $5 \times 10^{-4}$ M, $10^{-4}$ M, $5 \times 10^{-4}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In one embodiment, the antibody component of the MRD-containing antibodies have a dissociation constant or Kd of less than $5 \times 10^{-5}$ M. In another embodiment, antigen binding of the antibody component of the MRD-containing antibodies has a dissociation constant or Kd of less than $5 \times 10^{-8}$ M. In another embodiment, antigen binding of the antibody component of the MRD-containing antibodies has a dissociation constant or Kd of less than less than $5 \times 10^{-9}$ M. In another embodiment, the antibody component of the MRD-containing antibodies have a dissociation constant or Kd of less than $5 \times 10^{-10}$ M In another embodiment, the antibody component of the MRD-containing antibodies have a dissociation constant or Kd of less than $5 \times 10^{-11}$ M. In another embodiment, the antibody component of the MRD-containing antibodies have a dissociation constant or Kd of less than $5 \times 10^{-12}$ M.

In specific embodiments, the antibody component of the MRD-containing antibody binds its target with an off rate ($k_{off}$) of less than $5 \times 10^{-2}$ sec$^{-1}$, $10^{-2}$ sec$^{-1}$, $5 \times 10^{-3}$ sec$^{-1}$, or le sec$^{-1}$. More preferably, the antibody component of the MRD-containing antibody binds its target with an off rate ($k_{off}$) of less than $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$, or $10^{-7}$ sec$^{-1}$.

In other specific embodiments, the antibody component of the MRD-containing antibody binds its target with an on rate ($k_{on}$) of greater than $10^3$ M$^{-1}$sec$^{-1}$, $5 \times 10^3$ M$^{-1}$sec$^{-1}$, $10^4$ M$^{-1}$sec$^{-1}$, or $5 \times 10^4$ M$^{-1}$sec$^{-1}$. More preferably, the antibody component of the MRD-containing antibody binds its target with an on rate ($k_{on}$) of greater than $10^5$ M$^{-1}$ sec$^{-1}$, $5 \times 10^5$ M$^{-1}$sec$^{-1}$, $10^6$ M$^{-1}$sec$^{-1}$, or $5 \times 10^6$ M$^{-1}$sec$^{-1}$, or $10^{-7}$ M$^{-1}$sec$^{-1}$.

Affinity maturation strategies and chain shuffling strategies (see, e.g., Marks et al., Bio/Technology 10:779-783 (1992), which is herein incorporated by reference) are known in the art and can be employed to generate high affinity antibodies that can be used in the MRD-containing antibodies described herein.

Advantageously, the antibodies of the MRD-containing antibodies can also include variants and derivatives that improve antibody function and/or desirable pharmacodynamic properties.

Accordingly, certain embodiments of the invention include an antibody-MRD fusion, in which at least a fraction of one or more of the constant region domains has been altered so as to provide desired biochemical characteristics such as reduced or increased effector functions, the ability to non-covalently dimerize, increased ability to localize at the site of a tumor, reduced serum half-life, or increased serum half-life when compared with an unaltered antibody of approximately the same immunoreactivity. The alterations of the constant region domains can be amino acid substitutions, insertions, or deletions.

In some embodiments, a complex of the invention comprises an antibody and at least one MRD, wherein the antibody has an altered effector function. The complex can comprise MRDs that bind to at least 3 different targets. The complex can be a complex wherein the effector function of the antibody has been modified to: increased ADCC, decreased ADCC, increased CDC, decreased CDC, increased half-life, or decreased half-life. In some embodiments, a method for producing the complex comprises culturing a host cell transformed with polynucleotides encoding antibodies and MRDs of the complex under conditions wherein the nucleotide sequence encoding the MRDs and the antibody heavy and light chains are expressed as two or more proteins, and recovering the proteins. In some embodiments, a method of treating or preventing a disease or disorder in a subject in need thereof comprises administering a therapeutically acceptable amount of the complex to the subject.

In certain embodiments, the antibody component of the antibody-MRD fusion has been modified to increase antibody dependent cellular cytotoxicity (ADCC) (see, e.g., Bruhns et al., Blood 113:3716-3725 (2009); Shields et al., J. Biol. Chem. 276:6591-6604 (2001); Lazar et al., Proc. Natl. Acad. Sci USA 103:4005-4010 (2006); Stavenhagen et al., Cancer Res., 67:8882-8890 (2007); Horton et al., Cancer Res. 68:8049-8057 (2008); Zalevsky et al., Blood 113:3735-3743 (2009); Bruckheimer et al., Neoplasia 11:509-517 (2009); Allan et al., WO 2006/020114; Strohl, Curr. Op. Biotechnol. 20:685-691 (2009); and Watkins et al., WO 2004/074455, each of which is herein incorporated by reference). Examples of Fc sequence engineering modifications contained in the antibody component of the antibody-MRD fusions that increases ADCC include one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index as in Kabat.

In certain embodiments, the antibody component of the antibody-MRD fusion has been modified to decrease ADCC (see, e.g., Idusogie et al., J. Immunol. 166:2571-2575 (2001); Sazinsky et al., Proc. Natl. Acad. Sci USA 105: 20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-26 (2000); Cole et al., Transplantation 68:563-571 (1999); Hutchins et al., Proc. Natl. Acad. Sci USA 92:11980-11984 (1995); Reddy et al., J. Immunol. 164:1925-1933 (2000); Mueller et al., WO 1997/11971; Bell et al., WO 2007/106585; Strohl, US 2007/0148167A1; McEarchern et al., Blood 109:1185-1192 (2007); Strohl, Curr. Op. Biotechnol. 20:685-691 (2009); and Kumagai et al., J. Clin. Pharmacol. 47:1489-1497 (2007), each of which is herein incorporated by reference). Examples of Fc sequence engineering modifications contained in the antibody component of the antibody-MRD fusions that decreases ADCC include one or more modifications corresponding to: IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S.

In certain embodiments, the antibody component of the antibody-MRD fusion has been modified to increase antibody-dependent cell phagocytosis (ADCP); (see, e.g., Shields et al., J. Biol. Chem. 276:6591-6604 (2001); Lazar et al., Proc. Natl. Acad. Sci USA 103:4005-4010 (2006); Stavenhagen et al., Cancer Res., 67:8882-8890 (2007); Richards et al., Mol. Cancer Ther. 7:2517-2527 (2008); Horton et al., Cancer Res. 68:8049-8057 (2008), Zalevsky et al., Blood 113:3735-3743 (2009); Bruckheimer et al., Neoplasia 11:509-517 (2009); Allan et al., WO 2006/020114; Strohl, Curr. Op. Biotechnol. 20:685-691 (2009); and Watkins et al., WO 2004/074455, each of which is herein incorporated by reference). Examples of Fc sequence engineering modifications contained in the antibody component of the antibody-MRD fusions that increases ADCP include one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; IgG1-F243L, R292P, Y300L, V305I, P396L; IgG1-G236A, S239D, I332E.

In certain embodiments, the antibody component of the antibody-MRD fusion has been modified to decrease ADCP (see, e.g., Sazinsky et al., Proc. Natl. Acad. Sci USA 105:20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-20 (2000); Cole et al., Transplantation 68:563-571 (1999); Hutchins et al., Proc. Natl. Acad. Sci USA 92:11980-11984 (1995); Reddy et al., J. Immunol. 164:1925-1933 (2000); Mueller et al., WO 1997/11971; Bell et al., WO 2007/106585; Strohl et al., US 2007/0148167A1; McEarchern et al., Blood 109:1185-1192 (2007); Strohl, Curr. Op. Biotechnol. 20:685-691 (2009); and Kumagai et al., J. Clin. Pharmacol. 47:1489-1497 (2007), each of which is herein incorporated by reference). Examples of Fc sequence engineering modifications contained in the antibody component of the antibody-MRD fusions that decreases ADCP include one or more modifications corresponding to: IgG1-N297A; IgG1-L234A, L235A; IgG2-V234A, G237A; IgG4-L235A, G237A, E318A; IgG4-S228P, L236E; IgG2 EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S.

In certain embodiments, the antibody component of the antibody-MRD fusions have been modified to increase complement-dependent cytotoxicity (CDC) (see, e.g., (see, e.g., Idusogie et al., J. Immunol. 166:2571-2575 (2001); Strohl, Curr. Op. Biotechnol. 20:685-691 (2009); and Natsume et al., Cancer Res. 68:3863-3872 (2008), each of which is herein incorporated by reference). Examples of Fc sequence engineering modifications contained in the antibody component of the antibody-MRD fusions that increases CDC include one or more modifications corresponding to: IgG1-K326A, E333A; IgG1-K326W, E333S, IgG2-E333S; and IgG1/IgG3 fusion versions '1133' and '113F'.

In certain embodiments, the antibody component of the antibody-MRD fusions have been modified to increase inhibitory binding to FcgammaRIIb receptor (see, e.g., Chu et al., Mol. Immunol. 45:3926-3933 (2008)). An example of Fc sequence engineering modifications contained in the antibody component of the antibody-MRD fusions that increases binding to inhibitory FcgammaRIIb receptor is IgG1-S267E, L328F.

In certain embodiments, the antibody component of the antibody-MRD fusions have been modified to decrease CDC (see, e.g., Mueller et al., WO 1997/11971; Bell et al., WO 2007/106585; Strohl et al., US 2007/0148167A1; McEarchern et al., Blood 109:1185-1192 (2007); Hayden-Ledbetter et al., Clin. Cancer 15:2739-2746 (2009); Lazar et al., Proc. Natl. Acad. Sci USA 103:4005-4010 (2006); Bruckheimer et al., Neoplasia 11:509-517 (2009); Strohl, Curr. Op. Biotechnol. 20:685-691 (2009); and Sazinsky et al., Proc. Natl. Acad. Sci USA 105:20167-20172 (2008); each of which is herein incorporated by reference). Examples of Fc sequence engineering modifications contained in the antibody component of the antibody-MRD fusions that decreases CDC include one or more modifications corresponding to: IgG1-S239D, A330L, 1332E; IgG2 EU sequence 118-260; IgG4-EU sequence 261-447; IgG2-H268Q, V309L, A330S, A331S; IgG1-C226S, C229S, E233P, L234V, L235A; IgG1-L234F, L235E, P331S; and IgG1-C226S, P230S.

The half-life on an IgG is mediated by its pH-dependent binding to the neonatal receptor FcRn. In certain embodiments the antibody component of the antibody-MRD fusion has been modified to enhance binding to FcRn (see, e.g., Petkova et al., Int. Immunol. 18:1759-1769 (2006); Dall'Acqua et al., J. Immunol. 169:5171-5180 (2002); Oganesyan et al., Mol. Immunol. 46:1750-1755 (2009); Dall'Acqua et al., J. Biol. Chem. 281:23514-23524 (2006), Hinton et al., J. Immunol. 176:346-356 (2006); Datta-Mannan et al., Drug Metab. Dispos. 35:86-94 (2007); Datta-Mannan et al., J. Biol. Chem. 282:1709-1717 (2007); Ward WO 2006/130834; Strohl, Curr. Op. Biotechnol. 20:685-691 (2009); and Yeung et al., J. Immunol. 182:7663-7671 (2009) each of which is herein incorporated by reference).

In additional embodiments, the antibody of the antibody-MRD fusion has been modified to selectively bind FcRn at pH 6.0, but not pH 7.4. Examples of Fc sequence engineering modifications contained in the antibody component of the antibody-MRD fusions that increases half-life include one or more modifications corresponding to: IgG1-M252Y, S254T, T256E; IgG1-T250Q, M428L; IgG1-H433K, N434Y; IgG1-N434A; and IgG1-T307A, E380A, N434A.

In other embodiments the antibody component of the antibody-MRD fusion has been modified to decrease binding to FcRn (see, e.g., Petkova et al., Int. Immunol. 18:1759-1769 (2006); Datta-Mannan et al., Drug Metab. Dispos. 35:86-94 (2007); Dana-Mannan et al., J. Biol. Chem. 282:1709-1717 (2007); Strohl, Curr. Op. Biotechnol. 20:685-691 (2009); and Vaccaro et al., Nat. Biotechnol. 23:1283-1288 (2005), each of which is herein incorporated by reference). Examples of Fc sequence engineering modifications contained in the antibody component of the antibody-MRD fusions that decrease half-life include one or more modifications corresponding to: IgG1-M252Y, S254T, T256E; H433K, N434F, 436H; IgG1-1253A; and IgG1-P2571, N434H or D376V, N434H.

In certain embodiments, the antibody-MRD fusions have been glyocoengineered or the Fc portion of the MRD-containing antibody has been mutated to increase effector function using techniques known in the art.

For example, the inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well know immunological techniques without undue experimentation.

MRD-containing antibodies used according to the methods of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, or derivatization by known protecting/blocking groups. Any of numerous chemical modifications may be carried out by known techniques, including, but not limited to acetylation, formylation, etc. Additionally, the derivative may contain one or more non-classical amino acids.

In certain embodiments, the MRD-containing antibodies have been modified so as to not elicit a deleterious immune response in the animal to be treated, e.g., in a human. In one embodiment, the antibody is modified to reduce immunogenicity using art-recognized techniques. For example, antibody components of the MRD-containing antibodies can be humanized, primatized, deimmunized, or chimerized. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into human frameworks and constant regions with or without retention of critical framework residues; or (c) transplanting the entire non-human variable domains, but "cloaking" them with human-like sections by replacement of surface residues. Such methods are disclosed in Morrison et al., Proc. Natl. Acad. Sci. 81:6851-6855 (1984); Morrison et al., Adv. Immunol. 44:65-92 (1988); Verhoeyen et al., Science 239:1534-1536 (1988); Padlan, Molec. Immun. 28:489-498 (1991); Padlan, Molec. Immun. 31:169-217 (1994), and U.S. Pat. Nos. 5,585,089, 5,693,761, 5,693,762, and 6,190,370, all of which are herein incorporated by reference.

De-immunization can also be used to decrease the immunogenicity of an MRD-containing antibody. As used herein, the term "de-immunization" includes alteration of an MRD-containing antibody to modify T cell epitopes (see, e.g., WO9852976A1, and WO0034317A2, which are herein incorporated by reference). For example, VH and VL sequences from the starting antibody are analyzed and a human T cell epitope "map" is generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of antibodies for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Many different antibody components of the MRD-containing antibodies can be used in the methods described herein. It is contemplated that catalytic and non-catalytic antibodies can be used in the present invention. For example, Antibody 38C2 is an antibody-secreting hybridoma and has been previously described in WO 97/21803. 38C2 contains an antibody combining site that catalyzes the aldol addition reaction between an aliphatic donor and an aldehyde acceptor. In a syngeneic mouse model of neuroblastoma, systemic administration of an etoposide prodrug and intra-tumor injection of Ab 38C2 inhibited tumor growth.

The antibody target of the MRD-containing antibody (i.e., the target of the antigenic binding domain) can be any molecule that it is desirable for a MRD-antibody fusion to interact with. For example, the antibody target can be a soluble factor or the antibody target can be a transmembrane protein, such as a cell surface receptor. The antibody target can also be an extracellular component or an intracellular component. In certain nonexclusive embodiments, the antibody target is a factor that regulates cell proliferation, differentiation, or survival. In another nonexclusive embodiment, the antibody target is a cytokine. In another nonexclusive embodiment, the antibody target is a factor that regulates angiogenesis. In another nonexclusive embodiment, the antibody target is a factor that regulates one or more immune responses, such as, autoimmunity, inflammation and immune responses against cancer cells. In another nonexclusive embodiment, the antibody target is a factor that regulates cellular adhesion and/or cell-cell interaction. In certain nonexclusive embodiments, the antibody target is a cell signaling molecule. The ability of an antibody to bind to a target and to block, increase, or interfere with the biological activity of the antibody target can be determined using or routinely modifying assays, bioassays, and/or animal models known in the art for evaluating such activity.

In some embodiments the antibody target of the MRD-containing antibody is a disease-related antigen. The antigen can be an antigen characteristic of a particular cancer, and/or of a particular cell type (e.g., a hyperproliferative cell), and/or of a particular pathogen (e.g., a bacterial cell (e.g., tuberculosis, smallpox, anthrax), a virus (e.g., HIV), a parasite (e.g., malaria, leichmaniasis), a fungal infection, a mold, a mycoplasm, a prion antigen, or an antigen associated with a disorder of the immune system.

In some embodiments, the antibody target of the MRD-containing antibody is a target that has been validated in an animal model or clinical setting.

In other embodiments, the antibody target of the MRD-containing antibody is a cancer antigen.

In one embodiment, the antibody target of the MRD-containing antibody is: PDGFRa, PDGFRb, PDGF-A, PDGF-B, PDGF-CC, PDGF-C, PDGF-D, VEGFR1, VEGFR2, VEGFR3, VEGFC, VEGFD, neuropilin 2 (NRP2), betacellulin, PIGF, RET (rearranged during transfection), TIE1, TIE2 (TEK), CA125, CD3, CD4, CD7, CD10, CD13, CD25, CD32, CD32b, CD44, CD49e (integrin alpha 5), CD55, CD64, CD90 (THY1), CD133 (prominin 1), CD147, CD166, CD200, ALDH1, ESA, SHH, DHH, IHH, patched1 (PTCH1), smoothened (SMO), WNT1, WNT2B, WNT3A, WNT4, WNT4A, WNT5A, WNT5B, WNT7B, WNT8A, WNT10A, WNT10B, WNT16B, LRPS, LRP6, FZD1, FZD2, FZD4, FZD5, FZD6, FZD7, FZD8, Notch, Notch1, Notch3, Notch4, DLL4, Jagged, Jagged1, Jagged2, Jagged3, TNFSF1 (TNFb, LTa), TNFRSF1A (TNFR1, p55, p60), TNFRSF1B (TNFR2), TNFSF6 (Fas Ligand), TNFRSF6 (Fas, CD95), TNFRSF6B (DcR3), TNFSF7 (CD27 Ligand, CD70), TNFRSF7 (CD27), TNFSF8 (CD30 Ligand), TNFRSF8 (CD30), TNFSF11 (RANKL), TNFRSF11A (RANK), TNFSF12 (TWEAK), TNFRSF12 (TWEAKR), TNFSF13 (APRIL), TNFSF13B (BLYS), TNFRSF13B (TACI), TNFRSF13C (BAFFR), TNFSF15 (TL1A), TNFRSF17 (BCMA), TNFRSF19L (RELT), TNFRSF19 (TROY), TNFRSF21 (DR6), TNFRSF25 (DR3), ANG1 (ANGPT1), ANG3 (ANGPTL1), ANG4 (ANGPT4), IL1 alpha, IL1 beta, IL1R1, IL1R2, IL2, IL2R, IL5, IL5R, IL6, IL6R, IL8, IL8R, IL10, IL10R, IL12, IL12R, IL13, IL13R, IL15, IL15R, IL18, IL18R, IL19, IL19R, IL21R, IL23, IL23R, mif, XAG1, XAG3, REGIV, FGF1, FGF2, FGF3, FGF4, FGFR1, FGFR2, FGFR3, ALK, ALK1, ALK7, ALCAM, Artemin, Axl, TGFb, TGFb2, TGFb3, TGFBR1, IGFIIR, BMP2, BMPS, BMP6, BMPRI, GDF3, GDF8, GDF9, N-cadherin, E-cadherin, VE-cadherin, NCAM, L1CAM (CD171), ganglioside GM2, ganglioside GD2, calcitonin, PSGR, DCC, CDCP1, CXCR2, CXCR7, CCR3, CCR5, CCR7, CCR10, CXCL1, CXCL5, CXCL6, CXCL8, CXCL12, CCL3, CCL4, CCL5, CCL11, Claudin1, Claudin2, Claudin3, Claudin4, TMEFF2, neuregulin, MCSF, CSF, CSFR (fms), GCSF, GCSFR, BCAM, HPV, hCG, SR1F, PSA, FOLR2 (folate receptor beta), BRCA1, BRCA2, HLA-DR, ABCC3, ABCBS, HM1.24, LFA1, LYNX, S100A8, S100A9, SCF, Von Willebrand factor, Lewis Y6 receptor, Lewis Y, CA G250 (CA9), integrin avb3 (CNTO95), integrin avb5, activin B1 alpha, leukotriene B4 receptor (LTB4R), neurotensin NT receptor (NTR), 5T4 oncofetal antigen, Tenascin C, MMP, MMP2, MMP7, MMP9, MMP12, MMP14, MMP26, cathepsin G, cathepsin H, cathepsin L, SULF1, SULF2, MET, UPA, MHC1, MN (CA9), TAG-72, TM4SF1, Heparanse (HPSE), syndecan (SDC1), Ephrin B2, Ephrin B4, or relaxin2. An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention. The above antibody and MRD targets and those otherwise described herein are intended to be illustrative and not limiting.

In another embodiment, the antibody target of the MRD-containing antibody is CD19, CD22, CD30, CD33, CD38, CD44v6, TNFSF5 (CD40 Ligand), TNFRSF5 (CD40), CD52, CD54 (ICAM), CD74, CD80, CD200, EPCAM (EGP2), neuropilin 1 (NRP1), TEM1, mesothelin, TGFbeta 1, TGFBRII, phosphatidlyserine, folate receptor alpha (FOLR1), TNFRSFIOA (TRAIL R1 DR4), TNFRSF10B (TRAIL R2 DR5), CXCR4, CCR4, CCL2, HGF, CRYPTO, VLA5, TNFSF9 (41BB Ligand), TNFRSF9 (41BB, CD137), CTLA4, HLA-DR, IL6, TNFSF4 (OX40 Ligand), TNFRSF4 (OX40), MUC1, MUC18, mucin CanAg, ganglioside GD3, EGFL7, PDGFRa, IL21, IGF1, IGF2, CD117 (cKit), PSMA, SLAMF7, carcinoembryonic antigen (CEA), FAP, integrin avb3, or integrin α5β3. An MRD that binds to one of the above targets are encompassed by the invention. Additionally, MRD-containing antibodies having 1, 2, 3, 4, 5, 6, or more MRDs that bind to 1, 2, 3, 4, 5, 6, or more of the above targets are also encompassed by the invention.

In particular embodiments, the antibody of the MRD-containing antibody competes for target binding with an antibody selected from: siplizumab CD2 (e.g., MEDI-507, MedImmune), blinatumomab CD19 CD3 (e.g., MT103, Micromet/MedImmune); XMAB®5574 CD19 (Xencor), SGN-19A CD19 (Seattle Genetics), ASG-5ME (Agenesys and Seattle Genetics), MEDI-551 CD19 (MedImmune), epratuzumab CD22 (e.g., hLL2, Immunomedics/UCB), inotuzumab ozogamicin CD22 (Pfizer), iratumumab CD30 (e.g., SGN-30 (Seattle Genetics) and MDX-060 (Medarex)), XMAB®2513 CD30 (Xencor), brentuximab vedotin CD30 (e.g., SGN-35, Seattle Genetics), gemtuzumab ozogamicin CD33 (e.g., MYLOTARG®, Pfizer), lintuzumab CD33 (e.g., antibody of Seattle Genetics), MOR202, CD38 (MorphoSys), daratumumab CD38 (e.g., Genmab antibody), CP870893 CD40 (Pfizer), dacetuzumab CD40 (e.g., SGN40, Seattle Genetics), ANTOVA® CD40 (Biogen Idec), lucatumumab CD40 (e.g., HCD122, Novartis) XMAB®5485 CD40 (Xencor), teneliximub, ruplizumab CD40L (e.g., ANTOVA®) bivatuzumab mertansine CD44v6, alemtuzumab CD52 (e.g., CAMPATH®/MABCAMPATH®, Genzyme/Bayer), BI505 ICAM1 (Bioinvent), milatuzumab CD74 (e.g., antibody of Immunomedics), galiximab CD80 (Biogen Idec), BMS663513 4-1BB (Bristol-Myers Squibb), Alexion CD200 antibody (Alexion), edrecolomab EPCAM (e.g., MAb17-1A, PANOREX® (GlaxoSmithKline), AT003 EPCAM (Affitech)), adecatumumab EPCAM (e.g., MT201, Micromet), oportuzumab monatox EPCAM, Genentech anti-NRP1 antibody, MORAB004 TEM1 (Morphotek), MORAB009 mesothelin (Morphotek), lerdelimumab TGFb1 (e.g., CAT-152, Cambridge Antibody Technology), metelimumab TGFb1 (e.g., CAT-192, Cambridge Antibody Technology), ImClone anti-TGFBRII antibody, bavituximab phosphatidylserine (e.g., antibody of Peregrine (Peregrine Pharmaceuticals)), AT004 phosphatidylserine (Affitech), AT005 phosphatidylserine (Affitech), MORAB03 folate receptor alpha (Morphotek), farletuzumab folate receptor alpha cancer (e.g., MORAB003, Morphotek), CS1008 DR4 (Sankyo), mapatumumab DR4 (e.g., HGS-ETR1, Human Genome Sciences), LBY135 DR5 (Novartis), AMG66 DR5 (Amgen), Apomab DR5 (Genentech), PRO95780 (Genentech), lexatumumab DR5, (e.g., HGS-ETR2, Human Genome Sciences), conatumumab DR5, (e.g., AMG655, Amgen), tigatuzumab (e.g., CS-1008), AT009 CXCR4 (Affitech), AT008 CCR4 (Affitech), CNTO-888 CCL2 (Centocor), AMG102 HGF (Amgen), CRYPTO antibody (Biogen Idec), M200 antibody VLA5 (Biogen Idec), ipilimumab CTLA4 (e.g., MDX010, Bristol-Myers Squibb/Medarex), belatacept CTLA4 ECD (e.g., CP-675,206, Pfizer), IMMU114 HLA-DR (Immunomedics), apolizumab HLA-DR, toclizumab IL-6R (e.g., ACTEMRA®/ROACTEMRA®, Hoffmann-La Roche), OX86 OX40, pemtumomab PEM/MUC1 (Theragyn), ABX-MA1 MUC-18 (Abgenix), clivatuzumab MUC-18 (e.g., hPAM4, Immunomedics), cantuzumab mertansine mucin CanAg, ecromeximab (Ludwig Institute), Genentech anti-EGFL7 antibody, AMG820 CSFR (Amgen), olaratumab PDGFRa (e.g., antibody of Imclone (Imclone)), IL21 antibody Zymogenetics (Zymogenetics), MEDI-573 IGF1/IGF2 (MedImmune), AMG191 cKit (Amgen), etaracizumab (e.g., MEDI-522, MedImune), and MLN591 PSMA (Millennium Pharmaceuticals), elotuzumab SLAMF7 (e.g., HuLuc63, PDL), labetuzumab CEA (CEA-CIDE®, Immunomedics), sibrotuzumab FAP, CNTO95 integrin avb3 (Centocor), VITAXIN® integrin avb3 (MedImmune), and voloximab α5β1 MRDs that compete for target binding with one of the above antibodies are encompassed by the invention. Additionally, MRD-containing antibodies having 1, 2, 3, 4, 5, 6, or more MRDs that compete for target binding with 1, 2, 3, 4, 5, 6, or more of the above antibodies are also encompassed by the invention.

In particular embodiments, the antibody of the MRD-containing antibody is an antibody selected from: siplizumab CD2 (e.g., MEDI-507, MedImmune), blinatumomab CD19 CD3 (e.g., MT103, Micromet/MedImmune); XMAB®5574 CD19, (Xencor), SGN-19A CD19 (Seattle Genetics), ASG-5ME (Agenesys and Seattle Genetics), MEDI-551 CD19 (MedImmune), epratuzumab CD22 (e.g., hLL2, Immunomedics/UCB), inotuzumab ozogamicin CD22, iratumumab CD30 (e.g., SGN-30 (Seattle Genetics) and MDX-060 (Medarex)), XMAB®2513 CD30 (Xencor), brentuximab vedotin CD30 (e.g., SGN-35, Seattle Genetics), gemtuzumab ozogamicin CD33 (e.g., MYLOTARG®, Pfizer), lintuzumab CD33 (e.g., antibody of Seattle Genetics), MOR202 CD38 (MorphoSysdaratumumab CD38 (e.g., Genmab antibody), CP870893 CD40 (Pfizer), dacetuzumab CD40 (e.g., SGN40, Seattle Genetics), ANTOVA® CD40 (Biogen Idec), lucatumumab CD40 (e.g., HCD122, Novartis) XMAB®5485 CD40 (Xencor), teneliximub, ruplizumab CD40L (e.g., ANTOVA®), bivatuzumab mertansine CD44v6, alemtuzumab CD52 (e.g., CAMPATH®/MAB-CAMPATH®, Genzyme/Bayer), BI505 ICAM1 (Bioinvent), milatuzumab CD74 (e.g., antibody of Immunomedics), galiximab CD80 (Biogen Idec), BMS663513 4-1BB (Bristol-Myers Squibb), Alexion CD200 antibody (Alexion), edrecolomab EPCAM (e.g., MAb17-1A, PANOREX® (GlaxoSmithKline), AT003 EPCAM (Affitech)), adecatumumab EPCAM (e.g., MT201, Micromet), oportuzumab monatox EPCAM, Genentech anti-NRP1 antibody, MORAB004 TEM1 (Morphotek), MORAB009 mesothelin (Morphotek), lerdelimumab TGFb1 (e.g., CAT-152, Cambridge Antibody Technology), metelimumab TGFb1 (e.g., CAT-192, Cambridge Antibody Technology), ImClone anti-TGFBRII antibody, bavituximab phosphatidylserine (e.g., antibody of Peregrine (Peregrine Pharmaceuticals)), AT004 phosphatidylserine (Affitech), AT005 phosphatidylserine (Affitech), MORAB03 folate receptor alpha (Morphotek), farletuzumab folate receptor alpha cancer (e.g., MORAB003, Morphotek), CS1008 DR4 (Sankyo), mapatumumab DR4 (e.g., HGS-ETR1, Human Genome Sciences), LBY135 DR5 (Novartis), AMG66 DR5 (Amgen), Apomab DR5 (Genentech), PRO95780 (Genentech), lexatumumab DR5 (e.g., HGS-ETR2, Human Genome Sciences), conatumumab DR5 (e.g., AMG655, Amgen), tigatuzumab (e.g., CS-1008), AT009 CXCR4 (Affitech), AT008 CCR4 (Affitech), CNTO-888 CCL2 (Centocor), AMG102 HGF (Amgen), CRYPTO antibody (Biogen Idec), M200 antibody VLA5 (Biogen Idec), ipilimumab CTLA4 (e.g., MDX010, Bristol-Myers Squibb/Medarex), belatacept CTLA4 ECD (e.g., CP-675,206, Pfizer), IMMU114 HLA-DR (Immunomedics), apolizumab HLA-DR, toclizumab IL-6R (e.g., ACTEMRA®/ROACTEMRA®, Hoffmann-La Roche) OX86 OX40, pemtumomab PEM/MUC1 (Theragyn), ABX-MA1 MUC-18 (Abgenix), cantuzumab mertansine mucin CanAg, ecromeximab (Ludwig Institute), Genentech anti-EGFL7 antibody, AMG820 CSFR (Amgen), olaratumab PDGFRa (e.g., antibody of Imclone (Imclone)), IL21 antibody Zymogenetics (Zymogenetics), MEDI-573 IGF1/IGF2 (MedImmune), AMG191 cKit (Amgen), etaracizumab (e.g., MEDI-522, MedImmuune), MLN591 PSMA (Millennium Pharmaceuticals), elotuzumab SLAMF7 (e.g., HuLuc63, PDL), labetuzumab CEA (CEA-CIDE®, Immunomedics), sibrotuzumab FAP, CNTO95 integrin avb3 (Centocor), VITAXIN® integrin avb3 (MedImmune), and voloximab α5β1 (e.g., M200, PDL and Biogen Idec) (antibody targets are italicized).

In an additional embodiment, the antibody target of the MRD-containing antibody is ALK1. In one embodiment, the antibody is PF-3,446,962 (Pfizer). In another embodiment, the antibody binds to the same epitope as PF-3,446,962. In a further embodiment, the antibody competitively inhibits binding of PF-3,446,962 to ALK1. Additionally, MRD-containing antibodies having 1, 2, 3, 4, 5, 6, or more MRDs that compete for ALK1 binding with PF-3,446,962 are also encompassed by the invention.

In an additional embodiment, the antibody target of the MRD-containing antibody is CD22. In one embodiment, the antibody is inotuzumab (e.g., inotuzumab ozogamicin CMC-544, PF-5,208,773; Pfizer). In one embodiment, the antibody binds to the same epitope as inotuzumab. In another embodiment, the antibody competitively inhibits binding of inotuzumab to CD22. Additionally, MRD-containing antibodies having 1, 2, 3, 4, 5, 6, or more MRDs that compete for CD22 binding with inotuzumab are also encompassed by the invention.

In an additional embodiment, the antibody target of the MRD-containing antibody is CRYPTO. In one embodiment, the antibody is the Biogen CRYPTO antibody that has advanced to phase I clinical trials (Biogen Idec). In another embodiment, the antibody binds to the same epitope as the Biogen CRYPTO antibody. In a further embodiment, the antibody competitively inhibits binding of the Biogen CRYPTO antibody to CRYPTO. Additionally, MRD-containing antibodies having 1, 2, 3, 4, 5, 6, or more MRDs that compete for CRYPTO binding with the Biogen CRYPTO antibody are also encompassed by the invention.

In an additional embodiment, the antibody target of the MRD-containing antibody is CD40L. In one embodiment, the antibody is the Biogen CD40L antibody that has advanced to phase I clinical trials (Biogen Idec). In another embodiment, the antibody binds to the same epitope as the Biogen CD40L antibody. In a further embodiment, the antibody competitively inhibits binding of the Biogen CD40L antibody to CD40L. Additionally, MRD-containing antibodies having 1, 2, 3, 4, 5, 6, or more MRDs that compete for CD40L binding with the Biogen CD40L antibody are also encompassed by the invention.

In an additional embodiment, the antibody target of the MRD-containing antibody is CD80. In one embodiment, the antibody is galiximab (Biogen Idec). In another embodiment, the antibody binds to the same epitope as galiximab. In a further embodiment, the antibody competitively inhibits binding of galiximab to CD80. Additionally, MRD-containing antibodies having 1, 2, 3, 4, 5, 6, or more MRDs that compete for CD80 binding with galiximab are also encompassed by the invention.

In an additional embodiment, the antibody target of the MRD-containing antibody is MCSF. In one embodiment, the antibody is PD-360,324 (Pfizer). In another embodiment, the antibody binds to the same epitope as PD-360,324. In a further embodiment, the antibody competitively inhibits binding of PD-360,324 to MCSF. Additionally, MRD-containing antibodies having 1, 2, 3, 4, 5, 6, or more MRDs that compete for MCSF binding with PD-360,324 are also encompassed by the invention.

In an additional embodiment, the antibody target of the MRD-containing antibody is CD44. In one embodiment, the antibody is PF-3,475,952 (Pfizer). In another embodiment, the antibody binds to the same epitope as PF-3,475,952. In a further embodiment, the antibody competitively inhibits binding of PF-3,475,952 to CD44. Additionally, MRD-containing antibodies having 1, 2, 3, 4, 5, 6, or more MRDs that compete for CD44.binding with PF-3,475,952 are also encompassed by the invention.

In an additional embodiment, the antibody target of the MRD-containing antibody is p-cadherin (CDH3). In one embodiment, the antibody is PF-3,732,010 (Pfizer). In another embodiment, the antibody binds to the same epitope as PF-3,732,010. In a further embodiment, the antibody competitively inhibits binding of PF-3,732,010 to p-cadherin. Additionally, MRD-containing antibodies having 1, 2, 3, 4, 5, 6, or more MRDs that compete for p-cadherin binding with PF-3,732,010 are also encompassed by the invention.

In another embodiment, the antibody target of the MRD-containing antibody is: ANG2 (ANGPT2). In one embodiment, the antibody is MEDI3617 (MedImmune). In one embodiment, the antibody binds to the same epitope as MEDI3617. In another embodiment, the antibody competitively inhibits binding of MEDI3617 to ANG2. Additionally, MRD-containing antibodies having 1, 2, 3, 4, 5, 6, or more MRDs that compete for ANG2 binding with MEDI3617 are also encompassed by the invention.

In certain embodiments, the antibody target of the MRD-containing antibody is EGFR, ErbB2, ErbB3, ErbB4, CD20, insulin-like growth factor-I receptor, prostate specific membrane antigen, an integrin, or cMet.

In one embodiment, the antibody in the MRD-containing antibody specifically binds EGFR. In a specific embodiment, the antibody is ERBITUX® (IMC-C225). In one embodiment, the antibody binds to the same epitope as ERBITUX®. In another embodiment, the antibody competitively inhibits binding of ERBITUX® to EGFR. In another embodiment, the antibody in the MRD-containing antibody inhibits EGFR dimerization. In another specific embodiment, the antibody is matuzimab (e.g., EMD 72000, Merck Serono) or panitumumab (e.g., VECTIBIX®, Amgen). In another embodiment, the antibody binds to the same epitope as matuzimab or panitumumab. In another embodiment, the antibody competitively inhibits binding of matuzimab or panitumumab to EGFR. In another embodiment, the antibody is ABX-EGF (Immunex) or MDX-214 (Medarex). In another embodiment, the antibody binds to the same epitope as ABX-EGF or MDX-214. In another embodiment, the antibody competitively inhibits binding of ABX-EGF or MDX-214 to EGFR.

In one embodiment the MRD-containing antibody specifically binds ErbB2 (Her2). In a specific embodiment, the antibody is trastuzumab (e.g., HERCEPTIN®, Genentech/Roche). In one embodiment, the antibody binds to the same epitope as trastuzumab. In another embodiment, the antibody competitively inhibits binding of trastuzumab to ErbB2. An MRD that competes for target binding with one of the above antibodies is also encompassed by the invention. Additionally, MRD-containing antibodies having 1, 2, 3, 4, 5, 6, or more MRDs that compete for target binding with 1, 2, 3, 4, 5, 6, or more of the above antibodies are also encompassed by the invention.

In other embodiments, the antibody in the MRD-containing antibody specifically binds to ErbB2. In one embodiment, the antibody in the MRD-containing antibody is an antibody that specifically binds to the same epitope as the anti-ErbB2 antibody trastuzumab (e.g., HERCEPTIN®, Genentech). In another embodiment, the antibody in the MRD-containing antibody is an antibody that competitively inhibits ErbB2 binding by the anti-ErbB2 antibody trastuzumab. In yet another embodiment, the antibody in the MRD-containing antibody is the anti-ErbB2 antibody trastuzumab. In another embodiment, the antibody in the MRD-containing antibody inhibits HER2 dimerization. In another embodiment, the antibody in the MRD-containing antibody inhibits HER2 heterodimerization with HER3 (ErbB3). In a specific embodiment, the antibody is pertuzumab (e.g., OMNITARG® and phrMab2C4, Genentech). In another embodiment, the antibody specifically binds to the same epitope as pertuzumab. In another embodiment, the antibody in the MRD-containing antibody is an antibody that competitively inhibits binding of ErbB2 by pertuzumab. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention. Accordingly, in one embodiment the antibody in the MRD-containing antibody is trastuzumab and 1, 2, 3, 4, 5, 6, or more MRDs in the MRD-containing antibody competitively inhibit binding of ErbB2 by pertuzumab.

In another embodiment, the antibody in the MRD-containing antibody is an ErbB2 binding antibody selected from the group: MDX-210 (Medarex), tgDCC-E1A (Targeted Genetics), MGAH22 (MacroGenics), and pertuzumab (OMNITARG™, 2C4; Genentech). An MRD that competes for target binding with one of the above antibodies is also encompassed by the invention. Additionally, MRD-containing antibodies having 1, 2, 3, 4, 5, 6, or more MRDs that compete for target binding with 1, 2, 3, or 4 of the above antibodies are also encompassed by the invention.

In some embodiments, the antibody in the MRD-containing antibody comprises the CDRs of the anti-ErbB2 antibody trastuzumab. The CDR, VH, and VL sequences of trastuzumab are provided in Table 1.

TABLE 1

| CDR | Sequence |
|---|---|
| VL-CDR1 | RAS<u>QDVNTAVAW</u> (SEQ ID NO: 59) |
| VL-CDR2 | <u>SAS</u>FLYS (SEQ ID NO: 60) |
| VL-CDR3 | QQ<u>HYTTPPT</u> (SEQ ID NO: 61) |
| VH-CDR1 | GRNIKDTYIH (SEQ ID NO: 62) |
| VH-CDR2 | RI<u>YPTN</u>GYTRYADSVKG (SEQ ID NO: 63) |
| VH-CDR3 | W<u>GGDGFYAMDY</u> (SEQ ID NO: 64) |
| VL | DIQMTQSPSSLSASVGDRVTITCRASQDVNTAVAWYQQKPGK APKLLIYSASFLYSGVPSRFSGSRSGTDFTLTISSLQPEDFA TYYCQQHYTTPPTFGQGTKVEIKRT (SEQ ID NO: 65) |
| VH | EVQLVESGGGLVQPGGSLRLSCAASGFNIKDTYIHWVRQAPG KGLEWVARIYPTNGYTRYADSVKGRFTISADTSKNTAYLQMN SLRAEDTAVYYCSRWGGDGFYAMDYWGQGTLVTVSS (SEQ ID NO: 66) |

In one embodiment the MRD-containing antibody specifically binds ErbB3 (Her3). In a specific embodiment, the antibody is MM121 (Merrimack Pharmaceuticals) or AMG888 (Amgen). In one embodiment, the antibody binds to the same epitope as MM121 or AMG888. In another embodiment, the antibody competitively inhibits binding of MM121 or AMG888 to ErbB3. An MRD that competes for target binding with one of the above antibodies is also encompassed by the invention. Additionally, MRD-containing antibodies having 1, 2, 3, 4, 5, 6, or more MRDs that compete for target binding with 1 or both of the above antibodies are also encompassed by the invention In one embodiment the MRD-containing antibody specifically binds VEGFA. In a specific embodiment, the antibody is bevacizumab (e.g., AVASTIN®, Genentech/Roche). In one embodiment, the antibody binds to the same epitope as bevacizumab. In another embodiment, the antibody competitively inhibits binding of bevacizumab to VEGFA. In another embodiment the MRD-containing antibody is AT001 (Affitech). In one embodiment, the antibody binds to the same epitope as AT001. In another embodiment, the antibody competitively inhibits binding of AT001 to VEGFA. An MRD that competes for target binding with one of the above antibodies is also encompassed by the invention. Additionally, MRD-containing antibodies having 1, 2, 3, 4, 5, 6, or more MRDs that compete for target binding with 1 or both of the above antibodies are also encompassed by the invention.

In some embodiments, the antibody in the MRD-containing antibody comprises the CDRs of the anti-VEGF antibody bevacizumab. The CDR, VH, and VL sequences of bevacizumab are provided in Table 2.

TABLE 2

| CDR | Sequence |
|---|---|
| VL-CDR1 | SASQDISNYLN (SEQ ID NO: 72) |
| VL-CDR2 | FTSSLHS (SEQ ID NO: 73) |
| VL-CDR3 | QQYSTVPWT (SEQ ID NO: 74) |
| VH-CDR1 | GYTFTNYGMN (SEQ ID NO: 75) |
| VH-CDR2 | WINTYTGEPTYAADFKR (SEQ ID NO: 76) |
| VH-CDR3 | YPHYYGSSHWYFDV (SEQ ID NO: 77) |
| VL | DIQMTQSPSSLSASVGDRVTITCSASQDISNYLNWYQQKPGK APKVLIYFTSSLHSGVPSRFSGSGSGTDFTLTISSLQPEDFA TYYCQQYSTVPWTFGQGTKVEIKR (SEQ ID NO: 78) |
| VH | EVQLVESGGGLVQPGGSLRLSCAASGYTFTNYGMNWVRQAPG KGLEWVGWINTYTGEPTYAADFKRRFTFSLDTSKSTAYLQMN SLRAEDTAVYYCAKYPHYYGSSHWYFDVWGQGTLVTVSS (SEQ ID NO: 79) |

In one embodiment the MRD-containing antibody specifically binds VEGFR1. In one embodiment, the antibody competitively inhibits binding of Aflibercept (Regeneron) to VEGFR1. In another embodiment, the antibody in the MRD-containing antibody inhibits VEGFR1 dimerization. An MRD that competes for target binding with Aflibercept is also encompassed by the invention. Additionally, MRD-containing antibodies having 1, 2, 3, 4, 5, 6, or more MRDs that compete for target binding with Aflibercept are also encompassed by the invention.

In one embodiment, the MRD-containing antibody specifically binds VEGFR2. In a specific embodiment, the antibody is ramucirumab (e.g., IMC1121B and IMC1C11, ImClone). In another embodiment, the antibody in the MRD-containing antibody inhibits VEGFR2 dimerization. In one embodiment, the antibody binds to the same epitope as ramucirumab. In another embodiment, the antibody competitively inhibits binding of ramucirumab to VEGFR2. In another embodiment, the antibody competitively binding of Aflibercept to VEGFR2. An MRD that competes for target binding with ramucirumab is also encompassed by the invention. Additionally, MRD-containing antibodies having 1, 2, 3, 4, 5, 6, or more MRDs that compete for target binding with ramucirumab or Aflibercept are also encompassed by the invention In one embodiment, the antibody in the MRD-containing antibody specifically binds CD20. In a specific embodiment the antibody is rituximab (e.g., RITUXAN®/MAB-THERA®, Genentech/Roche/Biogen Idec). In one embodiment, the antibody binds to the same epitope as rituximab. In another embodiment, the antibody competitively inhibits binding of rituximab to CD20. In an additional embodiment, the antibody is GA101 (Biogen Idec/Roche/Glycart). In one embodiment, the antibody binds to the same epitope as GA101. In another embodiment, the antibody competitively inhibits binding of GA101 to CD20. In an additional embodiment, the antibody is PF-5,230,895 (SBI-087; Pfizer) . In one embodiment, the antibody binds to the same epitope as PF-5,230,895. In another embodiment, the antibody competitively inhibits binding of PF-5,230,895 to CD20. In another specific embodiment, the antibody is ocrelizumab (e.g., 2H7; Genentech/Roche/Biogen Idec). In one embodiment, the antibody binds to the same epitope as ocrelizumab. In another embodiment, the antibody competitively inhibits binding of ocrelizumab to CD20. In another specific embodiment, the MRD-containing antibody is selected from: obinutuzumab (e.g., GA101; Biogen Idec/Roche/Glycart), ofatumumab (e.g., ARZERRA® and HuMax-CD20 Genmab), veltuzumab (e.g., IMMU-160, Immunomedics), AME-133 (Applied Molecular Evolution), SGN35 (Millennium), TG-20 (GTC Biotherapeutics), afutuzumab (Hoffmann-La Roche), and PRO131921 (Genentech). In another embodiment, the antibody binds to the same epitope as an antibody selected from: obinutuzumab, ofatumumab, veltuzumab, AME-133, SGN35, TG-20 and PRO131921. In another embodiment, the antibody competitively inhibits CD20 binding by an antibody selected from: obinutuzumab, ofatumumab, veltuzumab, AME-133, SGN35, TG-20, afutuzumab, and PRO131921. An MRD that competes for target binding with one of the above antibodies is also encompassed by the invention. Additionally, MRD-containing antibodies having 1, 2, 3, 4, 5, 6, or more MRDs that compete for target binding with 1, 2, 3, 4, 5, 6, or more of the above antibodies are also encompassed by the invention.

In one embodiment the MRD-containing antibody specifically binds IGF1R. In a specific embodiment, the antibody is selected from: cixutumumab (e.g., IMC-A12, Imclone), figitumumab (e.g., CP-751,871, Pfizer), AMG479 (Amgen), BIIB022 (Biogen Idec), SCH 717454 (Schering-Pough), and R1507 (Hoffmann-La Roche). In one embodiment, the antibody binds to the same epitope as an antibody selected from: cixutumumab, figitumumab, AMG479, BIIB022, SCH 717454, and R1507. In another embodiment, the antibody competitively inhibits IGF1R binding by an antibody selected from: cixutumumab, figitumumab, AMG479, BIIB022, SCH 717454, and R1507. In a specific embodiment, the antibody is figitumumab. In another specific embodiment, the antibody binds to the same epitope as figitumumab. In a further specific embodiment, the antibody competitively inhibits IGF1R binding by figitumumab. In an additional specific embodiment, the antibody is BIIB022. In another specific embodiment, the antibody binds to the same epitope as BIIB022. In a further specific embodiment, the antibody competitively inhibits IGF binding by BIIB022. In another embodiment, the antibody in the MRD-containing antibody inhibits IGF dimerization. An MRD that competes for target binding with one of the above antibodies is also encompassed by the invention. Additionally, MRD-containing antibodies having 1, 2, 3, 4, 5, 6, or more MRDs that compete for IGF1R binding with 1, 2, 3, 4, 5, 6, or more of the above antibodies are also encompassed by the invention.

In one embodiment, the antibody in the MRD-containing antibody specifically binds integrin. In a specific embodiment, the antibody is selected from: MEDI-522 avb3 (VITAXIN®, MedImmune), CNTO 95 a5b3 (Centocor), JC7U αvβ3, and volociximab a5b1 (e.g., M200, PDL and Biogen Idec). In another embodiment, the antibody binds to the same epitope as an antibody selected from: MEDI-522, CNTO 95, JC7U αvβ3, and volociximab. In another embodiment, the antibody competitively inhibits integrin binding by an antibody selected from: MEDI-522, CNTO 95, JC7U, and M200. In a specific embodiment, the antibody is natalizumab (e.g., TSABRI®, Biogen Idec). In one embodiment, the antibody binds to the same epitope as natalizumab. In another embodiment, the antibody competitively inhibits integrin binding by natalizumab. An MRD that competes for target binding with one of the above antibodies is also encompassed by the invention. Additionally, MRD-containing antibodies having 1, 2, 3, 4, 5, 6, or more MRDs that compete for target binding with 1, 2, 3, 4, 5, 6, or more of the above antibodies are also encompassed by the invention.

In one embodiment, the antibody in the MRD-containing antibody specifically binds cMet. In a specific embodiment, the antibody is selected from: MetMab (OA-5D5, Genentech), AMG-102 (Amgen) and DN30. In another embodiment, the antibody binds to the same epitope as an antibody selected from: MetMab (OA-5D5), AMG-102 and DN30. In another embodiment, the antibody competitively inhibits cMET binding by an antibody selected from: MetMab (OA-5D5), AMG-102 and DN30. An MRD that competes for target binding with one of the above antibodies is also encompassed by the invention. Additionally, MRD-containing antibodies having 1, 2, 3, 4, 5, 6, or more MRDs that compete for target binding with 1, 2, or 3 of the above antibodies are also encompassed by the invention.

In an additional embodiment, the antibody in the MRD-containing antibody specifically binds a5b1 integrin (VLA5). In a specific embodiment, the antibody is volociximab (e.g., M200 Biogen Idec). In another embodiment, the antibody binds to the same epitope as volociximab. In a further embodiment, the antibody competitively inhibits a5b1 integrin binding by volociximab. An MRD that competes for a5b1 integrin binding with volociximab is also encompassed by the invention. Additionally, MRD-containing antibodies having 1, 2, 3, 4, 5, 6, or more MRDs that compete for a5b1 integrin binding with volociximab are also encompassed by the invention.

In other specific embodiments, the antibody in the MRD-containing antibody specifically binds VEGF. In a specific embodiment, the antibody is bevacizumab (e.g., AVASTIN®, Genentech). In one embodiment, the antibody binds to the same epitope as bevacizumab. In another embodiment, the antibody competitively inhibits binding of bevacizumab to VEGF. In another specific embodiment, the antibody is r84 (Peregrine) or 2C3 (Peregrine). In another embodiment, the antibody binds to the same epitope as r84 or 2C3. In another embodiment, the antibody competitively inhibits VEGF binding by r84 or 2C3. An MRD that competes for target binding with one of the above antibodies is also encompassed by the invention. Additionally, MRD-containing antibodies having 1, 2, 3, 4, 5, 6, or more MRDs that compete for target binding with 1, 2, or 3 of the above antibodies are also encompassed by the invention.

In another embodiment, the antibody target of the MRD-containing antibody is an antigen associated with an autoimmune disorder, inflammatory or other disorder of the immune system or is associated with regulating an immune response.

In one embodiment the antibody target of the MRD-containing antibody is an immunoinhibitory target selected from: IL-1, IL-1B, IL-1Ra, L-5, IL6, IL-6R, CD26L, CD28, CD80, FcRn, or FcGamma RIIB. An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention.

In another embodiment the antibody target of the MRD-containing antibody is an immunostimulatory target selected from: CD25, CD28, CTLA-4, PD1, PD11, B7-H1, B7-H4, IL-10, TGFbeta, TNFSF4 (OX40 Ligand), TNFRSF4 (OX40), TNFSF5 (CD40 Ligand), TNFRSF5 (CD40), TNFSF9 (41BB Ligand), TNFRSF9 (41BB, CD137), TNFSF14 (LIGHT, HVEM Ligand), TNFRSF14 (HVEM), TNFSF15 (TL1A), TNFRSF25 (DR3), TNFSF18 (GITR Ligand), and TNFRSF18 (GITR). An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention.

In another embodiment the antibody target of the MRD-containing antibody is cytokine selected from: IL-1 alpha, IL-1 beta, IL-18, TNFSF2 (TNFa), LTalpha, LT beta, TNFSF11 (RANKL), TNFSF13B (BLYS), TNFSF13 (APRIL), IL-6, IL-7, IL-10, IL-12, IL-15, IL-17A, IL-23, OncoStatinM, TGFbeta, BMP2-15, PDGF, an FGF family member, VEGF, MIF, and a type I interferon. In an additional embodiment, the antibody target of the MRD-containing antibody is a member selected from: interferon-gamma, TNFSF15 (TL1A), IL-21, IL-13, IL-4, IL-5, IL-2, IL-8, IL-11, and LIF (HILDA): An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention.

In another embodiment the antibody target of the MRD-containing antibody is cytokine selected from: TNF-alpha (TNFSF1A), CD25, CD28, CTLA-4, PD1, PD11, B7-H1, B7-H4, IL-10, TGFbeta, TNFSF4 (OX40 Ligand), TNFRSF4 (OX40), TNFSF5 (CD40 Ligand), TNFRSF5 (CD40), TNFSF9 (41BB Ligand), TNFRSF9 (41BB, CD137), TNFSF14 (LIGHT, HVEM Ligand), TNFRSF14 (HVEM), TNFSF15 (TL1A), TNFRSF25 (DR3), TNFSF18 (GITR Ligand), and TNFRSF18 (GITR). An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention.

In one embodiment the antibody target of the MRD-containing antibody is IL1Ra, IL1Rb, IL-2, IL-3, IL-4, IL-7, IL-10, IL-11, IL-15, IL-16, IL-17, IL-17A, IL-17F, IL-18, IL-19, IL-25, IL-32, IL-33, interferon beta, SCF, BCA1/CXCL13, CXCL1, CXCL2, CXCL6, CXCL13, CXCL16, C3AR, CSAR, CXCR1, CXCR2, CCR1, CCR3, CCR7, CCR8, CCR9, CCR10, ChemR23, CCL3, CCL5, CCL11, CCL13, CCL17, CCL18, CCL19, CCL20, CCL21, CCL22, CCL24, CCL25, CCL26, CCL27, MPL, GP130, TLR2, TLR3, TLR4, TLR5, TLR7, TLR8, TLR9, TREM1, TREM2, FcRn, FcGamma RIIB, oncostatin M, lymphotoxin alpha (LTa), integrin beta 7 subunit, CD49a (integrin alpha 1), integrin a5b3, MIF, ESM1, WIF1, cathepsin B, cathepsin D, cathepsin K, cathepsin S, TNFSF2 (TNFa), TNFSF3 (LTb), TNFRSF3 (LTBR), TNFSF6 (Fas Ligand), TNFRSF6 (Fas, CD95), TNFRSF6B (DcR3), TNFSF8 (CD30 Ligand), TNFRSF8 (CD30), TNFSF9 (41BB Ligand), TNFRSF9 (41BB, CD137), TNFSF11 (RANKL), TNFRSF11A (RANK), TNFSF14 (LIGHT, HVEM Ligand), TNFRSF14 (HVEM), TNFRSF16 (NGFR), TNFSF18 (GITR Ligand), TNFRSF18 (GITR), TNFRSF19L (RELT), TNFRSF19 (TROY), TNFRSF21 (DR6), CD14, CD23 CD25, CD28, CD36, CD36L, CD39, CD52, CD91, CD137, CD153, CD164, CD200, CD200R, BTLA, B7-1 (CD80), B7-2 (CD86), B7h, ICOS, ICOSL, MHC, CD, B7-H2, B7-H3, B7-H4, B7x, SLAM, KIM-1, SLAMF2, SLAMF3, SLAMF4, SLAMF5, SLAMF6, or SLAMF7. An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention. The above antibody and MRD targets and those otherwise described herein are intended to be illustrative and not limiting.

In another embodiment, the antibody target of the MRD-containing antibody is TNFSF1A (TNF-alpha), TNFRSF1A (TNFR1, p55, p60), TNFRSF1B (TNFR2), TNFSF7 (CD27 Ligand, CD70), TNFRSF7 (CD27), TNFSF13B (BLYS), TNFSF13 (APRIL), TNFRSF13B (TACI), TNFRSF13C (BAFFR), TNFRSF17 (BCMA), TNFSF15 (TL1A), TNFRSF25 (DR3), TNFSF12 (TWEAK), TNFRSF12 (TWEAKR), TNFSF4 (OX40 Ligand), TNFRSF4 (OX40), TNFSF5 (CD40 Ligand), TNFRSF5 (CD40), IL-1, IL-1 beta, IL1R, IL-2R, IL4-Ra, IL-5, IL-5R, IL-6, IL6R, IL9, IL12, IL-13, IL-14, IL-15, IL-15R, IL-17f, IL-17R, Il-17Rb, IL-17RC, IL-20, IL-21, IL-22RA, IL-23, IL-23R, IL-31, TSLP, TSLPR, interferon alpha, interferon gamma, B7RP-1, cKit, GMCSF, GMCSFR, CTLA-4, CD2, CD3, CD4, CD11a, CD18, CD20, CD22, CD26L, CD30, CD40, CD80, CD86, CXCR3, CXCR4, CCR2, CCR4, CCR5, CCR8, CCL2, CXCL10, PlGF, PD1, B7-DC (PDL2), B7-H1 (PDL1), alpha4 integrin, A4B7 integrin, C5, RhD, IgE, or Rh. An MRD that binds to one of the above targets is encompassed by the invention. Additionally, MRD-containing antibodies having 1, 2, 3, 4, 5, 6, or more MRDs that bind to 1, 2, 3, 4, 5, 6, or more of the above targets are also encompassed by the invention.

In particular embodiments, the antibody target of the MRD-containing antibody competes for target binding with: SGN-70 CD70 (Seattle Genetics), SGN-75 CD70 (Seattle Genetics), Belimumab BLYS (e.g., BENLYSTA®, Human Genome Sciences/GlaxoSmithKline), Atacicept BLYS/APRIL (Merck/Serono), TWEAK (e.g., Biogen mAb), TL1a antibodies of CoGenesys/Teva (e.g., hum11D8, hum25B9, and hum1B4 (U.S. Patent Application Publication 2009/0280116), OX40 mAb, humAb OX40L (Genentech), rilonacept IL1 trap (e.g., ARCALYST®, Regeneron), catumaxomab IL1 beta (e.g., REMOVAB®, Fresenius Biotech GmbH), Xoma052 IL1 beta (Lilly), canakinumab IL1 beta (e.g., ILARIS® (Novartis) and ACZ885 (Novartis)), AMG108 IL1R (Amgen), daclizumab IL2Ra (e.g., ZENAPAX®, Hoffmann-La Roche), basiliximab IL2Ra (e.g., SIMULECT®, Novartis), AMGN-317 IL-4a (Amgen), pascolizumab IL-4 (PDL), mepolizumab IL5 (e.g., BOSATRIA®, GlaxoSmithKline), reslizumab IL5 (e.g., SCH55700, Ception Therapeutics), MEDI-563 IL-5R (MedImmune), BIW-8405, IL-5R (BioWa), etanercept TNFR2-fc (e.g., ENBREL®, Amgen), siltuximab IL6 (e.g., CNTO328, Centocor), CNTO-136 IL6 (Centocor), CDP-6038 IL6 (UCB), AMGN-220 IL6 (Amgen), REGN-88 IL6R (Regeneron), tocilizumab IL6R (e.g., ACTEMRA®/RO- ACTEMRA®, Chugai/Roche), MEDI-528 IL9 (MedImmune), briakinumab IL-12/13 (e.g., ABT-874, Abbott), ustekinumab IL-12, IL-23 (e.g., STELARA® and CNTO 1275, Centocor), TNX-650 IL-13 (Tanox), lebrikizumab IL-13 (Genentech), CAT354 IL-13 (Cambridge Antibody Technology), AMG714 IL-15 (Amgen), CRB-15 IL-15R (Hoffmann-La Roche), AMG827 IL-17R (Amgen), IL-17RC antibody of Zymogenetics/Merck Serono, IL-20 antibody of Zymogenetics, IL-20 antibody of Novo Nordisk, IL-21 antibody of Novo Nordisk (e.g., NCT01038674), IL-21 antibody Zymogenetics (Zymogenetics), IL-22RA antibody of Zymogenetics, IL-31 antibody of Zymogenetics, AMG157 TSLP (Amgen), MEDI-545 interferon alpha (Medimmune), MEDI-546 interferon alpha pathway component (MedImmune), AMG811 interferon gamma (Amgen), INN0202 interferon gamma (Innogenetics/Advanced Biotherapy), HuZAF interferon-gamma (PDL), AMG557 B7RP1 (Amgen), AMG191 cKit (Amgen), MOR103 GMCSF (MorphoSys), CAM-3001 GMCSFR (Medimmune), tremelimumab CTLA4 (e.g., CP-675,206, Pfizer), iplimumab CTLA4 (e.g., MDX-010, BMS/Medarex), alefacept CD2 (e.g., AMEVIVE®, Astellas), siplizumab CD2 (e.g., MEDI-507, MedImmune), otelixizumab CD3 (e.g., TRX4, Tolerx/GlaxoSmithKline), teplizumab CD3 (e.g., MGA031, MacroGenics/Eli Lilly), visilizumab CD3 (e.g., NUVION®, PDL), muromonab-CD3 CD3 (Ortho), ibalizumab (e.g., TMB-355 and TNX-355, TaiMed Biologics), zanolimumab CD4 (e.g., HUMAX-CD4®, Genmab), cedelizumab CD4 (Euroasian Chemicals), keliximab CD4, priliximab CD4 (e.g., cMT412, Centocor), BT-061 CD4 (BioTest AG), efalizumab CD11a (e.g., RAPTIVA®/XANELIM™, Genentech/Roche/Merck-Serono), MLN01 CD18 (Millennium Pharmaceuticals), epratuzumab CD22 (e.g., Amgen antibody) and hLL2; (Immunomedics/UCB)), aselizumab CD26L, iratumumab CD30 (e.g., SGN30 (Seattle Genetics) and MDX-060 (Medarex), SGN40 CD40 (Seattle Genetics), ANTOVA® CD40 ligand (Biogen Idec), abatacept CD80 CD86 (e.g., ORENCIA®, Bristol-Myers Squibb), CT-011 PD1 (Cure Tech), AT010 CXCR3 (Affitech), MLN1202 CCR2 (Millennium Pharmaceuticals), AMG-761 CCR4 (Amgen), HGS004 CCR5 (Human Genome Sciences), PRO 140 (Progenics), MDX-1338 CXCR4 (Medarex), CNTO-888 CCL2 (Centocor), ABN912 CCL2 (Novartis), MDX-1100 CXCL10 (Medarex), TB-403 P1GF (Biolnvent), natalizumab integrin Alpha4 subunit (e.g., TYSABRI®, Biogen Idec/Elan), vedolizumab integrin A4B7 (e.g., MLN2, Millennium Pharmaceuticals/Takeda), eculizumab C5 Compliment (e.g., SOLIRIS®, Alexion), pexelizumab C5 Compliment (Alexion), omalizumab IgE (e.g., XOLAIR®, Genentech/Roche/Novartis), talizumab (e.g., TNX-901, Tanox), toralizumab (IDEC 131, IDEC), bertilimumab eotaxin (e.g., iCo-008, iCo Therapeutics Inc.), ozrolimupab RhD (e.g., Sym001, Symphogen A/S), atorolimumab or morolimumab (Rh factor). An MRD that competes for target binding with one of the above antibodies is also encompassed by the invention. Additionally, MRD-containing antibodies having 1, 2, 3, 4, 5, 6, or more MRDs that compete for target binding with 1, 2, 3, 4, 5, 6, or more of the above antibodies are also encompassed by the invention.

In particular embodiments, the antibody of the MRD-containing antibody is: SGN-70 CD70 (Seattle Genetics), SGN-75 CD70 (Seattle Genetics), Belimumab BLYS (e.g., BENLYSTA®, Human Genome Sciences/GlaxoSmithKline), BIIB023 TWEAK (Biogen Idec), TL1a antibodies of CoGenesys/Teva (e.g., 11D8, 25B9, and 1B4 (U.S. Patent Application Publication 2009/0280116), OX40 mAb, humAb OX40L (Genentech), catumaxomab IL1 beta (e.g., REMOVAB®, Fresenius Biotech GmbH), canakinumab IL1 beta (e.g., ILARIS® (Novartis) and ACZ885 (Novartis)), AMG108 IL1R (Amgen), daclizumab IL2Ra (e.g., ZENAPAX®, Hoffmann-La Roche), basiliximab IL2Ra (e.g., SIMULECT®, Novartis), AMGN-317 IL-4a (Amgen), pascolizumab IL-4 (PDL), mepolizumab IL5 (e.g., BOSATRIA®, GlaxoSmithKline), reslizumab IL5 (e.g., SCH55700, Ception Therapeutics), MEDI-563 IL-5R (MedImmune), benralizumab IL-5R (MedImmune), BIW-8405, IL-5R (BioWa), siltuximab IL6 (e.g., CNTO328, Centocor), CNTO-136 IL6 (Centocor), CDP-6038 IL6 (UCB), AMGN-220 IL6 (Amgen), REGN-88 IL6R (Regeneron), tocilizumab IL6R (e.g., ACTEMRA®/ROACTEMRA®, Chugai/Roche), MEDI-528 IL9 (MedImmune), briakinumab IL-12/13 (e.g., ABT-874, Abbott), ustekinumab IL-12, IL-23 (e.g., CNTO 1275, Centocor), lebrikizumab IL-13 (Genentech), TNX-650 IL-13 (Tanox), CAT354 IL-13 (Cambridge Antibody Technology), AMG714 IL-15 (Amgen), CRB-15 IL-15R (Hoffmann-La Roche), AMG827 IL-17R (Amgen), IL-17RC antibody of Zymogenetics/Merck Serono, IL-20 antibody of Zymogenetics, IL-20 antibody of Novo Nordisk, IL-21 antibody of Novo Nordisk, IL-21 antibody Zymogenetics (Zymogenetics), IL-22RA antibody of Zymogenetics, IL-31 antibody of Zymogenetics, AMG157 TSLP (Amgen), MEDI-545 interferon alpha (MedImmune), MEDI-546 interferon alpha pathway component (MedImmune), AMG811 interferon gamma (Amgen), INNO202 interferon gamma (Innogenetics/Advanced Biotherapy), HuZAF interferon-gamma (PDL), AMG557 B7RP1 (Amgen), AMG191 cKit (Amgen), MOR103 GMCSF (MorphoSys), CAM-3001 GMCSFR (MedImmune), tremelimumab CTLA4 (e.g., CP-675,206, Pfizer), iplimumab CTLA4 (e.g., MDX-010, BMS/Medarex), siplizumab CD2 (e.g., MEDI-507, MedImmune), otelixizumab CD3 (e.g., TRX4, Tolerx/GlaxoSmithKline), muromonab-CD3 CD3 (Ortho), teplizumab CD3 (e.g., MGA031, MacroGenics/Eli Lilly), visilizumab CD3 (e.g., NUVION®, PDL), zanolimumab CD4 (e.g., HUMAX-CD4®, Genmab), cedelizumab CD4 (Euroasian Chemicals), keliximab CD4, priliximab CD4 (e.g., cMT412, Centocor), BT-061 CD4 (BioTest AG), ibalizumab (e.g., TMB-355 and TNX-355, TaiMed Biologics), efalizumab CD11a (e.g., RAPTIVA®/XANELIM™, Genentech/Roche/Merck-Serono), MLN01 CD18 (Millennium Pharmaceuticals), epratuzumab CD22 (e.g., Amgen antibody) and hLL2 (Immunomedics/UCB)), aselizumab CD26L iratumumab CD30 (e.g., SGN30 (Seattle Genetics) and MDX-060 (Medarex), SGN40 CD40 (Seattle Genetics), ANTOVA® CD40 ligand (Biogen Idec), CT-011 PD1 (Cure Tech), AT010 CXCR3 (Affitech), MLN3897 CCR1 (Millennium Pharmaceuticals), MLN1202 CCR2 (Millennium Pharmaceuticals), AMG-761 CCR4 (Amgen), HGS004 CCR5 (Human Genome Sciences), PRO 140 (Progenics), MDX-1338 CXCR4 (Medarex), CNTO-888 CCL2 (Centocor), ABN912 CCL2 (Novartis), MDX-1100 CXCL10 (Medarex), TB-403 P1GF (Biolnvent), natalizumab integrin Alpha4 subunit (e.g., TYSABRI®, Biogen Idec/Elan), vedolizumab integrin A4B7 (e.g., MLN02, Millennium Pharmaceuticals/Takeda), eculizumab C5 Compliment (e.g., SOLIRIS®, Alexion pharmaceuticals), omalizumab IgE (e.g., XOLAIR®, Genentech/Roche/Novartis), talizumab (e.g., TNX-901, Tanox), toralizumab (IDEC 131, IDEC), bertilimumab eotaxin (e.g., iCo-008, iCo Therapeutics Inc.), ozrolimupab RhD (e.g., Sym001, Symphogen A/S), atorolimumab or morolimumab (Rh factor).

In an additional embodiment, the antibody in the MRD-containing antibody specifically binds CTLA4. In a specific embodiment, the antibody is tremelimumab (e.g., CP-675, 206, Pfizer). In another embodiment, the antibody binds to the same epitope as tremelimumab. In a further embodiment, the antibody competitively inhibits binding of tremelimumab to CTLA4. In an additional specific embodiment, the antibody is ipilimumab (e.g., MDX010, Bristol-Myers Squibb/Medarex). In one embodiment, the antibody binds to the same epitope as ipilimumab. In a further embodiment, the antibody competitively inhibits binding of ipilimumab to CTLA4. Additionally, MRD-containing antibodies having 1, 2, 3, 4, 5, 6, or more MRDs that compete for CTLA4 binding with tremelimumab or ipilimumab are also encompassed by the invention.

In an additional embodiment, the antibody in the MRD-containing antibody specifically binds TWEAK (TNFSF12). In a specific embodiment, the antibody is the TWEAK antibody of Biogen that has advanced to Phase I clinical trials. In another embodiment, the antibody binds to the same epitope as the Biogen TWEAK antibody. In a further embodiment, the antibody competitively inhibits binding of the Biogen TWEAK antibody to TWEAK. Additionally, MRD-containing antibodies having 1, 2, 3, 4, 5, 6, or more MRDs that compete for TWEAK binding with the Biogen TWEAK antibody are also encompassed by the invention.

In an additional embodiment, the antibody in the MRD-containing antibody specifically binds IL2Ra (CD25). In a specific embodiment, the antibody is daclizumab (e.g., ZENAPAX®). In another embodiment, the antibody binds to the same epitope as daclizumab. In a further embodiment, the antibody competitively inhibits binding of daclizumab to IL2Ra (CD25). Additionally, MRD-containing antibodies having 1, 2, 3, 4, 5, 6, or more MRDs that compete for IL2Ra (CD25) binding with daclizumab are also encompassed by the invention.

In an additional embodiment, the antibody in the MRD-containing antibody specifically binds CD40 (TNFRSF5). In a specific embodiment, the antibody is CP-870893 CD40 (Pfizer). In another embodiment, the antibody binds to the same epitope as CP-870893. In a further embodiment, the antibody competitively inhibits binding of CP-870893 to CD40. Additionally, MRD-containing antibodies having 1, 2, 3, 4, 5, 6, or more MRDs that compete for CD40 binding with CP-870893 are also encompassed by the invention.

In an additional embodiment, the antibody in the MRD-containing antibody specifically binds Alpha4 integrin. In a specific embodiment, the antibody is natalizumab (e.g., TYSABRI®; Biogen Idec/Elan). In one embodiment, the antibody binds to the same epitope as natalizumab. In a further embodiment, the antibody competitively inhibits binding of natalizumab to Alpha4 integrin. Additionally, MRD-containing antibodies having 1, 2, 3, 4, 5, 6, or more MRDs that compete for Alpha4 integrin binding with natalizumab are also encompassed by the invention.

In an additional embodiment, the antibody in the MRD-containing antibody specifically binds IL-22. In a specific embodiment, the antibody is PF-5,212,367 (ILV-094) (Pfizer). In another embodiment, the antibody binds to the same epitope as PF-5,212,367. In a further embodiment, the antibody competitively inhibits binding of PF-5,212,367 to IL-22. Additionally, MRD-containing antibodies having 1, 2, 3, 4, 5, 6, or more MRDs that compete for IL-22 binding with PF-5,212,367 are also encompassed by the invention.

In an additional embodiment, the antibody in the MRD-containing antibody specifically binds MAdCAM. In a specific embodiment, the antibody is PF-547,659 (Pfizer). In another embodiment, the antibody binds to the same epitope as PF-547,659. In a further embodiment, the antibody competitively inhibits binding of PF-547,659 to MAdCAM. Additionally, MRD-containing antibodies having 1, 2, 3, 4, 5, 6, or more MRDs that compete for MAdCAM binding with PF-547,659 are also encompassed by the invention.

In one embodiment, the antibody in the MRD-containing antibody specifically binds TNF. In a specific embodiment, the antibody is adalimumab (e.g., HUMIRA®/TRUDEXA®, Abbott). In one embodiment, the antibody binds to the same epitope as adalimumab. In another embodiment, the antibody competitively inhibits binding of adalimumab to TNF. In another specific embodiment, the antibody is ATN-103 (Pfizer). In one embodiment, the antibody binds to the same epitope as ATN-103. In another embodiment, the antibody competitively inhibits binding of ATN-103 to TNF. In another specific embodiment, the antibody is infliximab. In one embodiment, the antibody binds to the same epitope as infliximab. In another embodiment, the antibody competitively inhibits binding of infliximab to TNF. In another specific embodiment, the antibody is selected from: certolizumab (e.g., CIMZIA®, UCB), golimumab (e.g., SIMPONI®, Centocor), or AME-527 (Applied Molecular Evolution). In one embodiment, the antibody binds to the same epitope as certolizumab, golimumab, or AME-527. In another embodiment, the antibody competitively inhibits binding of certolizumab, golimumab, or AME-527, to TNF. An MRD that competes for target binding with one of the above antibodies is also encompassed by the invention. Additionally, MRD-containing antibodies having 1, 2, 3, 4, 5, 6, or more MRDs that compete for target binding with 1, 2, 3, 4, or 5, of the above antibodies are also encompassed by the invention.

In some embodiments, the antibody in the MRD-containing antibody comprises the CDRs of the anti-TNF antibody adalimumab. The CDR, VH, and VL sequences of adaliumumab are provided in Table 3.

TABLE 3

| CDR | Sequence |
|---|---|
| VL-CDR1 | RASQGIRNYLA (SEQ ID NO: 80) |
| VL-CDR2 | AASTLQS (SEQ ID NO: 81) |
| VL-CDR3 | QRYNRAPYT (SEQ ID NO: 82) |
| VH-CDR1 | DYAMH (SEQ ID NO: 83) |
| VH-CDR2 | AITWNSGHIDYADSVEG (SEQ ID NO: 84) |
| VH-CDR3 | VSYLSTASSLDY (SEQ ID NO: 85) |
| VL | DIQMTQSPSSLSASVGDRVTITCRASQGIRNYLAWYQQKPGK APKLLIYAASTLQSGVPSRFSGSGSGTDFTLTISSLQPEDVA TYYCQRYNRAPYTFGQGTKVEIKR (SEQ ID NO: 86) |
| VH | EVQLVESGGGLVQPGRSLRLSCAASGFTFDDYAMHWVRQAPG KGLEWVSAITWNSGHIDYADSVEGRFTISRDNAKNSLYLQMN SLRAEDTAVYYCAKVSYLSTASSLDYWGQGTLVTVSS (SEQ ID NO: 87) |

In other embodiments, the target of the antibody of the MRD-containing antibody is IL6. In some embodiments, the antibody of the MRD-containing antibody is siltuximab (CNTO328, Centocor), CNTO-136 (Centocor), CDP-6038 (UCB), or AMGN-220 (Amgen). In other embodiments, the antibody of the MRD-containing antibody competes with siltuximab (CNTO328, Centocor), CNTO-136 (Centocor), CDP-6038 (UCB), or AMGN-220 (Amgen) for binding to IL6. An MRD that competes for target binding with one of the above antibodies is also encompassed by the invention.

Additionally, MRD-containing antibodies having 1, 2, 3, 4, 5, 6, or more MRDs that compete for target binding with 1, 2, or more of the above antibodies are also encompassed by the invention.

In other embodiments, the target of the antibody of the MRD-containing antibody is IL6R. In some embodiments, the antibody of the MRD-containing antibody is REGN-88 (Regeneron) or tocilizumab (ACTEMRA®/RO-ACTEMRA®, Chugai/Roche). In other embodiments, the antibody of the MRD-containing antibody competes with siltuximab REGN-88 (Regeneron) or tocilizumab (ACTEMRA®/ROACTEMRA®, Chugai/Roche) for binding to IL6R. An MRD that competes for target binding with one of the above antibodies is also encompassed by the invention. Additionally, MRD-containing antibodies having 1, 2, 3, 4, 5, 6, or more MRDs that compete for target binding with 1 or both of the above antibodies are also encompassed by the invention.

In additional embodiments, an MRD-containing antibody binds to 2, 3, 4, 5 or more targets associated with abnormalities of the immune system including inflammation and autoimmune disease that include IL6, IL6R, TNF alpha (TNFSF1A), IL-1, cadherin 11, fibronectin, BLYS (TNFSF13B), Ang-2, VEGF, VEGFR1, integrin avb3, CD80/CD86, TL1a (TNFSF15), S1PR, CD19, CD20, CD22, CD70, CD32b, CD40, CD4, INF gamma, IL-10R, IL-10, CD80, CD86, ILTs, ICOS, PD1, CD4, IL-4R, IL5R, and IL19R. These MRD-containing antibodies have applications in treating, ameliorating diseases and disorders of the immune system, including inflammation and autoimmune disease.

According to one embodiment, an MRD-containing antibody binds to 2, 3, 4, 5 or more targets selected from IL6, IL6R, TNF alpha (TNFSF1A), IL-1, cadherin 11, fibronectin, BLyS (TNFSF13B), Ang-2, VEGF, VEGFR1, integrin avb3, and CD80/CD86. These MRD-containing antibodies have applications in treating, preventing, or ameliorating inflammation, such as autoimmune related inflammation in for example, rheumatoid arthritis.

According to another embodiment, an MRD-containing antibody binds to 1, 2, 3, or more targets selected from BLYS (TNFSF13B), S1pr, IFNbR, and IFNaR. These MRD-containing antibodies have applications in treating, preventing, or ameliorating inflammation, such as autoimmune related inflammation associated with systemic lupus erythematosus.

According to another embodiment, an MRD-containing antibody binds to 1, 2, or 3 targets selected from TNF alpha (TNFSF1A), TL1a (TNFSF15), and Ang-2. These MRD-containing antibodies have applications in treating, preventing, or ameliorating inflammation, such as autoimmune related inflammation associated with inflammatory bowel disease.

In another embodiment, an MRD-containing antibody binds to 1, 2, 3, 4, 5 or more targets selected from CD19, CD20, CD22, CD70, CD32b, CD40, CD4, IFNg, IL10R, and IL-10R. Members of this group are associated with cancer, hematologic disorders, inflammation and autoimmune disease, and B cell related diseases and disorders and these MRD-containing antibodies have applications in treating, preventing, or ameliorating such disorders.

According to one embodiment, an MRD-containing antibody binds to 1, 2, 3 or more targets selected from CD4, IFNg, IL10R, and IL10(R). Members of this group are associated with TH1 mediated immune responses and these MRD-containing antibodies have applications in treating, preventing, or ameliorating B cell associated autoimmune diseases and B cell associated diseases.

According to an additional embodiment, an MRD-containing antibody binds to 1, 2, or 3 targets selected from CD4, IL4R, IL5R, and IL9R. Members of this group are associated with TH2 mediated immune responses and these MRD-containing antibodies have applications in treating, preventing, or ameliorating for example, autoimmune disease and inflammation.

According to another embodiment, an MRD-containing antibody binds to 1, 2, 3, 4, 5 or more targets selected from CD80/86, ILTs, ICOS, and PD1. Members of this group are associated with stimulation of the immune response and these MRD-containing antibodies have applications in for example, in treating, preventing immune disorders such as those associated with autoimmune disease.

In particular embodiments, the target of the antibody of the MRD-containing antibody is: amyloid beta (Abeta), beta amyloid, complement factor D, PLP, ROBO4, ROBO, GDNF, NGF, LINGO, or myostatin. In specific embodiments, the antibody in the MRD-containing antibody is gantenerumab (e.g., R1450, Hoffmann-La Roche), bapineuzumab beta amyloid 9 (Elan and Wyeth), solanezumab beta amyloid 9 (Lilly), tanezumab NGF (e.g., RN624, Pfizer), BIIB033 LINGO (Biogen Idec), PF-3,446,879 myostatin (Pfizer), or stamulumab myostatin (Wyeth). In another embodiment, the antibody specifically binds to the same epitope as gantenerumab, bapineuzumab, solarezumab, tanezumab, the Biogen LINGO antibody, or stamulumab. In another embodiment, the antibody in the MRD-containing antibody is an antibody that competitively inhibits target binding by gantenerumab, bapineuzumab, solarezumab, tanezumab, BIIB033, or stamulumab. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention.

In an additional embodiment, the target of the antibody of the MRD-containing antibody is beta amyloid. In a specific embodiment, the antibody in the MRD-containing antibody is RN1219 (PF-4,360,365; Pfizer). In another embodiment, the antibody specifically binds to the same epitope as RN1219. In a further embodiment, the antibody in the MRD-containing antibody is an antibody that competitively inhibits beta amyloid binding by RN1219. An MRD that competes for beta amyloid binding with RN1219 is also encompassed by the invention. Additionally, MRD-containing antibodies having 1, 2, 3, 4, 5, 6, or more MRDs that compete for beta amyloid binding with RN1219 are also encompassed by the invention.

In an additional embodiment, the target of the antibody of the MRD-containing antibody is NGF. In a specific embodiment, the antibody in the MRD-containing antibody is tanezumab (e.g., RN624, Pfizer). In another embodiment, the antibody specifically binds to the same epitope as tanezumab. In a further embodiment, the antibody in the MRD-containing antibody is an antibody that competitively inhibits NGF binding by tanezumab. An MRD that competes for NGF binding with tanezumab is also encompassed by the invention. Additionally, MRD-containing antibodies having 1, 2, 3, 4, 5, 6, or more MRDs that compete for NGF binding with tanezumab are also encompassed by the invention.

In an additional embodiment, the target of the antibody of the MRD-containing antibody is LINGO (e.g., LINGO1). In a specific embodiment, the antibody in the MRD-containing antibody is BIIB033 (Biogen Idec). In another embodiment, the antibody specifically binds to the same epitope as BIIB033. In a further embodiment, the antibody in the MRD-containing antibody is an antibody that competitively inhibits LINGO binding by BIIB033. An MRD that competes for LINGO binding with BIIB033 is also encompassed by the invention. Additionally, MRD-containing antibodies having 1, 2, 3, 4, 5, 6, or more MRDs that compete for LINGO binding with BIIB033 are also encompassed by the invention.

In an additional embodiment, the MRD-containing antibody binds to LINGO and DR6 (TNFRSF21). These MRD-containing antibodies are expected to have applications in treating multiple sclerosis.

In another embodiment, the target of the antibody of the MRD-containing antibody is: oxidized LDL, gpIIB, gpIIIa, PCSK9, Factor VIII, integrin a2bB3, AOC3, or mesothelin. In specific embodiments, the antibody in the MRD-containing antibody is BI-204 oxidized LDL (Biolnvent), abciximab gpIIB, gpIIIa (e.g., REOPRO, Eli Lilly), AMG-145 PCSK9 (Amgen), TB-402 Factor VIII (Biolnvent), vapaliximab, or tadocizumab integrin a2bB3 (Yamonochi Pharma). In another embodiment, the antibody specifically binds to the same epitope as BI-204, abciximab, AMG-145, TB-402, or tadocizumab. In another embodiment, the antibody in the MRD-containing antibody is an antibody that competitively inhibits binding of BI-204, abciximab, AMG-145, TB-402, vapaliximab, or tadocizumab. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention.

In other embodiments, the antibody of the MRD-containing antibody is associated with bone growth and/or metabolism. In certain embodiments the antibody target of the MRD-containing antibody is RANKL. In other embodiments the antibody target of the MRD-containing antibody is: DKK1, osteopontin, cathepsin K, TNFRSF19L (RELT), TNFRSF19 (TROY), or sclerostin (CDP-7851 UCB Celltech). In another embodiment antibody target of the MRD-containing antibody is RANKL. In a specific embodiment, the antibody in the MRD-containing antibody is denosumab (e.g., AMG-162, Amgen). In another embodiment, the antibody specifically binds to the same epitope as denosumab. In another embodiment, the antibody in the MRD-containing antibody is an antibody that competitively inhibits binding of RANKL by denosumab. In another specific embodiment, the antibody is AMG617 or AMG785 (e.g., CDP7851, Amgen). In another embodiment, the antibody specifically binds to the same epitope as AMG617 or AMG785. In another embodiment, the antibody in the MRD-containing antibody is an antibody that competitively inhibits binding of sclerostin by AMG617 or AMG785. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention.

In additional embodiments, an MRD-containing antibody binds to 2, 3, 4, 5, 6, or more targets selected from TNFSF11 (RANKL), TNF-alpha (TNFSF1A), integrin avB3, Cad 11, fibronectin, DKK1, osteopontin, cathepsin K, TNFRSF19L (RELT), TNFRSF19 (TROY), and sclerostin. These MRD-containing antibodies have applications in treating an ameliorating musculoskeletal disorders such as osteoporosis and other degenerative bone disorders and other musculoskeletal diseases and disorders described herein or otherwise known in the art.

In additional embodiments, the antibody target of the MRD-containing antibody is a bacterial antigen, a viral antigen, a mycoplasm antigen, a prion antigen, or a parasite antigen (e.g., one infecting a mammal).

In other embodiments, the target of the antibody of the MRD-containing antibody is a viral antigen. In one embodiment, the target of the antibody of the MRD-containing antibody is anthrax, hepatitis b, rabies, Nipah virus, west nile virus, a mengititis virus, or CMV. In other embodiments, the antibody of the MRD-containing antibody competes with antigen binding with ABTHRAX® (Human Genome Sciences), exbivirumab, foravirumab, libivirumab, rafivirumab, regavirumab, sevirumab (e.g., MSL-109, Protovir), tuvirumab, raxibacumab, Nipah virus M102.4, or MGAWN 1® (MacroGenics) for target binding. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention.

In other embodiments, the target of the antibody of the MRD-containing antibody is RSV. In other embodiments, the antibody of the MRD-containing antibody is motavizumab (e.g., NUMAX®, MEDI-577; MedImmune) or palivizumab RSV fusion f protein (e.g., SYNAGIS®, MedImmune). In other embodiments, the antibody of the MRD-containing antibody competes with motavizumab or palivizumab RSV fusion f protein, for target binding. In other embodiments, the antibody of the MRD-containing antibody is felvizumab. In other embodiments, the antibody of the MRD-containing antibody competes with felvizumab for target binding. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention.

In other embodiments, the target of the antibody of the MRD-containing antibody is a bacterial or fungal antigen. In other embodiments, the antibody of the MRD-containing antibody competes for antigen binding with nebacumab, edobacomab (e.g., E5), tefibazumab (Inhibitex), panobacumab (e.g., KBPA101, Kenta), pagibaximab (e.g., BSYX-A110, Biosynexus), urtoxazumab, or efungumab (e.g., MYCOGRAB®, Novartis). In other embodiments, the antibody of the MRD-containing antibody is nebacumab, edobacomab, tefibazumab (lnhibitex), panobacumab, pagibaximab, urtoxazumab, or efungumab. An MRD that competes for target binding with one of the above antibodies is also encompassed by the invention. Additionally, MRD-containing antibodies having 1, 2, 3, 4, 5, 6, or more MRDs that compete for target binding with 1, 2 or more of the above antibodies are also encompassed by the invention.

In another specific embodiment, the antibody in the MRD-containing antibody is the catalytic antibody 38C2. In another embodiment, the antibody binds to the same epitope as 38C2. In another embodiment, the antibody competitively inhibits 38C2.

Other antibodies of interest include A33 binding antibodies. Human A33 antigen is a transmembrane glycoprotein of the Ig superfamily. The function of the human A33 antigen in normal and malignant colon tissue is not yet known. However, several properties of the A33 antigen suggest that it is a promising target for immunotherapy of colon cancer. These properties include (i) the highly restricted expression pattern of the A33 antigen, (ii) the expression of large amounts of the A33 antigen on colon cancer cells, (iii) the absence of secreted or shed A33 antigen, (iv) the fact that upon binding of antibody A33 to the A33 antigen, antibody A33 is internalized and sequestered in vesicles, and (v) the targeting of antibody A33 to A33 antigen expressing colon cancer in preliminary clinical studies. Fusion of a MRD directed toward A33 to a catalytic or non-catalytic antibody would increase the therapeutic efficacy of A33 targeting antibodies.

In some embodiments, the antibody in the MRD-containing antibody binds to a human target protein. In some embodiments, the MRD binds to both a human protein and its ortholog in mouse, rat, rabbit, or hamster.

The antibodies in the MRD-containing antibodies are able to bind their respective targets when the MRDs are attached to the antibody. In certain embodiments, the antibody binds its target independently. In some embodiments, the antibody is a target agonist. In other embodiments, the antibody is a target antagonist. In certain embodiments, the antibody can be used to localize an MRD-containing antibody to an area where the antibody target is located.

It is contemplated that the antibodies used in the present invention may be prepared by any method known in the art. For example, antibody molecules and MRD-containing antibodies can be "recombinantly produced," i.e., produced using recombinant DNA technology.

Monoclonal antibodies that can be used as the antibody component of the MRD-containing antibodies can be prepared using hybridoma methods, such as those described by Kohler and Milstein, Nature 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbant assay (ELISA)) can then be propagated either in vitro, for example, using standard methods (Goding, Monoclonal Antibodies: Principles and Practice, Academic Press, 1986) or in vivo, for example, as ascites tumors in an animal. The monoclonal antibodies can then be purified from the culture medium or ascites fluid as described for polyclonal antibodies above.

Alternatively monoclonal antibodies can also be made using recombinant DNA methods, for example, as described in U.S. Pat. No. 4,816,567. For example, in one approach polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. In other approaches, recombinant monoclonal antibodies or antibody fragments having the desired immunoreactivity can be isolated from phage display libraries expressing CDRs of the desired species using techniques known in the art (McCafferty et al., Nature 348:552-554 (1990); Clackson et al., Nature 352:624-628 (1991); and Marks et al., J. Mol. Biol. 222:581-597 (1991)).

The polynucleotide(s) encoding a monoclonal antibody can further be modified in a number of different manners, using recombinant DNA technology to generate alternative antibodies. For example, polynucleotide sequences that encode one or more MRDs and optionally linkers, can be operably fused, for example, to the 5' or 3' end of sequence encoding monoclonal antibody sequences. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. Techniques for site-directed and high-density mutagenesis of the variable region are known in the art and can be used to optimize specificity, affinity, etc. of a monoclonal antibody.

In certain embodiments, the antibody of the MRD-containing antibody is a human antibody. For example, human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., J. Immunol. 147 (1):86-95 (1991); and U.S. Pat. Nos. 5,750,373 and 6,787,637). In one embodiment, the human antibody can be derived from the "minilocus approach" in which an exogenous Ig locus is mimicked through inclusion of individual genes from the Ig locus (see e.g., U.S. Pat. No. 5,545,807). Methods of preparing a human antibody from a phage library, and optionally optimizing binding affinity are known in the art and described, for example, in Vaughan et al., Nat. Biotech. 14:309-314 (1996); Sheets et al., Proc. Nat'l. Acad. Sci. 95:6157-6162 (1998); Hoogenboom Nat. Biotechnology 23:1105-1116 (2005); Hoogenboom and Winter, J. Mol. Biol. 227:381 (1991); Persic et al., Gene 187:9-18 (1997); Jostock et al., J. Immunol. Methods 289:65-80 (2004); Marks et al., J. Mol. Biol., 222:581 (1991)); Barbas III, C. F., Kang, A. S., Lerner, R. A. and Benkovic, S. J., Proc. Natl. Acad. Sci. USA, 88:7978-7982 (1991); Barbas III, C. F., Hu, D., Dunlop, N., Sawyer, L., Cababa, D., Hendry, R. M., Nara, P. L. and Burton, D. R., Proc. Natl. Acad. Sci. USA 91:3809-3813 (1994); Yang, W.-P., Green, K., Pinz-Sweeney, S., Briones, A. T., Burton, D. R., and Barbas III, C. F., J. Mol. Biol. 254:392-403 (1995); and Barbas III, C. F., Bain, J. D., Hoekstra, D. M. and Lerner, R. A. Proc. Natl. Acad. Sci. USA 89:4457-4461 (1992). Techniques for the generation and use of antibody phage libraries are also described in: U.S. Pat. Nos. 5,545,807, 5,969,108, 6,172,197, 5,885,793, 6,521,404, 6,544,731, 6,555,313, 6,582,915, 6,593,081, 6,300,064, 6,653,068, 6,706,484, and 7,264,963; and Rothe et al., J. Mol. Bio. 130:448-54 (2007) (each of which is herein incorporated by reference). Affinity maturation strategies and chain shuffling strategies (Marks et al., Bio/Technology 10:779-783 (1992) (which is herein incorporated by reference) are known in the art and can be employed to generate high affinity human antibodies.

Antibodies can also be made in mice that are transgenic for human immunoglobulin genes or fragments of these genes and that are capable, upon immunization, of producing a broad repertoire of human antibodies in the absence of endogenous immunoglobulin production. This approach is described in: Lonberg, Nat. Biotechnol 23:1117-1125 (2005), Green, Nature Genet. 7:13-21 (1994), and Lonberg, Nature 368:856-859 (1994); U.S. Pat. Nos. 5,545,807, 5,545,806, 5,569,825, 5,625,126, 5,633,425, 5,661,016, 6,596,541, 7,105,348, and 7,368,334 (each of which is herein incorporated by reference).

IV. Linkers

MRD-containing antibodies can contain a single linker, multiple linkers, or no linker. Thus, a MRD may be operably attached (linked) to the antibody directly, or operably attached through an optional linker peptide. Similarly, a MRD may be operably attached to one or more MRD(s) directly, or operably attached to one or more MRD(s) through one or more optional linker peptide(s). Linkers can be of any size or composition so long as they are able to operably attach an MRD and an antibody such that the MRD enables the MRD containing antibody to bind the MRD target. In some embodiments, linkers have about 1 to 20 amino acids, about 1 to 15 amino acids, about 1 to 10 amino acids, about 1 to 5 amino acids, about 2 to 20 amino acids, about 2 to 15 amino acids, about 2 to 10 amino acids, or about 2 to 5 amino acids. The linker can also have about 4 to 15 amino acids.

In certain embodiments, the linker peptide contains a short linker peptide with the sequence GGGS (SEQ ID NO:1), a medium linker peptide with the sequence SSGGGGSGGGGGSS (SEQ ID NO:2), or a long linker peptide with the sequence SSGGGGSGGGGGSSRSS (SEQ ID NO:19). In another embodiment, the MRD is inserted into the fourth loop in the light chain constant region. For example, the MRD can be inserted between the underlined letters in the following amino acid sequence: RTVAAPSVFIFPPSDEQL KSGTASVVCLLNNFYPREA-KVQWKVDK<u>LG</u>TNSQESVTEQDSKDSTYSLSSTLTLS-KADYEKHKVYACEVTHQGLSLPVTKSFNRGEC (SEQ ID NO:102).

The linker can also be a non-peptide linker such as an alkyl linker, or a PEG linker. For example, alkyl linkers such as —NH—$(CH_2)$s-C(O)—, wherein s=2-20 can be used. These alkyl linkers may further be substituted by any non-sterically hindering group such as lower alkyl (e.g., $C_1$ $C_6$) lower acyl, halogen (e.g., Cl, Br), CN, $NH_2$, phenyl, etc. An exemplary non-peptide linker is a PEG linker. In certain embodiments, the PEG linker has a molecular weight of about 100 to 5000 kDa, or about 100 to 500 kDa.

Linker optimization can be evaluated using the techniques described in Examples 1-18 and techniques otherwise known in the art. Linkers preferably should not disrupt the ability of an MRD and/or an antibody to bind target molecules.

V. Antibodies Containing MRDs

Using the methods described herein, multi-specificity and greater multi-valency can be achieved through the fusion of MRDs to antibodies.

The MRDs of the MRD-containing antibodies prepared according to the present invention, may be operably linked to an antibody through the peptide's N-terminus or C-terminus. The MRD may be operably linked to the antibody at the C-terminal end of the heavy chain of the antibody, the N-terminal end of the heavy chain of the antibody, the C-terminal end of the light chain of the antibody, or the N-terminal end of the light chain of the antibody. Optimization of the MRD composition, MRD-antibody attachment location and linker composition can be performed using the binding assays described in Examples 1-18 and bioassays and other assays known in the art for the appropriate target related biological activity.

In one embodiment, MRD-containing antibodies contain an MRD operably linked to either the antibody heavy chain, the antibody light chain, or both the heavy and the light chain. In one embodiment an MRD-containing antibody contains at least one MRD linked to one of the antibody chain terminals. In another embodiment, an MRD-containing antibody of the invention contains at least one MRD operably linked to two of the antibody chain terminals. In another embodiment, an MRD-containing antibody contains at least one MRD operably linked to three of the antibody chain terminals. In another embodiment, an MRD-containing antibody contains at least one MRD operably attached to each of the four antibody chain terminals (i.e., the N and C terminals of the light chain and the N and C terminals of the heavy chain).

In certain specific embodiments, the MRD-containing antibody has at least one MRD operably attached to the N-terminus of the light chain. In another specific embodiment, the MRD-containing antibody has at least one MRD operably attached to the N-terminus of the heavy chain. In another specific embodiment, the MRD-containing antibody has at least one MRD operably attached to the C-terminus of the light chain. In another specific embodiment, the MRD-containing antibody has at least one MRD operably attached to the C-terminus of the heavy chain.

An MRD-containing antibody can be "multispecific" (e.g., bispecific, trispecific tetraspecific, pentaspecific or of greater multispecificity), meaning that it recognizes and binds to two or more different epitopes present on one or more different antigens (e.g., proteins). Thus, whether an MRD-containing antibody is "monospecific" or "multispecific," (e.g., bispecific, trispecific, and tetraspecific) refers to the number of different epitopes that the MRD-containing antibody binds. Multispecific antibodies may be specific for different epitopes of a target polypeptide (e.g., as described herein) or may be specific for a target polypeptide as well as for a heterologous epitope, such as a heterologous polypeptide target or solid support material. The present invention contemplates the preparation of mono-, bi-, tri-, tetra-, and penta-specific antibodies as well as antibodies of greater multispecificity. In one embodiment, the MRD-containing antibody binds two different epitopes. In an additional embodiment the MRD-containing antibody binds two different epitopes simultaneously. In another embodiment, the MRD-containing antibody binds three different epitopes. In an additional embodiment the MRD-containing antibody binds three different epitopes simultaneously. In another embodiment, the MRD-containing antibody binds four different epitopes. In an additional embodiment the MRD-containing antibody binds four different epitopes simultaneously. In another embodiment, the MRD-containing antibody binds five different epitopes (see, e.g., FIG. 2D). In an additional embodiment the MRD-containing antibody binds five different epitopes simultaneously.

In other embodiments two MRDs of the MRD-containing antibody bind the same antigen. In other embodiments three, four, five, six, seven, eight, nine or ten MRDs of the MRD-containing antibody bind the same antigen. In other embodiments at least two MRDs of the MRD-containing antibody bind the same antigen. In other embodiments at least three, four, five, six, seven, eight, nine or ten MRDs of the MRD-containing antibody bind the same antigen. In other embodiments two MRDs of the MRD-containing antibody bind the same epitope. In other embodiments three, four, five, six, seven, eight, nine or ten MRDs of the MRD-containing antibody bind the same epitope. In other embodiments at least two MRDs of the MRD-containing antibody bind the same epitope. In other embodiments at least three, four, five, six, seven, eight, nine or ten MRDs of the MRD-containing antibody bind the same epitope.

In other embodiments, the antibody and one MRD of the MRD-containing antibody bind the same antigen. In other embodiments the antibody and two, three, four, five, six, seven, eight, nine or ten MRDs of the MRD-containing antibody bind the same antigen. In other embodiments, the antibody and at least one MRD of the MRD-containing antibody bind the same antigen. In other embodiments the antibody and at least two, three, four, five, six, seven, eight, nine or ten MRDs of the MRD-containing antibody bind the same antigen. In other embodiments, the antibody and one MRD of the MRD-containing antibody bind the same epitope. In other embodiments the antibody and two, three, four, five, six, seven, eight, nine or ten MRDs of the MRD-containing antibody bind the same epitope. In other embodiments, the antibody and at least one MRD of the MRD-containing antibody bind the same epitope. In other embodiments the antibody and at least two, three, four, five, six, seven, eight, nine or ten MRDs of the MRD-containing antibody bind the same epitope.

The present invention also provides for two or more MRDs which are linked to any terminal end of the antibody. Thus, in one non-exclusive embodiment, two, three, four, or more MRDs are operably linked to the N-terminal of the heavy chain. In another non-exclusive embodiment, two, three, four, or more MRDs are operably linked to the N-terminal of the light chain. In another non-exclusive embodiment, two, three, four, or more MRDs are operably linked to the C-terminal of the heavy chain. In another non-exclusive embodiment, two, three, four, or more MRDs are operably linked to the C-terminal of the light chain. It is envisioned that these MRDs can be the same or different. In addition, any combination of MRD number and linkages can be used. For example, two MRDs can be operably linked to the N-terminal of the heavy chain of an antibody which contains one MRD linked to the C-terminal of the light chain. Similarly, three MRDs can be operably linked to the C-terminal of the light chain and two MRDs can be operably linked to the N-terminal of the light chain.

MRD-containing antibodies can contain one, two, three, four, five, six, seven, eight, nine, ten or more than ten MRDs.

Figure 1:
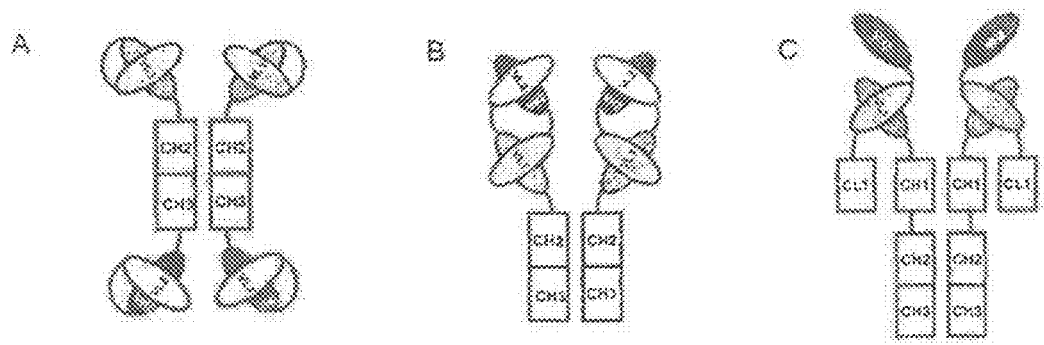
FIGS. 1A-1C show the schematic representation of different designs of multi-specific and multi-valent molecules. MRDs are depicted as triangles, circles, diamonds, and squares.
Figure 2:
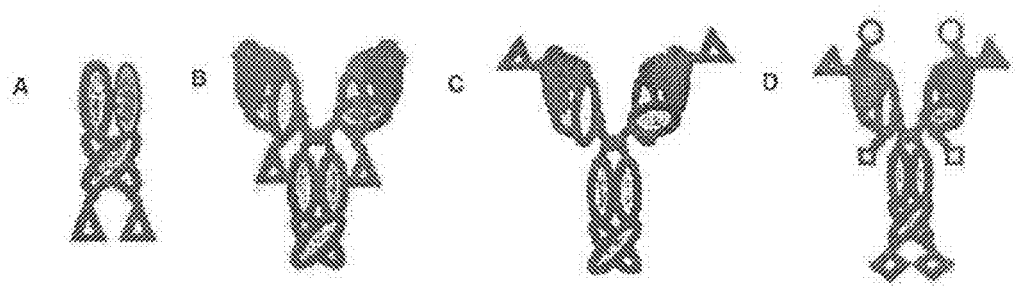
FIG. 2A shows a typical peptibody as a C-terminal fusion with the heavy chain of Fc.
FIG. 2B shows an MRD containing antibody with a C-terminal MRD fusion with the light chain of the antibody.
FIG. 2C shows an MRD containing antibody with an N-terminal MRD fusion with the light chain of the antibody.
FIG. 2D shows an MRD containing antibody with unique MRD peptides fused to each terminus of the antibody.

In one embodiment, the MRD-containing antibody contains one MRD (see, e.g., FIGS. 2B and 2C). In another embodiment, the MRD-containing antibody contains two MRDs. In another embodiment, the MRD-containing antibody contains three MRDs. In another embodiment, the MRD-containing antibody contains four MRDs (see, e.g., FIGS. 2B and 2C). In another embodiment, the MRD-containing antibody contains five MRDs. In another embodiment, the MRD-containing antibody contains six MRDs. In an additional embodiment, the MRD-containing antibody contains between two and ten MRDs.

In one embodiment, the MRD-containing antibody contains at least one MRD. In another embodiment, the MRD-containing antibody contains at least two MRDs. In another embodiment, the MRD-containing antibody contains at least three MRDs. In another embodiment, the MRD-containing antibody contains at least four MRDs. In another embodiment, the MRD-containing antibody contains at least five MRDs. In another embodiment, the MRD-containing antibody contains at least six MRDs.

In another embodiment, the MRD-containing antibody contains two different MRDs. In another embodiment, the MRD-containing antibody contains three different MRDs. In another embodiment, the MRD-containing antibody contains four different MRDs. In another embodiment, the MRD-containing antibody contains five different MRDs. In another embodiment, the MRD-containing antibody contains six different MRDs. In an additional embodiment, the MRD-containing antibody contains between two and ten different MRDs.

In another embodiment, the MRD-containing antibody contains at least two different MRDs. In another embodiment, the MRD-containing antibody contains at least three different MRDs. In another embodiment, the MRD-containing antibody contains at least four different MRDs. In another embodiment, the MRD-containing antibody contains at least five different MRDs. In another embodiment, the MRD-containing antibody contains at least six different MRDs.

Thus, the MRD-containing antibodies can be MRD monomeric (i.e., containing one MRD at the terminus of a peptide chain optionally connected by a linker) or MRD multimeric (i.e., containing more than one MRD in tandem optionally connected by a linker). The multimeric MRD-containing antibodies can be homo-multimeric (i.e., containing more than one of the same MRD in tandem optionally connected by linker(s) (e.g., homodimers, homotrimers, homotetramers etc.)) or hetero-multimeric (i.e., containing two or more MRDs in which there are at least two different MRDs optionally connected by linker(s) where all or some of the MRDs linked to a particular terminus are different (e.g., heterodimer, heterotrimer, heterotetramer etc.)). In one embodiment, the MRD-containing antibody contains two different monomeric MRDs located at different immunoglobulin termini. In another embodiment, the MRD-containing antibody contains three different monomeric MRDs located at different immunoglobulin termini. In another embodiment, the MRD-containing antibody contains four different monomeric MRDs located at different immunoglobulin termini. In another embodiment, the MRD-containing antibody contains five different monomeric MRDs located at different immunoglobulin termini. In another embodiment, the MRD-containing antibody contains six different monomeric MRDs located at different immunoglobulin termini.

In an alternative embodiment, the MRD-containing antibody contains at least one dimeric and one monomeric MRD located at different immunoglobulin termini. In another alternative embodiment, the MRD-containing antibody contains at least one homodimeric and one monomeric MRD located at different immunoglobulin termini. In another alternative embodiment, the MRD-containing antibody contains at least one heterodimeric and one monomeric MRD located at different immunoglobulin termini.

In an alternative embodiment, the MRD-containing antibody contains at least one multimeric and one monomeric MRD located at different immunoglobulin termini. In another alternative embodiment, the MRD-containing antibody contains at least one homomultimeric and one monomeric MRD located at different immunoglobulin termini. In another alternative embodiment, the MRD-containing antibody contains at least one heteromultimeric and one monomeric MRD located at different immunoglobulin termini.

In an alternative embodiment, the MRD-containing antibody contains MRDs operably linked to at least two different immunoglobulin termini. In a specific embodiment, the MRDs fused to at least one of the immunoglobulins is a multimer. In one embodiment, the MRDs fused to a least one of the immunoglobulins is a homomultimer (i.e., more than one of the same MRD operably linked in tandem, optionally linked via a linker), In another embodiment, the MRDs fused to at least one of the immunoglobulins is a heteromultimer (i.e., two or more different MRDs operably linked in tandem, optionally linked via a linker). In an additional embodiment, the MRDs fused to at least one of the immunoglobulins is a dimer. In another embodiment, the MRDs fused to a least one of the immunoglobulins is a homodimer. In another embodiment, the MRDs fused to at least one of the immunoglobulins is a heterodimer.

The multiple MRDs can target the same target binding site, or two or more different target binding sites. Where the MRDs bind to different target binding sites, the binding sites may be on the same or different target molecules.

Similarly, the antibody and the MRD in a MRD-containing antibody may bind to the same target molecule or to different target molecules.

In some embodiments, at least one MRD and the antibody in the MRD-containing antibody can bind to their targets simultaneously. In one embodiment, each MRD in the MRD-containing antibody and the antibody can bind to its target simultaneously. Therefore, in some embodiments, the MRD-containing antibody binds two, three, four, five, six, seven, eight, nine, ten or more target molecules simultaneously.

The ability of a MRD-containing antibody to bind to multiple targets simultaneously can be assayed using methods known in the art, including, for example, those methods described in the examples below.

In some embodiments, the MRD(s) and the antibody in the MRD-containing antibody are antagonists of their respective target molecules. In other embodiments, the MRD(s) and the antibody in the MRD-containing antibody are agonists of their respective target molecules. In yet other embodiments, at least one of the MRDs in the MRD-containing antibody is an antagonist of its target molecule and the antibody is an agonist of its target molecule. In yet another embodiment, at least one of the MRDs in the MRD-containing antibody is an agonist of its target molecule, and the antibody is an antagonist of its target molecule.

In some embodiments, both the MRD(s) and the antibody in the MRD-containing antibody bind to soluble factors. In some embodiments, both the MRD(s) and the antibody in the MRD-containing antibody bind to cell surface molecules. In some embodiments, at least one MRD in the MRD-containing antibody binds to a cell surface molecule and the antibody in the MRD-containing antibody binds to a soluble factor. In some embodiments, at least one MRD in the MRD-containing antibody binds to a soluble factor and the antibody in the MRD-containing antibody binds to a cell surface molecule.

An improved MRD-containing antibody that specifically binds a desired target or targets can also be prepared based on a previously known MRD or MRD-containing antibody. For example, 1, 2, 3, 4, 5, 6, 7, 8, 9, 10, 10-20, 20-30, 30-50, 50-100, 100-150 or more than 150 amino acid substitutions, deletions or insertions can be introduced into an MRD or MRD-containing antibody sequence and the resulting MRD or MRD-containing antibody can be screened for binding to the desired target or targets, for antagonizing target activity, or for agonizing target activity as described in the examples or using techniques known in the art.

Additional peptide sequences may be added, for example, to enhance the in vivo stability of the MRD or affinity of the MRD for its target.

In preferred embodiments, the MRD-containing antibody retains particular activities of the parent antibody. Thus, in certain embodiments, the MRD-containing antibody is capable of inducing complement dependent cytotoxicity. In certain embodiments, the MRD-containing antibody is capable of inducing antibody dependent cell mediated cytotoxicity (ADCC). In additional embodiments, the MRD-containing antibody is capable of inducing apoptosis. In additional embodiments, the MRD-containing antibody is capable of reducing tumor volume. In additional embodiments, the MRD-containing antibodies are capable of inhibiting tumor growth.

In some embodiments, the MRD-containing antibody shows improved activity or pharmacodynamic properties compared to the corresponding antibody without the attached MRD. Thus, in certain embodiments, the MRD-containing antibody has greater avidity than the corresponding antibody without the attached MRD. In other embodiments, the MRD-containing antibody results in increased receptor aggregation compared to the corresponding antibody without the attached MRD. In another embodiment, the MRD-containing antibody antagonizes target activity to a greater extent than the corresponding antibody without the attached MRD. In another embodiment, the MRD-containing antibody agonizes target activity to a greater extent than the corresponding antibody without the attached MRD. In another embodiment, the MRD-containing antibody has an improved pharmacodymamic profile than the corresponding antibody without the attached MRD.

In another embodiment, the MRD-containing antibody has a greater therapeutic efficacy than the corresponding antibody without the attached MRD.

In other embodiments, the MRD-containing antibodies have one or more of the following effects: inhibit proliferation of tumor cells, reduce the tumorigenicity of a tumor, inhibit tumor growth, increase subject survival, trigger cell death of tumor cells, differentiate tumorigenic cells to a non-tumorigenic state, or prevent metastasis of tumor cells.

In certain embodiments, the MRD-containing antibody is at least as stable as the corresponding antibody without the attached MRD. In certain embodiments, the MRD-containing antibody is more stable than the corresponding antibody without the attached MRD. MRD-antibody stability can be measured using methods known to those in the art, including, for example, ELISA techniques. In some embodiments, the MRD-containing antibody is stable in whole blood at 37° C. for at least about 10 hours, at least about 15 hours, at least about 20 hours, at least about 24 hours, at least about 25 hours, at least about 30 hours, at least about 35 hours, at least about 40 hours, at least about 45 hours, at least about 48 hours, at least about 50 hours, at least about 55 hours, at least about 60 hours, at least about 65 hours, at least about 70 hours, at least about 72 hours, at least about 75 hours, at least about 80 hours, at least about 85 hours, at least about 90 hours, at least about 95 hours, or at least about 100 hours.

In certain embodiments, the MRD-containing antibody has at least the same affinity for Fc receptors as the corresponding parent antibody. In other nonexclusive embodiments, the MRD-containing antibody has at least the same affinity for complement receptors as the corresponding parent antibody. In other nonexclusive embodiments, the MRD-containing antibody has at least the same half-life as the corresponding parent antibody. In other embodiments, the MRD-containing antibody can be expressed at levels commensurate with the corresponding parent antibody.

In additional, embodiments, the MRD-containing antibody has an increased affinity for Fc receptors compared to the corresponding parent antibody. In other nonexclusive embodiments, the MRD-containing antibody has an increased affinity for complement receptors compared to the corresponding parent antibody. In other nonexclusive embodiments, the MRD-containing antibody has an increased half-life compared to the corresponding parent antibody. In other embodiments, the MRD-containing antibody can be expressed at increased levels compared to that of the corresponding parent antibody.

In other embodiments, the MRD-containing antibody is conjugated to a cytotoxin. Cytotoxins include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Chemotherapeutic agents useful in the generation of such immunoconjugates also include antitubulin drugs, such as auristatins, including monomethyl auristatin E (MMAE) and monomethyl auristatin F (MMAF). Enzymatically active toxins and fragments thereof that can be used according to the invention include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. In some embodiments, the heteromultimeric molecules can be conjugated to radioisotopes, such as $^{90}$Y, $^{125}$I/$^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the MRD-containing antibody is coupled to drugs, prodrugs or lymphokines such as interferon. Conjugates of the MRD-containing antibody and cytotoxin can routinely be made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). In specific embodiments, the toxin is conjugate to an MRD-containing antibody through an enzyme-cleavable linker system (e.g., such as that present in SGN-35). Conjugates of an MRD-containing antibody and one or more small molecule toxins, such as a calicheamicin, maytansinoids, a trichothene, and CC1065, and the derivatives of these toxins that have toxin activity, can also be used. In some embodiments, the MRD-containing antibody can be complexed, or have MRDs that bind with other immunologically active ligands (e.g., chemokines, cytokines, and antibodies or fragments thereof) wherein the resulting molecule binds to both the neoplastic cell or other target as well as the chemokine, cytokine, or an effector cell such as a T cell.

In some embodiments, the N-terminus or C-terminus of the antibody to which the MRD is operably linked in the MRD-antibody fusions is truncated. In preferred embodiments, this truncation does not prevent or reduce the ability of the antibody to bind to its target antigen via its antigen binding domain. In other embodiments, the truncation does not prevent or reduce Fc effector function, half-life and/or ADCC activity. In other embodiments, MRDs are attached in the terminal region of the antibody chain. More particularly, in certain embodiments, the MRD is attached within 1, 2, 3, 4, 5, 10, 15, 20, 25, 30, 35, 40, 45, or 50 residues of the C-terminal amino acid of the heavy chain. In other embodiments, the MRD is attached within 1, 2, 3, 4, 5, 10, 15, 20, 25, 30, 35, 40, 45, or 50 residues of the C-terminal amino acid of the light chain. In additional embodiments, the MRD is attached within 1, 2, 3, 4, 5, 10, 15, 20, 25, 30, 35, 40, 45, or 50 residues of the N-terminal amino acid of the heavy chain. In other embodiments, the MRD is attached within 1, 2, 3, 4, 5, 10, 15, 20, 25, 30, 35, 40, 45, or 50 residues of the N-terminal amino acid of the light chain. Thus, for example, a MRD that is linked to the N-terminal end of the heavy chain can be linked to the first, second, third, fourth, fifth, or tenth amino acid of the N-terminal chain of the heavy chain. For example, an MRD-antibody fusion containing an MRD linked to the N-terminal of the heavy chain may contain amino acids 1-3 of the heavy chain sequence linked to the MRD, which is linked to amino acid 4 of the heavy chain sequence.

In certain embodiments, one or more MRDs are attached to the antibody at locations other than the termini of the antibody light and heavy chains. The MRD can be attached to any portion of the antibody that does not prevent the ability of the antibody to bind its target. Thus, in some embodiments, the MRD is located outside the antibody combining site. For example, the MRD can be located within a heavy chain sequence or within a light chain sequence. By way of example only, the MRD can be located between the Fc domain and the hinge region, between the hinge region and the CH1 domain of the heavy chain, between the CH1 domain and the variable region of the heavy chain, or between the constant region and the variable region of the light chain.

In specific embodiments, the MRD-containing antibody targets ErbB2 and an angiogenic factor. In specific embodiments, the MRD-containing antibody targets ErbB2 and IGF1R. In another embodiment, the antibody targets ErbB2, and at least one MRD targets an angiogenic factor and/or IGF1R. In one embodiment, an antibody that binds to the same ErbB2 epitope as trastuzumab is operably linked to at least one MRD that targets an angiogenic factor and/or IGF1R. In an additional embodiment, an antibody that competitively inhibits trastuzumab binding is operably linked to at least one MRD that targets an angiogenic factor and/or IGF1R. In additional embodiments, an antibody that comprises the sequences of SEQ ID NOS:59-64 is operably linked to at least one MRD that targets an angiogenic factor and/or IGF1R. In additional embodiments, the trastuzumab antibody is operably linked to at least one MRD that targets an angiogenic factor and/or IGF1R.

In some embodiments, an antibody that binds to ErbB2 is operably linked to an MRD that targets Ang2. In some embodiments, the antibody that binds to ErbB2 is linked to an Ang2 binding MRD that binds to the same Ang2 epitope as an MRD comprising the sequence of SEQ ID NO:8. In some embodiments, the antibody that binds to ErbB2 is linked to an Ang2 binding MRD that competitively inhibits an MRD comprising the sequence of SEQ ID NO:8. In some embodiments, the antibody that binds to ErbB2 is linked to an MRD comprising the sequence of SEQ ID NO:8.

In some embodiments, at least one Ang2 binding MRD is operably linked to the C-terminus of the heavy chain of an antibody that binds to ErbB2. In some embodiments, at least one Ang2 binding MRD is operably linked to the N-terminus of the heavy chain of an antibody that binds to ErbB2. In some embodiments, at least one Ang2 binding MRD is operably linked to the C-terminus of the light chain of an antibody that binds to ErbB2. In some embodiments, at least one Ang2 binding MRD is operably linked to the N-terminus of the light chain of an antibody that binds to ErbB2.

In some embodiments, at least one Ang2 binding MRD is operably linked directly to an antibody that binds to ErbB2. In additional embodiments, at least one Ang2 binding MRD is operably linked to an antibody that binds to ErbB2 via a linker.

In some embodiments, an antibody that binds to ErbB2 is operably linked to an MRD that targets IGF1R. In some embodiments, the antibody that binds to ErbB2 is linked to an IGF1R binding MRD that binds to the same IGF1R epitope as an MRD comprising the sequence of SEQ ID NO:14. In some embodiments, the antibody that binds to ErbB2 is linked to an IGF1R binding MRD that competitively inhibits an MRD comprising the sequence of SEQ ID NO:14. In some embodiments, the antibody that binds to ErbB2 is linked to an MRD comprising the sequence of SEQ ID NO:14. In some embodiments, the antibody that binds ErbB2 is linked to an MRD encoding the sequence SLFVPRPERK (SEQ ID NO:103). In some embodiments, the antibody that binds ErbB2 is linked to an MRD encoding the sequence ESDVLHFTST (SEQ ID NO:104). In some embodiments, the antibody that binds to ErbB2 is linked to an MRD encoding the sequence LRKYADGTL (SEQ ID NO:105).

In some embodiments, at least one IGF1R binding MRD is operably linked to the C-terminus of the heavy chain of an antibody that binds to ErbB2. In some embodiments, at least one IGF1R binding MRD is operably linked to the N-terminus of the heavy chain of an antibody that binds to ErbB2. In some embodiments, at least one IGF1R binding MRD is operably linked to the C-terminus of the light chain of an antibody that binds to ErbB2. In some embodiments, at least one IGF1R binding MRD is operably linked to the N-terminus of the light chain of an antibody that binds to ErbB2.

In some embodiments, at least one IGF1R binding MRD is operably linked directly to an antibody that binds to ErbB2. In additional embodiments, at least one IGF1R binding MRD is operably linked to an antibody that binds to ErbB2 via a linker.

In some embodiments, an MRD-containing antibody targets ErbB2 and HER2/3. In some embodiments, an MRD-containing antibody can bind to ErbB2 and HER2/3 simultaneously. In some embodiments, an antibody that binds to ErbB2 is operably linked to an MRD that targets HER2/3. In additional embodiments, at least one HER2/3-binding MRD is operably linked to the C-terminus of the heavy chain of an antibody that binds to ErbB2. In further embodiments, at least one HER2/3-binding MRD is operably linked to the N-terminus of the heavy chain of an antibody that binds to ErbB2. In additional embodiments, at least one HER2/3-binding MRD is operably linked to the C-terminus of the light chain of an antibody that binds to ErbB2. In additional embodiments, at least one HER2/3-binding MRD is oper- ably linked to the N-terminus of the light chain of an antibody that binds to ErbB2.

In some embodiments, at least one HER2/3-binding MRD is operably linked directly to an antibody that binds to ErbB2. In additional embodiments, at least one HER2/3-binding MRD is operably linked to an antibody that binds to ErbB2 via a linker.

In some embodiments, an MRD-containing antibody targets ErbB2 and HER2/3. In some embodiments, an MRD-containing antibody can bind to ErbB2 and HER2/3 simultaneously. In some embodiments, an antibody that binds to HER2/3 is operably linked to an MRD that targets ErbB2. In additional embodiments, at least one ErbB2-binding MRD is operably linked to the C-terminus of the heavy chain of an antibody that binds to HER2/3. In further embodiments, at least one ErbB2-binding MRD is operably linked to the N-terminus of the heavy chain of an antibody that binds to HER2/3. In additional embodiments, at least one ErbB2-binding MRD is operably linked to the C-terminus of the light chain of an antibody that binds to HER2/3. In additional embodiments, at least one ErbB2-binding MRD is operably linked to the N-terminus of the light chain of an antibody that binds to HER2/3.

In some embodiments, the MRD-containing antibody targets ErbB2, Ang2, and IGF1R. In some embodiments, the MRD-containing antibody comprises an antibody that targets ErbB2, an MRD that targets Ang2, and an MRD that targets IGF1R. In some embodiments, the Ang2 and IGF1R MRDs are attached to the same location on the anti-ErbB2 antibody. In some embodiments, the Ang2 and IGF1R MRDs are attached to different locations on the anti-ErbB2 antibody. In some embodiments, the Ang2 and IGF1R MRDs are on the light chain of the anti-ErbB2 antibody. In some embodiments, the Ang2 and IGF1R MRDs are on the heavy chain of the anti-ErbB2 antibody. In some embodiments, the Ang2 MRD is on the light chain of the ErbB2 antibody, and the IGF1R MRD is on the heavy chain of the anti-ErbB2 antibody. In some embodiments, the Ang2 MRD is on the heavy chain of the ErbB2 antibody, and the IGF1R MRD is on the light chain of the anti-ErbB2 antibody. In some embodiments, the Ang2 MRD is on the N-terminus of the heavy chain of the ErbB2 antibody, and the IGF1R MRD is on the C-terminus of the light chain of the anti-ErbB2 antibody. In some embodiments, the IGF1R MRD is on the N-terminus of the heavy chain of the ErbB2 antibody, and the Ang2 MRD is on the C-terminus of the light chain of the anti-ErbB2 antibody. MRD-containing antibodies comprising an antibody that targets Ang2, an MRD that targets ErbB2, and an MRD that targets IGF1R; and MRD-containing antibodies comprising an antibody that targets IGF1R, an MRD that targets ErbB2, and an MRD that targets Ang2 are also encompassed by the invention.

In some embodiments, the anti-ErbB2 antibody operably linked to an Ang2 binding MRD binds to both ErbB2 and Ang2 simultaneously. In some embodiments, the anti-ErbB2 antibody operably linked to an IGF1R binding MRD binds to both ErbB2 and IGF1R simultaneously. In some embodiments, the anti-ErbB2 antibody operably linked to an Ang2 MRD and an IGF1R MRD binds to ErbB2, Ang2, and IGF1R simultaneously. In some embodiments, the anti-ErbB2 antibody operably linked to an Ang2 and/or IGF1R binding MRD(s) exhibits ADCC activity. In additional embodiments, the anti-ErbB2 antibody operably linked to an Ang2 and/or, IGF1R binding MRD(s) down-regulates Akt signaling. In additional embodiments, the anti-ErbB2 antibody operably linked to an Ang2 binding MRD inhibits Ang2 binding to Tie2. In additional embodiments, the anti- ErbB2 antibody operably linked to an Ang2 and/or IGF1R binding MRD(s) down-regulates IGF1R signaling. In additional embodiments, the anti-ErbB2 antibody operably linked to an Ang2 and/or IGF1R binding MRD(s) inhibits cell proliferation. In additional embodiments, the anti-ErbB2 antibody operably linked to an Ang2 and/or IGF1R binding MRD(s) inhibits tumor growth.

According to some embodiments, the MRD-containing antibody binds 2, 3, 4, 5 or more targets selected from the group: EGFR, ErbB2, ErbB3, cMet, IGF1R, PDGFR, FGFR1, FGFR2, FGFR3, VEGFR1, and Ang2. MRD-containing antibodies having 1, 2, 3, 4, 5, 6, or more MRDs that bind to 1, 2, 3, 4, 5, 6, or more of the above targets are also encompassed by the invention. Accordingly, for example, in one embodiment, the MRD-containing antibody is an anti-ErbB2 antibody operably linked to MRDs that bind Her3, EGFR, IGF1R, Ang2, and PDGFR. According to another embodiment, an anti-EGFR antibody is operably linked to MRDs that bind Her3, ErbB2, VEGR, IGF1R, Ang2, and PDGFR. Such MRD containing antibodies are expected to have particular use in treating cancers including solid tumors and an treating disorders associated with neovascularization, such as those indications described herein or otherwise known in the art. In additional embodiments these MRD-containing antibodies contain an MRD or antibody that binds MAGE, Meloe-1 and/or CD20. Such MRD-containing antibodies have applications in, for example treating cancers such as, melanoma. In additional embodiments these MRD-containing antibody additionally contain an MRD or antibody that binds PSMA. Such MRD-containing antibodies have applications in, for example treating prostate cancer and other disorders associated with the prostate.

In additional embodiments these MRD-containing antibodies contain an MRD or antibody that binds PMSA. Such MRD-containing antibodies have applications in, for example treating prostate cancer and other disorders associated with the prostate. In additional embodiments these MRD-containing antibody additionally contain an MRD or antibody that binds PMSA. Such MRD-containing antibodies have applications in, for example treating prostate cancer and other disorders associated with the prostate.

In specific embodiments, the MRD-containing antibody targets VEGF and an angiogenic factor. In specific embodiments, the MRD-containing antibody targets VEGF and IGF1R. In another embodiment, the antibody targets VEGF, and at least one MRD targets an angiogenic factor and/or IGF1R. In one embodiment, an antibody that binds to the same VEGF epitope as bevacizumab is operably linked to at least one MRD that targets an angiogenic factor and/or IGF1R. In an additional embodiment, an antibody that competitively inhibits bevacizumab binding is operably linked to at least one MRD that targets an angiogenic factor and/or IGF1R. In additional embodiments, an antibody that comprises the sequences of SEQ ID NOS:78-79 is operably linked to at least one MRD that targets an angiogenic factor and/or IGF1R. In additional embodiments, the bevacizumab antibody is operably linked to at least one MRD that targets an angiogenic factor and/or IGF1R.

In some embodiments, an antibody that binds to VEGF is operably linked to an MRD that targets Ang2. In some embodiments, the antibody that binds to VEGF is linked to an Ang2 binding MRD that binds to the same Ang2 epitope as an MRD comprising the sequence of SEQ ID NO:8. In some embodiments, the antibody that binds to VEGF is linked to an Ang2 binding MRD that competitively inhibits an MRD comprising the sequence of SEQ ID NO:8.

In some embodiments, at least one Ang2 binding MRD is operably linked to the C-terminus of the heavy chain of an antibody that binds to VEGF. In some embodiments, at least one Ang2 binding MRD is operably linked to the N-terminus of the heavy chain of an antibody that binds to VEGF. In some embodiments, at least one Ang2 binding MRD is operably linked to the C-terminus of the light chain of an antibody that binds to VEGF. In some embodiments, at least one Ang2 binding MRD is operably linked to the N-terminus of the light chain of an antibody that binds to VEGF.

In some embodiments, at least one Ang2 binding MRD is operably linked directly to an antibody that binds to VEGF. In additional embodiments, at least one Ang2 binding MRD is operably linked to an antibody that binds to VEGF via a linker.

In some embodiments, an antibody that binds to VEGF is operably linked to an MRD that targets IGF1R. In some embodiments, the antibody that binds to VEGF is linked to an IGF1R binding MRD that binds to the same IGF epitope as an MRD comprising the sequence of SEQ ID NO:14. In some embodiments, the antibody that binds to VEGF is linked to an IGF1R binding MRD that competitively inhibits an MRD comprising the sequence of SEQ ID NO:14. In some embodiments, the antibody that binds to VEGF is linked to an MRD comprising the sequence of SEQ ID NO:14. In some embodiments, the antibody that binds ErbB2 is linked to an MRD encoding the sequence SLFVPRPERK (SEQ ID NO:103). In some embodiments, the antibody that binds ErbB2 is linked to an MRD encoding the sequence ESDVLHFTST (SEQ ID NO:104). In some embodiments, the antibody that binds ErbB2 is linked to an MRD encoding the sequence LRKYADGTL (SEQ ID NO:105).

In some embodiments, at least one IGF1R binding MRD is operably linked to the C-terminus of the heavy chain of an antibody that binds to VEGF. In some embodiments, at least one IGF1R binding MRD is operably linked to the N-terminus of the heavy chain of an antibody that binds to VEGF. In some embodiments, at least one IGF1R binding MRD is operably linked to the C-terminus of the light chain of an antibody that binds to VEGF. In some embodiments, at least one IGF1R binding MRD is operably linked to the N-terminus of the light chain of an antibody that binds to VEGF.

In some embodiments, at least one IGF1R binding MRD is operably linked directly to an antibody that binds to VEGF. In additional embodiments, at least one IGF1R binding MRD is operably linked to an antibody that binds to VEGF via a linker.

In some embodiments, the MRD-containing antibody targets VEGF, Ang2, and IGF1R. In some embodiments, the MRD-containing antibody comprises an antibody that targets VEGF, an MRD that targets Ang2, and an MRD that targets IGF1R. In some embodiments, the Ang2 and IGF1R MRDs are attached to the same location on the anti-VEGF antibody. In some embodiments, the Ang2 and IGF1R MRDs are attached to different locations on the anti-VEGF antibody. In some embodiments, the Ang2 and IGF1R MRDs are on the light chain of the anti-VEGF antibody. In some embodiments, the Ang2 and IGF1R MRDs are on the heavy chain of the anti-VEGF antibody. In some embodiments, the Ang2 MRD is on the light chain of the anti-VEGF antibody, and the IGF1R MRD is on the heavy chain of the anti-VEGF antibody. In some embodiments, the Ang2 MRD is on the heavy chain of the anti-VEGF antibody, and the IGF1R MRD is on the light chain of the anti-VEGF antibody. In some embodiments, the Ang2 MRD is on the N-terminus of the heavy chain of the anti-VEGF antibody, and the IGF1R MRD is on the C-terminus of the light chain of the anti-VEGF antibody. In some embodiments, the IGF1R MRD is on the N-terminus of the heavy chain of the anti-VEGF antibody, and the Ang2 MRD is on the C-terminus of the light chain of the anti-VEGF antibody.

In some embodiments, the anti-VEGF antibody operably linked to an Ang2 binding MRD binds to both anti-VEGF and Ang2 simultaneously. In some embodiments, the anti-VEGF antibody operably linked to an IGF1R binding MRD binds to both anti-VEGF and IGFR1 simultaneously. In some embodiments, the anti-VEGF antibody operably linked to an Ang2 binding MRD and an IGF1R binding MRD binds to VEGF, Ang2, and IGF1R simultaneously. In some embodiments, the anti-VEGF antibody operably linked to an Ang2 and/or IGF1R binding MRD(s) exhibits ADCC activity. In additional embodiments, the anti-VEGF antibody operably linked to an Ang2 and/or IGF1R binding MRD(s) down-regulates VEGF signaling. In additional embodiments, the anti-VEGF antibody operably linked to an Ang2 binding MRD inhibits Ang2 binding to Tie2. In additional embodiments, the anti-VEGF antibody operably linked to an IGF1R binding MRD inhibits IGF1R signaling. In additional embodiments, the anti-VEGF antibody operably linked to an Ang2 and/or IGF1R binding MRD(s) inhibits cell proliferation. In additional embodiments, the anti-VEGF antibody operably linked to an Ang2 and/or IGF1R binding MRD(s) inhibits tumor growth.

In some embodiments, the anti-ErbB2 antibody or the VEGF antibody contains and MRD that inhibits the binding of pertuzumab to ErbB2. In some embodiments, an anti-ErbB2 antibody contains at least one MRD that binds to Ang2 or IGF and one MRD that inhibits the binding of pertuzumab to ErbB2. In some embodiments, an anti-VEGF antibody contains at least one MRD that binds to Ang2 or IGF1R and one MRD that inhibits the binding of pertuzumab to ErbB2. In some embodiments, an anti-ErbB2 antibody contains an MRD that binds Ang2, an MRD that binds IGF1R, and an MRD that inhibits the binding of pertuzumab to ErbB2. In some embodiments, an anti-VEGF antibody contains an MRD that binds Ang2, an MRD that binds IGF1R, and an MRD that inhibits the binding of pertuzumab to ErbB2.

In specific embodiments, the MRD-containing antibody targets TNF and an angiogenic factor. In another embodiment, the antibody targets TNF (i.e., TNF-alpha (TNFSF1A)), and at least one MRD targets an angiogenic factor. In one embodiment, an antibody that binds to the same TNF epitope as adalimumab is operably linked to at least one MRD that targets an angiogenic factor. In an additional embodiment, an antibody that competitively inhibits adalimumab binding is operably linked to at least one MRD that targets an angiogenic factor. In additional embodiments, an antibody that comprises the sequences of SEQ ID NOS:80-85 is operably linked to at least one MRD that targets an angiogenic factor. In additional embodiments, the adalimumab antibody is operably linked to at least one MRD that targets an angiogenic factor. In one embodiment, an antibody that binds to the same TNF epitope as golimumab is operably linked to at least one MRD that targets an angiogenic factor. In an additional embodiment, an antibody that competitively inhibits golimumab binding is operably linked to at least one MRD that targets an angiogenic factor. In additional embodiments, the golimumab antibody is operably linked to at least one MRD that targets an angiogenic factor.

In some embodiments, an antibody that binds to TNF is operably linked to an MRD that targets Ang2. In some embodiments, the antibody that binds to TNF is linked to an Ang2 binding MRD that binds to the same Ang2 epitope as an MRD comprising the sequence of SEQ ID NO:8. In some embodiments, the antibody that binds to TNF is linked to an Ang2 binding MRD that competitively inhibits an MRD comprising the sequence of SEQ ID NO:8. In some embodiments, the antibody that binds to TNF is linked to an MRD comprising the sequence of SEQ ID NO:8.

In some embodiments, at least one Ang2 binding MRD is operably linked to the C-terminus of the heavy chain of an antibody that binds to TNF. In some embodiments, at least one Ang2 binding MRD is operably linked to the N-terminus of the heavy chain of an antibody that binds to TNF. In some embodiments, at least one Ang2 binding MRD is operably linked to the C-terminus of the light chain of an antibody that binds to TNF. In some embodiments, at least one Ang2 binding MRD is operably linked to the N-terminus of the light chain of an antibody that binds to TNF.

In some embodiments, at least one Ang2 binding MRD is operably linked directly to an antibody that binds to TNF. In additional embodiments, at least one Ang2 binding MRD is operably linked to an antibody that binds to TNF via a linker.

In some embodiments, the anti-TNF antibody operably linked to an Ang2 binding MRD binds to both TNF and Ang2 simultaneously. In some embodiments, the anti-TNF antibody operably linked to an Ang2 binding MRD exhibits ADCC activity. In additional embodiments, the anti-TNF antibody operably linked to an Ang2 binding MRD inhibits binding of TNF to the p55 and p75 cell surface TNF receptors. In additional embodiments, the anti-TNF antibody operably linked to an Ang2 binding MRD lyses surface TNF-expressing cells in vitro in the presence of complement. In additional embodiments, the anti-TNF antibody operably linked to an Ang2 binding MRD inhibits Ang2 binding to Tie2. In additional embodiments, the anti-TNF antibody operably linked to an Ang2 binding MRD reduces the signs and symptoms of arthritis.

In some embodiments, the MRD-containing antibody targets TNF and IL6. In some embodiments, the MRD-containing antibody is capable of binding TNF and IL6 simultaneously. Thus, in some embodiments, an antibody that binds to TNF is operably linked to an MRD that targets IL6. In other embodiments, an antibody that binds to IL6 is operably linked to an MRD that targets TNF.

In some embodiments, at least one IL6-binding MRD is operably linked to the C-terminus of the heavy chain of an antibody that binds TNF. In some embodiments, at least one IL6-binding MRD is operably linked to the N-terminus of the heavy chain of an antibody that binds to TNF. In some embodiments, at least one IL6-binding MRD is operably linked to the C-terminus of the light chain of an antibody that binds to TNF. In some embodiments, at least one IL6-binding MRD is operably linked to the N-terminus of the light chain of an antibody that binds to TNF.

In some embodiments, at least one TNF-binding MRD is operably linked to the C-terminus of the heavy chain of an antibody that binds IL6. In some embodiments, at least one TNF-binding MRD is operably linked to the N-terminus of the heavy chain of an antibody that binds to IL6. In some embodiments, at least one TNF-binding MRD is operably linked to the C-terminus of the light chain of an antibody that binds to IL6. In some embodiments, at least one TNF-binding MRD is operably linked to the N-terminus of the light chain of an antibody that binds to IL6.

In some embodiments, at least one IL6-binding MRD is operably linked directly to an antibody that binds to TNF. In additional embodiments, at least one IL6-binding MRD is operably linked to an antibody that binds to TNF via a linker.

In some embodiments, at least one TNF-binding MRD is operably linked directly to an antibody that binds to IL6. In additional embodiments, at least one TNF-binding MRD is operably linked to an antibody that binds to IL6 via a linker.

In some embodiments, at least one IL-1 beta-binding MRD is operably linked directly to an antibody that binds to IL-6. In additional embodiments, at least one IL6-binding MRD is operably linked to an antibody that binds to IL-1 beta via a linker.

In some embodiments, at least one TNF-binding MRD is operably linked directly to an antibody that binds to IL6. In additional embodiments, at least one TNF-binding MRD is operably linked to an antibody that binds to IL6 via a linker.

In some embodiments, the MRD-containing antibody targets TNF and IL-17 (e.g., IL-17A). In some embodiments, the MRD-containing antibody is capable of binding TNF and IL-17 simultaneously. Thus, in some embodiments, an antibody that binds to TNF is operably linked to an MRD that targets IL17. In other embodiments, an antibody that binds to IL-17 is operably linked to an MRD that targets TNF.

In some embodiments, at least one IL-17-binding MRD is operably linked to the C-terminus of the heavy chain of an antibody that binds TNF. In some embodiments, at least one IL-17-binding MRD is operably linked to the N-terminus of the heavy chain of an antibody that binds to TNF. In some embodiments, at least one IL-17-binding MRD is operably linked to the C-terminus of the light chain of an antibody that binds to TNF. In some embodiments, at least one IL-17-binding MRD is operably linked to the N-terminus of the light chain of an antibody that binds to TNF.

In some embodiments, at least one TNF-binding MRD is operably linked to the C-terminus of the heavy chain of an antibody that binds IL-17. In some embodiments, at least one TNF-binding MRD is operably linked to the N-terminus of the heavy chain of an antibody that binds to IL-17. In some embodiments, at least one TNF-binding MRD is operably linked to the C-terminus of the light chain of an antibody that binds to IL-17. In some embodiments, at least one TNF-binding MRD is operably linked to the N-terminus of the light chain of an antibody that binds to IL17.

In some embodiments, at least one IL-17-binding MRD is operably linked directly to an antibody that binds to TNF. In additional embodiments, at least one IL-17-binding MRD is operably linked to an antibody that binds to TNF via a linker.

In some embodiments, at least one TNF-binding MRD is operably linked directly to an antibody that binds to IL-17. In additional embodiments, at least one TNF-binding MRD is operably linked to an antibody that binds to IL-17 via a linker.

In some embodiments, the MRD-containing antibody targets TNF and IL-1 beta. In some embodiments, the MRD-containing antibody is capable of binding TNF and IL-1 beta simultaneously. Thus, in some embodiments, an antibody that binds to TNF is operably linked to an MRD that targets IL-1 beta. In other embodiments, an antibody that binds to IL-1 beta is operably linked to an MRD that targets TNF.

In some embodiments, at least one IL-1 beta-binding MRD is operably linked to the C-terminus of the heavy chain of an antibody that binds TNF. In some embodiments, at least one IL-1 beta-binding MRD is operably linked to the N-terminus of the heavy chain of an antibody that binds to TNF. In some embodiments, at least one IL-1 beta-binding MRD is operably linked to the C-terminus of the light chain of an antibody that binds to TNF. In some embodiments, at least one IL-1 beta-binding MRD is operably linked to the N-terminus of the light chain of an antibody that binds to TNF.

In some embodiments, at least one TNF-binding MRD is operably linked to the C-terminus of the heavy chain of an antibody that binds IL-1 beta. In some embodiments, at least one TNF-binding MRD is operably linked to the N-terminus of the heavy chain of an antibody that binds to IL-1 beta. In some embodiments, at least one TNF-binding MRD is operably linked to the C-terminus of the light chain of an antibody that binds to IL-1 beta. In some embodiments, at least one TNF-binding MRD is operably linked to the N-terminus of the light chain of an antibody that binds to IL-1 beta.

In some embodiments, at least one IL-1 beta-binding MRD is operably linked directly to an antibody that binds to TNF. In additional embodiments, at least one IL-1 beta-binding MRD is operably linked to an antibody that binds to TNF via a linker.

In some embodiments, at least one TNF-binding MRD is operably linked directly to an antibody that binds to IL-1 beta. In additional embodiments, at least one TNF-binding MRD is operably linked to an antibody that binds to IL-1 beta via a linker.

In some embodiments, at least one IL-17 (e.g., IL-17A)-binding MRD and at least one IL1 beta binding MRD are operably linked directly to the same or different termini of an antibody that binds to TNF. In additional embodiments at least one IL-17-binding MRD and at least one IL1 beta binding MRD are operably linked to the same or different termini of an antibody that binds to TNF via a linker.

In additional embodiments, at least one IL-17 (e.g., IL-17A)-binding MRD and at least one TNF-binding MRD are operably linked directly to the same or different termini of an antibody that binds to IL-1 beta. In additional embodiments, at least one IL-17-binding MRD and at least one TNF-binding MRD are operably linked to the same or different termini of an antibody that binds to IL-1 beta via a linker.

In additional embodiments, at least one IL-1 beta-binding MRD and at least one TNF-binding MRD are operably linked directly to the same or different termini of an antibody that binds to IL-17 (e.g., IL-17A). In additional embodiments, at least one IL-1 beta-binding MRD and at least one TNF-binding MRD are operably linked to the same or different termini of an antibody that binds to IL-17 via a linker.

In some embodiments, the MRD-containing antibody targets TNF and BLyS. In some embodiments, the MRD-containing antibody is capable of binding TNF and BLyS simultaneously. In some embodiments, an antibody that binds to TNF is operably linked to an MRD that targets BLyS. In other embodiments, an antibody that binds to BLyS is operably linked to an MRD that targets TNF.

In some embodiments, at least one BLyS-binding MRD is operably linked to the C-terminus of the heavy chain of an antibody that binds TNF. In some embodiments, at least one BLyS-binding MRD is operably linked to the N-terminus of the heavy chain of an antibody that binds to TNF. In some embodiments, at least one BLyS-binding MRD is operably linked to the C-terminus of the light chain of an antibody that binds to TNF. In some embodiments, at least one BLyS-binding MRD is operably linked to the N-terminus of the light chain of an antibody that binds to TNF.

In some embodiments, at least one TNF-binding MRD is operably linked to the C-terminus of the heavy chain of an antibody that binds BLyS. In some embodiments, at least one TNF-binding MRD is operably linked to the N-terminus of the heavy chain of an antibody that binds to BLyS. In some embodiments, at least one TNF-binding MRD is operably linked to the C-terminus of the light chain of an antibody that binds to BLyS. In some embodiments, at least one TNF-binding MRD is operably linked to the N-terminus of the light chain of an antibody that binds to BLyS.

In some embodiments, at least one BLyS-binding MRD is operably linked directly to an antibody that binds to TNF. In additional embodiments, at least one BLyS-binding MRD is operably linked to an antibody that binds to TNF via a linker.

In other embodiments, at least one TNF-binding MRD is operably linked directly to an antibody that binds to BLyS. In additional embodiments, at least one TNF-binding MRD is operably linked to an antibody that binds to BLyS via a linker.

In some embodiments, the MRD-containing antibody targets Ang2, TNF, and IL6. In some embodiments, the MRD-containing antibody is capable of binding Ang2, TNF, and IL6 simultaneously. In some embodiments, an antibody that binds to TNF is operably linked to an MRD that targets Ang2 and an MRD that targets IL6. In some embodiments, the Ang2- and IL6-binding MRDs are located on the same antibody chain. In some embodiments, the Ang2- and IL6-binding MRDs are located on the same antibody terminus. In some embodiments, the Ang2- and IL6-binding MRDs are located on different antibody chains. In some embodiments, the Ang2- and IL6-binding MRDs are located on different antibody termini.

In some embodiments, an antibody that binds to Ang2 is operably linked to an MRD that targets TNF and an MRD that targets IL6. In some embodiments, the TNF- and IL6-binding MRDs are located on the same antibody chain. In some embodiments, the TNF- and IL6-binding MRDs are located on the same antibody terminus. In some embodiments, the TNF- and IL6-binding MRDs are located on different antibody chains. In some embodiments, the TNF- and IL6-binding MRDs are located on different antibody termini.

In some embodiments, an antibody that binds to IL6 is operably linked to an MRD that targets Ang2 and an MRD that targets TNF. In some embodiments, the Ang2- and TNF-binding MRDs are located on the same antibody chain. In some embodiments, the Ang2- and TNF-binding MRDs are located on the same antibody terminus. In some embodiments, the Ang2- and TNF-binding MRDs are located on different antibody chains. In some embodiments, the Ang2- and TNF-binding MRDs are located on different antibody termini.

In some embodiments, the MRD-containing antibody targets Ang2, TNF, and BLyS. In some embodiments, the MRD-containing antibody is capable of binding Ang2, TNF, and BLyS simultaneously. In some embodiments, an antibody that binds to TNF is operably linked to an MRD that targets Ang2 and an MRD that targets BLyS. In other embodiments, an antibody that binds to BLyS is operably linked to an MRD that targets TNF and an MRD that targets Ang2. In other embodiments, an antibody that binds to Ang2 is operably linked to an MRD that targets TNF and an MRD that targets BLyS. In some embodiments, the Ang2-, BLyS, and/or TNF-binding MRDs are located on the same antibody chain. In some embodiments, the Ang2-, BLyS, and/or TNF-binding MRDs are located on the same antibody terminus. In some embodiments, the Ang2-, BLyS, and/or TNF-binding MRDs are located on different antibody chains. In some embodiments, the Ang2-, BLyS, and/or TNF-binding MRDs are located on different antibody termini.

In some embodiments, the MRD-containing antibody targets Ang2, TNF, IL6, and BLyS. In some embodiments, the MRD-containing antibody is capable of binding Ang2, TNF, IL6 and BLyS simultaneously. In some embodiments, an antibody that binds to TNF is operably linked to an MRD that targets Ang2, an MRD that targets IL6, and an MRD that targets BLyS. In some embodiments, an antibody that binds to Ang2 is operably linked to an MRD that targets TNF, an MRD that targets IL6, and an MRD that targets BLyS. In some embodiments, an antibody that binds to IL6 is operably linked to an MRD that targets Ang2, an MRD that targets TNF, and an MRD that targets BLyS. In some embodiments, an antibody that binds to BLyS is operably linked to an MRD that targets Ang2, an MRD that targets IL6, and an MRD that targets TNF. In some embodiments, the TNF-, Ang2-, IL6-, and/or BLyS-binding MRDs are located on the same antibody chain. In some embodiments, the TNF-, Ang2-, IL6- and/or BLyS-binding MRDs are located on the same antibody terminus. In some embodiments, the TNF-, Ang2-, IL6-, and/or BLyS-binding MRDs are located on different antibody chains. In some embodiments, the TNF-, Ang2-, IL6- and/or BLyS-binding MRDs are located on different antibody termini.

VI. Methods of Making Antibody-MRD Fusions

An additional advantage of MRD-containing antibodies is that they can be produced using protocols that are known in the art for producing antibodies. The antibody-MRD fusion molecules can be encoded by a polynucleotide comprising a nucleotide sequence. Thus, the polynucleotides described herein can encode an MRD, an antibody heavy chain, an antibody light chain, a fusion protein comprising an antibody heavy chain and at least one MRD, and/or a fusion protein comprising an antibody light chain and at least one MRD.

Also provided herein are an expression vector and/or a host cell that comprises one or more of the polynucleotides. Also provided herein, are methods of producing an MRD-containing antibody, the method comprising: culturing a host cell comprising one or more polynucleotides or an expression vector comprising one or more isolated polynucleotides in a medium under conditions allowing the expression of said one or more polynucleotide, wherein said one or more polynucleotides encodes one or more polypeptides that form part of MRD-containing antibody; and recovering said MRD-containing antibody.

Generally, any type of cultured cell line can be used to express the MRD-containing antibody of the present invention. In some embodiments, CHO cells, BHK cells, NS0 cells, SP2/0 cells, YO myeloma cells, P3X63 mouse myeloma cells, PER cells, PER.C6 cells or hybridoma cells, other mammalian cells, avian cells, yeast cells, insect cells, or plant cells are used as the background cell line to generate the engineered host cells of the invention.

In one embodiment, one or several polynucleotides encoding an MRD-containing antibody can be expressed under the control of a constitutive promoter or, alternately, a regulated expression system. Suitable regulated expression systems include, but are not limited to, a tetracycline-regulated expression system, an ecdysone inducible expression system, a lac-switch expression system, a glucocorticoid-inducible expression system, a temperature-inducible promoter system, and a metallothionein metal-inducible expression system. If several different nucleic acids encoding an MRD-containing antibody are comprised within the host cell system, some of them can be expressed under the control of a constitutive promoter, while others are expressed under the control of a regulated promoter. The maximal expression level is considered to be the highest possible level of stable polypeptide expression that does not have a significant adverse effect on cell growth rate, and will be determined using routine experimentation. Expression levels are determined by methods generally known in the art, including Western blot analysis and Northern blot analysis. In a further alternative, the polynucleotide may be operatively linked to a reporter gene; the expression levels of an MRD-containing antibody disclosed herein are determined by measuring a signal correlated with the expression level of the reporter gene. The reporter gene may be transcribed together with the nucleic acid(s) encoding said MRD-containing antibody as a single mRNA molecule; their respective coding sequences may be linked either by an internal ribosome entry site (IRES) or by a cap-independent translation enhancer. The nucleic acids encoding an MRD-containing antibody can be operatively linked to the reporter gene under the control of a single promoter, such that the nucleic acid encoding the MRD-containing antibody and the reporter gene are transcribed into an RNA molecule which is alternatively spliced into two separate messenger RNA (mRNA) molecules; one of the resulting mRNAs is translated into said reporter protein, and the other is translated into the MRD-containing antibody.

Methods which are well known to those skilled in the art can be used to construct expression vectors containing the coding sequence of an MRD-containing antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y. (1989). In some embodiments, the vectors used are pCEP4 (Invitrogen®) vectors. In some embodiments, the vectors used are pcDNA3 (Invitrogen®) vectors.

A variety of host-expression vector systems may be utilized to express the coding sequence an MRD-containing antibody. Mammalian cells can be used as host cell systems transfected with recombinant plasmid DNA or cosmid DNA expression vectors containing the coding sequence of the protein of interest and the coding sequence of the fusion polypeptide. Cells such as 293 cells (e.g., 293T and 293F), CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as host cell system. Some examples of expression systems and selection methods are described in the following references and references cited therein: Borth et al., Biotechnol. Bioen. 71(4):266-73 (2000-2001), in Werner et al., Arzneimittelforschung/Drug Res. 48(8):870-80 (1998), in Andersen and Krummen, Curr. Op. Biotechnol. 13:117-123 (2002), in Chadd and Chamow, Curr. Op. Biotechnol. 12:188-194 (2001), and in Giddings, Curr. Op. Biotechnol. 12: 450-454 (2001).

In alternate embodiments, other eukaryotic host cell systems may be used, including yeast cells transformed with recombinant yeast expression vectors containing the coding sequence of an MRD-containing antibody of the present invention, such as the expression systems taught in U.S. Pat. Appl. No. 60/344,169 and WO 03/056914 (methods for producing human-like glycoprotein in a non-human eukaryotic host cell) (the contents of each of which are incorporated by reference in their entirety); insect cell systems infected with recombinant virus expression vectors (e.g., baculovirus) containing the coding sequence of an MRD-containing antibody; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of an MRD-containing antibody, including, but not limited to, the expression systems taught in U.S. Pat. No. 6,815,184 (methods for expression and secretion of biologically active polypeptides from genetically engineered duckweed); WO 2004/057002 (production of glycosylated proteins in bryophyte plant cells by introduction of a glycosyl transferase gene) and WO 2004/024927 (methods of generating extracellular heterologous non-plant protein in moss protoplast); and U.S. Pat. Appl. Nos. 60/365,769, 60/368,047, and WO 2003/078614 (glycoprotein processing in transgenic plants comprising a functional mammalian GnTIII enzyme) (the contents of each of which is herein incorporated by reference in its entirety); or animal cell systems infected with recombinant virus expression vectors (e.g., adenovirus, vaccinia virus) including cell lines engineered to contain multiple copies of the DNA encoding an MRD-containing antibody either stably amplified (CHO/dhfr) or unstably amplified in double-minute chromosomes (e.g., murine cell lines). In one embodiment, the vector comprising the polynucleotide(s) encoding the MRD-containing antibody of the invention is polycistronic.

Stable expression typically achieves more reproducible results than transient expression and also is more amenable to large-scale production; however, it is within the skill of one in the art to determine whether transient expression is better for a particular situation. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:2026 (1962)), and adenine phosphoribosyltransferase (Lowy et al., Cell 22:817 (1980)) genes, which can be employed in tk$^-$, hgprt$^-$ or aprt$^-$ cells, respectively. Also, antimetabolite resistance can be used as the basis of selection for dhfr, which confers resistance to methotrexate (Wigler et al., Natl. Acad. Sci. USA 77:3567 (1989); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Colberre-Garapin et al., J. Mol. Biol. 150:1 (1981)); and hygro, which confers resistance to hygromycin (Santerre et al., Gene 30:147 (1984)) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047 (1988)); the glutamine synthase system; and ODC (ornithine decarboxylase) which confers resistance to the ornithine decarboxylase inhibitor, 2-(difluoromethyl)-DL-ornithine, DFMO (McConlogue, in: Current Communications in Molecular Biology, Cold Spring Harbor Laboratory ed. (1987)).

In some embodiments, the MRD-containing antibodies are expressed at levels (titers) comparable to those of antibodies. In some embodiments, the MRD-containing antibodies are expressed at least about 10 µg/ml, at least about 20 µg/ml, or at least about 30 µg/ml. In some embodiments, the MRD-containing antibodies are expressed at least about 40 µg/ml or at least about 50 µg/ml. In some embodiments, the MRD-containing antibodies are expressed at least about 60 µg/ml, at least about 70 µg/ml, at least about 80 µg/ml, at least about 90 µg/ml, at least about 95 µg/ml, at least about 100 µg/ml, at least about 110 µg/ml, at least about 120 µg/ml, at least about 130 µg/ml, at least about 140 µg/ml, at least about 150 µg/ml, at least about 160 µg/ml, at least about 170 µg/ml, at least about 180 µg/ml, at least about 190 µg/ml, or at least about 200 µg/ml.

The present invention is further directed to a method for modifying the glycosylation profile of an MRD-containing antibody that is produced by a host cell, comprising expressing in said host cell a nucleic acid encoding an MRD-containing antibody and a nucleic acid encoding a polypeptide with a glycosyltransferase activity, or a vector comprising such nucleic acids. Genes with glycosyltransferase activity include β(1,4)-N-acetylglucosaminyltransferase III (GnTIII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). In one embodiment, a combination of genes with glycosyltransferase activity are expressed in the host cell (e.g., GnTIII and Man II). Likewise, the method also encompasses expression of one or more polynucleotide(s) encoding the MRD-containing antibody in a host cell in which a glycosyltransferase gene has been disrupted or otherwise deactivated (e.g., a host cell in which the activity of the gene encoding α1-6 core fucosyltransferase has been knocked out). In another embodiment, the MRD-containing antibody can be produced in a host cell that further expresses a polynucleotide encoding a polypeptide having GnTIII activity to modify the glycosylation pattern. In a specific embodiment, the polypeptide having GnTIII activity is a fusion polypeptide comprising the Golgi localization domain of a Golgi resident polypeptide. In another embodiment, the expression of the MRD-containing antibody in a host cell that expresses a polynucleotide encoding a polypeptide having GnTIII activity results in an MRD-containing antibody with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an MRD-containing antibody of the present invention, such as a chimeric, primatized or humanized antibody. In another embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in U.S. Provisional Pat. Appl. No. 60/495,142 and U.S. Pat. Appl. Publ. No. 2004/0241817, each of which is herein incorporated by reference.

The MRD-containing antibodies with altered glycosylation produced by the host cells of the invention typically exhibit increased Fc receptor binding affinity and/or increased effector function as a result of the modification of the host cell (e.g., by expression of a glycosyltransferase gene). The increased Fc receptor binding affinity can be increased binding to a Fcγ activating receptor, such as the FcγRIIIa receptor. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

VII. Uses of Antibody-MRD Fusions

The MRD-containing antibodies described herein are useful in a variety of applications including, but not limited to, therapeutic treatment methods, such as the treatment of cancer. In certain embodiments, the MRD-containing antibodies are useful for inhibiting tumor growth, reducing neovascularization, reducing angiogenesis, inducing differentiation, reducing tumor volume, and/or reducing the tumorigenicity of a tumor. The methods of use may be in vitro, ex vivo, or in vivo methods.

In one embodiment, the MRD-containing antibodies are useful for detecting the presence of a factor or multiple factors (e.g., antigens or organisms) in a biological sample. The term "detecting" as used herein encompasses quantitative or qualitative detection. In certain embodiments, a biological sample comprises a cell or tissue. In certain embodiments, such tissues include normal and/or cancerous tissues.

The present invention contemplates therapeutic compositions useful for practicing the therapeutic methods described herein. In one embodiment, therapeutic compositions of the present invention contain a physiologically tolerable carrier together with at least one species of antibody comprising an MRD as described herein, dissolved or dispersed therein as an active ingredient. In another embodiment, therapeutic compositions of the present invention contain a physiologically tolerable carrier together with at least one species of an MRD as described herein, dissolved or dispersed therein as an active ingredient. In a preferred embodiment, the therapeutic composition is not immunogenic when administered to a human patient for therapeutic purposes.

The preparation of a pharmacological composition that contains active ingredients dissolved or dispersed therein is well understood in the art. Typically such compositions are prepared as sterile injectables either as liquid solutions or suspensions, aqueous or nonaqueous. However, solid forms suitable for solution, or suspensions, in liquid prior to use can also be prepared. The preparation can also be emulsified. Thus, an antibody—MRD containing composition can take the form of solutions, suspensions, tablets, capsules, sustained release formulations or powders, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water.

Exemplary of such additional liquid phases are glycerin, vegetable oils such as cottonseed oil, organic esters such as ethyl oleate, and water-oil emulsions.

In one embodiment, a therapeutic composition contains an antibody comprising a MRD of the present invention, typically in an amount of at least 0.1 weight percent of antibody per weight of total therapeutic composition. A weight percent is a ratio by weight of antibody total composition. Thus, for example, 0.1 weight percent is 0.1 grams of antibody-MRD per 100 grams of total composition.

An antibody-containing therapeutic composition typically contains about 10 micrograms (μg) per milliliter (ml) to about 100 milligrams (mg) per ml of antibody as active ingredient per volume of composition, and more preferably contains about 1 mg/ml to about 10 mg/ml (i.e., about 0.1 to 1 weight percent).

A therapeutic composition in another embodiment contains a polypeptide of the present invention, typically in an amount of at least 0.1 weight percent of polypeptide per weight of total therapeutic composition. A weight percent is a ratio by weight of polypeptide total composition. Thus, for example, 0.1 weight percent is 0.1 grams of polypeptide per 100 grams of total composition.

Preferably, a polypeptide-containing therapeutic composition typically contains about 10 micrograms (ug) per milliliter (ml) to about 100 milligrams (mg) per ml of polypeptide as active ingredient per volume of composition, and more preferably contains about 1 mg/ml to about 10 mg/ml (i.e., about 0.1 to 1 weight percent).

In view of the benefit of using human, humanized or chimeric antibodies in vivo in human patients, the presently described antibody-MRD molecules are particularly well suited for in vivo use as a therapeutic reagent. The method comprises administering to the patient a therapeutically effective amount of a physiologically tolerable composition containing an antibody-MRD molecule of the invention.

The dosage ranges for the administration of the antibody-MRD molecule of the invention are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

As shown in the examples herein, an antibody-MRD molecule can have a similar PK profile to the corresponding antibody. Thus, in some embodiments, an antibody-MRD is administered in a dosing concentration and regimen that is the same as the antibody component of the antibody-MRD molecule alone (e.g., a commercial antibody, biosimilar, or a biobetter thereof). In other embodiments, an antibody-MRD is administered in a dosing concentration and regimen that is similar, or substantially the same as the antibody component of the antibody-MRD molecule alone.

A therapeutically effective amount of an antibody-MRD molecule of the invention is typically an amount of antibody such that when administered in a physiologically tolerable composition is sufficient to achieve a plasma concentration of from about 0.1 microgram (gig) per milliliter (ml) to about 100 μg/ml, preferably from about 1 μg/ml to about 5 μg/ml, and usually about 5 μg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

In some embodiments, the antibody-MRD molecule is administered at about 1 mg/kg to about 50 mg/kg, about 1 mg/kg to about 25 mg/kg, about 1 mg/kg to about 20 mg/kg, about 1 mg/kg to about 15 mg/kg, about 1 mg/kg to about 10 mg/kg, or about 1 mg/kg to about 5 mg/kg.

In some embodiments, the interval between doses is about twice a week, about every week, about every other week, or about every three weeks.

In some embodiments, the antibody-MRD is administered first at a higher loading dose and subsequently at a lower maintenance dose.

The antibody-MRD molecule of the invention can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, antibody-MRD molecules of the invention can be administered intravenously, intraperitoneally, intramuscularly, subcutaneously, intracavity, transdermally, and can be delivered by peristaltic means. MRD-containing antibodies can also be delivered by aerosol to airways and lungs. In some embodiments, the antibody-MRD molecule is administered by intravenous infusion. In some embodiments, the antibody-MRD molecule is administered by subcutaneous injection.

The therapeutic compositions containing an antibody-MRD molecule of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. In a specific embodiment, the therapeutic compositions containing a human monoclonal antibody or a polypeptide are administered subcutaneously.

The compositions of the invention are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In other embodiments, the invention provides a method for treating or preventing a disease, disorder, or injury comprising administering a therapeutically effective amount or prophylactically effective amount of antibody-MRD molecule to a subject in need thereof. In some embodiments, the disease, disorder or injury is cancer. In other embodiments, the disease, disorder or injury is a disease or disorder of the immune system, such as inflammation or an autoimmune disease.

MRD-containing antibodies are expected to have at least the same therapeutic efficacy as the antibody contained in the MRD antibody containing antibody when administered alone. Accordingly, it is envisioned that the MRD-containing antibodies can be administered to treat or prevent a disease, disorder, or injury for which the antibody contained in the MRD-containing antibody, or an antibody that functions in the same way as the antibody contained in the MRD-containing antibody, demonstrates a reasonably correlated beneficial activity in treating or preventing such disease, disorder or injury. This beneficial activity can be demonstrated in vitro, in an in vivo animal model, or in human clinical trials. In one embodiment, an MRD-containing antibody is administered to treat or prevent a disease, disorder or injury for which the antibody component of the MRD-containing antibody, or an antibody that functions in the same way as the antibody contained in the MRD-containing antibody, demonstrates therapeutic or prophylactic efficacy in vitro or in an animal model. In another embodiment, an MRD-containing antibody is administered to treat or prevent a disease, disorder or injury for which the antibody component of the MRD-containing antibody, or an antibody that functions in the same way as the antibody contained in the MRD-containing antibody, demonstrates therapeutic or prophylactic efficacy in humans. In another embodiment, an MRD-containing antibody is administered to treat or prevent a disease, disorder or injury for which the antibody component of the MRD-containing antibody, or an antibody that functions in the same way as the antibody contained in the MRD-containing antibody, has been approved by a regulatory authority for use in such treatment or prevention.

In another embodiment, an MRD-containing antibody is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, demonstrates therapeutic or prophylactic efficacy in vitro or in an animal model. In another embodiment, an MRD-containing antibody is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, demonstrates therapeutic or prophylactic efficacy in humans. In another embodiment, an MRD-containing antibody, is administered in combination with another therapeutic to treat or prevent a disease, disorder or injury for which the antibody component of the MRD-containing antibody, or an antibody that functions in the same way as the antibody contained in the MRD antibody, in combination with the therapeutic, or a different therapeutic that functions in the same way as the therapeutic in the combination, has been approved by a regulatory authority for use in such treatment or prevention.

In one embodiment, the invention provides a method of treating cancer comprising administering a therapeutically effective amount of a VEGFA or VEGFR binding MRD-containing antibody to a patient in need thereof. In a specific embodiment, the invention provides a method of treating cancer comprising administering a therapeutically effective amount of bevacizumab comprising at least one MRD to a patient in need thereof. In one embodiment, the invention provides a method of treating colorectal cancer by administering a therapeutically effective amount of bevacizumab comprising at least one MRD to a patient having colorectal cancer. In another embodiment, the invention provides a method of treating breast cancer by administering a therapeutically effective amount of bevacizumab comprising at least one MRD to a patient having breast cancer. In another embodiment, the invention provides a method of treating non-small cell lung carcinoma by administering a therapeutically effective amount of bevacizumab comprising at least one MRD to a patient having non-small cell lung carcinoma. In other embodiments, therapeutic effective amounts of bevacizumab comprising at least one MRD are administered to treat a patient having metastatic colorectal cancer, metastatic breast cancer, metastatic pancreatic cancer, or metastatic non-small cell lung carcinoma. In another embodiment, the invention provides a method of treating cancer by administering a therapeutically effective amount of bevacizumab comprising at least one MRD to a patient having renal cell carcinoma, glioblastoma multiforme, ovarian cancer, prostate cancer, liver cancer or pancreatic cancer.

Combination therapy and compositions including MRD-containing antibodies of the invention and another therapeutic are also encompassed by the invention, as are methods of treatment using these compositions. In other embodiments, compositions of the invention are administered alone or in combination with one or more additional therapeutic agents. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the therapeutic compounds or agents given first, followed by the second. Accordingly, in one embodiment, a VEGFA or VEGFR binding MRD-containing antibody is administered in combination with 5-fluorouracil, carboplatin, paclitaxel, or interferon alpha. In another embodiment, bevacizumab comprising at least one MRD is administered in combination with 5-fluorouracil, carboplatin, paclitaxel, or interferon alpha.

In another embodiment, the invention provides a method of treating macular degeneration comprising administering a therapeutically effective amount of a VEGFA or VEGFR binding MRD-containing antibody to a patient in need thereof. In a specific embodiment, the invention provides a method of treating macular degeneration comprising administering a therapeutically effective amount of bevacizumab comprising at least one MRD to a patient in need thereof. In a specific embodiment, the invention provides a method of treating macular degeneration comprising administering a therapeutically effective amount of ranibizumab comprising at least one MRD to a patient in need thereof.

In some embodiments, the invention provides a method of treating cancer comprising administering a therapeutically effective amount of a ErbB2 (HER2) binding MRD-containing antibody to a patient in need thereof. In various embodiments, the ErbB2-binding MRD-containing antibodies are administered to patients who have been previously shown to respond to another ErbB2-based therapy (e.g., HERCEPTIN®, chemotherapy and/or radiation) or are predicted to respond to another ErbB2-based therapy. In other embodiments, the ErbB2-binding MRD-containing antibodies are administered to patients who have previously failed to respond to another ErbB2-based therapy or are predicted to fail to respond to another ErbB2-based therapy.

In a specific embodiment, the invention provides a method of treating cancer comprising administering a therapeutically effective amount of trastuzumab comprising at least one MRD to a patient in need thereof. In one embodiment, the invention provides a method of treating breast cancer by administering a therapeutically effective amount of trastuzumab comprising at least one MRD to a patient having breast cancer. In other embodiments, therapeutic effective amounts of trastuzumab comprising at least one MRD are administered to treat a patient having metastatic breast cancer.

In another embodiment, an ErbB2(HER2) binding MRD-containing antibody is administered in combination with cyclophosphamide, paclitaxel, docetaxel, carboplatin, anthracycline, or a maytansinoid. In a specific embodiment, trastuzumab comprising at least one MRD is administered in combination with cyclophosphamide, paclitaxel, docetaxel, carboplatin, anthracycline, or a maytansinoid.

In another embodiment, the invention provides a method of treating cancer comprising administering a therapeutically effective amount of a CD20-binding MRD-containing antibody to a patient in need thereof. In a specific embodiment, the invention provides a method of treating a hematologic cancer comprising administering a therapeutically effective amount of rituximab comprising at least one MRD to a patient in need thereof. In one embodiment, the invention provides a method of treating CD20 positive NHL by administering a therapeutically effective amount of bevacizumab comprising at least one MRD to a patient having CD20 positive NHL. In one embodiment, the invention provides a method of treating CD20 positive CLL by administering a therapeutically effective amount of bevacizumab comprising at least one MRD to a patient having CD20 positive CLL.

In another embodiments, a therapeutically effective amount of a CD20-binding MRD-containing antibody is administered in combination with: ludarabine, cyclophosphamide, FC (fludarabine and cyclophosphamide), anthracycline based chemotherapy regimen (e.g., CHOP (cyclophosphamide, adriamycin, vincristine and prednisone)), or CVP (cyclophosphamide, prednisone, and vincristine) chemotherapy. In a specific embodiment, a therapeutically effective amount of bevacizumab comprising at least one MRD is administered in combination with: ludarabine, cyclophosphamide, FC (fludarabine and cyclophosphamide), anthracycline based chemotherapy regimen (e.g., CHOP (cyclophosphamide, adriamycin, vincristine and prednisone)), or CVP (cyclophosphamide, prednisone, and vincristine) chemotherapy.

Any of the antibody-MRD fusions containing antibodies and/or MRDs that bind CD20 can be used according to the methods of treating a disorder associated with CD20, or that can be treated by targeting cells that express CD20 (e.g., hematological cancers and autoimmune disease). In some embodiments, the antibody component of the antibody-MRD-fusion is a member selected from rituximab, ocrelizumab, GA101, and PF-5,230,895.

In another embodiment, the invention provides a method of treating a disorder of the immune system comprising administering a therapeutically effective amount of a CD20-binding MRD-containing antibody to a patient in need thereof. In a specific embodiment, the invention provides a method of treating an autoimmune disease comprising administering a therapeutically effective amount of a CD20-binding MRD-containing antibody to a patient in need thereof. In one embodiment, the invention provides a method of treating an autoimmune disease comprising administering a therapeutically effective amount of a rituximab-MRD-containing antibody to a patient in need thereof. In another embodiment, the invention provides a method of treating rheumatoid arthritis comprising administering a therapeutically effective amount of a rituximab-MRD-containing antibody to a patient in need thereof. In another embodiment, the invention provides a method of treating systemic lupus erythematosus comprising administering a therapeutically effective amount of a rituximab-MRD-containing antibody to a patient in need thereof. In another embodiment, the invention provides a method of treating multiple sclerosis comprising administering a therapeutically effective amount of a rituximab-MRD-containing antibody to a patient in need thereof.

In an additional embodiment, the invention provides a method of treating an autoimmune disease comprising administering a therapeutically effective amount of a ocrelizumab-MRD-containing antibody to a patient in need thereof. In one embodiment, the invention provides a method of treating rheumatoid arthritis comprising administering a therapeutically effective amount of a ocrelizumab-MRD-containing antibody to a patient in need thereof. In a further embodiment, the invention provides a method of treating systemic lupus erythematosus comprising administering a therapeutically effective amount of a ocrelizumab-MRD-containing antibody to a patient in need thereof. In another embodiment, the invention provides a method of treating multiple sclerosis comprising administering a therapeutically effective amount of a ocrelizumab-MRD-containing antibody to a patient in need thereof.

In an additional embodiment, the invention provides a method of treating an autoimmune disease comprising administering a therapeutically effective amount of a PF5, 230,895-MRD-containing antibody to a patient in need thereof. In one embodiment, the invention provides a method of treating rheumatoid arthritis comprising administering a therapeutically effective amount of a PF5,230,895-MRD-containing antibody to a patient in need thereof. In a further embodiment, the invention provides a method of treating systemic lupus erythematosus comprising administering a therapeutically effective amount of a PF5,230,895-MRD-containing antibody to a patient in need thereof. In another embodiment, the invention provides a method of treating multiple sclerosis comprising administering a therapeutically effective amount of a PF5,230,895-MRD-containing antibody to a patient in need thereof.

In some embodiments, the invention provides a method of treating a disorder of the immune system comprising administering a therapeutically effective amount of a TNF-binding MRD-containing antibody to a patient in need thereof. In various embodiments, the TNF-binding MRD-containing antibodies are administered to patients who have been previously shown to respond to another TNF-based therapy or are predicted to respond to another TNF-based therapy (e.g., TNF antagonists such as Anti-TNFs (e.g., HUMIRA®), ENBREL®, CD28 antagonists, CD-20 antagonists, and IL6/IL6R antagonists). In other embodiments, the TNF-binding MRD-containing antibodies are administered to patients who have previously failed to respond to another TNF-based therapy or are predicted to fail to respond to another TNF-based therapy.

In other embodiments, the TNF-binding MRD-containing antibodies are administered to patients who have been previously shown to respond to an autoimmune disease based therapy or are predicted to respond to other autoimmune disease based therapies (e.g., TNF antagonists such as anti-TNFs (e.g., HUMIRA®), ENBREL®, CD28 antagonists, CD-20 antagonists, BLyS antagonists, and IL6/IL6R antagonists). In other embodiments, the TNF-binding MRD-containing antibodies are administered to patients who have previously failed to respond to another autoimmune disease based therapy or are predicted to fail to respond to another autoimmune disease based therapy.

In a specific embodiment, the invention provides a method of treating a disorder of the immune system comprising administering a therapeutically effective amount of adalimumab comprising at least one MRD to a patient in need thereof. In one embodiment, the invention provides a method of treating an autoimmune disease by administering a therapeutically effective amount of adalimumab comprising at least one MRD to a patient in need thereof. In one embodiment, the invention provides a method of treating rheumatoid arthritis, by administering a therapeutically effective amount of adalimumab comprising at least one MRD to a patient in need thereof. In one embodiment, the invention provides a method of treating an inflammatory disorder, by administering a therapeutically effective amount of adalimumab comprising at least one MRD to a patient in need thereof. In another embodiment, the invention provides a method of treating Crohn's disease, by administering a therapeutically effective amount of adalimumab comprising at least one MRD to a patient in need thereof. In another embodiment, the invention provides a method of treating ulcerative colitis, by administering a therapeutically effective amount of adalimumab comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of adalimumab comprising at least one MRD to a patient in need thereof.

In an additional embodiment, the invention provides a method of treating a disorder of the immune system comprising administering a therapeutically effective amount of ATN-103 comprising at least one MRD to a patient in need thereof. In one embodiment, the invention provides a method of treating an inflammatory disorder, by administering a therapeutically effective amount of ATN-103 comprising at least one MRD to a patient in need thereof. In another embodiment, the invention provides a method of treating an autoimmune disease, by administering a therapeutically effective amount of ATN-103 comprising at least one MRD to a patient in need thereof. In a further embodiment, the invention provides a method of treating rheumatoid arthritis, by administering a therapeutically effective amount of ATN-103 comprising at least one MRD to a patient in need thereof. In another embodiment, the invention provides a method of treating Crohn's disease, by administering a therapeutically effective amount of ATN-103 comprising at least one MRD to a patient in need thereof. In an additional embodiment, the invention provides a method of treating ulcerative colitis, by administering a therapeutically effective amount of ATN-103 comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of ATN-103 comprising at least one MRD to a patient in need thereof.

In a specific embodiment, the invention provides a method of treating a disorder of the immune system comprising administering a therapeutically effective amount of infliximab comprising at least one MRD to a patient in need thereof. In one embodiment, the invention provides a method of treating an inflammatory disorder, by administering a therapeutically effective amount of infliximab comprising at least one MRD to a patient in need thereof. In one embodiment, the invention provides a method of treating an autoimmune disease, by administering a therapeutically effective amount of infliximab comprising at least one MRD to a patient in need thereof. In one embodiment, the invention provides a method of treating rheumatoid arthritis, by administering a therapeutically effective amount of infliximab comprising at least one MRD to a patient in need thereof. In another embodiment, the invention provides a method of treating Crohn's disease, by administering a therapeutically effective amount of infliximab comprising at least one MRD to a patient in need thereof. In another embodiment, the invention provides a method of treating ulcerative colitis, by administering a therapeutically effective amount of infliximab comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of infliximab comprising at least one MRD to a patient in need thereof.

In an additional embodiment, the invention provides a method of treating a disorder of the immune system comprising administering a therapeutically effective amount of a IL22-binding MRD-containing antibody to a patient in need thereof. In a specific embodiment, the invention provides a method of treating a disorder of the immune system comprising administering a therapeutically effective amount of PF5,212,367 (ILV-094) comprising at least one MRD to a patient in need thereof. In one embodiment, the invention provides a method of treating an autoimmune disease by administering a therapeutically effective amount of PF5,212,367 comprising at least one MRD to a patient in need thereof. In one embodiment, the invention provides a method of treating rheumatoid arthritis, by administering a therapeutically effective amount of PF5,212,367 comprising at least one MRD to a patient in need thereof. In one embodiment, the invention provides a method of treating an inflammatory disorder, by administering a therapeutically effective amount of PF5,212,367 comprising at least one MRD to a patient in need thereof. In another embodiment, the invention provides a method of treating Crohn's disease, by administering a therapeutically effective amount of PF5,212,367 comprising at least one MRD to a patient in need thereof. In a further embodiment, the invention provides a method of treating ulcerative colitis, by administering a therapeutically effective amount of PF5,212,367 comprising at least one MRD to a patient in need thereof. In another embodiment, the invention provides a method of treating psoriatic arthritis, ankylosing spondylitis, psoriasis, or juvenile idiopathic arthritis by administering a therapeutically effective amount of PF5,212,367 comprising at least one MRD to a patient in need thereof.

In an additional embodiment, the invention provides a method of treating a disorder of the immune system comprising administering a therapeutically effective amount of a alpha4 integrin-binding MRD-containing antibody to a patient in need thereof. In a specific embodiment, the invention provides a method of treating a disorder of the immune system comprising administering a therapeutically effective amount of natalizumab comprising at least one MRD to a patient in need thereof. In one embodiment, the invention provides a method of treating an autoimmune disease by administering a therapeutically effective amount of natalizumab comprising at least one MRD to a patient in need thereof. In another embodiment, the invention provides a method of treating rheumatoid arthritis, by administering a therapeutically effective amount of natalizumab comprising at least one MRD to a patient in need thereof. In a further embodiment, the invention provides a method of treating systemic lupus erythematosus comprising administering a therapeutically effective amount of a natalizumab-MRD-containing antibody to a patient in need thereof. In another embodiment, the invention provides a method of treating multiple sclerosis comprising administering a therapeutically effective amount of a natalizumab-MRD-containing antibody to a patient in need thereof. In a further embodiment, the invention provides a method of treating an inflammatory disorder, by administering a therapeutically effective amount of natalizumab comprising at least one MRD to a patient in need thereof. In another embodiment, the invention provides a method of treating Crohn's disease, by administering a therapeutically effective amount of natalizumab comprising at least one MRD to a patient in need thereof. In an additional embodiment, the invention provides a method of treating ulcerative colitis, by administering a therapeutically effective amount of natalizumab comprising at least one MRD to a patient in need thereof. In another embodiment, the invention provides a method of treating multiple sclerosis, by administering a therapeutically effective amount of natalizumab comprising at least one MRD to a patient in need thereof. In an additional embodiment, the invention provides a method of treating psoriatic arthritis, ankylosing spondylitis, psoriasis, or juvenile idiopathic arthritis by administering a therapeutically effective amount of natalizumab comprising at least one MRD to a patient in need thereof.

In an additional embodiment, the invention provides a method of treating a disorder of the immune system comprising administering a therapeutically effective amount of a CD40L-binding MRD-containing antibody to a patient in need thereof. In a specific embodiment, the invention provides a method of treating a disorder of the immune system comprising administering a therapeutically effective amount of CDP7657 comprising at least one MRD to a patient in need thereof. In one embodiment, the invention provides a method of treating an autoimmune disease by administering a therapeutically effective amount of CDP7657 comprising at least one MRD to a patient in need thereof. In another embodiment, the invention provides a method of treating rheumatoid arthritis, by administering a therapeutically effective amount of CDP7657 comprising at least one MRD to a patient in need thereof. In a further embodiment, the invention provides a method of treating systemic lupus erythematosus comprising administering a therapeutically effective amount of a CDP7657-MRD-containing antibody to a patient in need thereof. In another embodiment, the invention provides a method of treating multiple sclerosis comprising administering a therapeutically effective amount of a CDP7657-MRD-containing antibody to a patient in need thereof. In one embodiment, the invention provides a method of treating an inflammatory disorder, by administering a therapeutically effective amount of CDP7657 comprising at least one MRD to a patient in need thereof. In another embodiment, the invention provides a method of treating Crohn's disease, by administering a therapeutically effective amount of CDP7657 comprising at least one MRD to a patient in need thereof. In a further embodiment, the invention provides a method of treating ulcerative colitis, by administering a therapeutically effective amount of CDP7657 comprising at least one MRD to a patient in need thereof. In an additional embodiment, the invention provides a method of treating psoriatic arthritis, ankylosing spondylitis, psoriasis, or juvenile idiopathic arthritis by administering a therapeutically effective amount of CDP7657 comprising at least one MRD to a patient in need thereof.

In another embodiment, the invention provides a method of treating a disorder of the immune system comprising administering a therapeutically effective amount of a TWEAK-binding MRD-containing antibody to a patient in need thereof. In a specific embodiment, the invention provides a method of treating a disorder of the immune system comprising administering a therapeutically effective amount of the Biogen TWEAK antibody (that has entered phase 1 clinical trials) comprising at least one MRD to a patient in need thereof. In one embodiment, the invention provides a method of treating an autoimmune disease by administering a therapeutically effective amount of the Biogen TWEAK antibody comprising at least one MRD to a patient in need thereof. In one embodiment, the invention provides a method of treating rheumatoid arthritis, by administering a therapeutically effective amount of the Biogen TWEAK antibody comprising at least one MRD to a patient in need thereof. In a further embodiment, the invention provides a method of treating systemic lupus erythematosus comprising administering a therapeutically effective amount of the Biogen TWEAK antibody comprising at least one MRD to a patient in need thereof. In another embodiment, the invention provides a method of treating multiple sclerosis comprising administering a therapeutically effective amount of the Biogen TWEAK antibody comprising at least one MRD to a patient in need thereof. In another embodiment, the invention provides a method of treating an inflammatory disorder, by administering a therapeutically effective amount of the Biogen TWEAK antibody comprising at least one MRD to a patient in need thereof. In an additional embodiment, the invention provides a method of treating Crohn's disease, by administering a therapeutically effective amount of the Biogen TWEAK antibody comprising at least one MRD to a patient in need thereof. In another embodiment, the invention provides a method of treating ulcerative colitis, by administering a therapeutically effective amount of the Biogen TWEAK antibody comprising at least one MRD to a patient in need thereof. In a further embodiment, the invention provides a method of treating psoriatic arthritis, ankylosing spondylitis, psoriasis, or juvenile idiopathic arthritis by administering a therapeutically effective amount of the Biogen TWEAK antibody comprising at least one MRD to a patient in need thereof.

In an additional embodiment, the invention provides a method of treating a disorder of the immune system comprising administering a therapeutically effective amount of a CD25-binding MRD-containing antibody to a patient in need thereof. In a specific embodiment, the invention provides a method of treating a disorder of the immune system comprising administering a therapeutically effective amount of daclizumab comprising at least one MRD to a patient in need thereof. In one embodiment, the invention provides a method of treating an autoimmune disease by administering a therapeutically effective amount of daclizumab comprising at least one MRD to a patient in need thereof. In another embodiment, the invention provides a method of treating rheumatoid arthritis, by administering a therapeutically effective amount of daclizumab comprising at least one MRD to a patient in need thereof. In a further embodiment, the invention provides a method of treating systemic lupus erythematosus comprising administering a therapeutically effective amount of a daclizumab-MRD-containing antibody to a patient in need thereof. In another embodiment, the invention provides a method of treating multiple sclerosis comprising administering a therapeutically effective amount of a daclizumab-MRD-containing antibody to a patient in need thereof. In one embodiment, the invention provides a method of treating an inflammatory disorder, by administering a therapeutically effective amount of daclizumab comprising at least one MRD to a patient in need thereof. In another embodiment, the invention provides a method of treating Crohn's disease, by administering a therapeutically effective amount of daclizumab comprising at least one MRD to a patient in need thereof. In a further embodiment, the invention provides a method of treating ulcerative colitis, by administering a therapeutically effective amount of daclizumab comprising at least one MRD to a patient in need thereof. In an additional embodiment, the invention provides a method of treating psoriatic arthritis, ankylosing spondylitis, psoriasis, or juvenile idiopathic arthritis by administering a therapeutically effective amount of daclizumab comprising at least one MRD to a patient in need thereof.

Antibody-MRD fusion proteins having antibodies and/or MRDs that bind cancer antigens or other targets associated with cancer establishment, progression, and/or metastasis are described herein or otherwise known in the art and may be used according to the methods of the invention to treat cancer.

In another embodiment, the invention provides a method of treating cancer comprising administering a therapeutically effective amount of a EGFR-binding MRD-containing antibody to a patient in need thereof. In a specific embodiment, the invention provides a method of treating cancer comprising administering a therapeutically effective amount of cetuximab comprising at least one MRD to a patient in need thereof. In one embodiment, the invention provides a method of treating cancer by administering a therapeutically effective amount of cetuximab comprising at least one MRD to a patient having colorectal cancer. In another embodiment, therapeutic effective amounts of cetuximab comprising at least one MRD are administered to treat a patient having metastatic colorectal cancer, metastatic breast cancer, metastatic pancreatic cancer, or metastatic non-small cell lung carcinoma. In one embodiment, the invention provides a method of treating cancer by administering a therapeutically effective amount of cetuximab comprising at least one MRD to a patient having squamous cell carcinoma of the head and neck.

In another embodiment, a therapeutically effective amount of an EGFR-binding MRD-containing antibody is administered in combination with irinotecan, FOLFIRI, platinum-based chemotherapy, or radiation therapy. In a specific embodiment, a therapeutically effective amount of cetuximab comprising at least one MRD is administered in combination with irinotecan, FOLFIRI, platinum-based chemotherapy, or radiation therapy In certain embodiments, the invention provides a method of treating cancer comprising administering a therapeutically effective amount of an MRD-antibody described herein to a patient in need thereof.

In one embodiment, the invention provides a method of treating a solid cancer by administering a therapeutically effective amount of a solid cancer binding MRD-antibody described herein to a patient in need thereof.

In some embodiments, the invention provides a method of treating a solid cancer by administering a therapeutically effective amount of an MRD-antibody that binds to a member selected from the group consisting of: IGFR1, ALK1, p-cadherin, CRYPTO, and alpha5 b1 integrin. In other embodiments, the antibody component of the administered MRD-antibody is a member selected from the group: figitumumab, CP-870893, PF-3,732,010, PF-3,446,962, volociximab, BIIB022, and the Biogen CRYPTO antibody.

In some embodiments, the MRD-containing antibodies described herein are useful for treating cancer. Thus, in some embodiments, the invention provides methods of treating cancer comprise administering a therapeutically effective amount of a MRD-containing antibody to a subject (e.g., a subject in need of treatment). In certain embodiments, the cancer is a cancer selected from the group consisting of colorectal cancer, pancreatic cancer, lung cancer, ovarian cancer, liver cancer, breast cancer, brain cancer, kidney cancer, prostate cancer, gastrointestinal cancer, melanoma, cervical cancer, bladder cancer, glioblastoma, and head and neck cancer. In certain embodiments, the cancer is breast cancer. In certain embodiments, the subject is a human.

Other examples of cancers or malignancies that may be treated with MRD containing antibodies and MRDs include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, and Wilms' Tumor.

In some embodiments, MRD-containing antibodies are useful for inhibiting tumor growth. In certain embodiments, the method of inhibiting the tumor growth comprises contacting the cell with a MRD-containing antibody in vitro. For example, an immortalized cell line or a cancer cell line that expresses an MRD target and/or an antibody target is cultured in medium to which is added the MRD-containing antibody to inhibit tumor growth. In some embodiments, tumor cells are isolated from a patient sample such as, for example, a tissue biopsy, pleural effusion, or blood sample and cultured in medium to which is added a MRD-containing antibody to inhibit tumor growth.

In some embodiments, the method of inhibiting tumor growth comprises contacting the tumor or tumor cells with a therapeutically effective amount of the MRD-containing antibody in vivo. In certain embodiments, contacting a tumor or tumor cell is undertaken in an animal model. For example, MRD-containing antibodies can be administered to xenografts in immunocompromised mice (e.g., NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a MRD-containing antibody to inhibit tumor cell growth. In some embodiments, the MRD-containing antibody is administered at the same time or shortly after introduction of tumorigenic cells into the animal to prevent tumor growth. In some embodiments, the MRD-containing antibody is administered as a therapeutic after the tumorigenic cells have grown to a specified size.

In certain embodiments, the method of inhibiting tumor growth comprises administering to a subject a therapeutically effective amount of a MRD-containing antibody. In certain embodiments, the subject is a human. In certain embodiments, the subject has a tumor or has had a tumor removed. In certain embodiments, the tumor expresses an antibody target. In certain embodiments, the tumor overexpresses the MRD target and/or the antibody target.

In certain embodiments, the inhibited tumor growth is selected from the group consisting of brain tumor, colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a breast tumor.

In additional embodiments, MRD-containing antibodies are useful for reducing tumorigenicity. Thus, in some embodiments, the method of reducing the tumorigenicity of a tumor in a subject, comprises administering a therapeutically effective amount of a MRD-containing antibody to the subject. In certain embodiments, the tumor comprises cancer stem cells. In certain embodiments, the frequency of cancer stem cells in the tumor is reduced by administration of the agent.

In other embodiments, MRD-containing antibodies are useful for diagnosing, treating or preventing a disorder of the immune system. In one embodiment, the disorder of the immune system is inflammation or an inflammatory disorder. In a more specific embodiment, the inflammatory disorder is selected from the group consisting of asthma, allergic disorders, and rheumatoid arthritis.

In another embodiment, the disorder of the immune system is an autoimmune disease. Autoimmune disorders, diseases, or conditions that may be diagnosed, treated or prevented using MRD-containing antibodies include, but are not limited to, autoimmune hemolytic anemia, autoimmune neonatal thrombocytopenia, idiopathic thrombocytopenia purpura, autoimmune neutiopenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis, systemic lupus erhythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders.

In another embodiment the disorder of the immune system diagnosed, treated or prevented using MRD-containing antibodies is selected from the group consisting of: Crohn's disease, Systemic lupus erythematosus (SLE), inflammatory bowel disease, psoriasis, diabetes, ulcerative colitis, multiple sclerosis, and rheumatoid arthritis. In a preferred embodiment, the autoimmune disease is rheumatoid arthritis.

In other embodiments, MRD-containing antibodies are useful for treating or preventing a metabolic disease or disorder.

In other embodiments, the MRD-containing antibodies are useful for treating or preventing a cardiovascular disease or disorder. In one embodiment, the MRD-containing antibodies are useful for treating or preventing thrombosis, atherosclerosis, heart attack, or stroke.

In other embodiments, the MRD-containing antibodies are useful for treating or preventing a musculoskeletal disease or disorder.

In other embodiments, the MRD-containing antibodies are useful for treating or preventing a skeletal disease or disorder. In one embodiment, the MRD-containing antibodies are useful for treating or preventing osteoporosis.

In other embodiments, the disease, disorder, or injury treated or prevented with an MRD-containing antibody or MRD of the invention is neurological. In one embodiment, the neurological disease, disorder or injury in pain such as, acute pain or chronic pain.

In some embodiments, the invention provides a method of treating or ameliorating pain by administering a therapeutically effective amount of a pain target binding MRD-antibody, to a patient in need thereof. In additional embodiments, the invention provides a method of treating or ameliorating pain by administering a therapeutically effective amount of an NGF binding MRD-antibody, to a patient in need thereof. In further embodiments, the invention provides a method of treating or ameliorating pain by administering a therapeutically effective amount of tanezumumab (e.g., Pfizer) comprising an MRD, to a patient in need thereof.

In additional embodiments, an MRD-containing antibody binds to 2, 3, 4, or 5 targets selected from NGF, IL6R, IL6, CB2, SCN9A (Naν1.7). These MRD-containing antibodies have applications in treating an ameliorating pain.

In additional embodiments, the invention provides a method of treating or ameliorating Alzheimer's by administering a therapeutically effective amount of an Alzheimer's target binding MRD-antibody, to a patient in need thereof. In additional embodiments, the invention provides a method of treating or ameliorating Alzheimer's by administering a therapeutically effective amount of a beta amyloid binding MRD-antibody, to a patient in need thereof. In additional embodiments, the invention provides a method of treating or ameliorating Alzheimer's by administering a therapeutically effective amount of RN1219 (PF-4,360,365; Pfizer) comprising an MRD, to a patient in need thereof.

In additional embodiments, an MRD-containing antibody binds to 1, 2, or 3 targets selected from NGF, beta amyloid and IGF1R. These MRD-containing antibodies have applications in treating, ameliorating and delaying the onset of pre-dementia and dementia, including Alzheimer's.

In additional embodiments, the invention provides a method of treating or ameliorating multiple sclerosis by administering a therapeutically effective amount of an multiple sclerosis target binding MRD-antibody, to a patient in need thereof. In additional embodiments, the invention provides a method of treating or ameliorating multiple sclerosis by administering a therapeutically effective amount of a LINGO binding MRD-antibody, to a patient in need thereof. In additional embodiments, the invention provides a method of treating or ameliorating multiple sclerosis by administering a therapeutically effective amount of the Biogen LINGO antibody comprising an MRD, to a patient in need thereof. In further embodiments, the invention provides a method of treating or ameliorating multiple sclerosis by administering a therapeutically effective amount of the natalizumab (e.g., TYSABRI®; Biogen) comprising an MRD, to a patient in need thereof. In an additional embodiment, the invention provides a method of treating or ameliorating multiple sclerosis by administering a therapeutically effective amount of the Biogen LINGO antibody comprising an MRD, to a patient in need thereof.

In an additional embodiment, the invention provides a method of treating or ameliorating multiple sclerosis by administering a therapeutically effective amount of a CD20 binding MRD-antibody, to a patient in need thereof. In one embodiment, the invention provides a method of treating or ameliorating multiple sclerosis by administering a therapeutically effective amount of the ocrelizumab (Biogen Idec) comprising an MRD, to a patient in need thereof.

In other embodiments, MRD-containing antibodies are useful for treating or preventing an infectious disease. Infectious diseases that may be treated or prevented with MRD-containing antibodies include diseases associated with yeast, fungal, viral and bacterial infections. Viruses causing viral infections which can be treated or prevented with MRD-containing antibodies include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), adrenoviruses (e.g., lassa fever virus), paramyxoviruses (e.g., morbilbivirus virus, human respiratory syncytial virus, mumps, and pneumovirus), adrenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C (including avian influenza, e.g., H5N1 subtype)), papovaviruses (e.g., papillomaviruses), picomaviruses (e.g., rhinoviruses, enteroviruses and hepatitis A viruses), poxviruses, reoviruses (e.g., rotaviruses), togaviruses (e.g., rubella virus), rhabdoviruses (e.g., rabies virus). Microbial pathogens causing bacterial infections include, but are not limited to, *Streptococcus pyogenes, Streptococcus pneumoniae, Neisseria* gonorrhoea, Neissetia *meningitidis, Corynebacterium diphtheriae, Clostridium botulinum, Clostridium pefringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (*Vibrio*) fetus, *Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigellaflexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia Lsutsugumushi, Chlamydia* spp., and *Helicobacter pylori.*

In a preferred embodiment, the he MRD-containing antibodies are administered to treat or prevent human immunodeficiency virus (HIV) infection or AIDS, botulism, anthrax, or *clostridium difficile.*

VIII MRD Linked Compounds that are not Antibodies

In a distinct group of embodiments, one or more MRDs of the invention are operably linked to the amino and/or carboxyl terminus of an immunoglobulin fragment, such as Fab, Fab', F(ab')2, pFc', or Fc. In some embodiments, MRDs are operably linked to a Fab or Fc polypeptide containing an additional Ig domain. In some embodiments, MRDs are operably linked to the amino and/or carboxyl terminus of an immunoglobulin fragment that is also operably linked to an scFv. In other embodiments, the MRDs of the invention are operably linked to an Fc-fusion protein.

According to this group of embodiments, one two, three, four, five, six, seven to ten, or more than ten MRDs are operably linked to the amino terminus and/or carboxyl terminus of the immunoglobulin fragment. These MRDs are optionally linked to one another or to the immunoglobulin fragment via a linker. In one embodiment, one, two, three, four, five, six, seven to ten, or more than ten, of the MRDs operably linked to the amino terminus and/or carboxyl terminus of the immunoglobulin fragment are the same. In another embodiment, one, two, three, four, five, six, seven to ten, or more than ten, of the MRDs operably linked to the amino terminus and/or carboxyl terminus of the immunoglobulin fragment are different.

The MRDs operably linked to the immunoglobulin fragment can be monomeric (i.e., containing one MRD at the terminus of a peptide chain optionally connected by a linker) or multimeric (i.e., containing more than one MRD in tandem optionally connected by a linker). The MRDs can be homo-multimeric (i.e., containing more than one of the same MRD in tandem optionally connected by linker(s) (e.g., homodimers, homotrimers, homotetramers etc.)) or hetero-multimeric (i.e., containing two or more MRDs in which there are at least two different MRDs optionally connected by linker(s) where all or some of the MRDs linked to a particular terminus are different (e.g., heterodimer)). In one embodiment, two different monomeric MRDs are located at different termini of the immunoglobulin fragment. In another embodiment, three, four, five, six, or more different monomeric MRDs are located at different termini of the immunoglobulin fragment.

In an alternative embodiment, the MRD-containing antibody contains at least one dimeric and one monomeric MRD located at different immunoglobulin termini. In another alternative embodiment, the MRD-containing antibody contains at least one homodimeric and one monomeric MRD located at different immunoglobulin termini. In another alternative embodiment, the MRD-containing antibody contains at least one heterodimeric and one monomeric MRD located at different immunoglobulin termini.

In an alternative embodiment, the MRD-containing antibody contains at least one multimeric and one monomeric MRD located at different immunoglobulin termini. In another alternative embodiment, the MRD-containing antibody contains at least one homomultimeric and one monomeric MRD located at different immunoglobulin termini. In another alternative embodiment, the MRD-containing antibody contains at least one heteromultimeric and one monomeric MRD located at different immunoglobulin termini.

Multiple MRDs that are operably linked to the immunoglobulin fragment can target the same target binding site, or two or more different target binding sites. Where the MRDs bind to different target binding sites, the binding sites may be on the same or different target molecules. Similarly, one or more of the MRDs may bind to the same target molecule as the immunoglobulin fragment.

In some embodiments, at least one of the MRDs and if applicable, the immunoglobulin fragment (e.g., where the immunoglobulin fragment is an Fab), bind to their targets simultaneously. In additional embodiments, two, three, four, five, six, seven, eight, nine, ten, or more than ten MRDs, and if applicable the immunoglobulin fragment, bind to their target molecules simultaneously.

The synthesis of MRDs operably linked to an immunoglobulin fragment and the assay of these MRDs and immunoglobulin fragment for their ability to bind, or compete for binding, with one or more targets simultaneously can be routinely accomplished using methods disclosed herein or otherwise known in the art.

In a specific embodiment, one or more of the operably linked MRDs or the immunoglobulin fragment, binds to VEGF. In another specific embodiment, one or more of the operably linked MRDs or the immunoglobulin fragment, binds to the same epitope as ranibizumab (LUCENTIS®). In another specific embodiment, one or more of the operably linked MRDs or the immunoglobulin fragment, competitively inhibits ranibizumab binding to VEGF. In an additional embodiment, the immunoglobulin fragment is an Fab. In a further specific embodiment, the immunoglobulin fragment is ranibizumab.

In another embodiment, the invention provides a method of treating macular degeneration comprising administering a therapeutically effective amount of a VEGFA or VEGFR binding MRD-immunoglobulin fragment fusion to a patient in need thereof. In a specific embodiment, the invention provides a method of treating macular degeneration comprising administering a therapeutically effective amount of a VEGFA or VEGFR binding MRD-Fab fusion to a patient in need thereof. In a specific embodiment, the invention provides a method of treating macular degeneration comprising administering a therapeutically effective amount of MRD-ranibizumab to a patient in need thereof.

In other embodiments the one or more MRDs of the invention are operably linked to the amino and/or carboxyl terminus of an Fc fusion protein. The Fc fusion protein can contain fusions to any protein or polypeptide sequence of therapeutic value, for example, any of the targets or receptors of the targets described herein. For example, the fusions can contain the extracellular domain of receptors or ligands that typically function or display improved cognate-partner binding in multimeric form, including for example, receptors corresponding to the TNF-R superfamily (e.g., TNFR2, TACI, BCMA, HVEM, etc.), IL receptor superfamily (e.g., IL1-R-IL-6R), VEGFR superfamily (e.g., VEGFR1-VEGR3), FGRFR superfamily (e.g., FGFR1-FGFR4), and B7 superfamily (e.g., CTLA)).

In a specific embodiment, one, two, three, four, five, six, or more MRDs are operably linked to a VEGR1/VEGFR2-Fc fusion protein. In another specific embodiment, one or more of the operably linked MRDs bind to the same epitope as aflibercept (Regeneron). In another specific embodiment, one or more of the operably linked MRDs competitively inhibit aflibercept binding to VEGFA or PLGF. In a further specific embodiment, the MRDs are operably linked to aflibercept.

In another embodiment, the invention provides a method of treating cancer comprising administering a therapeutically effective amount of an MRD-VEGFR1/VEGFR2-Fc fusion protein to a patient in need thereof. In a specific embodiment, the invention provides a method of treating colorectal cancer, prostate cancer, or non-small cell lung cancer comprising administering a therapeutically effective amount of a VEGFA or PLGF binding MRD-Fc fusion protein to a patient in need thereof. In a specific embodiment, the invention provides a method of treating macular degeneration comprising administering a therapeutically effective amount of a VEGFA or PLGF binding MRD-Fc fusion protein and irinotecan, 5FU, oxaliplatin, doxetaxel, or FOLFOX6, to a patient in need thereof.

In another embodiment, the invention provides a method of treating cancer comprising administering a therapeutically effective amount of MRD-aflibercept to a patient in need thereof. In a specific embodiment, the invention provides a method of treating colorectal cancer, prostate cancer, or non-small cell lung cancer comprising administering a therapeutically effective amount of MRD-aflibercept to a patient in need thereof. In a specific embodiment, the invention provides a method of treating macular degeneration comprising administering a therapeutically effective amount of MRD-aflibercept and irinotecan, 5FU, oxaliplatin, doxetaxel, or FOLFOX6, to a patient in need thereof.

In a specific embodiment, one, two, three, four, five, six, or more MRDs are operably linked to a CTLA4-Fc fusion protein. In another specific embodiment, one or more of the operably linked MRDs bind to the same epitope as abatacept (ORENCIA®). In another specific embodiment, one or more of the operably linked MRDs competitively inhibits abatacept binding to B7-1 (CD80) or B7-2 (CD86). In a further specific embodiment, the MRDs are operably linked to abatacept. In another specific embodiment, one or more of the operably linked MRDs bind to the same epitope as belatacept (Bristol Myers Squibb). In another specific embodiment, one or more of the operably linked MRDs competitively inhibits belatacept binding to B7-1 (CD80) or B7-2 (CD86). In an additional embodiment, the immunoglobulin fragment is an Fab. In a further specific embodiment, the MRDs are operably linked to belatacept.

In another embodiment, the invention provides a method of suppressing an immune response comprising administering a therapeutically effective amount of a MRD-CTLA4-Fc fusion protein to a patient in need thereof. In a specific embodiment, the invention provides a method suppressing an immune response comprising administering a therapeutically effective amount of MRD-abatacept to a patient in need thereof. In another specific embodiment, the invention provides a method of treating rheumatoid arthritis comprising administering a therapeutically effective amount of MRD-abatacept to a patient in need thereof. In another specific embodiment, the invention provides a method of suppressing an immune response to a graft rejection comprising administering a therapeutically effective amount of MRD-abatacept to a patient in need thereof.

In a specific embodiment, the invention provides a method of suppressing an immune response comprising administering a therapeutically effective amount of MRD-belatacept to a patient in need thereof. In another specific embodiment, the invention provides a method of suppressing an immune response to a graft rejection comprising administering a therapeutically effective amount of MRD-belatacept to a patient in need thereof.

In another specific embodiment, one, two, three, four, five, six, or more MRDs are operably linked to a TNFR2-Fc fusion protein. In another specific embodiment, one or more of the operably linked MRDs bind to the same epitope as etanercept (ENBREL®). In another specific embodiment, one or more of the operably linked MRDs competitively inhibits etanercept binding to TNF alpha. In another embodiment, one or more of the operably linked MRDs binds ANG2. In a further specific embodiment, the MRDs are operably linked to etanercept.

In another embodiment, the invention provides a method of suppressing an immune response comprising administering a therapeutically effective amount of a MRD-TNFR2-Fc fusion protein to a patient in need thereof. In one embodiment, the invention provides a method of treating an autoimmune disease by administering a therapeutically effective amount of a MRD-TNFR2-Fc fusion protein to a patient in need thereof. In one embodiment, the invention provides a method of treating rheumatoid arthritis, by administering a therapeutically effective amount of an MRD-TNFR2-Fc fusion protein to a patient in need thereof. In one embodiment, the invention provides a method of treating an inflammatory disorder, by administering a therapeutically effective amount of an MRD-TNFR2-Fc fusion protein to a patient in need thereof. In another embodiment, the invention provides a method of treating Crohn's disease, by administering a therapeutically effective amount of an MRD-TNFR2-Fc fusion protein to a patient in need thereof. In another embodiment, the invention provides a method of treating ulcerative colitis, by administering a therapeutically effective amount of an MRD-TNFR2-Fc fusion protein to a patient in need thereof. In another embodiment, the invention provides a method of treating psoriatic arthritis, ankylosing spondylitis, psoriasis, or juvenile idiopathic arthritis by administering a therapeutically effective amount of an MRD-TNFR2-Fc fusion protein to a patient in need thereof.

In another embodiment, the invention provides a method of suppressing an immune response comprising administering a therapeutically effective amount of a MRD-etanercept-Fc fusion protein to a patient in need thereof. In one embodiment, the invention provides a method of treating an autoimmune disease by administering a therapeutically effective amount of MRD-etanercept to a patient in need thereof. In one embodiment, the invention provides a method of treating rheumatoid arthritis, by administering a therapeutically effective amount of MRD-etanercept to a patient in need thereof. In one embodiment, the invention provides a method of treating an inflammatory disorder, by administering a therapeutically effective amount of MRD-etanercept to a patient in need thereof. In another embodiment, the invention provides a method of treating Crohn's disease, by administering a therapeutically effective amount of MRD-etanercept to a patient in need thereof. In another embodiment, the invention provides a method of treating ulcerative colitis, by administering a therapeutically effective amount of MRD-etanercept to a patient in need thereof. In another embodiment, the invention provides a method of treating psoriatic arthritis, ankylosing spondylitis, psoriasis, or juvenile idiopathic arthritis by administering a therapeutically effective amount of MRD-etanercept to a patient in need thereof.

In another specific embodiment, one, two, three, four, five, six, or more MRDs are operably linked to a TACI-Fc fusion protein. In another specific embodiment, one or more of the operably linked MRDs bind to the same epitope as atacicept (Merck/Serono). In another specific embodiment, one or more of the operably linked MRDs competitively inhibits atacicept binding to BLyS or APRIL. In a further specific embodiment, the MRDs are operably linked to atacicept.

In another embodiment, the invention provides a method of suppressing an immune response comprising administering a therapeutically effective amount of a MRD-TACI-Fc fusion protein to a patient in need thereof. In one embodiment, the invention provides a method of treating an autoimmune disease by administering a therapeutically effective amount of a MRD-TACI-Fc fusion protein to a patient in need thereof. In one embodiment, the invention provides a method of treating rheumatoid arthritis, by administering a therapeutically effective amount of a MRD-TACI-Fc fusion protein to a patient in need thereof. In one embodiment, the invention provides a method of treating systemic lupus erythematosus by administering a therapeutically effective amount of a MRD-TACI-Fc fusion protein to a patient in need thereof. In another embodiment, the invention provides a method of suppressing an immune response comprising administering a therapeutically effective amount of a MRD-atacicept fusion protein to a patient in need thereof. In one embodiment, the invention provides a method of treating an autoimmune disease by administering a therapeutically effective amount of a MRD-atacicept fusion protein to a patient in need thereof. In one embodiment, the invention provides a method of treating rheumatoid arthritis, by administering a therapeutically effective amount of a MRD-atacicept protein fusion protein to a patient in need thereof. In one embodiment, the invention provides a method of treating systemic lupus erythematosus, by administering a therapeutically effective amount of a MRD-atacicept fusion protein to a patient in need thereof.

In another specific embodiment, one, two, three, four, five, six, or more MRDs are operably linked to an IL-1R-Fc fusion protein. In another specific embodiment, one or more of the operably linked MRDs bind to the same epitope as rilonacept (Regeneron). In another specific embodiment, one or more of the operably linked MRDs competitively inhibits rilonacept binding to IL-1R. In a further specific embodiment, the MRDs are operably linked to rilonacept.

In another embodiment, the invention provides a method of preventing gout comprising administering a therapeutically effective amount of a MRD-IL-IR-Fc fusion protein to a patient in need thereof. In a specific embodiment, the invention provides a method of preventing gout comprising administering a therapeutically effective amount of a MRD-rilonacept-Fc fusion protein to a patient in need thereof.

The following examples are intended to illustrate but not limit the invention.

EXAMPLES

Example 1

Integrin Targeting Antibody-MRD Molecules

Novel antibody-MRD fusion molecules were prepared by fusion of an integrin αvβ3-targeting peptides to catalytic antibody 38C2. Fusions at the N-termini and C-termini of the light chain and the C-termini of the heavy chain were most effective. Using flow cytometry, the antibody conjugates were shown to bind efficiently to integrin αvβ3-expressing human breast cancer cells. The antibody conjugates also retained the retro-aldol activity of their parental catalytic antibody 38C2, as measured by methodol and doxorubicin prodrug activation. This demonstrates that cell targeting and catalytic antibody capability can be efficiently combined for selective chemotherapy.

Example 2

Angiogenic Cytokine Targeting Antibody-MRD Molecules

Angiogenic cytokine targeting antibody-MRD fusion molecules were constructed. The antibody used was 38C2, which was fused with a MRD containing the 2×Con4 peptide (AQQEECEWDPWTCEHMGSGSATGGSGSTASSGSGSATHQEECEWDPWTCEHMLE (SEQ ID NO:10)). The MRD-containing peptide was fused to either the N- or C-terminus of the light chain and the C-terminus of the heavy chain. Similar results were found with the other Ang2 MRD peptides. Additional Ang2 MRD peptides include: MGAQTNFMPMDNDELLLYEQ FILQQGLEGGSGSTASSGSGSSLGAQTNFMPMDNDELLLY (SEQ ID NO:20) (LM-2x-32); AQQEECEWDPWTCEHMG SGSATGGSGSTASSGSGSATHQEECEWDPWTCEHMLE (SEQ ID NO:10) (2×Con4); AQQEECEFAPWTCEHM (SEQ ID NO:21) ConFA; core XnEFAPWTXn where n is from about 0 to 50 amino acid residues (SEQ ID NO:22); AQQEECEFAPWTCEHMGSGSATGGSGSTASSGSGSATHQEECEFAPWTCEHMLE (SEQ ID NO:23) (2×ConFA); AQQEECELAPWTCEHM (SEQ ID NO:24) (ConLA); XnELAPWTXn where n is from about 0 to 50 amino acid residues (SEQ ID NO:25); AQQEECELAPWTCEHMG SGSATGGSGSTASSGSGSATHQEECELAPWTCEHMLE (SEQ ID NO:26) (2×ConLA); AQQEECEFSPWTCEHM ConFS (SEQ ID NO:27); XnEFSPWTXn where n is from about 0 to 50 amino acid residues (SEQ ID NO:28); AQQEECEFSPWTCEHMGSGSATGGSGS TASSGSGSATHQEECEFSPWTCEHMLE (SEQ ID NO:29) (2×ConFS); AQQEECELEPW TCEHM ConLE (SEQ ID NO:30); XnELEPWTXn where n is from about 0 to 50 amino acid residues (SEQ ID NO:31); and AQQEECELEPWTCEHMGSGSATGGSGSTASSGSGSATH QEECELEPWTCEHMLE (SEQ ID NO:32) (2×ConLE).

It should be understood that such peptides can be present in dimmers, trimers or other multimers either homologous or heterologous in nature. For example, one can dimerize identical Con-based sequences such as in 2×ConFA to provide a homologous dimer, or the Con peptides can be mixed such that ConFA is combined with ConLA to create ConFA-LA heterodimer with the sequence: AQQEECEFAP-WTCEHMGSGSATGGSGSTASSGSGSATHQEECELAP-WTCE HMLE (SEQ ID NO:33).

Another illustrative heterodimer is ConFA combined with ConFS to create ConFA-FS with the sequence: AQQEECE-FAPWTCEH-MGSGSATGGSGSTASSGSGSATHQEECEFSPW TCEH-MLE (SEQ ID NO:34).

One of skill in the art, given the teachings herein, will appreciate that other such combinations will create functional Ang2 binding MRDs as described herein.

Example 3

Antibody-MRD Fusions with Non-catalytic Antibodies

A humanized mouse monoclonal antibody, LM609, directed towards human integrin αvβ3 has been previously described (Rader et. al., PNAS 95:8910$^{-5}$ (1998)).

Figure 3:
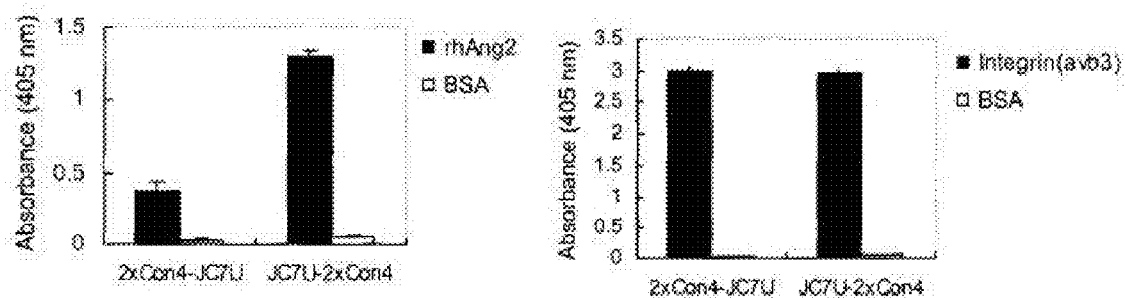
FIG. 3 depicts the results of an enzyme linked immunosorbant assay (ELISA) in which integrin and Ang2 were bound by an anti-integrin antibody (JC7U) fused to a Ang2 targeting MRD (2×Con4).
Figure 4:
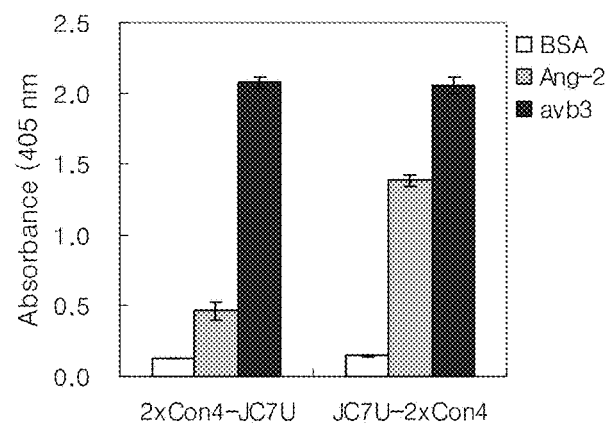
FIG. 4 depicts the results of an ELISA in which integrin and Ang2 were bound by an anti-integrin antibody (JC7U) fused to a Ang2 targeting MRD (2×Con4).

A human non-catalytic monoclonal Ab, JC7U was fused to an anti-Ang2 MRD containing 2×Con4 (AQQEECEWD-PWTCEHMGSGSATGGSGSTASSGSGSATHQEECE WDPWTCEHMLE (SEQ ID NO:10)) at either the N- or C-terminus of the light chain. 2×Con4 (AQQEECEWDP-WTCEHMGSGSATGGSGSTASSGSGSATHQEEC EWD-PWTCEHMLE (SEQ ID NO:10)) was studied as an N-terminal fusion to the Kappa chain of the antibody (2×Con4-JC7U) and as a C-terminal fusion (JC7U-2×Con4). Both fusions maintained integrin and Ang2 binding. As shown in the left panel of FIG. 3, both antibody constructs (2×Con4-JC7U and JC7U-2×Con4) specifically bound to recombinant Ang2 as demonstrated by ELISA studies. Binding to Ang2, however, is significantly higher with JC7U-2×Con4, which has the 2×Con4 (SEQ ID NO:10) fusion at the C-terminus of the light chain of the antibody. The right panel of FIG. 3 depicts the binding of Ang2-JC7U and JC7U-Ang2 to integrin αvβ3. The results show that fusion of 2×Con4 (SEQ ID NO:10) to either the N- or the C-light chain terminus does not affect mAb JC7U binding to integrin αvβ3. FIG. 4 depicts another ELISA study using the same antibody-MRD fusion constructs.

Example 4

HERCEPTIN®—MRD Fusion Molecules

Another example of MRD fusions to a non-catalytic antibody are HERCEPTIN®-MRD fusion constructs. The HERCEPTIN®-MRD fusions are multifunctional, both small-molecule αv integrin antagonists and the chemically programmed integrin-targeting antibody show remarkable efficacy in preventing the breast cancer metastasis by interfering with αv-mediated cell adhesion and proliferation. MRD fusions containing HERCEPTIN®-2×Con4 (which targets ErbB2 and Ang2) and HERCEPTIN®-V114 (which targets ErbB2 and VEGF targeting) and HERCEPTIN®-RGD-4C-2×Con4 (which targets ErbB2, ang2, and integrin targeting) are effective.

Example 5

VEGF Targeting Antibody-MRD Molecules

An antibody containing an MRD that targets VEGF was constructed. A MRD which targets vl 14 (SEQ ID NO:13) was fused at the N-terminus of the kappa chain of 38C2 and HERCEPTIN® using a linker. Expression and testing of the resulting antibody-MRD fusion constructs demonstrated strong VEGF binding.

Example 6

IGF1R Targeting Antibody-MRD Molecules

Fusion of an MRD which targets IGF1R (SFY-SCLESLVNGPAEKSRG QWDGCRKK (SEQ ID NO:14)) to the N-terminus of the kappa chain of 38C2 and HER-CEPTIN® using the long linker sequence as a connector was studied. Expression and testing of the resulting antibody-MRD fusion constructs demonstrated strong IGF1R binding. Additional clones showing high binding to IGR I R were identified after several rounds of mutagenesis and screening of the regions described in Table 4. The preferred sequences listed in Table 5 bind IGF1R and show no significant or no binding affinity to the insulin receptor, thereby suggesting specificity for IGF1R.

TABLE 4

Template for further mutagenesis.

| Name | DNA | AA |
|---|---|---|
| Rm2-2-218 | GTGGAGTGCAGGGCGCCG VECRAP (SEQ ID NO: 51)<br>(SEQ ID NO: 50) | |
| Rm2-2-316 | GCTGAGTGCAGGGCTGGG AECRAG (SEQ ID NO: 53)<br>(SEQ ID NO: 52) | |
| Rm2-2-319 | CAGGAGTGCAGGACGGGG QECRTG (SEQ ID NO: 55)<br>(SEQ ID NO: 54) | |

TABLE 5

| Mutant | Amino acid sequence | Template | SEQ ID NO |
|---|---|---|---|
| Rm4-31 | NFYQCIEMLASHPAEKSRGQWQECRTGG | Rm2-2-319 | 35 |
| Rm4-33 | NFYQCIEQLALRPAEKSRGQWQECRTGG | Rm2-2-319 | 36 |
| Rm4-39 | NFYQCIDLLMAYPAEKSRGQWQECRTGG | Rm2-2-319 | 37 |
| Rm4-310 | NFYQCIERLVTGPAEKSRGQWQECRTGG | Rm2-2-319 | 38 |
| Rm4-314 | NFYQCIEYLAMKPAEKSRGQWQECRTGG | Rm2-2-319 | 39 |
| Rm4-316 | NFYQCIEALQSRPAEKSRGQWQECRTGG | Rm2-2-319 | 40 |
| Rm4-319 | NFYQCIEALSRSPAEKSRGQWQECRTGG | Rm2-2-319 | 41 |
| Rm4-44 | NFYQCIEHLSGSPAEKSRGQWQECRTG | Rm2-2-319 | 42 |
| Rm4-45 | NFYQCIESLAGGPAEKSRGQWQECRTG | Rm2-2-319 | 43 |
| Rm4-46 | NFYQCIEALVGVPAEKSRGQWQECRTG | Rm2-2-319 | 44 |
| Rm4-49 | NFYQCIEMLSLPPAEKSRGQWQECRTG | Rm2-2-319 | 45 |
| Rm4-410 | NFYQCIEVFWGRPAEKSRGQWQECRTG | Rm2-2-319 | 46 |

TABLE 5-continued

| Mutant | Amino acid sequence | Template | SEQ ID NO |
|---|---|---|---|
| Rm4-411 | NFYQCIEQLSSGPAEKSRGQWQECRTG | Rm2-2-319 | 47 |
| Rm4-415 | NFYQCIELLSARPAEKSRGQ WAECRAG | Rm2-2-316 | 48 |
| Rm4-417 | NFYQCIEALARTPAEKSRGQWVECRAP | Rm2-2-218 | 49 |

Example 7

ErbB2 Binding, Ang2-Targeting Antibody-MRD Molecules

Figure 5:
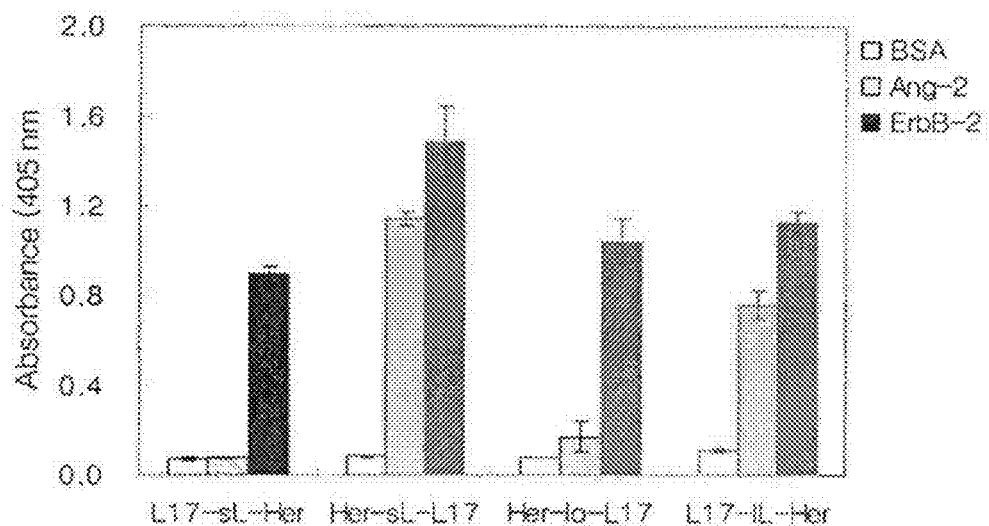
FIG. 5 depicts the results of an ELISA in which an anti-ErbB2 antibody was fused to an MRD which targets Ang2.

An antibody was constructed which contains an MRD that targets Ang2 (L17) (SEQ ID NO:7) fused to the light chain of an antibody which binds to ErbB2. Either the short linker sequence, the long linker sequence, or the 4th loop in the light chain constant region was used as a linker. FIG. 5 depicts the results of an ELISA using constructs containing an N-terminal fusion of an Ang2 targeting MRD with the ErbB2 antibody with the short linker peptide (GGGS (SEQ ID NO:1)) (L17-sL-Her), a C-terminal fusion of Ang2 targeting MRD with the ErbB2 antibody with the short linker peptide (Her-sL-L17), a C-terminal fusion of Ang2 targeting MRD with the ErbB2 antibody with the 4th loop in the light chain constant region (Her-lo-L17), or an N-terminal fusion of Ang2 targeting MRD with the ErbB2 antibody with the long linker peptide (SSGGGGSGGGGGGSSRSS (SEQ ID NO:19)) (L17-1L-Her). ErbB2 was bound with varying degrees by all of the constructs. However, Ang2 was bound only by Her-sL-L17 and L17-1L-Her.

Example 8

Figure 6:
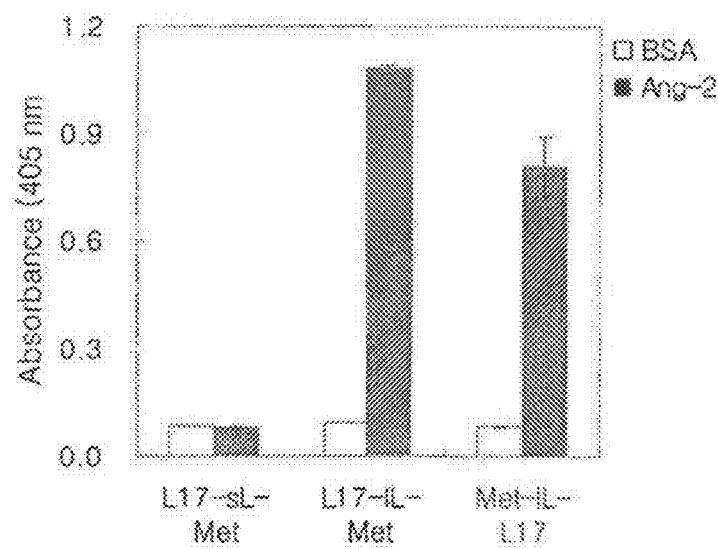
FIG. 6 depicts the results of an ELISA in which an Ang2 targeting MRD was fused to a hepatocyte growth factor receptor (cMET) binding antibody.

Hepatocyte Growth Factor Receptor Binding, Ang2-Targeting Antibody-MRD Molecules Fusion of an MRD which targets Ang2 (L17) (SEQ ID NO:7) was made to either the N-terminus or C-terminus of the light chain of the Met antibody, which binds to hepatocyte growth factor receptor. Either the short linker sequence or the long linker sequence were used as a connector. FIG. 6 depicts the results of an ELISA using constructs containing N-terminal fusion of Ang2 targeting MRD with the Met antibody with the short linker peptide (GGGS (SEQ ID NO:1)) (L17-sL-Met), N-terminal fusion of Ang2 targeting MRD with the Met antibody with the long linker peptide (SSGGGGSGGGGGGSSRSS (SEQ ID NO:19)) (L17-1L-Met), and C-terminal fusion of Ang2 targeting MRD with the Met antibody with the long linker peptide (Met-iL-L17). Expression and testing of the resulting antibody-MRD fusion constructs demonstrated strong Ang2 binding when the long linker peptide was used. Fusion of the Ang2 targeting MRD to the C-light chain terminus of the antibody resulted in slightly higher binding to Ang2 then fusion of the Ang2 targeting to the N-light chain terminus of the antibody.

Example 9

ErbB2 Binding, Integrin-Targeting Antibody-MRD Molecules

Figure 7:
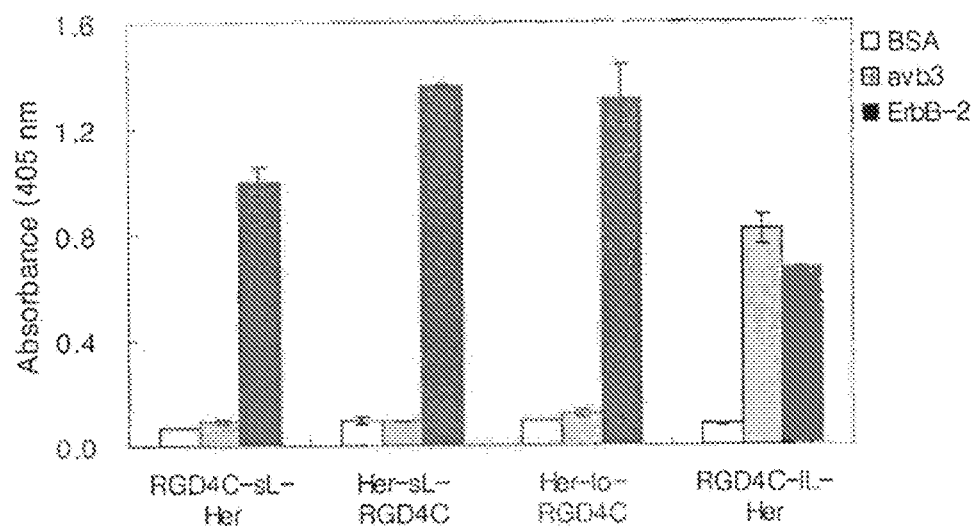
FIG. 7 depicts the results of an ELISA in which an integrin targeting MRD was fused to an ErbB2 binding antibody.

An antibody was constructed which contains an MRD that targets integrin αvβ3 (RGD4C) with the sequence CDCRGDCFC (SEQ ID NO:106) fused to the light chain of an antibody HERCEPTIN® which binds to ErbB2 (Her). Either the short linker sequence, the long linker sequence, or the 4th loop in the light chain constant region was used as a linker. FIG. 7 depicts the results of an ELISA using constructs containing an N-terminal fusion of integrin αvβ3 targeting MRD with the ErbB2 antibody with the short linker peptide (GGGS (SEQ ID NO:1)) (RGD4C-sL-Her), a C-terminal fusion of integrin αvβ3 targeting MRD with the ErbB2 antibody with the short linker peptide (Her-sL-RGD4C), a C-terminal fusion of integrin αvβ3 targeting MRD with the ErbB2 antibody with the 4th loop in the light chain constant region (Her-lo-RGD4C), or an N-terminal fusion of integrin αvβ3 targeting MRD with the ErbB2 antibody with the long linker peptide (SSGGGGSGGGGGGSSRSS (SEQ ID NO:19)) (RGD4C-1L-Her). ErbB2 was bound with varying degrees by all of the constructs. However, integrin αvβ3 was bound only by RGD4C-1L-Her.

Example 10

Figure 8:
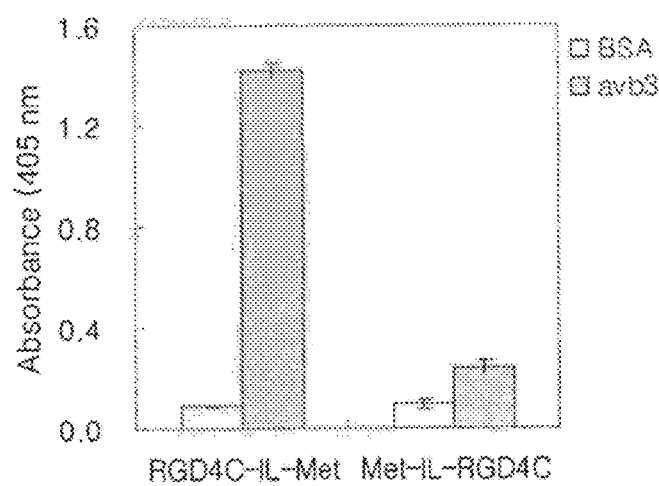
FIG. 8 depicts the results of an ELISA in which an integrin targeting MRD was fused to an hepatocyte growth factor receptor binding antibody.

Hepatocyte Growth Factor Receptor Binding, Integrin-Targeting Antibody-MRD Molecules An antibody was constructed which contains an MRD that targets integrin αvβ3 (RGD4C) (SEQ ID NO:106) fused to the light chain of an antibody which binds to the hepatocyte growth factor receptor (Met). Antibody-MRD constructs containing the long linker sequence were used. FIG. 8 depicts the results of an ELISA using constructs containing an N-terminal fusion of integrin αvβ3 targeting MRD with the hepatocyte growth factor receptor antibody (RGD4C-1L-Met), or a C-terminal fusion of integrin αvβ3 targeting MRD with the hepatocyte growth factor receptor antibody (Met-1L-RGD4C). The RGD4C-1L-Met demonstrated strong integrin αvβ3 binding.

Example 11

Figure 9:
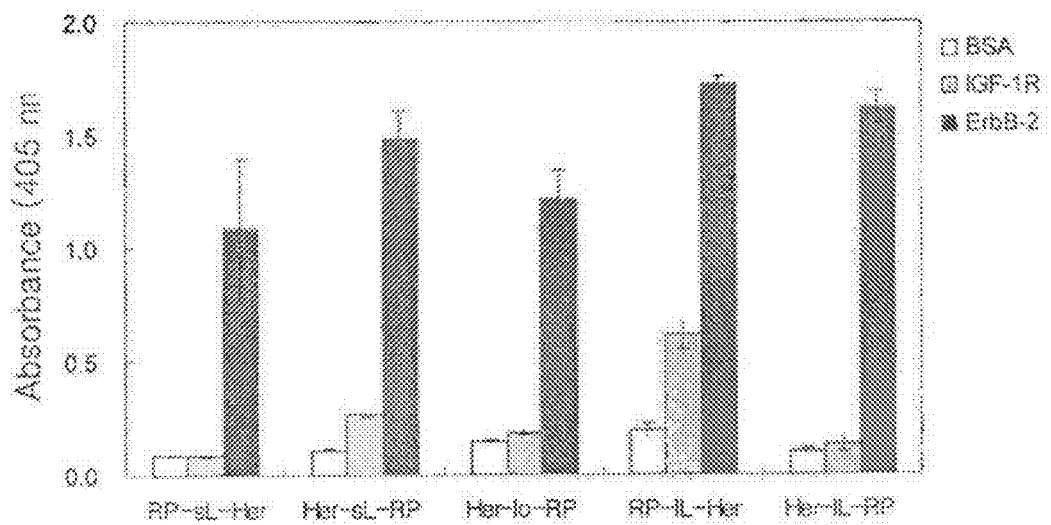
FIG. 9 depicts the results of an ELISA in which an insulin-like growth factor-I receptor targeting MRD was fused to an ErbB2 binding antibody.

ErbB2 Binding, Insulin-like Growth Factor-I Receptor—Targeting Antibody-MRD Molecules Antibodies were constructed which contains an MRD that targets insulin-like growth factor-I receptor (RP) (SEQ ID NO:14) fused to the light chain of an antibody which binds to ErbB2 (Her). Either the short linker peptide, the long linker peptide, or the 4th loop in the light chain constant region was used as a linker (Carter et al., *Proc Natl Acad Sci* 89:4285-9 (1992); U.S. Pat. No. 5,677,171; and ATCC Deposit 10463, each of which is herein incorporated by reference). FIG. 9 depicts the results of an ELISA using constructs containing an N-terminal fusion of insulin-like growth factor-I receptor targeting MRD with the ErbB2 antibody with the short linker peptide (RP-sL-Her), a C-terminal fusion of insulin-like growth factor-I receptor targeting MRD with the ErbB2 antibody and the short linker peptide (Her-sL-RP), a C-terminal fusion of insulin-like growth factor-I receptor targeting MRD with the ErbB2 antibody with the 4th loop in the light chain constant region (Her-lo-RP), an N-terminal fusion of insulin-like growth factor-I receptor targeting MRD with the ErbB2 antibody with the long linker peptide (RP-lL-Her), or a C-terminal fusion of insulin-like growth factor-I receptor targeting MRD with the ErbB2 antibody with the long linker peptide (Her-1L-RP). ErbB2 was bound with varying degrees by all of the constructs. Insulin-like growth factor-I receptor was bound by RP-1L-Her.

Example 12

ErbB2 Binding. VEGF-Targeting Antibody-MRD Molecules

Figure 10:
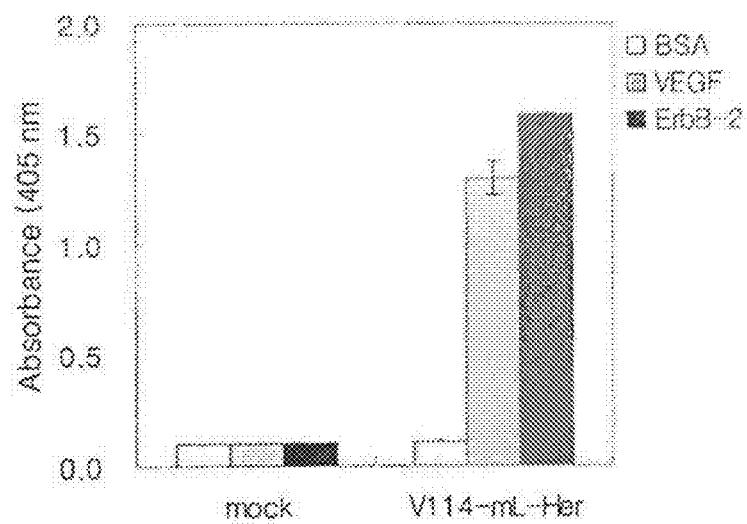
FIG. 10 depicts the results of an ELISA in which a VEGF-targeting MRD was fused to an ErbB2 binding antibody.

Fusion of an MRD which targets VEGF (Vl 14) (SEQ ID NO:13) (Fairbrother W. J., et al, Biochemistry 37:177754-64 (1998)) was made to the N-terminus of the light chain of a ErbB2-binding antibody (Her). A medium linker peptide (SSGGGGSGGGGGSS (SEQ ID NO:2)) was used as a connector. FIG. 10 depicts the results of an ELISA using a construct containing an N-terminal fusion of VEGF targeting MRD with the ErbB2-binding antibody with the medium linker peptide (Vl 14-mL-Her). Expression and testing of the resulting antibody-MRD fusion construct demonstrated strong VEGF and ErbB2 binding.

Example 13

Integrin Targeting Antibody-MRD Molecules

Figure 11:
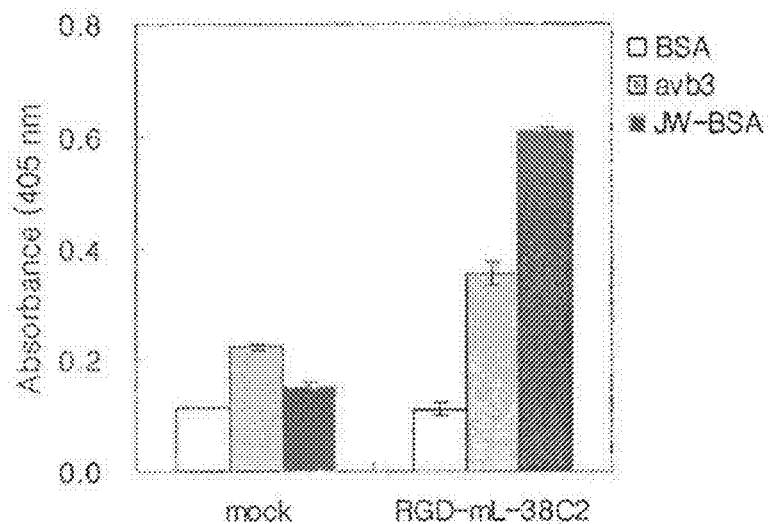
FIG. 11 depicts the results of an ELISA in which an integrin targeting MRD was fused to a catalytic antibody.

Fusion of an MRD which targets integrin αvβ3 (RGD) (SEQ ID NO:106) to the N-terminus of the light chain of 38C2 using the medium linker peptide as a connector was studied. FIG. 11 demonstrates that expression and testing of the resulting antibody-MRD fusion construct had strong integrin αvβ3 binding.

Example 14

Ang2 Targeting Antibody-MRD Molecules

Figure 12:
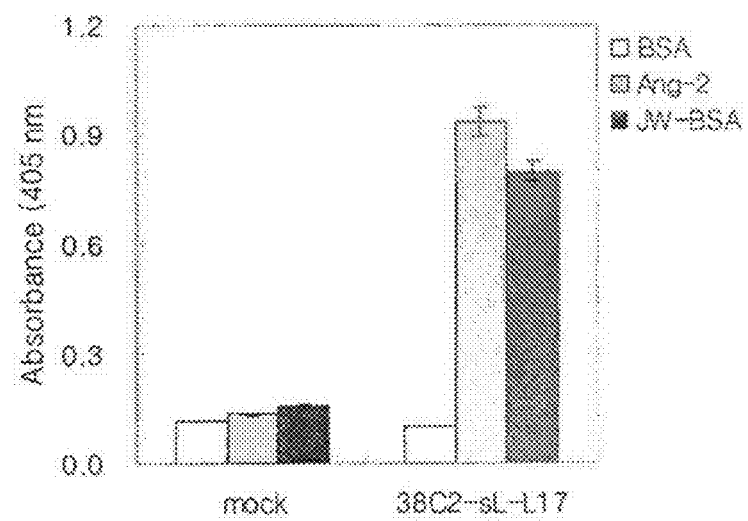
FIG. 12 depicts the results of an ELISA in which an Ang2-targeting MRD was fused to a catalytic antibody.

Fusion of an MRD which targets Ang2 (L 17) (SEQ ID NO:7) to the C-terminus of the light chain of 38C2 using the short linker sequence as a connector was studied. FIG. 12 demonstrates that expression and testing of the resulting antibody-MRD fusion construct had strong Ang2 binding.

Example 15

ErbB2 Binding, Integrin and Ang2 Targeting Antibody-MRD Molecules

Figure 13:
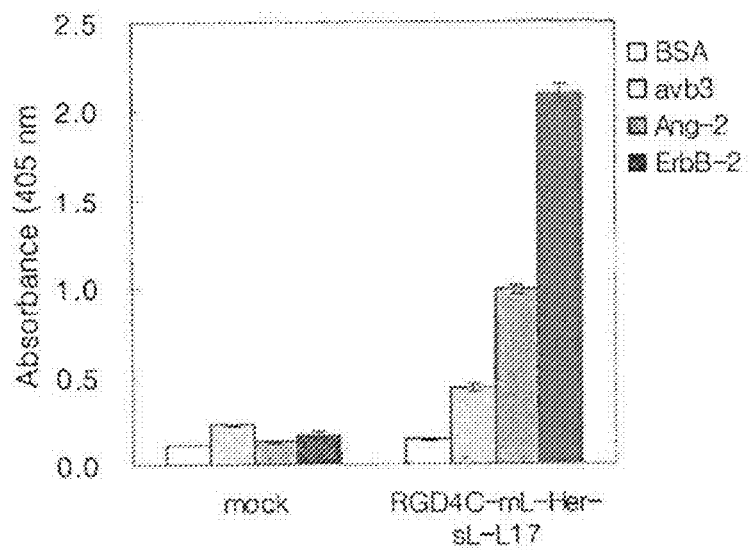
FIG. 13 depicts the results of an ELISA in which an integrin targeting MRD and an Ang2 targeting MRD were fused to an ErbB2 binding antibody.

An MRD which targets integrin αvβ3 (RGD4C) was connected to the N-terminus of the light chain of an ErbB2 targeting antibody (Her) with a medium linker, and an Ang2 (L17) targeting MRD was connected by a short linker to the C-terminus of the same ErbB2 targeting antibody (RGD4C-mL-Her-sL-L17). FIG. 13 demonstrates that the resulting antibody-MRD fusion construct bound to integrin, Ang2, and ErbB2.

Similarly, ErbB2 targeting antibodies (e.g., Her) with an IGF-1R MRD fused to the C-terminus of the heavy chain or the N-terminus of the light chain bound to immobilized IGF-1R at comparable rates. In addition, ErbB2 targeting antibodies containing an IGF-1R MRD fused to the N-terminus of the light chain and an Ang2 MRD fused to the C-terminus of the heavy chain bound to immobilized IGF-1R at comparable rates. Each of these three MRD-containing antibodies also inhibited the binding of IGF-1 to immobilized IGF-1R. The trispecific molecule (HERCEPTIN® with IGF-1R and Ang2 MRDs) bound to both cell surface ErbB2 and soluble Ang2.

Example 16

ErbB2 Binding, Integrin-Targeting Antibody-MRD Molecules

Figure 14:
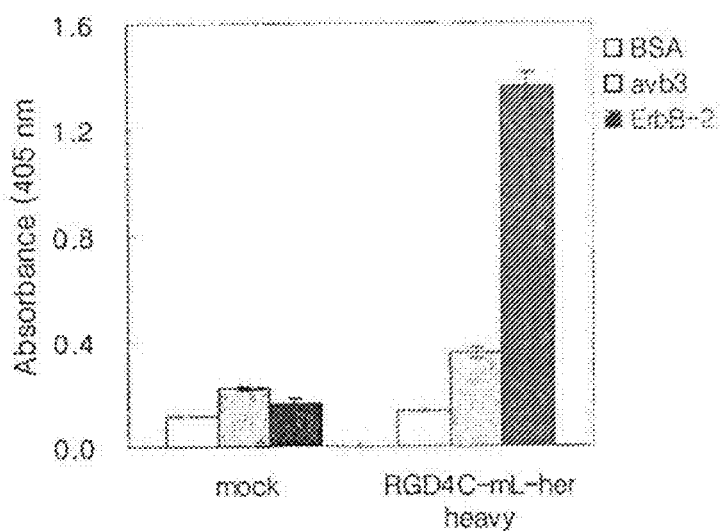
FIG. 14 depicts the results of an ELISA in which an integrin targeting MRD was fused to an ErbB2 binding antibody.

An antibody was constructed which contains an MRD that targets integrin αvβ3 (RGD4C) fused to the N-terminus of the heavy chain of an antibody which binds to ErbB2 (Her) using the medium linker as a connector (RGD4C-mL-her-heavy). FIG. 14 depicts the results of an ELISA using the construct. Both integrin and ErbB2 were bound by the construct.

Example 17

Figure 15:
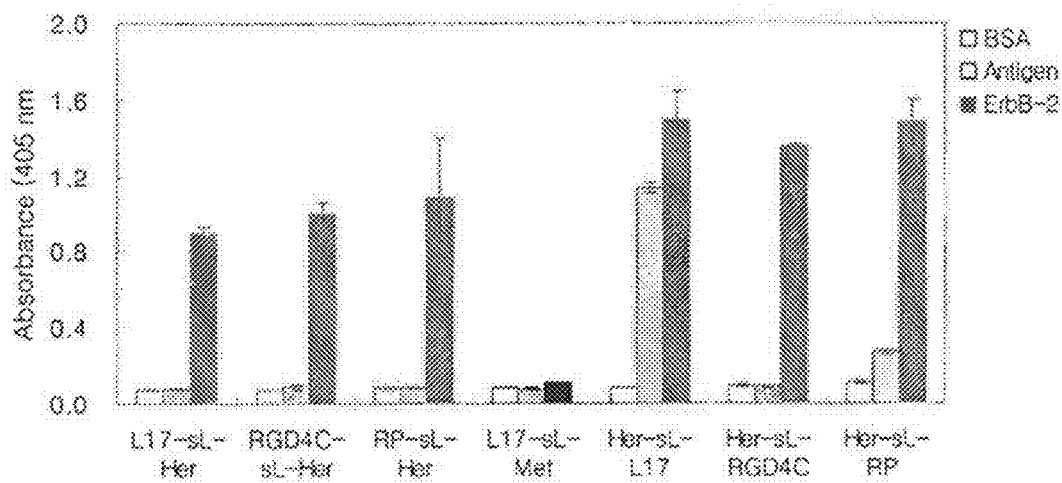
FIG. 15 depicts the results of an ELISA in which an integrin, Ang2, or insulin-like growth factor-I receptor-targeting MRD was fused to an ErbB2 or hepatocyte growth factor receptor-binding antibody with a short linker peptide.

ErbB2 or Hepatocyte Growth Factor Receptor Binding, and Integrin, Ang2 or Insulin-Like Growth Factor-I Receptor-Targeting Antibody-MRD Molecules with the Short Linker Peptide Antibody-MRD molecules were constructed which contain ErbB2 or hepatocyte growth factor receptor binding antibodies, and integrin αvβ3, Ang2 or insulin-like growth factor-I receptor-targeting MRD regions were linked with the short linker peptide to the light chain of the antibody. FIG. 15 depicts the results of an ELISA using constructs containing an N-terminal fusion of Ang2 targeting MRD fused to the ErbB2 antibody (L17-sL-Her), an N-terminal fusion of integrin-targeting MRD with the ErbB2 antibody (RGD4C-sL-Her), an N-terminal fusion of insulin-like growth factor-I receptor targeting MRD with the ErbB2 binding antibody (RP-sL-Her), a C-terminal fusion of Ang2 targeting MRD with the hepatocyte growth factor receptor binding antibody (L17-sL-Met), a C-terminal fusion of Ang2 targeting MRD with the ErbB2 binding antibody (Her-sL-L17), a C-terminal fusion of integrin targeting MRD with the ErbB2 binding antibody (Her-sL-RGD4C), or a C-terminal fusion of insulin-like growth factor-I receptor targeting MRD with the ErbB2 binding antibody (Her-sL-RP). ErbB2 was bound with varying degrees by the antibody-MRD constructs, with the exception of the construct containing the hepatocyte growth factor receptor-binding antibody. Antigen was bound only by the Her-sL-L17 construct.

Example 18

Figure 16:
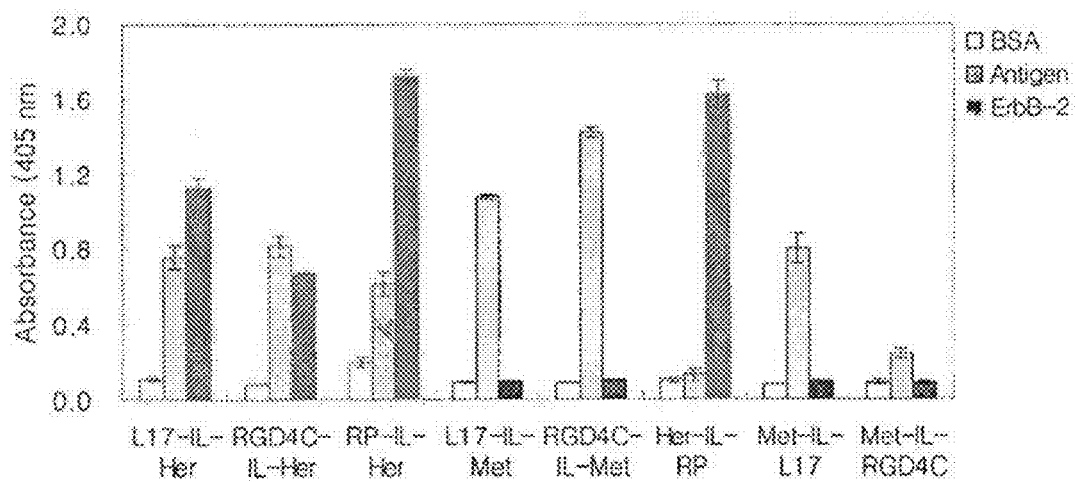
FIG. 16 depicts the results of an ELISA in which an integrin, Ang2, or insulin-like growth factor-I receptor-targeting MRD was fused to an ErbB2 or hepatocyte growth factor receptor-binding antibody with a long linker peptide.

ErbB2 or Hepatocyte Growth Factor Receptor Binding, and Integrin, Ang2 or Insulin-Like Growth Factor-I Receptor-Targeting Antibody-MRD Molecules with the Long Linker Peptide Antibody-MRD molecules were constructed which contain ErbB2 or hepatocyte growth factor receptor binding antibodies, and integrin αvβ3, Ang2 or insulin-like growth factor-I receptor-targeting MRD regions linked with the long linker peptide to the light chain of the antibody. FIG. 16 depicts the results of an ELISA using constructs containing an N-terminal fusion of Ang2 targeting MRD fused to the ErbB2 antibody (L17-1L-Her), an N-terminal fusion of integrin-targeting MRD with the ErbB2 antibody (RGD4C-1L-Her), an N-terminal fusion of insulin-like growth factor-I receptor-targeting MRD with the ErbB2 binding antibody (RP-1L-Her), a C-terminal fusion of Ang2 targeting MRD with the hepatocyte growth factor receptor binding antibody (L17-1L-Met), a C-terminal fusion of integrin targeting MRD with the hepatocyte growth factor receptor binding antibody (RGD4C-1L-Met), a C-terminal fusion of Ang2 targeting MRD with the insulin-like growth factor-I receptor binding antibody (Her-IL-RP), a C-terminal fusion of Ang2 targeting MRD with the hepatocyte growth factor receptor binding antibody (Met-1L-L17), or a C-terminal fusion of integrin targeting MRD with the hepatocyte growth factor receptor binding antibody (Met-1L-RGD4C). As shown in FIG. 16, antibody-MRD fusions are effective to bind antigen and ErbB2. Lu et al. J Biol Chem 280(20)(2005): 19665-72. Epub 2005 Mar. 9; Lu et al. J Biol Chem 279(4):2856-65 (2004). Epub 2003 Oct. 23.

Example 19

Cloning and Expression of Ang2 MRDs Fused to Maltose Binding Protein

A. Cloning of MBP Fusions

Monomer and dimer peptides were expressed as protein fusions to maltose binding protein (MBP) using a modified form of the pMAL-p2 vector and expression system from New England Biolabs (NEB; Beverly, Mass.) The PCR-generated MRD sequence was inserted into a pMAL vector down-stream from the malE gene, which encodes MBP. This results in a vector that encodes an MRD-MBP-fusion protein. The pMAL vector contains a strong Ptac promoter and is inducible by IPTG. The pMAL-p2 series contains the normal malE signal sequence, which directs the fusion protein through the cytoplasmic membrane. pMAL-p2 fusion proteins capable of being exported can be purified from the periplasm through osmotic shock. Further purification can be performed, for example by binding to amylose resin.

B. Expression of MBP Fusion Proteins and Osmotic Shock Fractionation

For expression of fusion proteins, bacterial cultures grown overnight were back-diluted into fresh media to an OD A600 of approximately 0.1. Cultures were grown to an OD of approximately 0.8 and induced with IPTG at a concentration of 0.3 mM. Cultures were incubated with shaking for approximately 4 hours, after which bacteria were centrifuged for 15 minutes at 4700 g. Pelleted bacteria were resuspended in 30 mM Tris-HCL pH 7.4, 20% sucrose, 1 mM EDTA. Cells were incubated for 20 minutes at room temperature (RT) prior to centrifugation for 15 minutes at 4700 g. Pelleted bacteria were then resuspended in ice cold $MgSO_4$, and incubated for 20 minutes on ice, with periodic mixing. Cell suspensions were sonicated (Misonix XL2020) for 90 seconds. Cells were centrifuged at 4° C. for 20 minutes at 4700 g. The supernatant ("osmotic shock fraction") was adjusted to 1×PBS using 10x PBS (Quality Biologics, cat #119-069-131) and filtered through 0.2 micron filter. These osmotic shock fractions were assayed directly for binding to Ang2.

C. Direct Binding of MBP Fusion Proteins

For detection of direct binding of MRD-MBP fusions to Ang2, the following ELISA was performed. Ninety-six-well plates were coated overnight with rhAng2 (R&D cat#623-AN) at 320 ng/ml (100 µl/well). Wells were blocked for 3.25 hours with 250 µl Blocking buffer (Thermo Cat# N502), followed by 4 washes with 300 µl wash buffer (PBS, 0.1% tween). MBP fusion proteins were serially diluted in Blocking buffer and added to wells for 2 hours at RT. After washing (8×300 µl wash buffer), samples were treated with HRP-mouse anti MBP mAb (NEB, cat # E8038S), diluted 1:4000 in Blocking buffer. After incubation for 1 hour at RT, wells were washed (8×300 µl wash buffer) prior to receiving 100 µl of TMB substrate (KPL Laboratories). Color development was stopped with 100 µl of $H_2SO_4$, and absorbance was read at 450 nm.

D. Results

MRD-MBP fusions were assayed for direct binding to Ang2. Osmotic shock fractions of induced bacterial cultures were serially diluted and added to Ang2 coated wells. Bound fusion proteins were detected with anti-MBP mAb. The dose response curves are presented in FIGS. 17A and B. Assayed proteins represent mutational variants of the sequence MGAQTNFMPMDDDELLLYEQFILQQGLE (L17D) (SEQ ID NO:107). In this series, the motif MDD within L17D was mutated at the first D to all other possible amino acids (except cysteine). Other MRDs tested were "Lm32 KtoS" and a dimer of Lm32 (2×Lm32). As presented in FIG. 17C, several MXD mutants exhibit binding in the 0.1 to 100 nm range. The Lm32 dimer (2×Lm32) exhibits greater than 10 fold higher affinity for Ang2 than either L17D or "Lm32 KtoS".

Example 21

Expression and Purification of Antibodies Containing MRDs

Molecular recognition domains were constructed and expressed in a pcDNA 3.3 vector as fusion proteins with either the heavy or light chains of antibodies. For protein production, plasmid DNAs encoding the heavy and light chains of the antibodies containing MRDs were first transformed into chemically competent bacteria in order to produce large amounts of DNA for transient transfection. Single transformants were propagated in LB media and purified using Qiagen's Endotoxin Free Plasmid Kits. Briefly, cells from an overnight culture were lysed; lysates were clarified and applied to an anion-exchange column, and then subjected to a wash step and eluted with high salt. Plasmids were precipitated, washed, and resuspended in sterile water.

HEK293T cells were expanded to the desired final batch size (about 5 L) prior to transfection. The purified plasmid (lmg per liter of production) was complexed with the polyethylenimine (PEI) transfection reagent, added to the shake flask culture, and incubated at 37° C. The culture was monitored daily for cell count, cell diameter, and viability. The conditioned medium was harvested and stored at −80° C. until purification.

Antibodies containing MRDs were purified from the conditioned medium using affinity chromatography. Culture supernatant was filter clarified and applied directly to a chromatography column containing recombinant Protein A Sepharose (GE Healthcare). The column was washed, and bound antibodies containing MRDs were eluted by lowering buffer pH. Following elution, eluate fractions were immediately adjusted to physiologic pH. Following Protein A affinity purification, an additional optional polishing chromatographic step can be performed as needed.

Purified proteins were dialyzed into PBS, concentrated to ~1-4 mg/ml, sterile filtered, aliquoted aseptically, and stored frozen at −80° C. All steps of the purification were monitored by SDS-PAGE-Coomassie, and precautions were taken during the purification to keep endotoxin levels as minimal as possible.

The final product was analyzed for endotoxin levels (EndoSafe), purity (SDS-PAGE-coomassie, analytical SEC-HPLC), protein identity (Western blot), and yield (Bradford assay). An additional size exclusion HPLC analysis was performed to assess the level of aggregates.

The data presented in Table 6 indicate that the antibodies containing MRDs can be expressed and purified using conventional techniques.

TABLE 6

| Zybody | Yield (mg) | Purity | Aggregates (%) | Endotoxin (EU/ml) |
|---|---|---|---|---|
| HER2xCon4(H) | 36 | >90% | 4.6 | <1 |
| HER-lm32(H) | 57 | >90% | 1 | 2.02 |
| HER-lm32(L) | 98 | >90% | 2 | 3.26 |
| AVA-lm32(H) | 12 | >90% | 0 | <1 |

Example 22

Simultaneous Binding of HER Lm32(H) and HER Lm32 (L) to Her2 and Ang2

A. Methods

Ninety-six-well plates were coated overnight with rHER2-Fc (R&D cat#1129-ER-050) at 20 ng/ml (100µl/well). Wells are blocked for 3.25 hours with 250 µl Blocking buffer (Thermo Cat# N502), followed by 4 washes with 300 µl wash buffer (PBS, 0.1% tween). Antibodies containing MRDs (HER-lm32(H), HER-lm32(L), and AVA-lm32(H)) and antibodies (HERCEPTIN®) were serially diluted in Blocking buffer, containing 1.94 µg/ml biotinylated Ang2 (R&D cat#BT633) and added to wells for 2 hours at RT. After washing (8×300 µl wash buffer), parallel samples received either HRP-conjugated anti-human kappa chain mAb- (Abcam, cat # ab79115-1) diluted 1:1000 in Blocking buffer or HRP-conjugated streptavidin (Thermo Scientific cat#N100) diluted 1:4000 in Blocking buffer. After incubation for 1 hour at RT, wells were washed (8×300 µl wash buffer) prior to receiving 100 µl of TMB substrate (KPL Laboratories). Color development was stopped with 100 µl of $H_2SO_4$, and absorbance was read at 450 nm.

B. Results

As detected with anti-human kappa chain mAb, both a HERCEPTIN®-based antibody or HERCEPTIN®-based antibodies containing MRDs bind to Her2 Fc in the presence of Ang2 in a dose dependent manner (FIG. 18A). Only the HERCEPTIN®-based antibodies containing MRDs (HER-lm32(H) and HER-lm32(L)) exhibit simultaneous binding to Her2 Fc and Ang2, as detected by HRP-conjugated streptavidin (FIG. 18B).

Example 23

Simultaneous Binding of AVA-Lm32(H) to VEGF and Ang2

A. Methods:

Ninety-six-well plates were coated overnight with human VEGF (PeproTech, Inc. cat#100-20) at 30 ng/ml (100 µl/well). Wells were blocked for 3.25 hours with 250 µl Blocking buffer (Thermo Cat# N502), followed by 4 washes with 300 µl wash buffer (PBS, 0.1% tween). Antibodies containing MRDs (HER-lm32(H) and AVA-lm32(H)) and antibodies (AVASTIN®) were serially diluted in Blocking buffer, containing 3.876 µg/ml biotinylated Ang2 (R&D cat#BT633) and added to wells for 2 hours at RT. After washing (8×300 µl wash buffer), parallel samples received either HRP-conjugated anti-human kappa chain mAb (Abcam, cat # ab79115) diluted 1:1000 in Blocking buffer or HRP-conjugated streptavidin (Thermo Scientific cat#N100) diluted 1:4000 diluted in Blocking buffer. After incubation for 1 hour at RT, wells were washed (8×300 µl wash buffer) prior to receiving 100 µl of TMB substrate (KPL Laboratories). Color development was stopped with 100 µl of $H_2SO_4$, and absorbance was read at 450 nm.

B. Results

As detected with anti-human kappa chain mAb, both AVASTIN® and AVASTIN®-based antibodies containing MRDs bind to VEGF in the presence of Ang2 in a dose dependent manner (FIG. 19A). Only the AVASTIN®-based antibodies containing MRDs (AVA-lm32(H)) exhibited simultaneous binding to VEGF and Ang2, as detected by HRP-conjugated streptavidin (FIG. 19B).

Example 24

Simultaneous Binding of HER-Lm32 (H) and HER-Lm32 (L) to HER2 and Angiopoietin-2

The ability of HER-lm32 (H) and HER-lm32 (L) simultaneously bind to Her2 expressed on the surface of breast carcinoma cells BT-474, and to Ang2 in solution, was determined by flow cytometry. Mouse anti-human Ig-FITC was used for detection of the heavy chain of the antibodies containing MRDs, and Ang2-biotin/streptavidin-PE was used for detection of the lm32 MRD. Cells that bind Her2 and Ang2 simultaneously are expected to be detected as double positive for FITC and PE fluorescence.

One million HER2 positive breast carcinoma cells BT-474 were incubated with 1 µg HER-lm32(H) or HER-lm32(L) for 25 minutes at RT. After washing, cells were incubated with 200 ng/mL Ang2 biotin (R&D systems) for 25 minutes at RT and then with 20 µL of mouse anti-human Ig-FITC and Streptavidin-PE for 15 minutes. After washing with 2 mL buffer, cells were analyzed by flow cytometry (FACS Canto II, BD).

In order to confirm the specificity of binding of HER-lm32(H) and HER-lm32(L) to HER2 on BT-474 cells, binding was determined in the presence of 10-fold excess of HERCEPTIN®. In these experiments, antibodies containing MRDs (1 µg) were incubated with one million BT-474 cells in the absence or presence of 10 µg HERCEPTIN® for 25 minutes at RT. Binding of antibodies containing MRDs to HER2 was determined by incubating with 200 ng/mL Ang2 biotin followed by detection with streptavidin-PE.

The data presented in FIG. 20A demonstrate that both HER-lm32(H) and HER-lm32(L), bind simultaneously to HER2 and Ang2. In both cases, the cells exhibited bright dual fluorescence in the FITC and PE fluorescence channels. The fact that HER-lm32(H) and HER-lm32(L) binding to HER2 is completely inhibited by HERCEPTIN® (FIG. 20B) indicates that the binding is specific.

Example 25

Antibody-MRDs Containing Heavy Chain Fusions Bind to Targets

To assess the ability of lm32-containing antibodies to block the interaction of Ang2 with its receptor Tie2, their effect on the binding of soluble Tie2 to plate-bound Ang2 was determined by ELISA.

Ang2 (R&D Systems, catalog#623-AN) was coated on a 96-well plate (Thermo Electron, cat#3855) at 200 ng/mL in PBS overnight at 4° C. The plate was then incubated with 100 µL of blocking solution (Thermo Scientific, cat#N502)

for 1 hour at RT. After washing the plate 4 times with 0.1% Tween-20 in PBS, the plate bound Ang2 was incubated with 0.5 µg/mL soluble Tie2 (R&D Systems, cat#313-TI) in the absence or presence of various concentrations of serially diluted antibodies containing MRDs for 1 hour at RT. After washing 4 times, 100 µL of 0.5 µg/mL anti Tie2 antibody (cat#BAM3313, R&D Systems) was added and incubated at RT for 1 hour. Tie2 binding to Ang2 was detected by incubation with 1:1000 diluted goat anti-mouse-HRP (BD Pharmingen, cat#554002) for 1 hour at RT. The plate was washed 4 times and incubated with 100 µL TMB reagent for 10 minutes at RT. After stopping the reaction with 100 µL of 0.36N $H_2SO_4$, the plate was read at 450 nm using a spectrophotometer.

As presented in FIG. 21A, HER-lm32(H), HER-lm32(L), and AVA-lm32(H) inhibited Tie2 binding to plate-bound Ang2 in a dose-dependent fashion. All tested lm32-containing antibodies demonstrated comparable inhibitory effects with IC-50 values of 4 nM for HER-lm32 (H), 8 nM for HER-lm32(L) and 3.3 nM for AVA-lm32(H).

Example 26

Antibody-MRDs Containing Heavy Chain Fusions Bind to Targets

To determine the specificity and relative affinity of AVA-lm32 (H) binding to VEGF, a competitive binding assay was performed using biotin labeled AVASTIN®.

AVASTIN® was labeled with biotin using EZ-Link NHS-LC-Biotin (Pierce, cat#21336). VEGF (Peprotech, cat#100-20) was coated on a 96-well plate (Thermo Electron, cat#3855) at 100 ng/mL in PBS overnight at 4° C. The plate was then incubated with 100 µl of blocking solution (Thermo Scientific, cat#N502) for 1 hour at RT. After washing the plate 4 times with 0.1% Tween 20 in PBS, 50 µL of AVASTIN®-biotin at 150 ng/mL and 50 µL of various concentrations of AVA-lm32(H) or unlabeled AVASTIN® were added and incubated at RT for 1 hour. The plate was washed 4 times and incubated with Streptavidin-HRP (Thermo, cat#N100) at 1:1000 dilution for 1 hour at RT. The plate was washed 4 times and 100 µL of TMB reagent was added. After 10 minutes incubation at RT, 100 µL of 0.36N $H_2SO_4$ was added to stop the reaction and the plate was read at 450 nm.

The data presented in FIG. 22 demonstrate that AVA-lm32 (H) specifically binds to VEGF-2. It inhibits binding of biotinylated AVASTIN® to VEGF in a dose dependent manner. The dose response curves generated by AVA-lm32 (H) and unlabeled AVASTIN® are superimposable and indicate similar binding affinities.

Example 27

Binding of HER-Lm32(H) and HER-lm32(L) to HER2 Expressed on Breast Cancer Cells

To determine the relative binding affinity of HERCEPTIN®-based antibodies containing MRDs to cell surface HER2 compared to HERCEPTIN®, a competitive binding assay was performed with Eu-labeled HERCEPTIN®.

HERCEPTIN® was labeled with Eu3+ using a dissociation-enhanced lanthanide fluorescence immunoassay (DEL-FIA) Europium-labeling kit (Perkin Elmer Life Sciences, cat#1244-302) following the manufacturer's instructions. The labeling agent is the Eu-chelate of N1-(p-isothiocynateobenzyl) diethylenetriamine N1, N2, N3, N3-tetraacetic acid (DTTA). The DTTA group forms a stable complex with Eu3+, and the isothiocynate group reacts with amino groups on the protein at alkaline pH to form a stable, covalent thio-urea bond. HERCEPTIN® (0.2 mg in 200 mL sodium bicarbonate buffer pH 9.3) was labeled with 0.2 mg of labeling agent at 4° C. overnight. Eu-labeled HERCEPTIN® was purified by spin column using 50 mmol/L tris-HCl pH 7.5 and 0.9% NaCl elution buffer.

The Eu-HERCEPTIN® binding assay was performed by incubating 0.5-1 million BT-474 or SK-BR3 breast cancer cells per well in a 96-well plate with 2-5 nM Eu-HERCEPTIN® in the presence of various concentrations of unlabeled HERCEPTIN®-based antibodies containing MRDs or HERCEPTIN® for 1 hour at RT. Unbound Eu-HERCEPTIN® was removed by washing using 200 µL complete medium. Cells were then resuspended in 100 µL complete medium and 80 µL of cell suspension transferred to a 96-well isoplate. Cells were incubated with 100 µL Delfia enhancer solution at RT for 10 minutes and cell bound Eu-HERCEPTIN® was detected by Envison (Perkin Elmer).

The inhibition of binding curves obtained using BT-474 cells are presented in FIG. 23. Eu-HERCEPTIN® binding to BT-474 was inhibited by HERCEPTIN® and HERCEPTIN®-based antibodies containing MRDs in a dose-dependent fashion. Comparable IC-50 values were observed: 4.7 nM for HER-lm32(H), 5.7 nM for HER-lm32(L), and 3.7 nM for unlabeled HERCEPTIN®.

Example 28

Inhibition of Breast Cancer Cells Proliferation by HERCEPTIN®-Based Antibodies Containing MRDs HERCEPTIN® sensitive breast cancer cells SK-BR-3 expressing HER2neo receptor were also tested in a bioassay. SK-BR-3 cells (2000 cell/well) were plated in 96 well plates (Costar) in complete McCoy's growth medium containing 2 mM glutamine, pen/strep (Invitrogen) and 10% FBS (Hy-Clone). The cells were cultured for 24 hours at 37° C., 5% $CO_2$, 85% humidity. On the following day, the growth medium was replaced with starvation medium (McCoy's medium containing 2 mM glutamine, pen/strep, 0.5% FBS). Nine serial dilutions (concentration range 5000-7.8 ng/ml) of HERCEPTIN® and HERCEPTIN®-based antibodies containing MRDs were prepared in complete growth medium. After 24 hours of incubation, the starvation medium was removed, and the serial dilutions of HERCEPTIN® and HERCEPTIN®-based antibodies containing MRDs were transferred to the plates in triplicates. The cells were cultured for 6 days. The proliferation was quantified using the CellTiter Glo luminescence method.

The IC50 values determined using a four-parameter logistic model were as follows: 0.49+/−0.17 nm for HER-lm32 (H), 0.81+/−0.19 nm for HER-lm32(L), a and 0.67+/−0.15 nm for HER-con4(H). All tested HERCEPTIN®-based antibodies containing MRDs were able to inhibit the proliferation of the SK-BR-3 breast carcinoma cells with subnanomolar IC-50 values. The representative fitted dose response curves shown in FIGS. 24A-C demonstrate that HERCEPTIN®-based antibodies containing MRDs inhibit cell proliferation with similar potency to HERCEPTIN®.

Example 29

Antibody Dependent Cytotoxicity of HERCEPTIN®-Based Antibodies Containing MRDs To assess the ability of antibodies containing MRDs to mediate ADCC in vitro, a cytotoxicity assay based on the "DELFIA EUTDA Cytotoxicity reagents AD0116" kit (PerkinElmer) was used. In this assay, the target cells were labeled with a hydrophobic fluorescence enhancing ligand (BADTA, bis (acetoxymethyl) 2,2':6',2"-terpyridine-6,6"-dicarboxylate). Upon entering the cells, BADTA is converted to a hydrophilic compound (TDA, 2,2':6',2"-terpyridine-6,6"-dicarboxylic acid) by cytoplasmic esterases mediated cleavage and no longer can cross the membrane. After cell lysis, TDA is released into a medium containing Eu3+ solution to form a fluorescent chelate (EuTDA). The fluorescence intensity is directly proportional to the number of lysed cells.

HERCEPTIN® and HERCEPTIN®-based antibodies containing MRDs can mediate ADCC on Her2 positive breast cancer cells by binding to the HER2 receptor on the surface of the target cells and activating the effector cells present in human PBMCs by interacting with their FcγRIII receptors. A HER2 positive human breast cancer cell line SK-BR-3 was used as a target cell line in the ADCC assay to demonstrate this.

SK-BR-3 cells were detached with 0.05% trypsin-versene and resuspended at $1\times10^6$ cells/mL in RPMI1640 medium containing 2 mM glutamine, pen/strep and 10% FBS (complete growth medium). $2\times10^6$ cells in 2 mL of media were transferred into 15 mL tube and 10 µl of BADTA reagent was added. The cell suspension was mixed gently and placed in the incubator at 37° C., 5% $CO_2$ and 85% humidity for 15 minutes. Seven 10x serial dilutions starting with 5 µg/mL of HERCEPTIN® or HERCEPTIN®-based antibodies containing MRDs were prepared during cell labeling.

After incubation with BADTA, cells were washed 4 times in complete growth medium containing 2.5 mM Probenecid. Between washes, cells were spun down by centrifugation at 1000 rpm for 3 minutes. After the last wash, labeled SK-BR-3 cells were resuspended in 10 mL complete growth medium and 50 µl of cells were added to each well of 96 well plate, except background wells. 50 µl of serial dilutions of HERCEPTIN® or HERCEPTIN®-based antibodies containing MRDs were added to the designated wells. The plates were transferred to the incubator at 37° C., 5% $CO_2$ and 85% humidity for 30 minutes.

PBMCs that were purified from human peripheral blood one day prior the ADCC assay, were washed once in RPMI1640 with 2 mM glutamine, pen/strep, 10% FBS. 10 mL of the PBMCs suspension with $2.5\times10^6$ cells/mL was prepared. 100 µl of PBMC suspension was transferred into wells containing target cells and HERCEPTIN® or HERCEPTIN®-based antibodies containing MRDs in triplicate. The following controls were placed in designated wells: Spontaneous release (target cells without effector cells), Maximum release (lysed target cells) and Background (media without cells). The plates were incubated for 2.5 hours an incubator with 37° C., 5% $CO_2$ and 85% humidity.

After incubation 20 µl of the supernatant was transferred to another plate and 200 µl of Europium solution was added. The plates were incubated on a plate shaker at RT for 15 minutes. The time resolved fluorescence was measured using PerkinElmer EnVision 2104 Multilabel Reader.

The following formula was used to calculate percentage of Specific release:

$$\frac{\text{Experimental release(counts)} - \text{Spontaneous release (counts)}}{\text{Maximum release(counts)} - \text{Spontaneous release (counts)}} \times 100$$

The IC50 values calculated by a four-parameter logistic model were as follows: 0.213+/−0.077 nM for HER-lm32 (H), 0.204+/−0.036 nM for HER-lm32(L), and 0.067+/−0.015 nM for HER-con4(H). All tested antibodies containing MRDs demonstrated robust ADCC activity with subnanomolar IC-50 values. The representative fitted dose response curves shown in FIGS. 25A and 25B demonstrate that antibodies containing MRDs are able to mediate cell dependent cytotoxicity with comparable potency to HERCEPTIN®.

A similar experiment was conducted in the presence of Ang2. Human PBMCs were activated with 20 ng/ml of IL-2 overnight and added to freshly plated (10,000 cells/well) BADTA labeled SK-BR-3 cells. The effector/target ratio was 25/1. After a 4-hour incubation with serial dilutions of HER-lm32(H) or HUMIRA® in the presence of 2 µg/ml Ang2, Eu was added to the medium and TRFI measured on Envision reader (Perkin-Elmer). HER-lm32 was more potent in mediating ADCC in the presence of Ang2.

Example 30

Inhibition of Endothelial Cell Proliferation by AVA-lm32(H)

The biological activities of the AVASTIN®-based antibodies containing MRDs AVA-lm32(H) were tested to determine if they could inhibit VEGF-induced proliferation of Human Umbilical Vein Endothelial Cells (HUVEC) assay.

HUVEC were obtained from GlycoTech (Gaithersburg, Md.) and Lonza on passage 1 and passage 3 respectively. Cells were grown on Endothelial cell basal medium (EBM-2) with addition of 2% fetal bovine serum (FBS) and single quotes (Lonza) at 37° C., 5% $CO_2$, 85% humidity. For inhibition of proliferation experiments, cells were plated in 96-well plates (Costar) at 2000 cells per well in EBM-2 medium with 2% FBS and cultivated for 24 hours. Nine serial dilutions of AVASTIN® or AVA-lm32(H) were prepared starting with 5 µg/mL on EBM-2 medium with 2% FBS. VEGF (R & D Systems) was added at a final concentration of 10 ng/mL to all serial dilutions. After incubation for 15 minutes at 37° C., 5% $CO_2$, 85% humidity, serial dilutions were added to the cells. After 96 hours, CellTiter Glo was added to the cells. After incubation at RT for 15 minutes, the cell suspension was transferred into 96 well white opaque plates, and luminescence was measured using PerkinElmer EnVision 2104 Multilabel Reader.

As shown in FIGS. 26A and 26B, AVA-lm32(H) exhibited dose dependent anti-proliferative activity on HUVECs from both sources. IC50 values calculated from 4 PL fitted curves indicate similar potency for AVA-lm32(H) and AVASTIN® (IC50 values 0.36+/−0.42 nM and 0.33+/−0.38 nM, respectively).

Example 31

MRD-Containing Antibodies Inhibit Tumor Proliferation In Vivo

In order to determine the effectiveness of MRD-containing antibodies in vivo, their efficacy in a mouse Colo5 tumor model was assessed. In these experiments, tumors were implanted into the right flank of six-week old female athymic nude mice by injecting 5×10⁶ Colo205 cells suspended in 100 μL PBS. Three groups of eight animals each received intraperitoneal injections of 5 mg/kg of antibody (HERCEPTIN®, RITUXAN®) or an MRD-containing antibody (HER-2×Con4; "H2×Con4") in 100 μL PBS every third day starting at day 6 after tumor implantation. The results, shown in FIG. 27, demonstrate that the MRD-containing antibody was more efficient at inhibiting tumor growth than either rituximab or HERCEPTIN®.

HERCEPTIN® with lm32 fused to the C-terminus of the heavy chain also inhibited tumor growth in both Her2 dependent and angiogenesis dependent xenograft tumor models. The HERCEPTIN®-lm32 fusion had a similar PK to HERCEPTIN® in both mice and monkeys after single dose injections. Furthermore, the HERCEPTIN®-lm32 fusion was stable in whole blood at 37° C. for up to 72 hours.

Example 32

Molecular Assays to Evaluate MRD-Containing Antibodies

Novel MRD-containing antibodies are generated by altering the sequence of the MRD and/or the antibody, by altering the location at which the antibody is linked to the MRD, and/or by altering the linker through which the MRD is connected to the antibody. The binding potential, structure, and functional properties of the MRD-containing antibodies are evaluated using known techniques to measure protein binding and function. The MRD-containing antibodies are compared to the MRD alone, the antibody alone, and to other MRD-containing antibodies.

An MRD-containing antibody is tested using a solid phase assay in which a target of the MRD and/or antibody is immobilized on a solid surface and then exposed to increasing concentrations of a fluorescently labeled MRD-containing antibody. The solid surface is washed to remove unbound MRD-containing antibody and the amount of target-bound MRD-containing antibody is determined directly by quantitating fluorescence. In another experiment, the immobilized target is exposed to increasing concentrations of an unlabeled MRD-containing antibody and the amount of target-bound MRD-containing antibody is determined indirectly by use of a labeled reagent that binds to the MRD-containing antibody.

An MRD-containing antibody is tested using a liquid phase assay in which a target of the MRD and/or antibody is added to various concentrations of an MRD-containing antibody is a solution. The interaction of the target with the MRD-containing antibody is detected by the appearance of a molecular complex comprised of a target and MRD-containing antibody that differs in molecular mass (and mobility) from unbound target and unbound MRD-containing antibody.

An MRD-containing antibody is also assayed in a cell based assay in which target-expressing cells are incubated in the presence of increasing concentrations of MRD-containing antibody. The binding of the MRD-containing antibody is detected by fluorescence activated cell sorting. In addition, cellular proliferation, cellular differentiation, protein phosphorylation, protein expression, mRNA expression, membrane composition, signaling pathway activity, and cellular viability are assessed.

Useful MRD-containing antibodies bind to both the MRD target and to the antibody target. In addition, useful MRD-containing antibodies affect at least one cellular process.

Example 33

Identification of MRDs with Improved Characteristics

Two potential T cell epitopes were identified in LM32. In order to identify LM32 variants that did not containing T cell epitopes, and therefore, were less likely to produce immunogenic responses, mutational and deletional variants of the LM32 peptide were created. The LM32 variants listed in Table 7 MRDs were expressed as MBP fusion proteins and tested for the ability to bind Ang2.

TABLE 7

| MRD expressed as a MBP fusion protein | EC50 (nM) | SEQ ID NO |
|---|---|---|
| KSLSLSPGSGGGSMGAQTNFMPMDNDELLLYEQFI | 1.080 | 86 (142) |
| KSLSLSPGSGGGSMGAQTNFMPMDNEELLLYEQFI | 20.700 | 87 (143) |
| KSLSLSPGSGGGSMGAQTNFMPMDNDEGLLYEQFILQQGLE | 1.040 | 88 |
| KSLSLSPGSGGGSMGAQTNFMPMDNDELGLYEQFILQQGLE | na | 89 |
| KSLSLSPGSGGGSMGAQTNFMPMDNDEALLYEQFILQQGLE | 0.182 | 90 |
| KSLSLSPGSGGGSMGAQTNFMPMDNDELTLYEQFILQQGLE | 1.420 | 91 |
| KSLSLSPGSGGGSMGAQTNFMPMDNDELLLYEQFIYQQGLE | na | 92 |
| KSLSLSPGSGGGSMGAQTNFMPMDNDEGLLYEQFIYQQGLE | 0.902 | 93 |
| KSLSLSPGSGGGSMGAQTNFMPMDNDEALLYEQFIYQQGLE | 0.392 | 94 |

TABLE 7-continued

| MRD expressed as a MBP fusion protein | EC50(nM) | SEQ ID NO |
|---|---|---|
| KSLSLSPGSGGGSMGAQTNFMPMDNEELTLYEQFIFQQG | na | 95 |
| KSLSLSPGSGGGSMGAQTNFMPMDNDEGLLYEEFILQQGLE | 0.922 | 96 |
| KSLSLSPGSGGGSMGAQTNFMPMDNDEALLYEEFILQQGLE | 0.426 | 97 |
| KSLSLSPGSGGGSMGAQTNFMPMDNEELTLYEEFILQQGLE | na | 98 |
| KSLSLSPGSGGGSMGAQTNFMPMDQDELLLYEQFILQQGLE | 0.383 | 99 |
| KSLSLSPGSGGGSMGAQTNFMPMDDDELLLYEQFILQQGLE | 0.240 | 100 |

The LM32 variants are then tested for their ability to induce proliferation and/or cytokine release. LM32 variants that are functionally active and have reduced immunogenic potential are identified. An MRD-containing antibody comprising the LM32 variant fused to the light chain of HERCEPTIN®, an MRD-containing antibody comprising the LM32 variant fused to the heavy chain of HERCEPTIN®, an MRD-containing antibody comprising the LM32 variant fused to the light chain of HUMIRA®, an MRD-containing antibody comprising the LM32 variant fused to the heavy chain of HUMIRA®, MRD-containing antibody comprising the LM32 variant fused to the light chain of AVASTIN®, and an MRD-containing antibody comprising the LM32 variant fused to the heavy chain of AVASTIN® are created. The LM32-variant containing antibodies are administered to animal models and the plasma protein representation and plasma and tissue residence are measured and compared to those of HERCEPTIN®, HUMIRA®, and AVASTIN®. In addition, the effects of the LM32-variant containing antibodies on cellular proliferation, angiogenesis, tumorigenicity, arthritic indicators are compared to the effects of HERCEPTIN®, HUMIRA®, and AVASTIN®.

Example 34

In Vivo Assays to Evaluate MRD-Containing Antibodies

In order to determine the efficacy of MRD-containing antibodies in vivo, animal models are treated with an antibody and an MRD-containing antibody and the results are compared.

MRD-containing anti-HER2 antibodies are tested in the following in vivo model. NIH 3T3 cells transfected with a HER2 expression plasmid are injected into nu/nu athymic mice subcutaneously at a dose of $10^6$ cells in 0.1 ml of phosphate-buffered saline as described in U.S. Pat. No. 6,399,063, which is herein incorporated by reference in its entirety. On days, 0, 1, 5, and every 4 days thereafter 100 µg of a HER2 antibody, an ang2-containing HER2 antibody, an igflr-containing HER2 antibody and an ang2-igflr-containing HER2 antibody are injected intraperitoneally. Tumor occurrence and size are monitored for one month. Increases in efficacy of MRD-containing antibodies compared to antibodies are observed.

MRD-containing anti-VEGF antibodies are tested in the following in vivo model. RIP-TβAg mice are provided with high-sugar chow and 5% sugar water as described in U.S. Published Application No. 2008/0248033, which is herein incorporated by reference in its entirety. At 9-9.5 or 11-12 weeks of age, the mice are treated twice-weekly with intra-peritoneal injections of 5 mg/kg of an anti-VEGF antibody, ang2-containing VEGF antibody, ifg 1r-containing VEGF antibody or ang2- and igflr-containing antibody. The 9-9.5 week mice are treating for 14 days and then examined. The 11-12 week mice are examined after 7, 14, and 21 days of treatment. The pancreas and spleen of the mice are removed and analyzed. Tumor number is determined by dissecting out each spherical tumor and counting. Tumor burden is determined by calculating the sum of the volume of all tumors within the pancreas of a mouse. The effect on angiogenesis is determined by calculating the mean number of angiogenic islets observed. Increases in efficacy of MRD-containing antibodies compared to antibodies are observed.

MRD-containing anti-TNF antibodies are tested in the following in vivo model. Transgenic mice (Tg197) are treated with three intra-peritoneal injections of anti-TNF antibody or ang2-containing TNF antibody at 1.5 µg/g, 15 µg/g, or 30 µg/g as in U.S. Pat. No. 6,258,562, which is incorporated herein by reference in its entirety. Injections continue for about 10 weeks and macroscopic changes in joint morphology are recorded each week. At 10 weeks, mice are sacrificed and microscopic examination of tissue is performed. Joint size is established as an average measurement on the hind right ankle using a micrometer device and arthritic scores are recorded as follows: 1=no arthritis; +/−=mild (joint distortion); ++=moderate arthritis (swelling, joint deformation); and +++=heavy arthritis (ankylosis detected on flexion and severely impaired movement). Histopathological scoring based on haematoxylinleosin staining of joint sections is based as follows; 0=No detectable disease; 1=proliferation of the synovial membrane; 2=heavy synovial thickening 3=cartilage destruction and bone erosion. Increases in efficacy of MRD-containing antibodies compared to antibodies are observed.

Although the invention has been described with reference to the above examples, it will be understood that modifications and variations are encompassed within the spirit and scope of the invention. Accordingly, the invention is limited only by the following claims.

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

The invention claimed is:

1. A complex comprising a modular recognition domain (MRD) capable of binding angiopoietin-2 (ANG-2), wherein the MRD comprises amino acid sequence AQTNFMPMDQEEALLYEEFI (SEQ ID NO:108) or amino acid sequence AQTNFMPMDQDEALLYEEFI (SEQ ID NO:109).

2. The complex of claim 1, wherein the MRD is fused to a heterologous protein.

3. The complex of claim 1, which further comprises an antibody.

4. The complex of claim 3, wherein the MRD and the antibody are covalently bound.

5. The complex of claim 4, wherein the antibody binds ANG-2.

6. The complex of claim 4, wherein the MRD and the antibody bind different targets.

7. The complex of claim 6, wherein the antibody binds a target selected from: vascular endothelial growth factor (VEGF), epidermal growth factor (EGF), type 1 insulin-like growth factor 1 (IGF1), fibroblast growth factor 1 (FGF1), fibroblast growth factor 2 (FGF2), fibroblast growth factor 3 (FGF3), fibroblast growth factor 4 (FGF4), fibroblast growth factor receptor 1 (FGFR1), fibroblast growth factor receptor 2 (FGFR2), fibroblast growth factor receptor 3 (FGFR3), vascular endothelial growth factor receptor 1 (VEGFR1), epidermal growth factor receptor (EGFR), platelet-derived growth factor receptor (PDGFR), erb b2 receptor tyrosine kinase 2 (ErbB2), erb b2 receptor tyrosine kinase 3 (ErbB3), type 1 insulin-like growth factor 1 receptor (IGF1R), hepatocyte growth factor receptor (cMET), cluster of differentiation 19 (CD19), and cluster of differentiation 20 (CD20).

8. The complex of claim 7, wherein the antibody competitively inhibits:

(a) binding of trastuzumab to ErbB2;
(b) binding of pertuzumab to ErbB2;
(c) binding of bevacizumab to VEGF;
(d) binding of cetuximab to EGFR;
(e) binding of panitumumab to EGFR;
(f) binding of zalutumumab to EGFR;
(g) binding of nimotuzumab to EGFR;
(h) binding of matuzumab to EGFR;
(i) binding of figitumumab to IGF1R;
(j) binding of AMG 479 to IGF1R;
(k) binding of cixutumumab to IGF1R;
(l) binding of dalotuzumab to IGF1;
(m) binding of BIIB022 to IGF1; or
(n) binding of MEDI-573 to IGF1.

9. The complex of claim 6, wherein the antibody binds a target selected from: interferon-alpha, interferon alpha receptor, interferon beta, interferon beta receptor, interferon-gamma, sphingosine 1 phosphate receptor (S1PR), integrin avb3, Interleukin-1B (IL-1B), Interleukin-2 (IL-2), Interleukin-4 (IL-4), Interleukin 4 Receptor (IL-4R), Interleukin-5 (IL-5), Interleukin-5 Receptor (IL-5R), Interleukin-6 (IL-6), Interleukin 6-Receptor (IL-6R), Interleukin-7 (IL-7), Interleukin-8 (IL-8), Interleukin-9 (IL-9), Interleukin-9 Receptor (IL-9R), Interleukin-10 Receptor (IL-10R), Interleukin-11 (IL-11), Interleukin-12 (IL-12), Interleukin-13 (IL-13), Interleukin-23 (IL-23), Interleukin-15 (IL-15), Interleukin-18 (IL-18), Interleukin-21 (IL-21), Inducible T-cell COStimulator (ICOS), programmed cell death protein-1 (PD-1), and Leukemia Inhibitory Factor (LIF).

10. The complex of claim 6, wherein the antibody binds to tumor necrosis factor alpha (TNF).

11. The complex of claim 10, wherein the antibody competitively inhibits binding of adalimumab, golumimab, or infliximab to TNF.

12. A pharmaceutical composition comprising the complex of claim 3.

* * * * *